(12) United States Patent
Karuppasamy

(10) Patent No.: US 11,998,708 B2
(45) Date of Patent: Jun. 4, 2024

(54) METHOD AND APPARATUSES FOR ACCESSING AND/OR MODIFYING A TARGET PATIENT TISSUE SITE

(71) Applicant: THE CLEVELAND CLINIC FOUNDATION, Cleveland, OH (US)

(72) Inventor: Karunakaravel Karuppasamy, Cleveland, OH (US)

(73) Assignee: THE CLEVELAND CLINIC FOUNDATION, Cleveland, OH (US)

( * ) Notice: Subject to any disclaimer, the term of this patent is extended or adjusted under 35 U.S.C. 154(b) by 580 days.

(21) Appl. No.: 17/323,578

(22) Filed: May 18, 2021

(65) Prior Publication Data
US 2021/0322739 A1  Oct. 21, 2021

Related U.S. Application Data

(63) Continuation of application No. 16/341,975, filed as application No. PCT/US2017/056564 on Oct. 13, 2017, now Pat. No. 11,020,573.

(60) Provisional application No. 62/469,566, filed on Mar. 10, 2017, provisional application No. 62/416,844, (Continued)

(51) Int. Cl.
*A61M 29/00* (2006.01)
*A61M 25/09* (2006.01)

(52) U.S. Cl.
CPC ............ *A61M 29/00* (2013.01); *A61M 25/09* (2013.01)

(58) Field of Classification Search
CPC .. A61M 29/00; A61M 25/09; A61M 25/0662; A61M 25/0668; A61M 2025/0687; A61B 17/3415; A61B 17/3421; A61B 17/3431
See application file for complete search history.

(56) References Cited

U.S. PATENT DOCUMENTS

| 4,846,791 A | 7/1989 | Hattler et al. |
| 5,221,256 A | 6/1993 | Mahurkar |

(Continued)

FOREIGN PATENT DOCUMENTS

WO    1997/29680 A1    8/1997

OTHER PUBLICATIONS

PCT International Search Report and Written Opinion for International Application Serial No. PCT/US2017/056564, dated Feb. 2, 2018, pp. 1-9.

*Primary Examiner* — Katherine H Schwiker
*Assistant Examiner* — Zehra Jaffri
(74) *Attorney, Agent, or Firm* — TAROLLI, SUNDHEIM, COVELL & TUMMINO L.L.P.

(57) ABSTRACT

A modular dilation device is provided for inserting multiple dilators into a target patient tissue site. The modular dilation device includes a first dilator and a second dilator. The first dilator has a first dilator distal end and a first dilator inner lumen. The first dilator has a first dilator side wall opening. The first dilator distal end has a first dilator open tip. The first dilator has a first dilator open slit. The first dilator open slit extends between the first dilator side wall opening and the first dilator open tip. The second dilator has a second dilator distal end and a second dilator inner lumen. The second dilator distal end has a second dilator open tip. When the second dilator is joined to the first dilator, the second dilator open tip is adjacent to the first dilator side wall opening.

8 Claims, 65 Drawing Sheets

Related U.S. Application Data filed on Nov. 3, 2016, provisional application No. 62/408,312, filed on Oct. 14, 2016.

(56) References Cited

U.S. PATENT DOCUMENTS

| | | | |
|---|---|---|---|
| 5,275,611 A * | 1/1994 | Behl | A61B 17/34 606/198 |
| 5,378,230 A | 1/1995 | Mahurkar | |
| 5,779,681 A | 7/1998 | Bonn | |
| 5,938,582 A | 8/1999 | Ciamacco, Jr. et al. | |
| 6,821,291 B2 | 11/2004 | Bolea et al. | |
| 6,966,886 B2 | 11/2005 | Appling | |
| 7,229,431 B2 | 6/2007 | Houser et al. | |
| 7,311,697 B2 | 12/2007 | Osborne | |
| 7,608,063 B2 | 10/2009 | Le et al. | |
| 7,615,034 B2 | 11/2009 | Difiore | |
| 7,938,795 B2 | 5/2011 | Difiore et al. | |
| 8,287,585 B2 | 10/2012 | Gurm | |
| 8,512,389 B2 | 8/2013 | Ayala et al. | |
| 8,845,675 B2 | 9/2014 | Johnson et al. | |
| 2002/0107482 A1 | 8/2002 | Rocamora et al. | |
| 2007/0244430 A1 | 10/2007 | Bedell | |
| 2014/0039586 A1 | 2/2014 | Barker et al. | |
| 2016/0174820 A1 | 6/2016 | Dejima et al. | |

\* cited by examiner

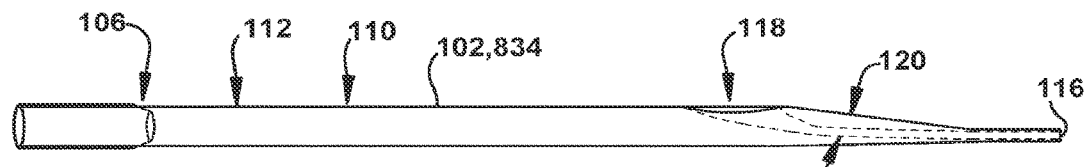
Fig. 9
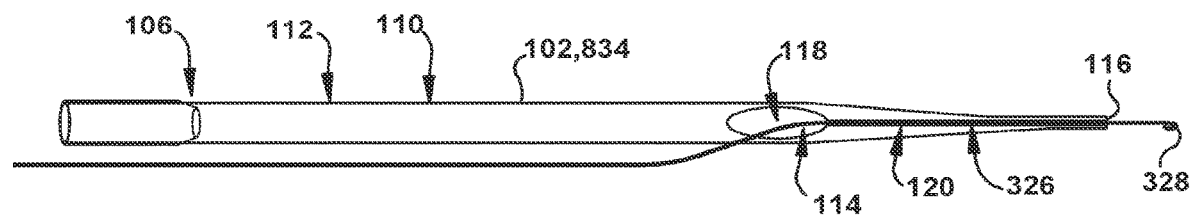
Fig. 10
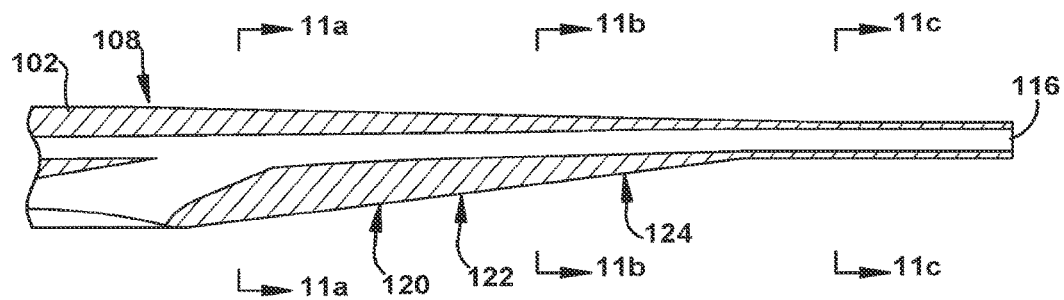
Fig. 11
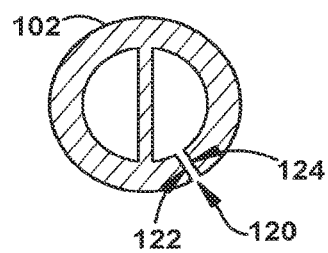 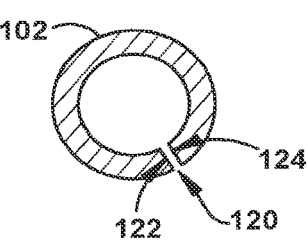 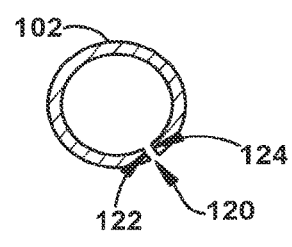
Fig. 11a    Fig. 11b    Fig. 11c

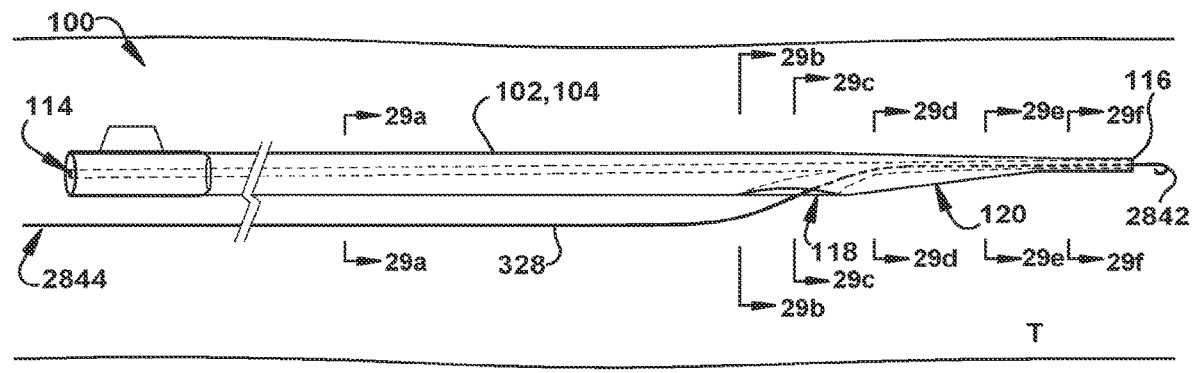
Fig. 29
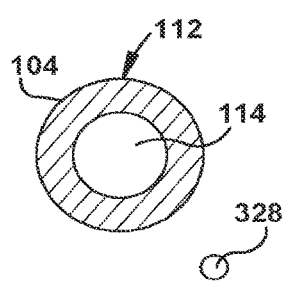 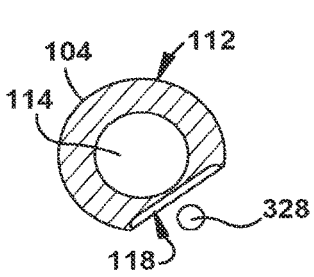 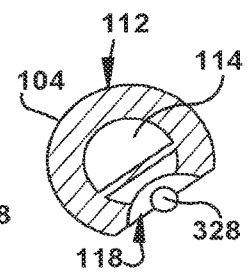 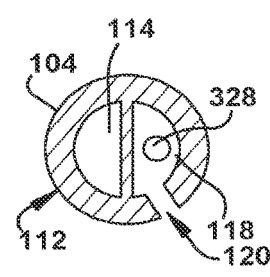
Fig. 29a  Fig. 29b  Fig. 29c  Fig. 29d
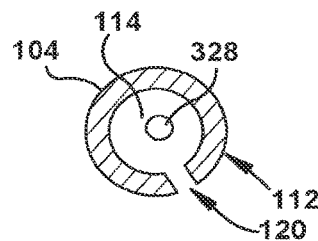 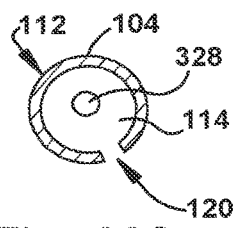
Fig. 29e  Fig. 29f

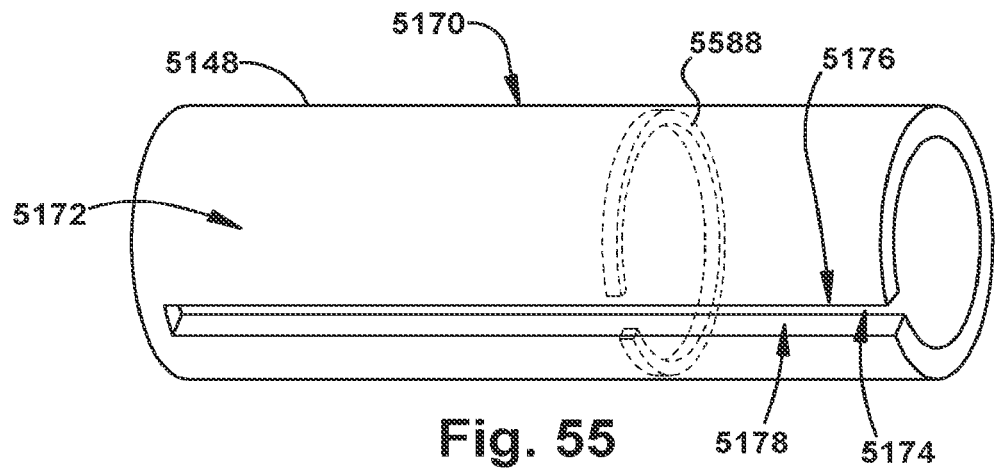
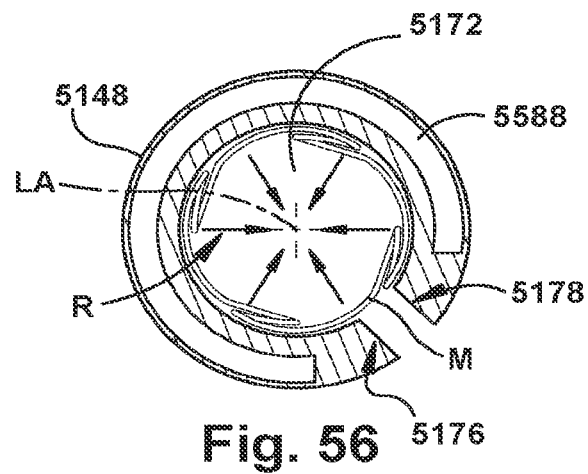
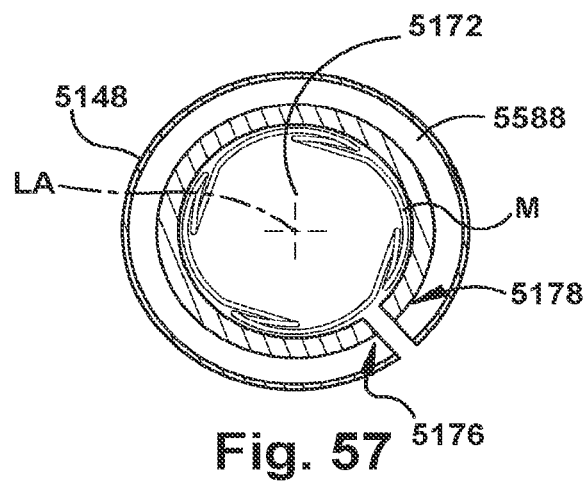

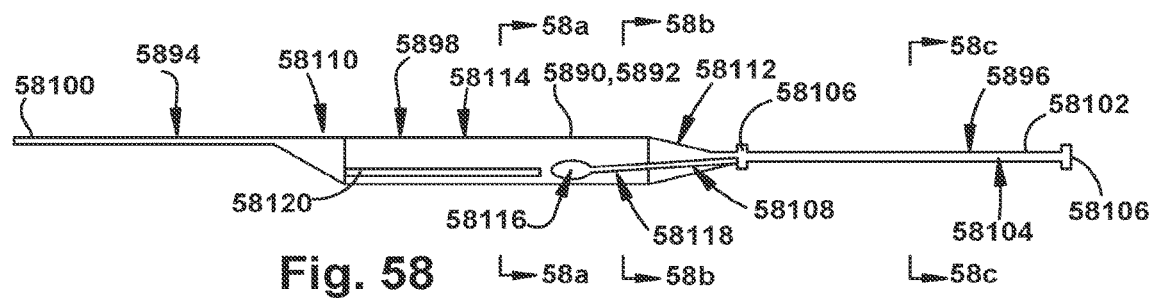
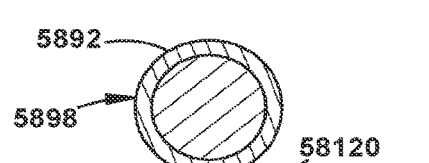 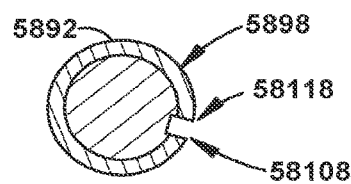 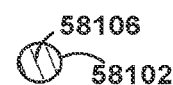
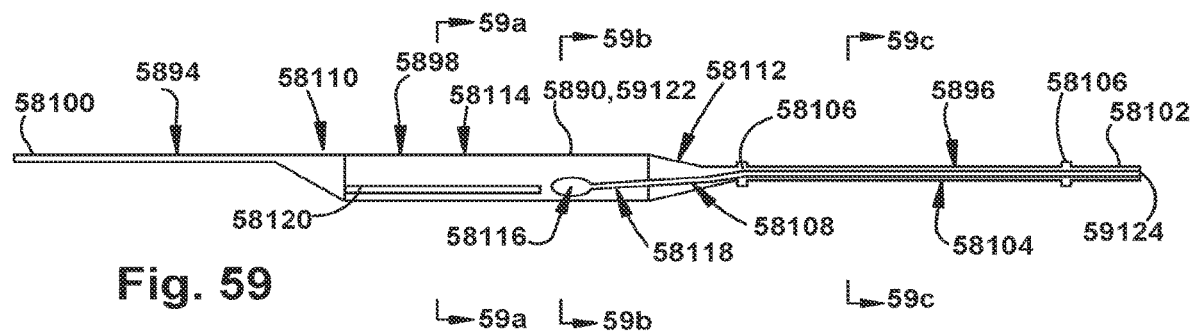
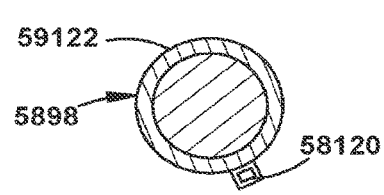 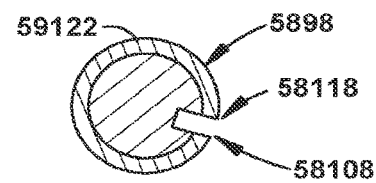 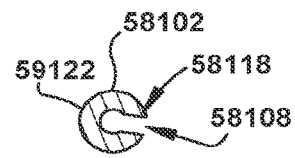

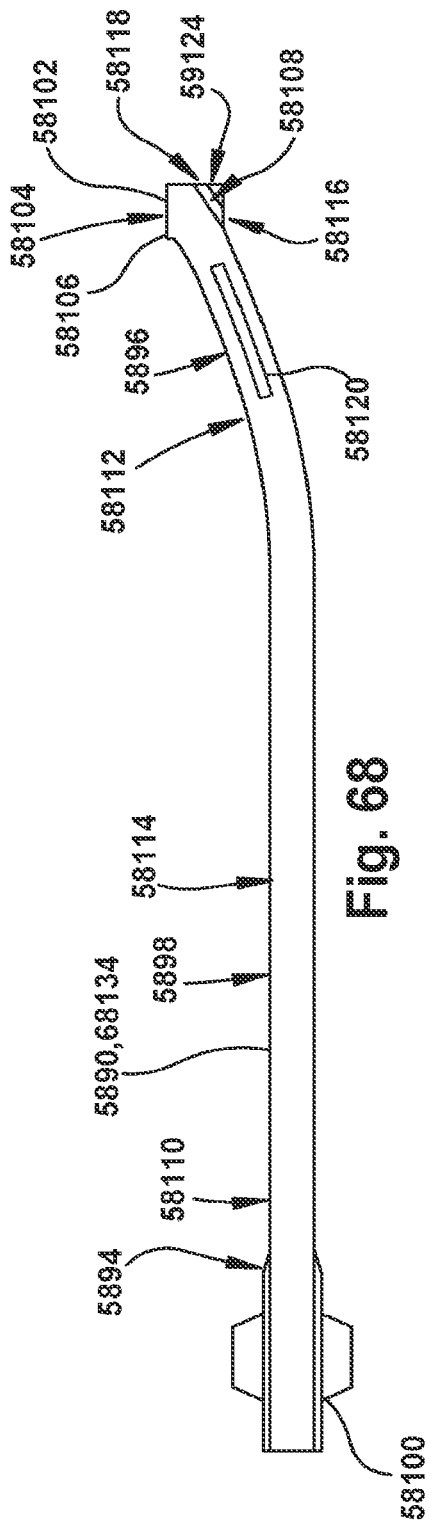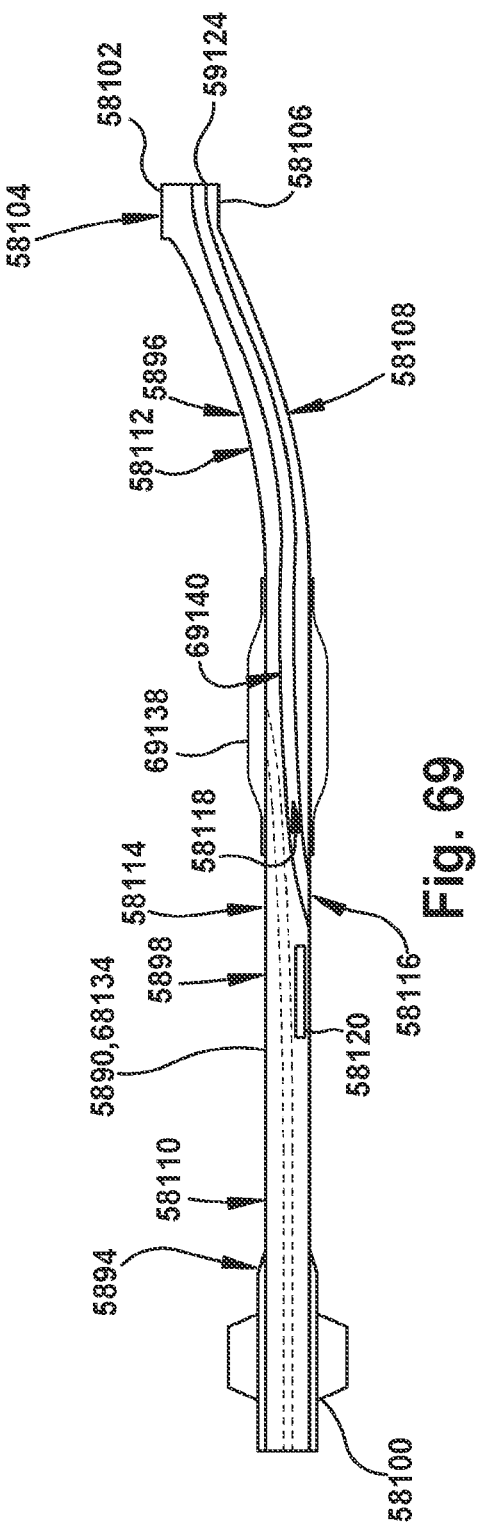

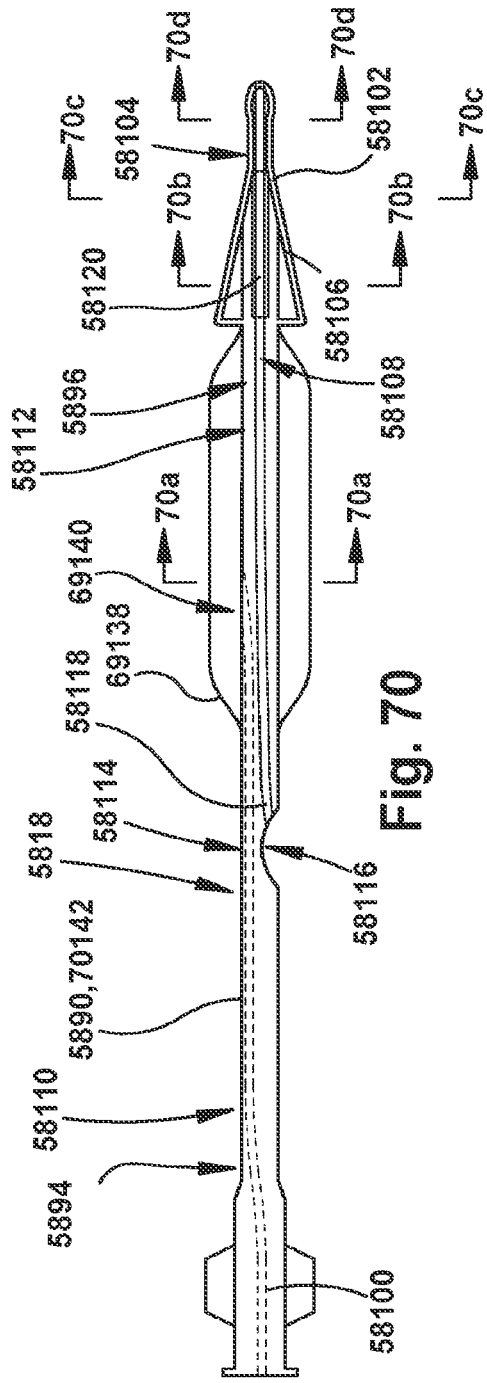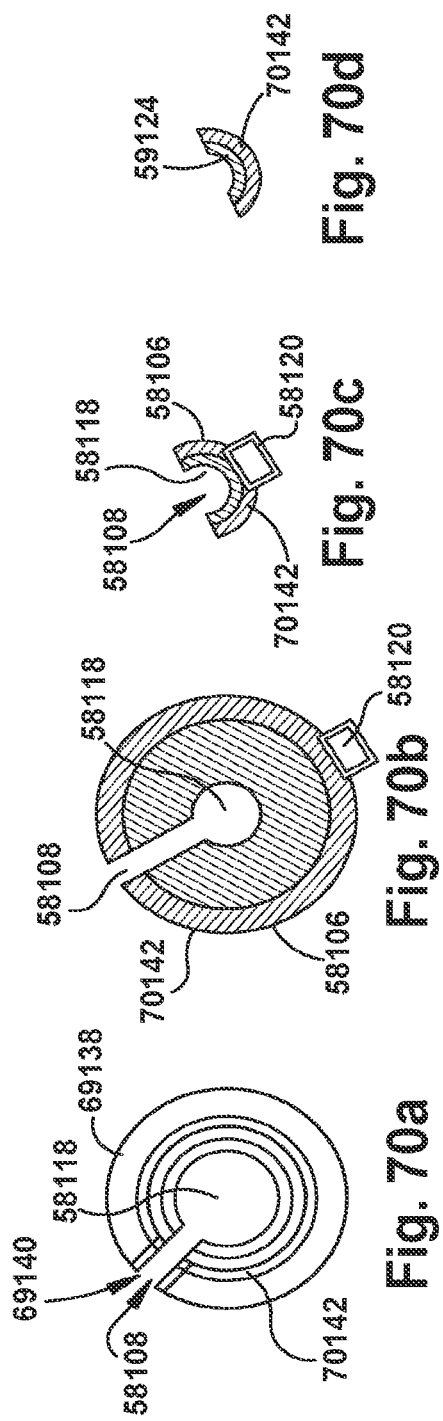

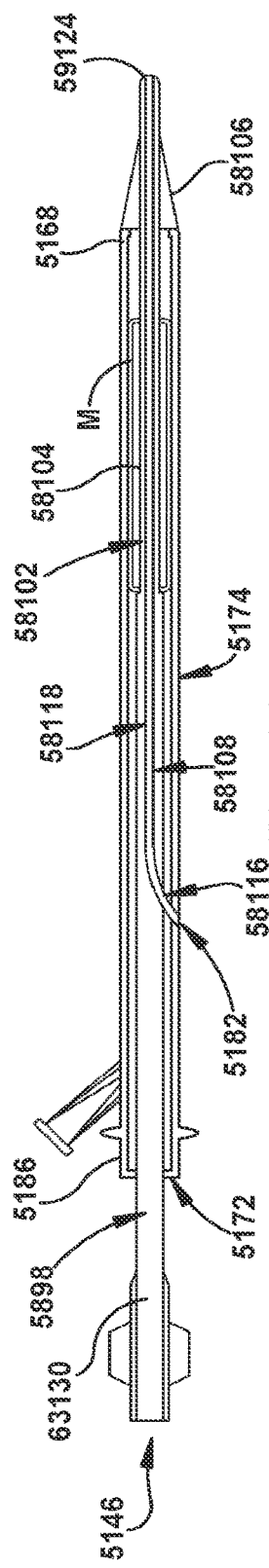
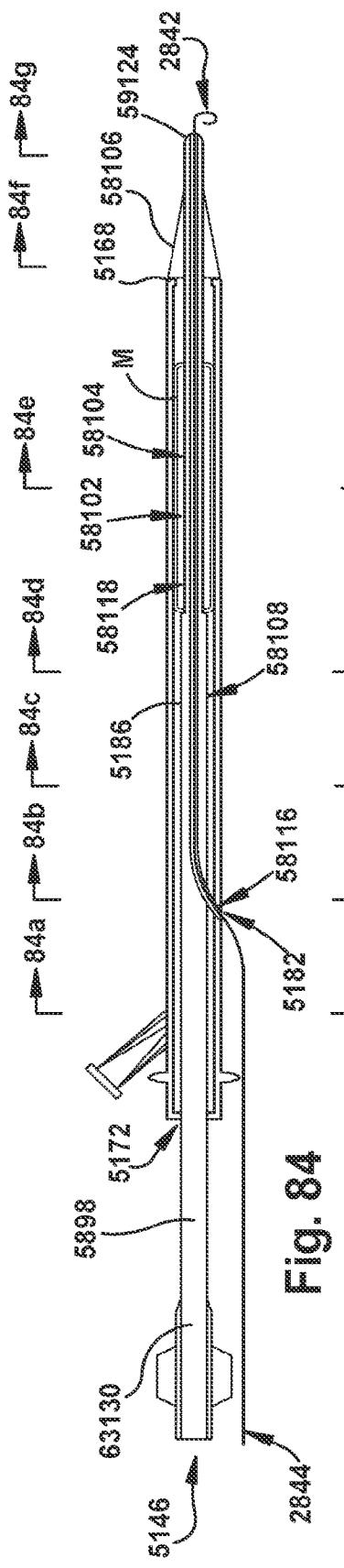
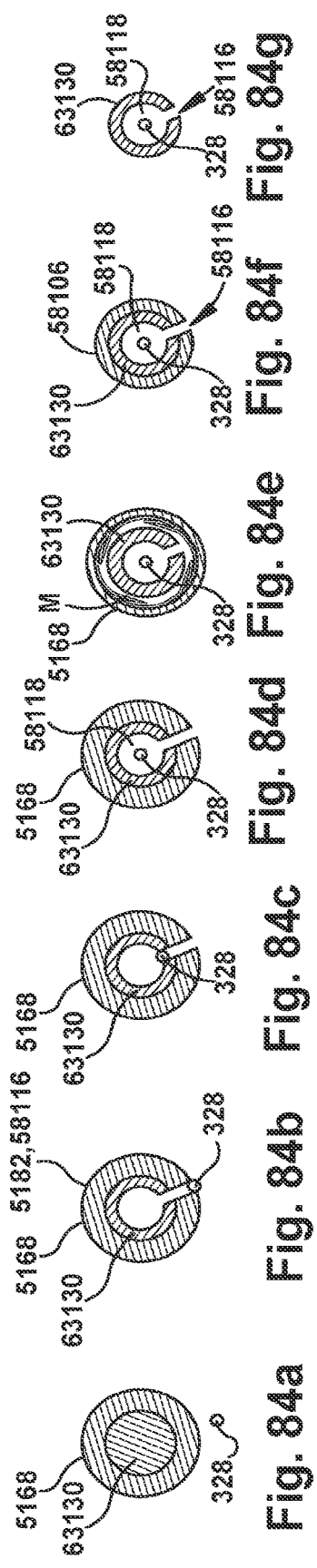

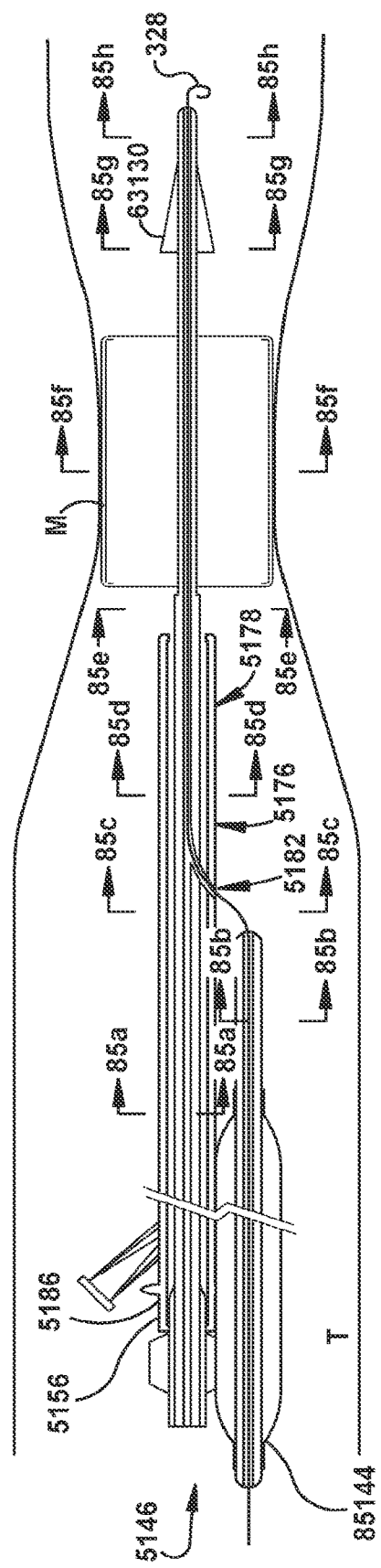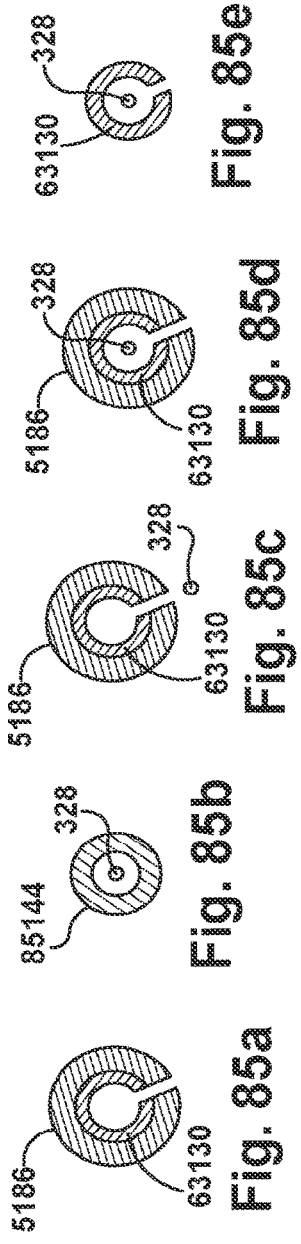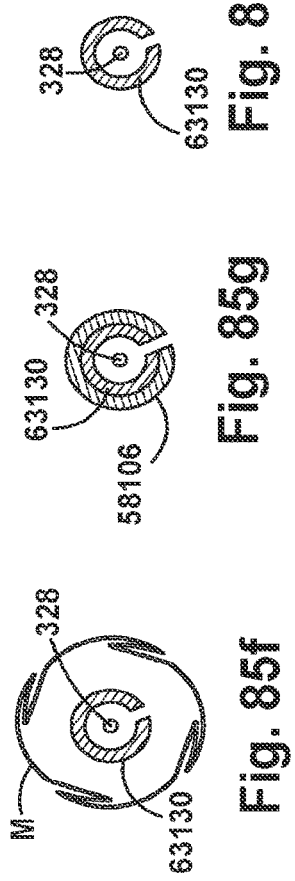

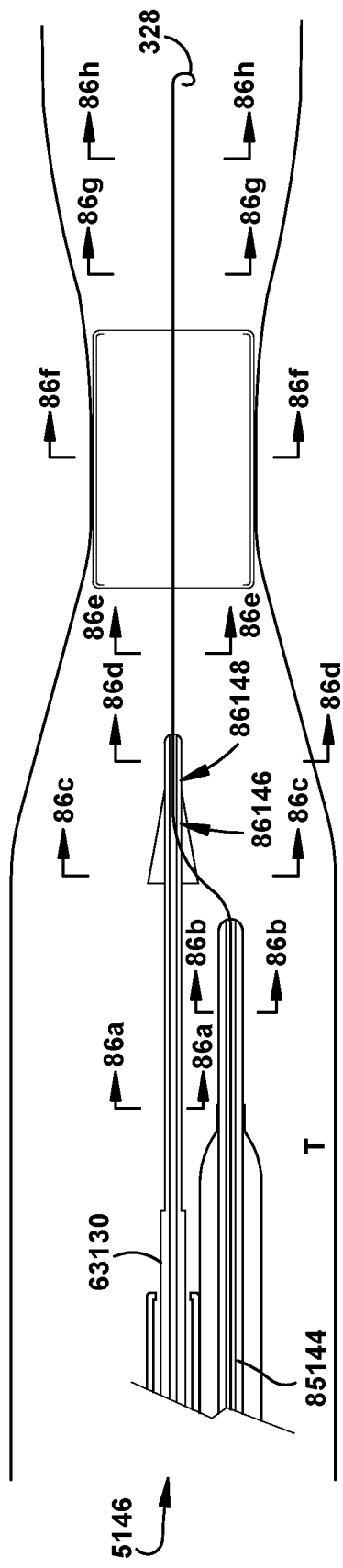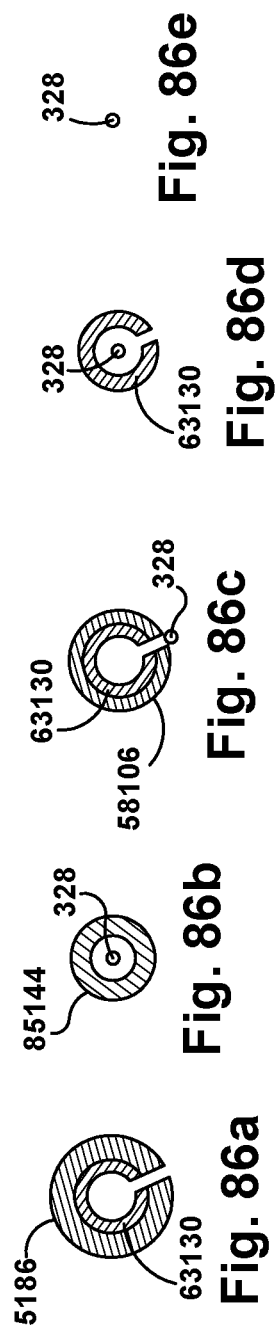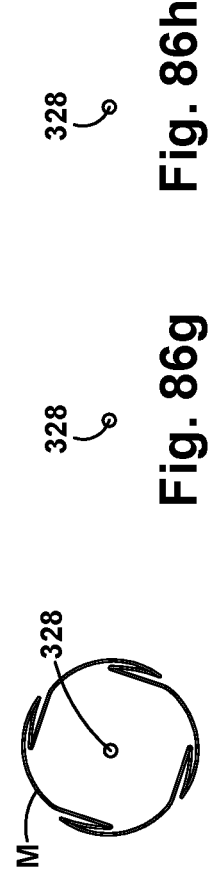

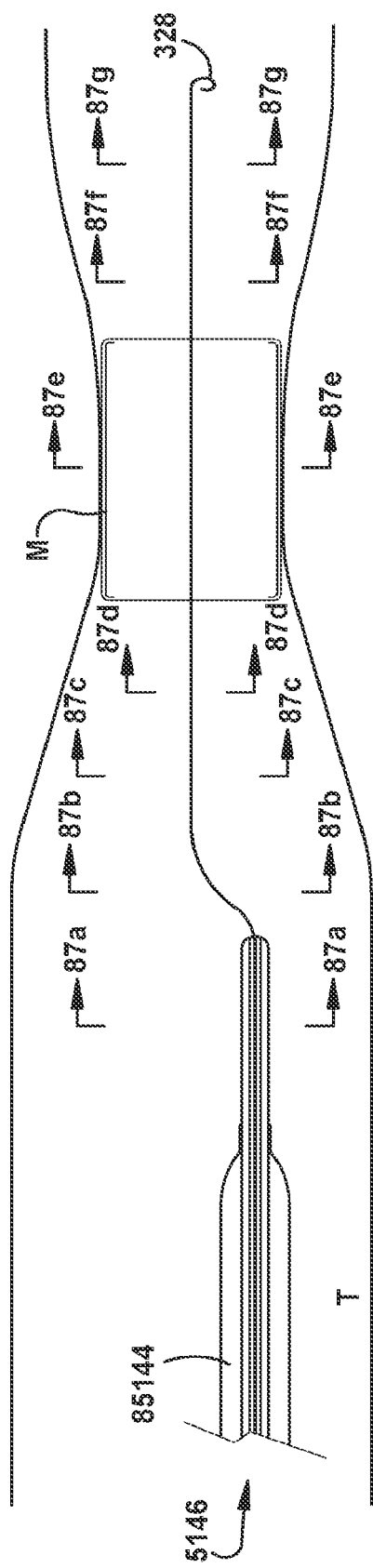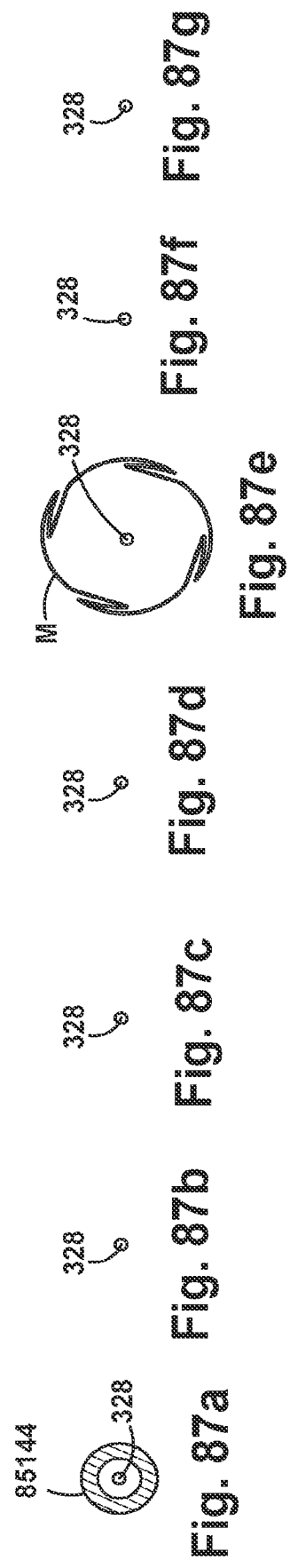
Fig. 87
Fig. 87a  Fig. 87b  Fig. 87c  Fig. 87d  Fig. 87e  Fig. 87f  Fig. 87g

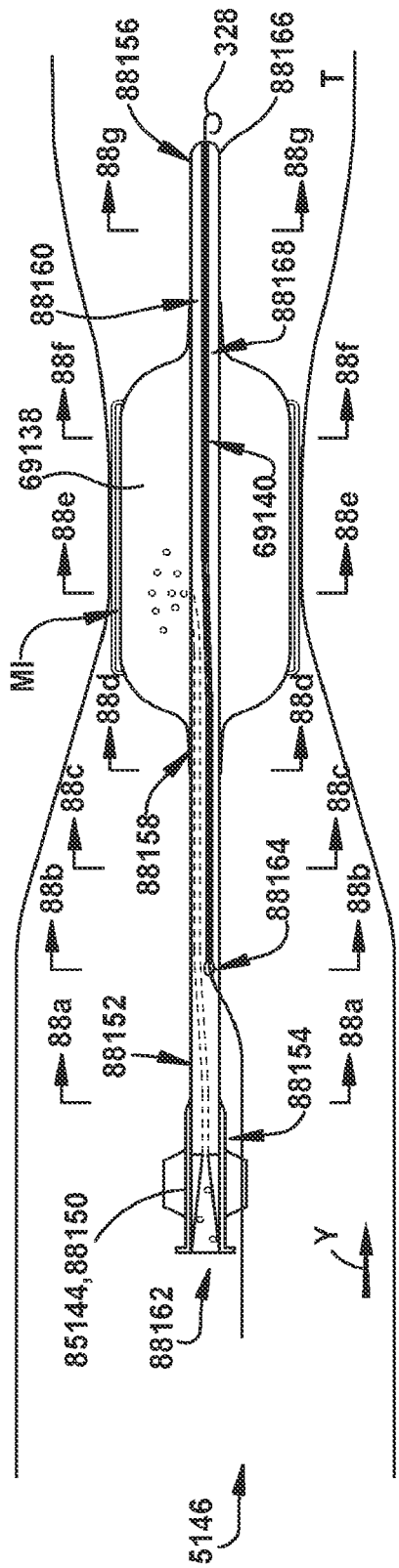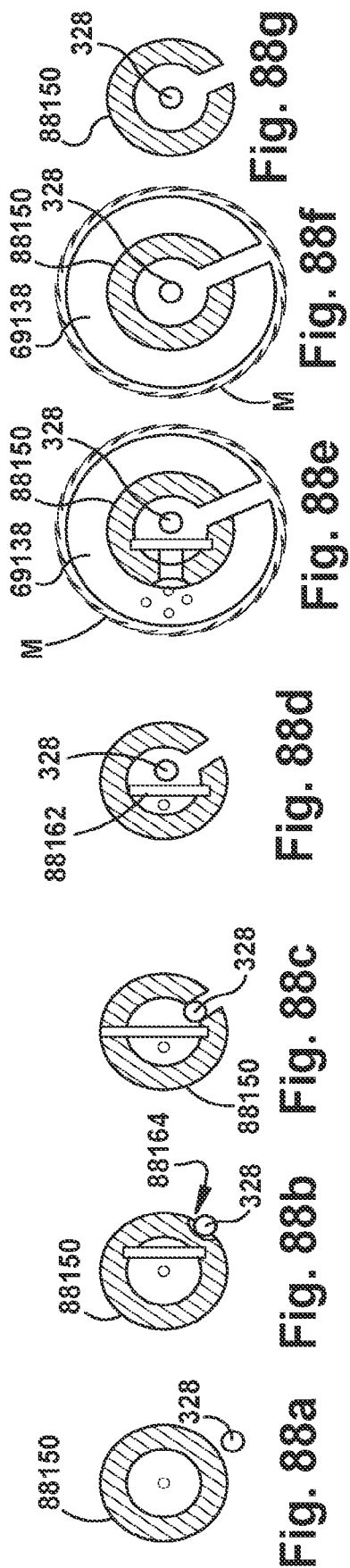

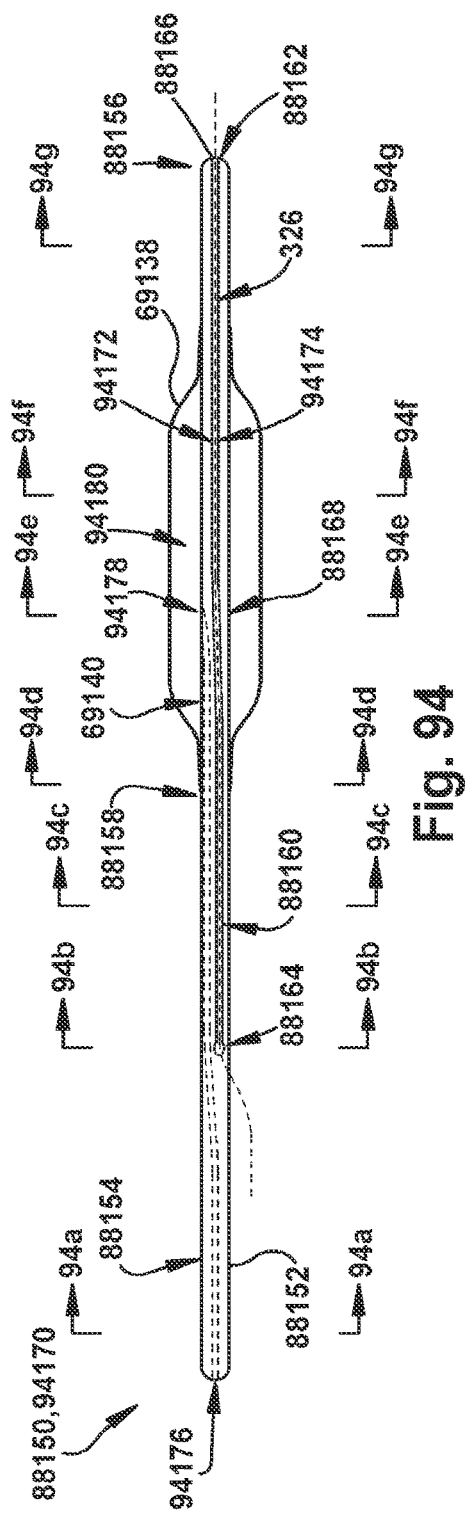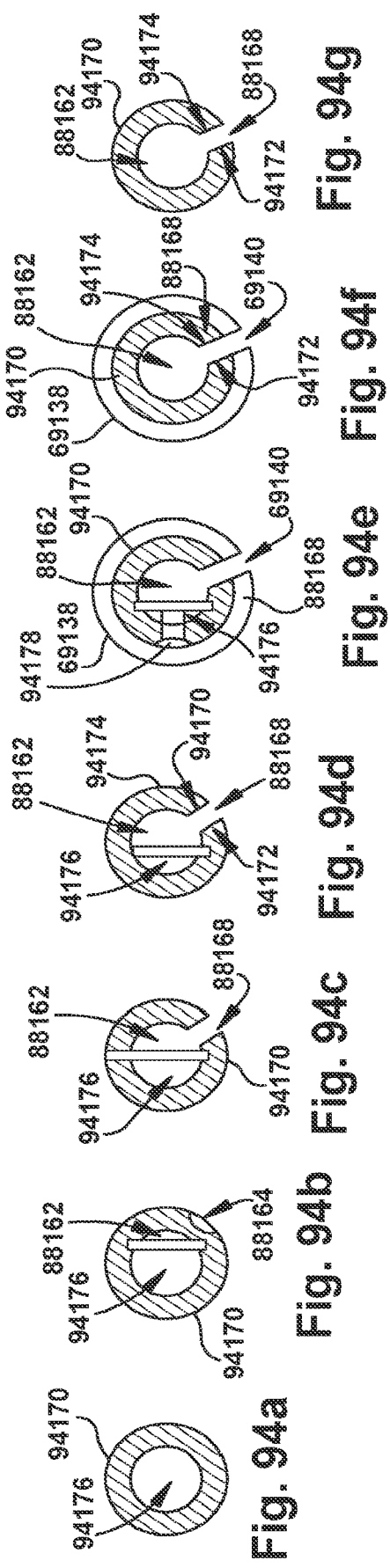

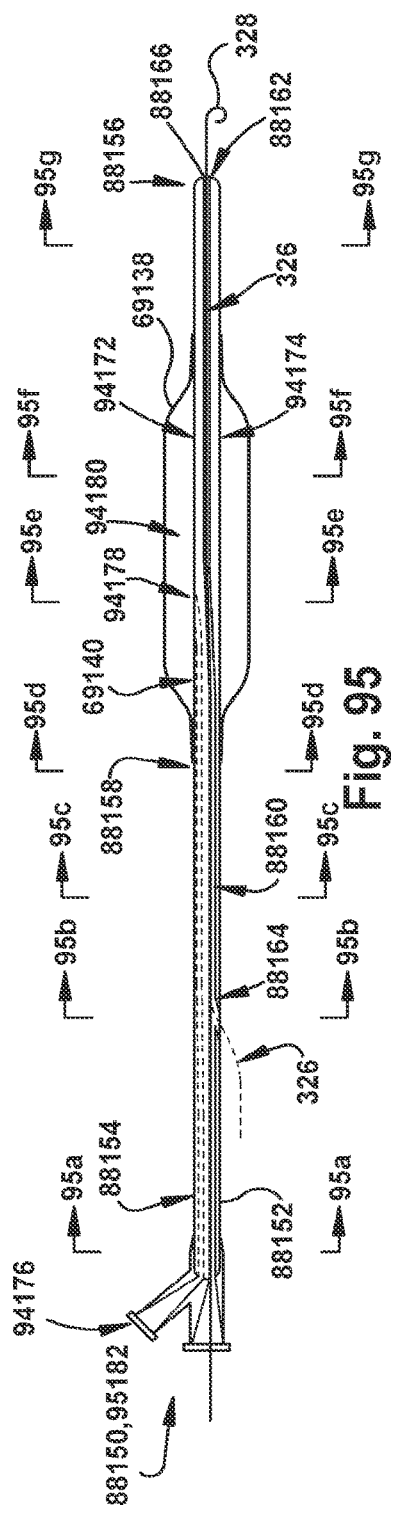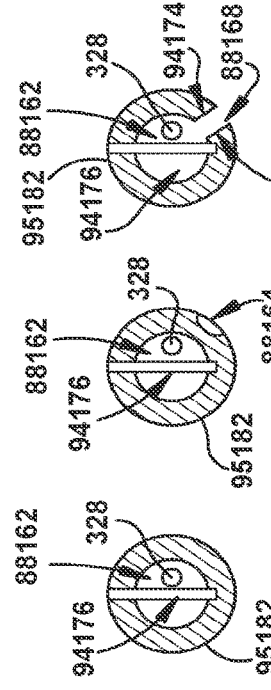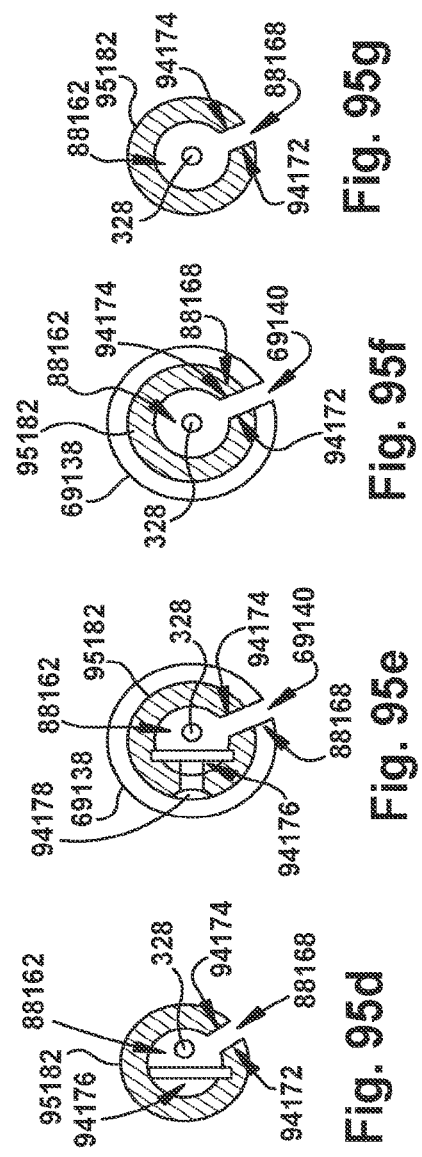

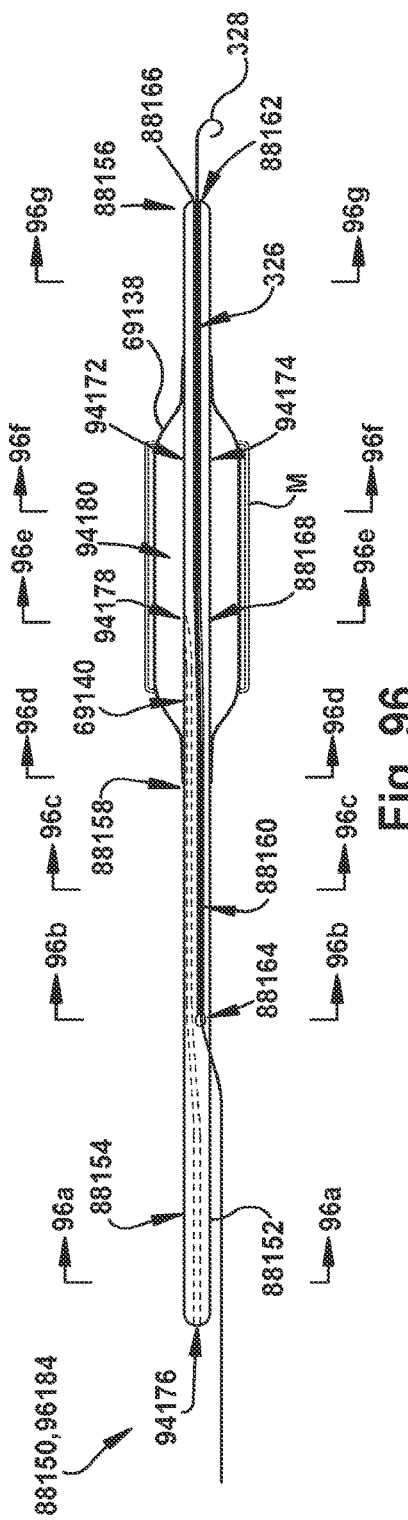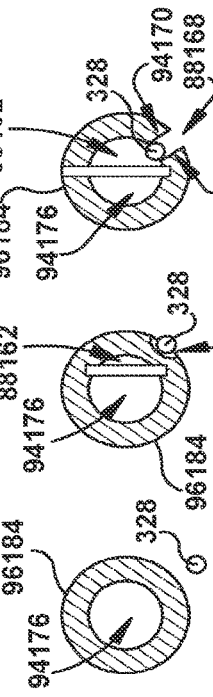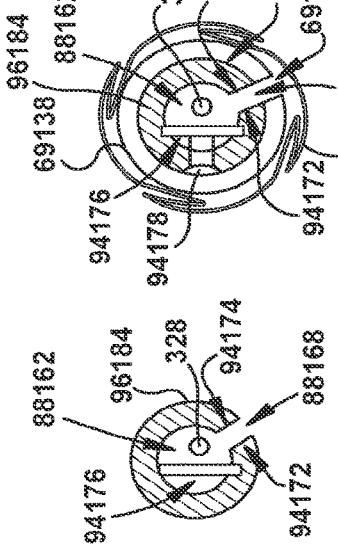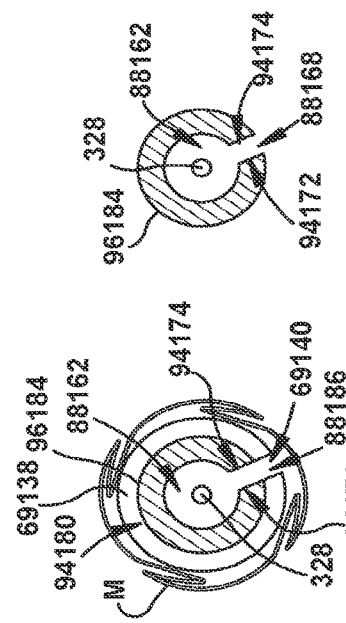

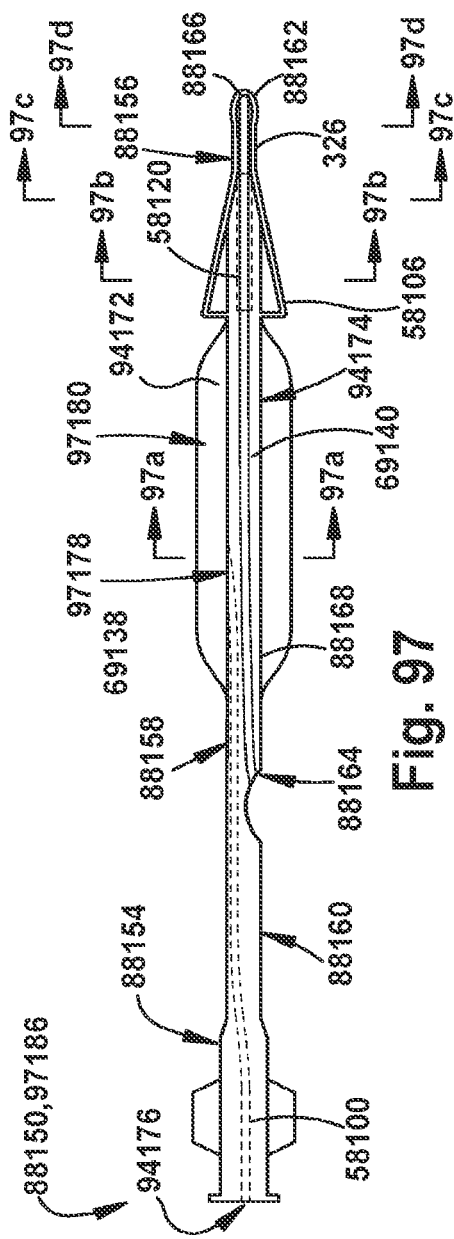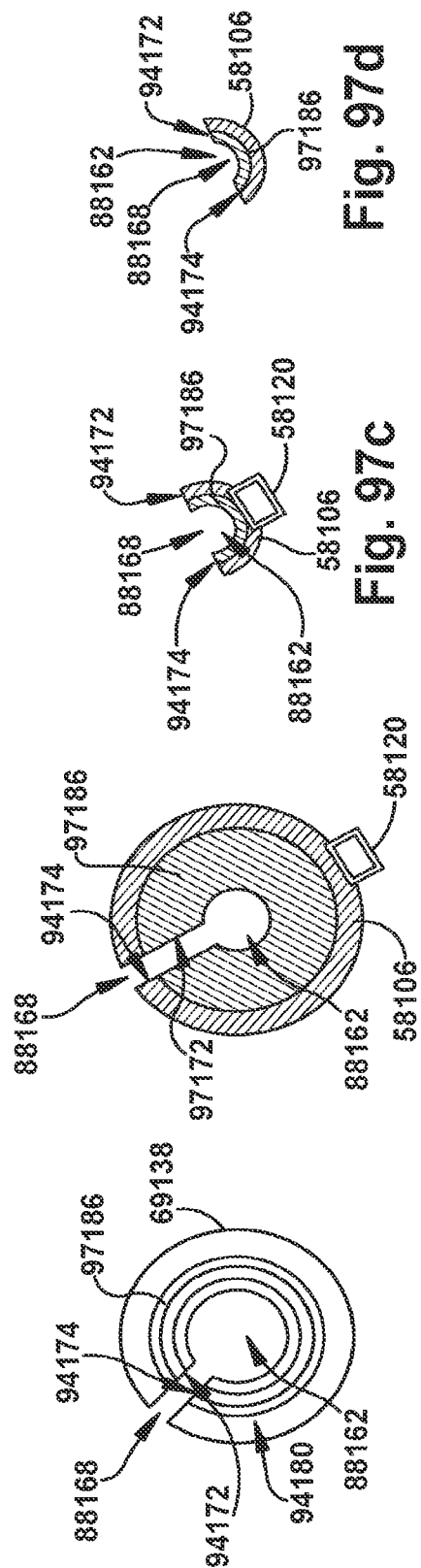

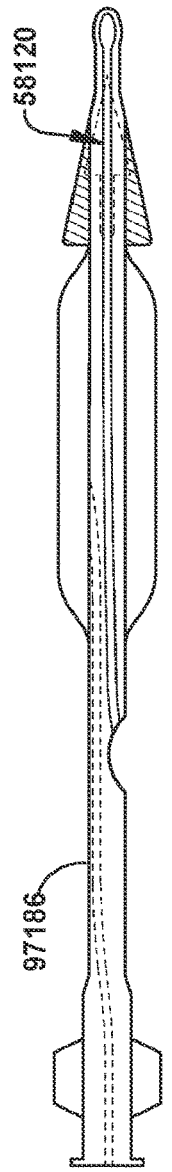
Fig. 98
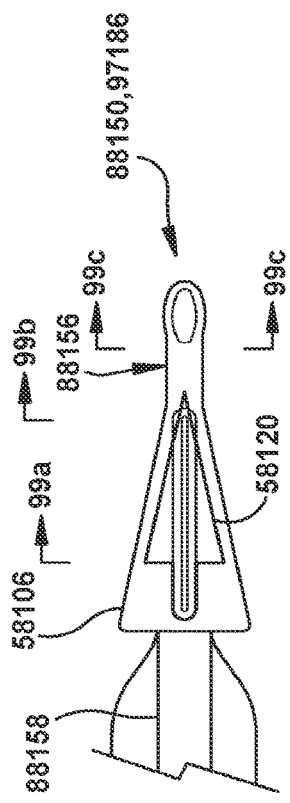
Fig. 99
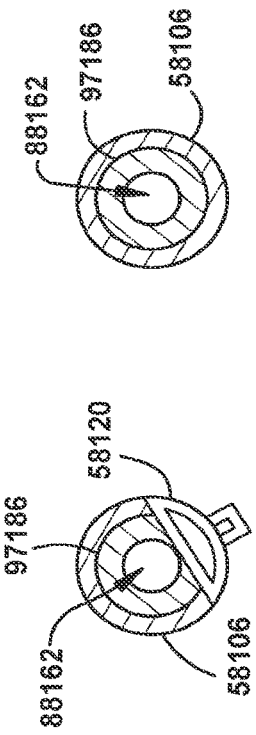
Fig. 99c
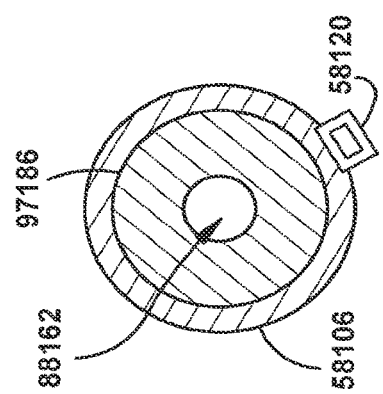
Fig. 99b
Fig. 99a

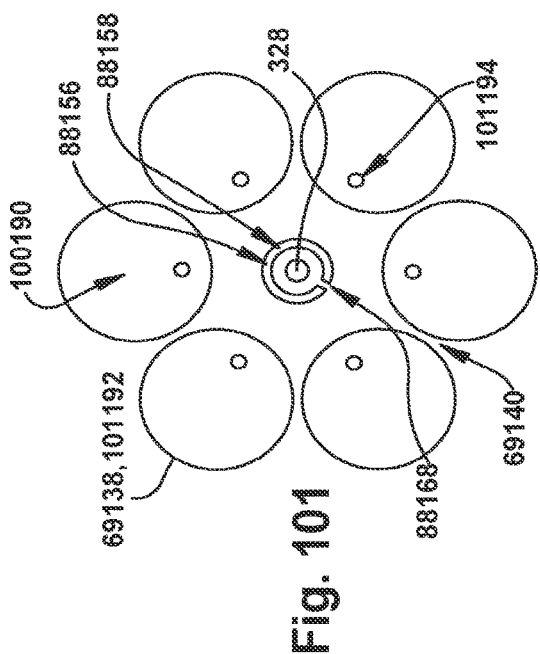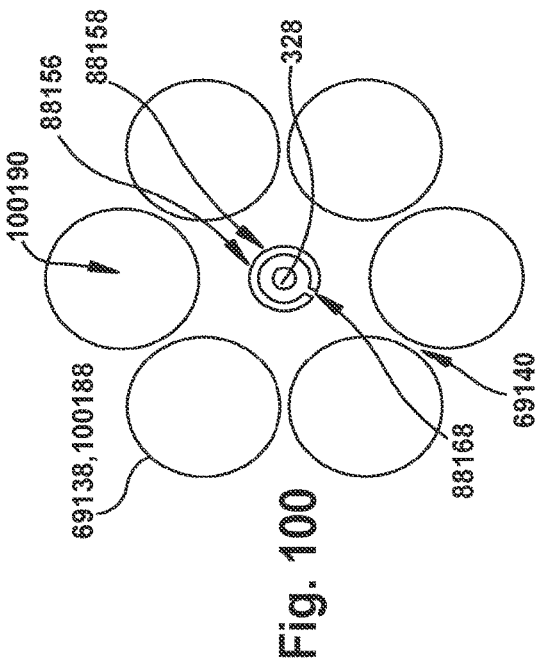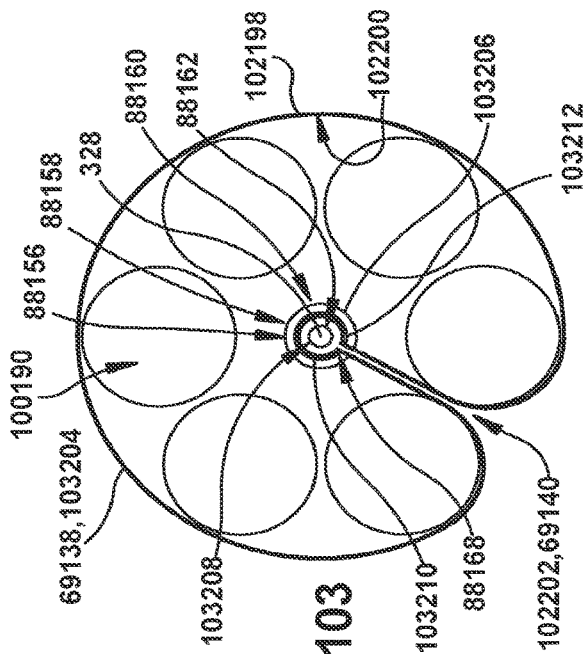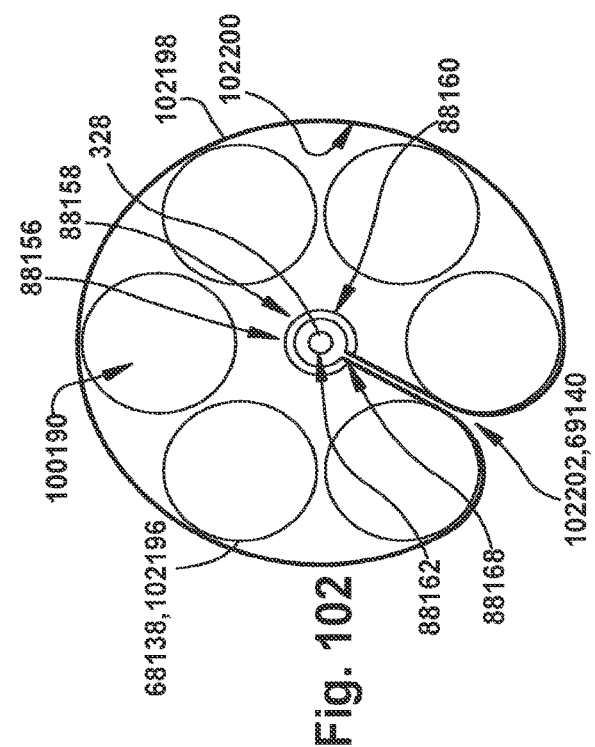

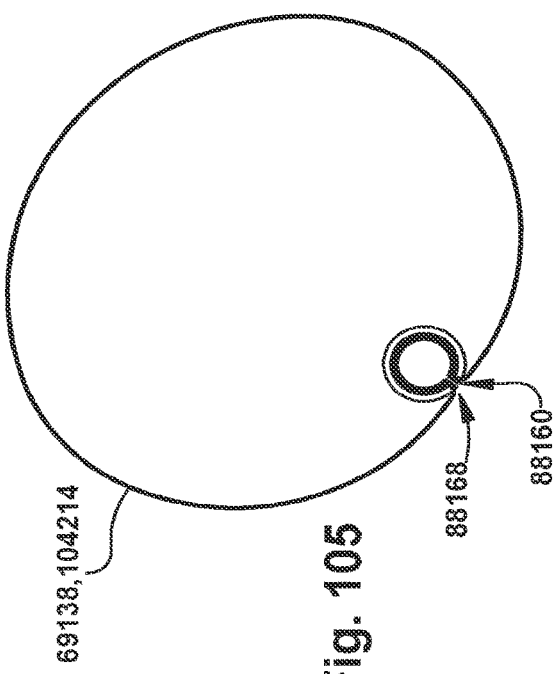
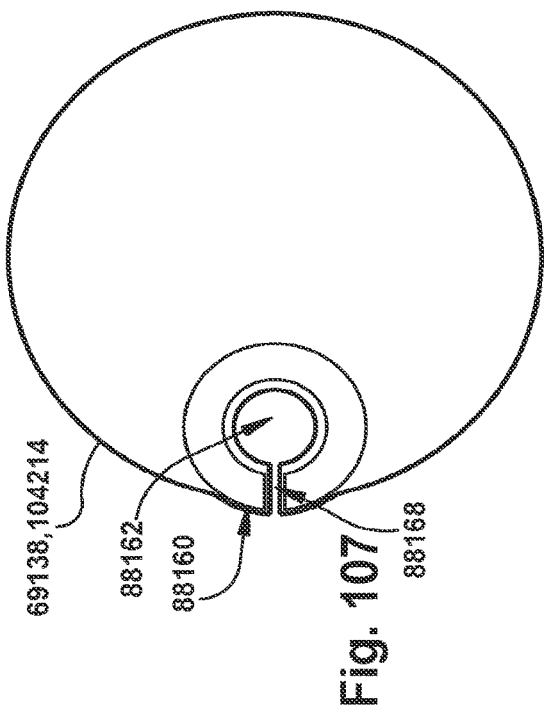
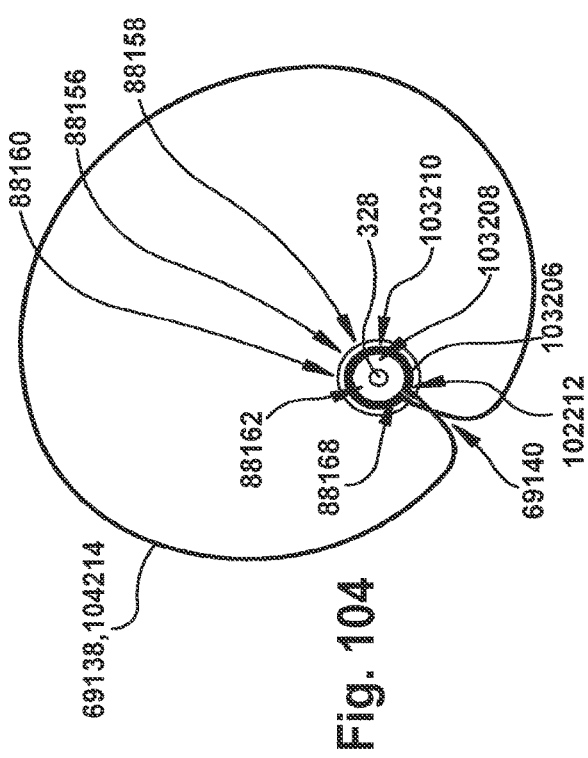
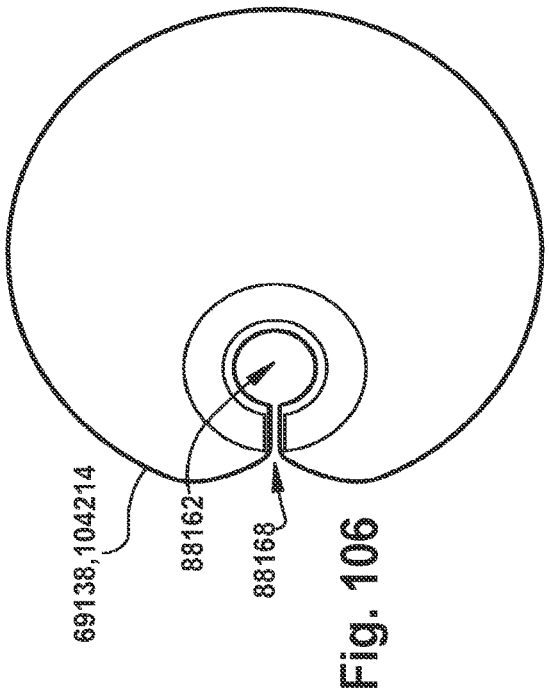

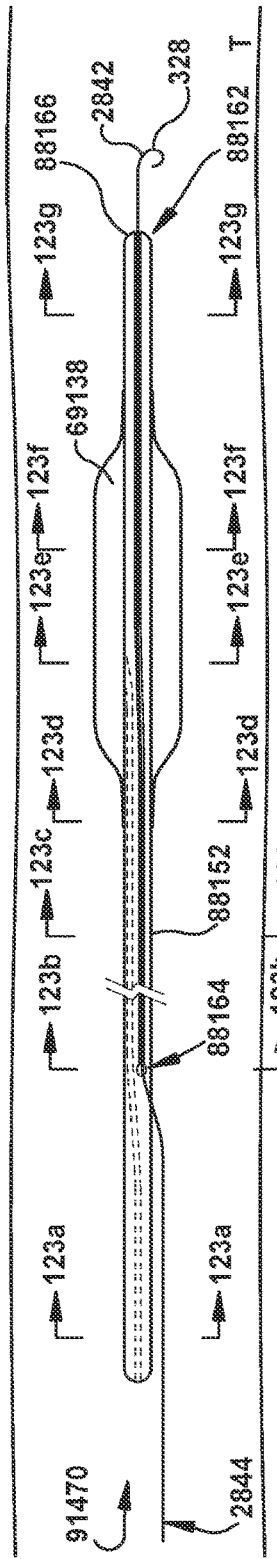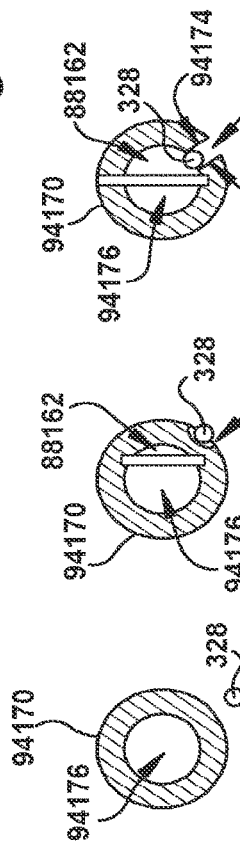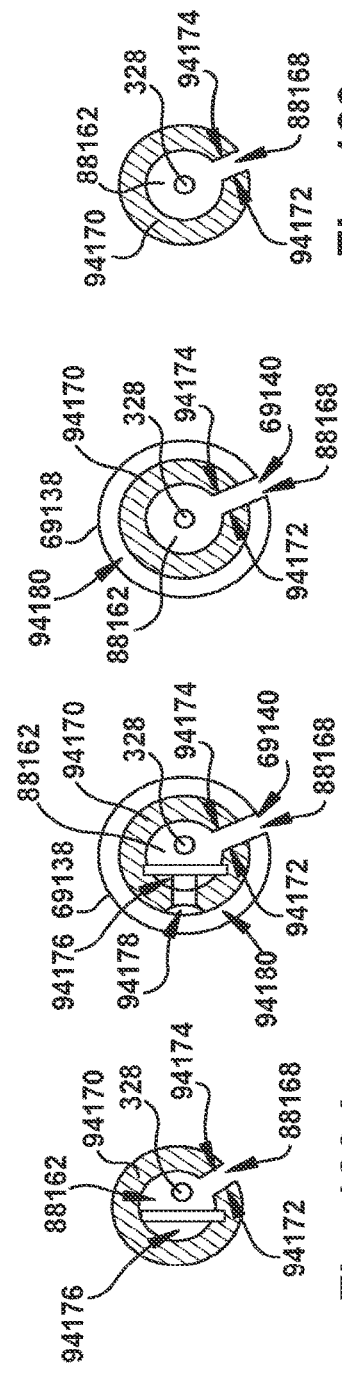

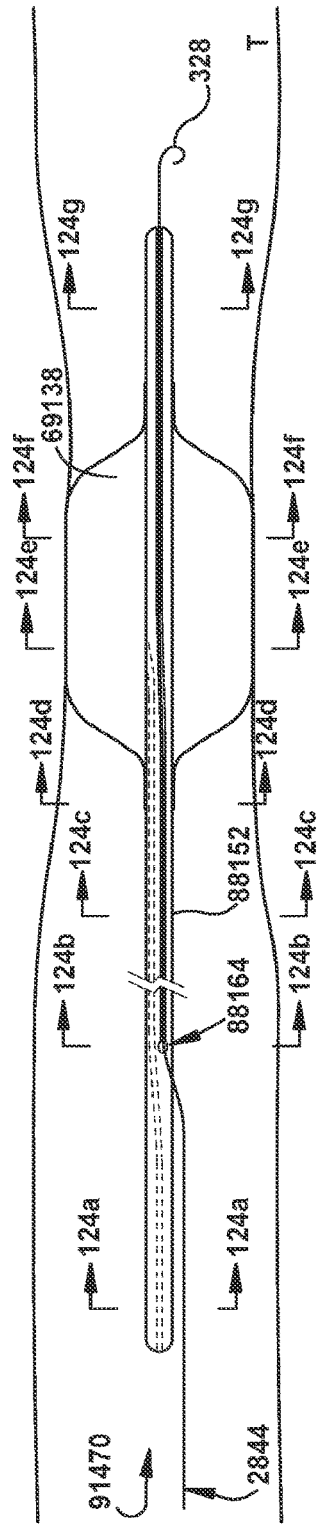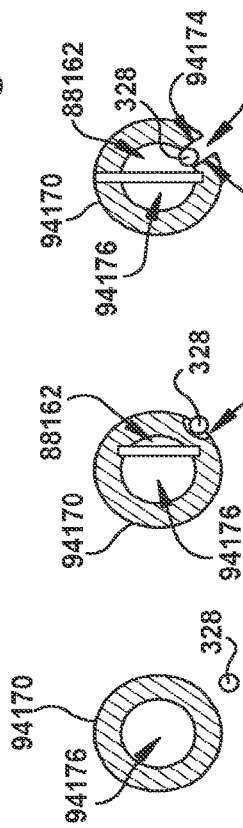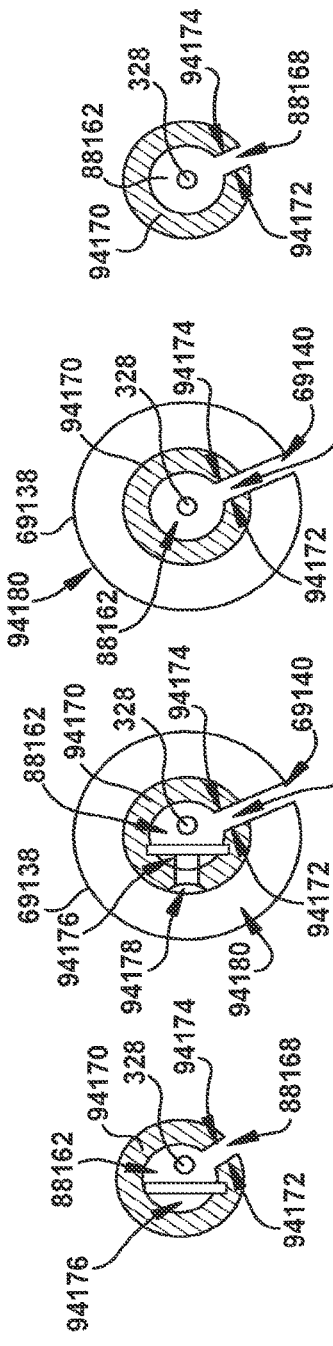

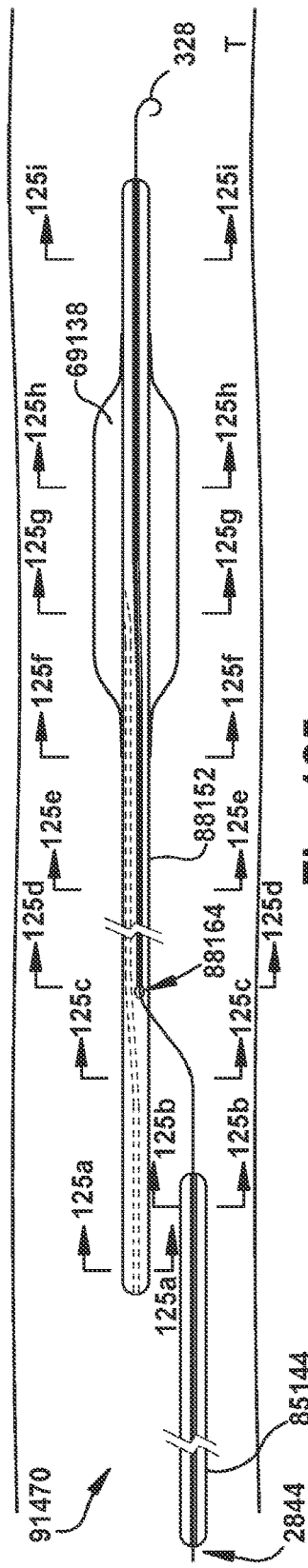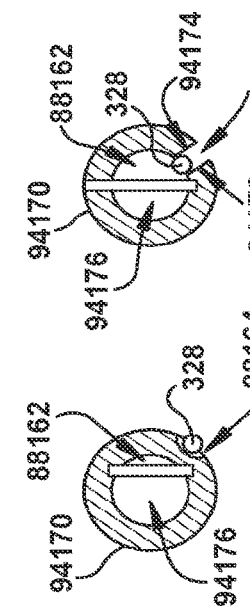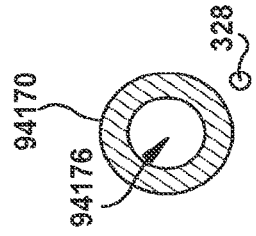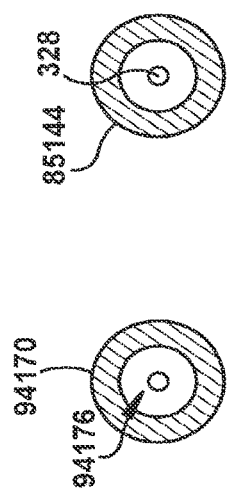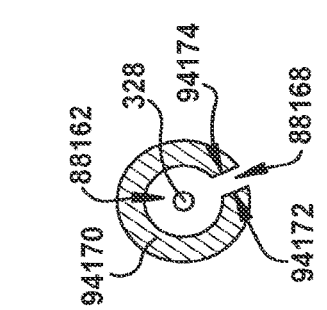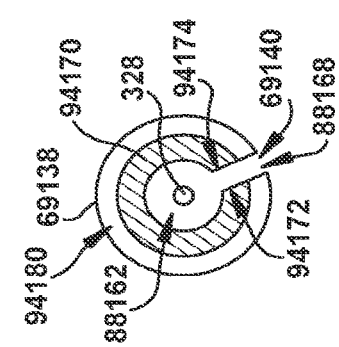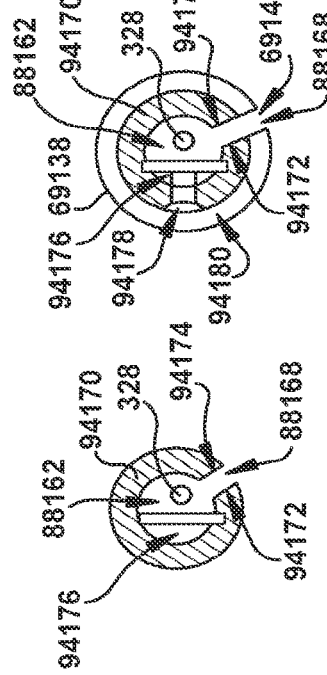

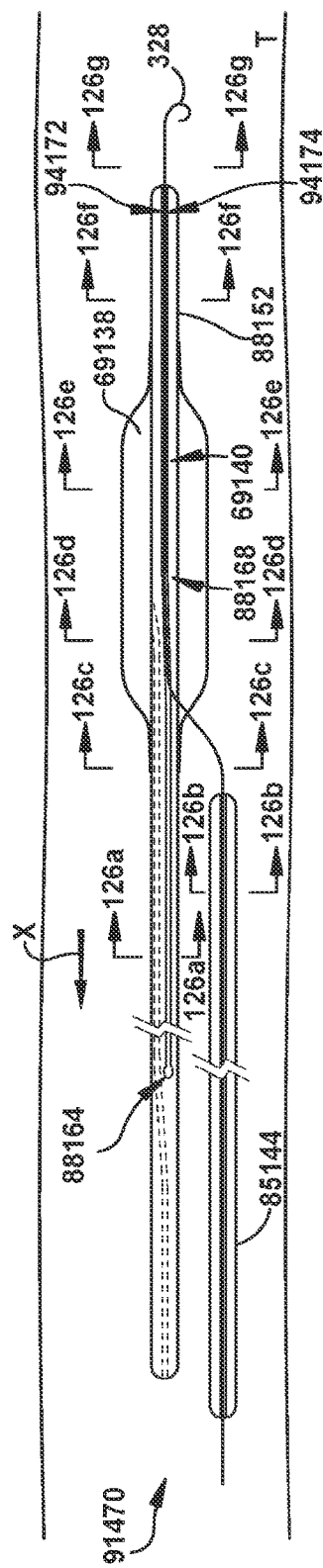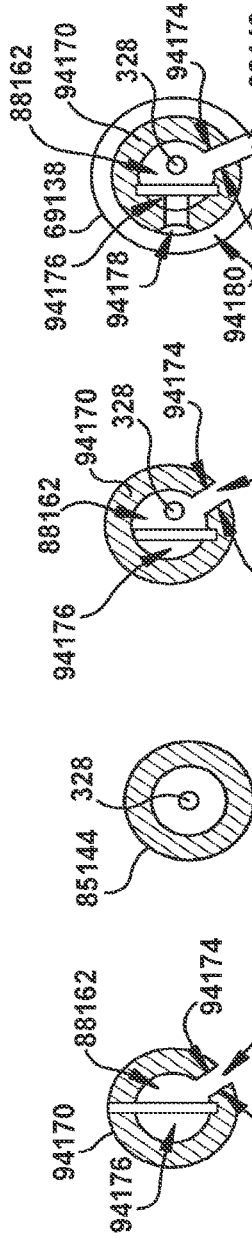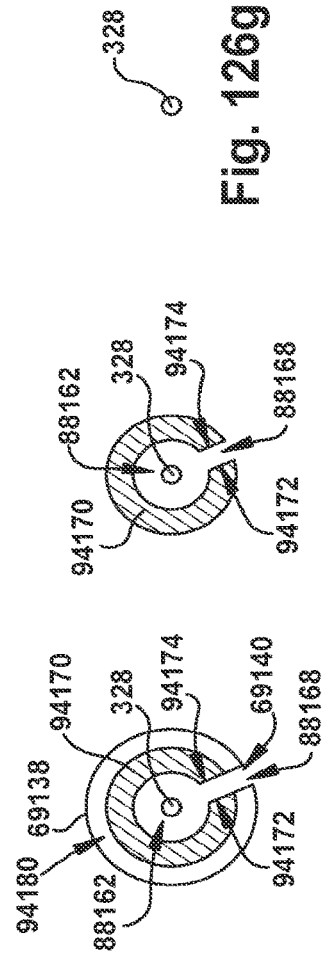

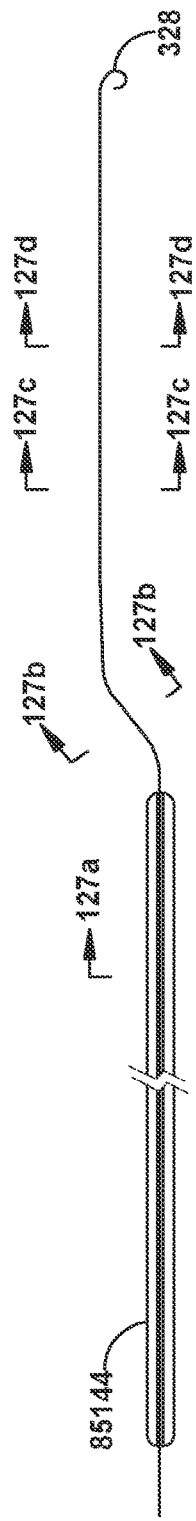 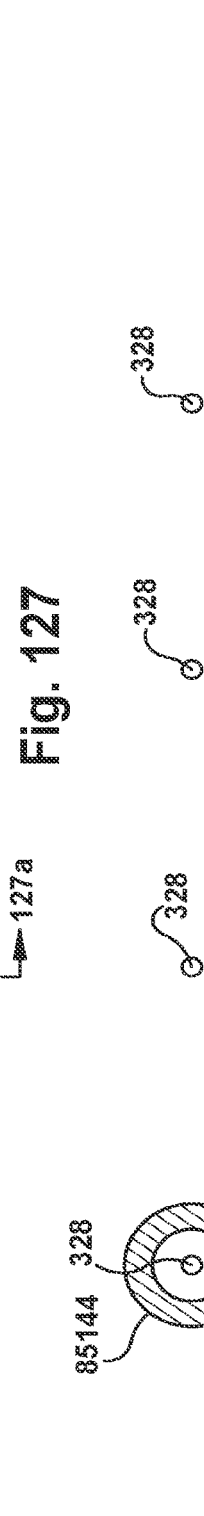 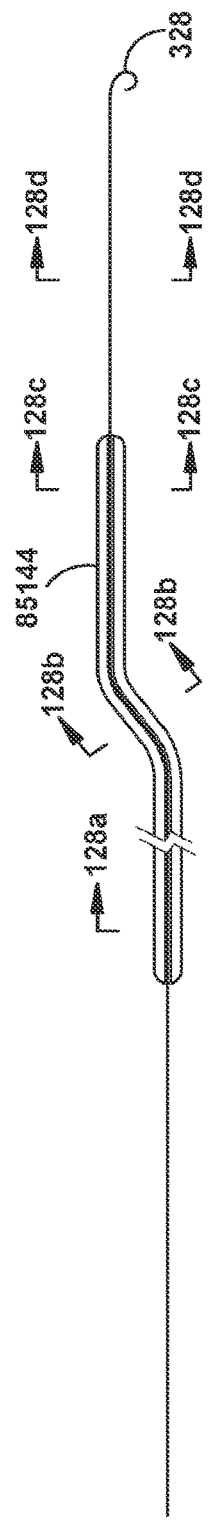 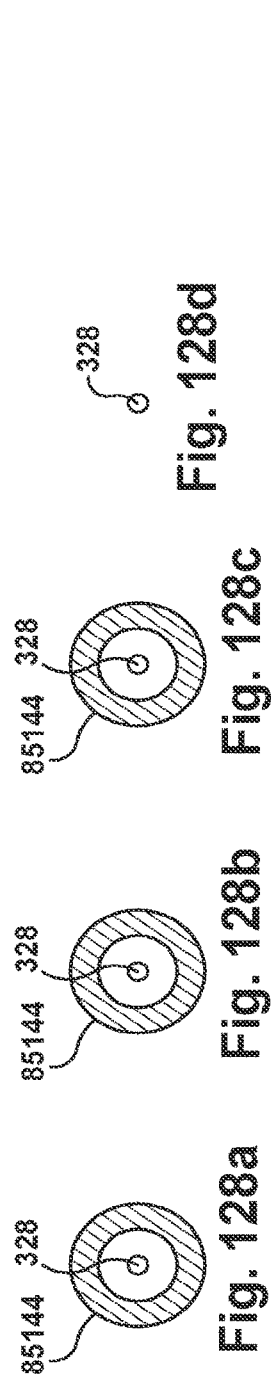

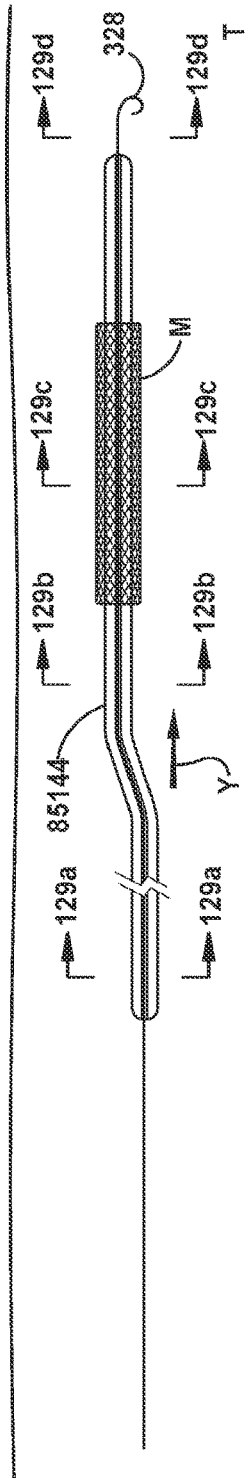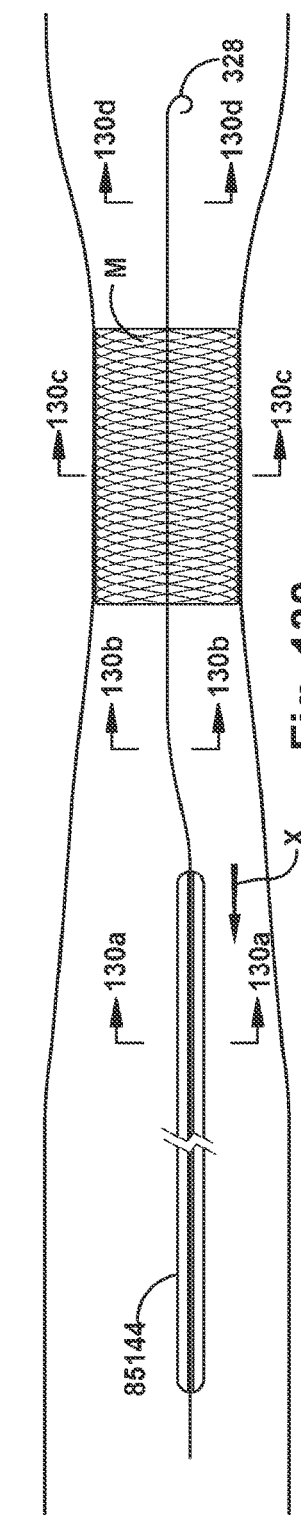

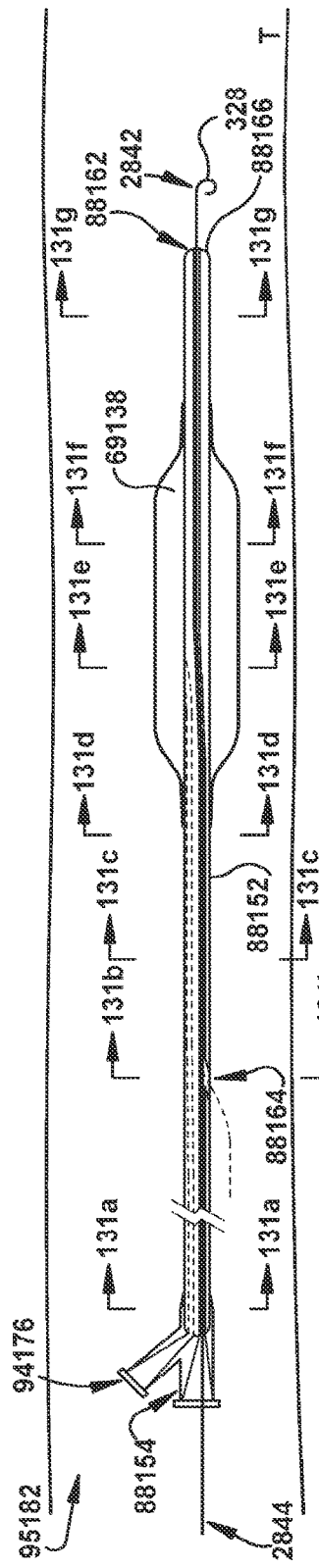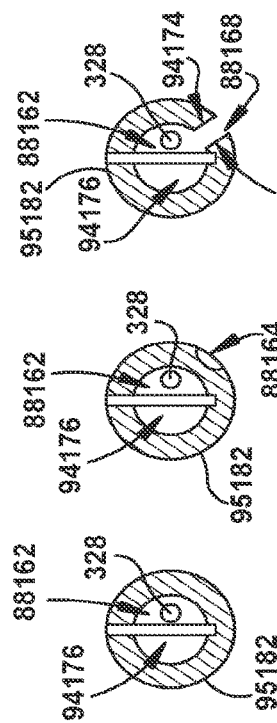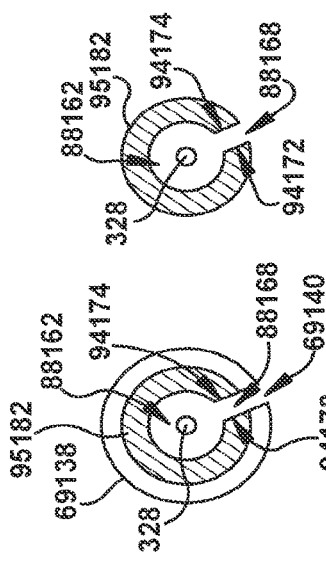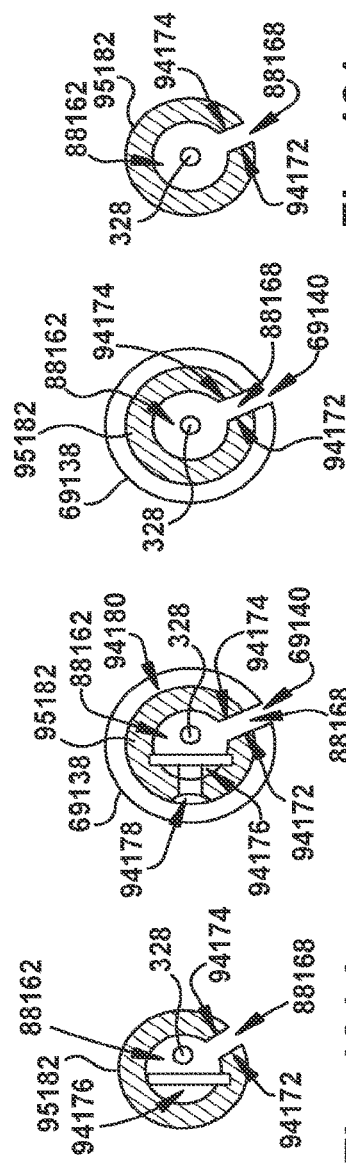

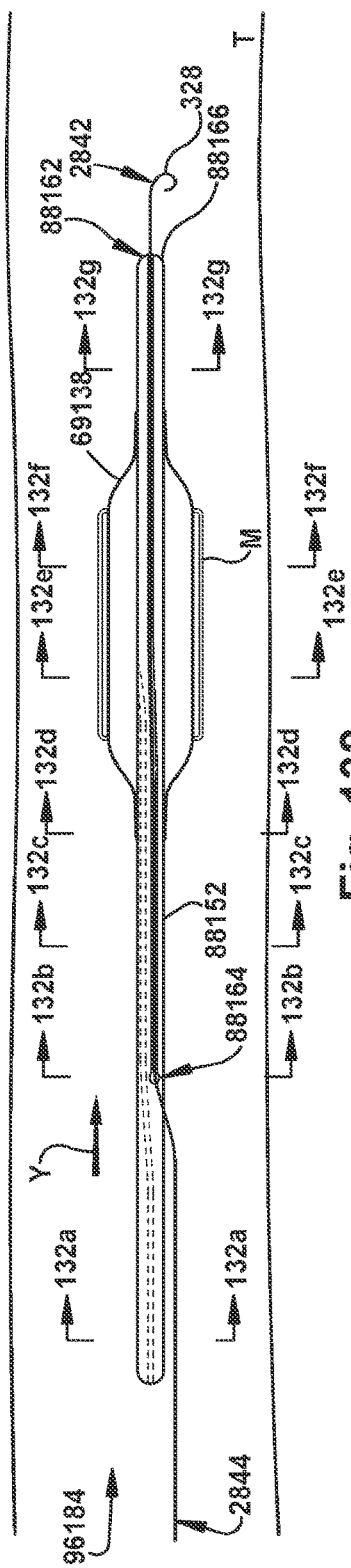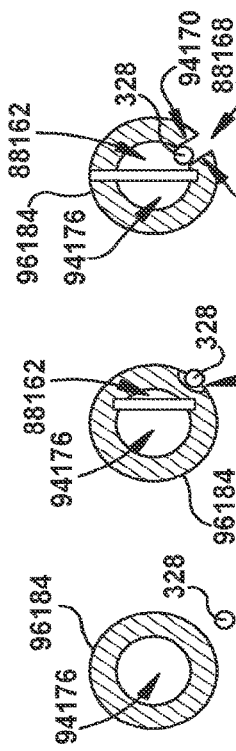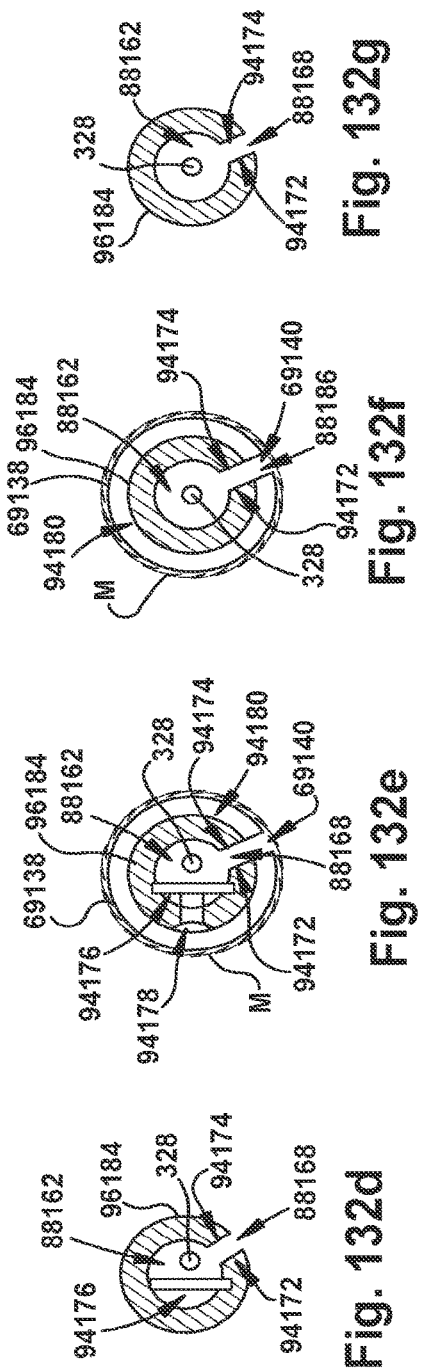

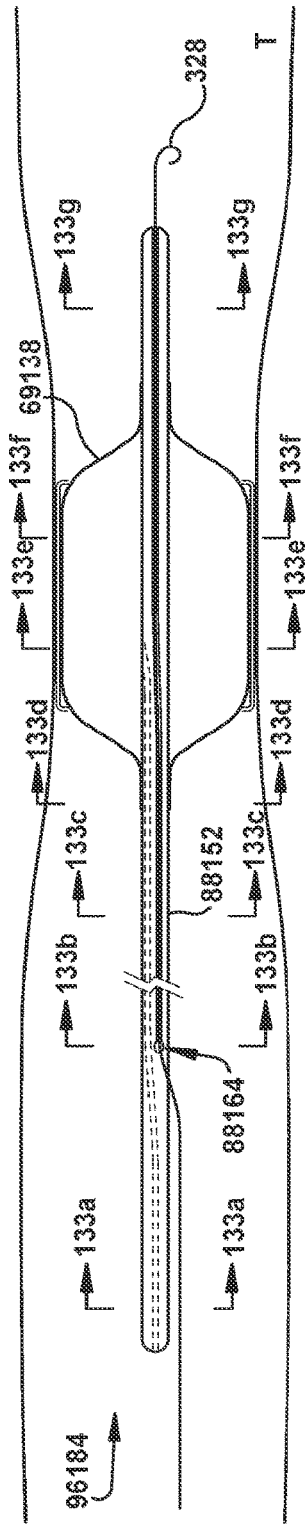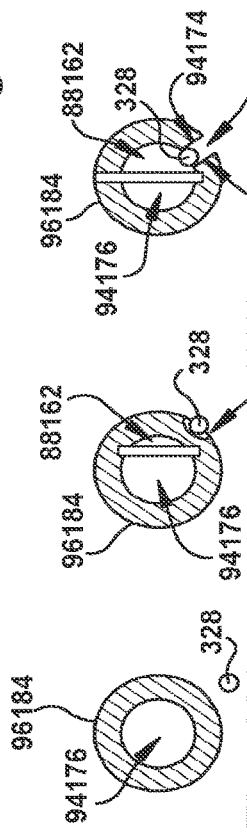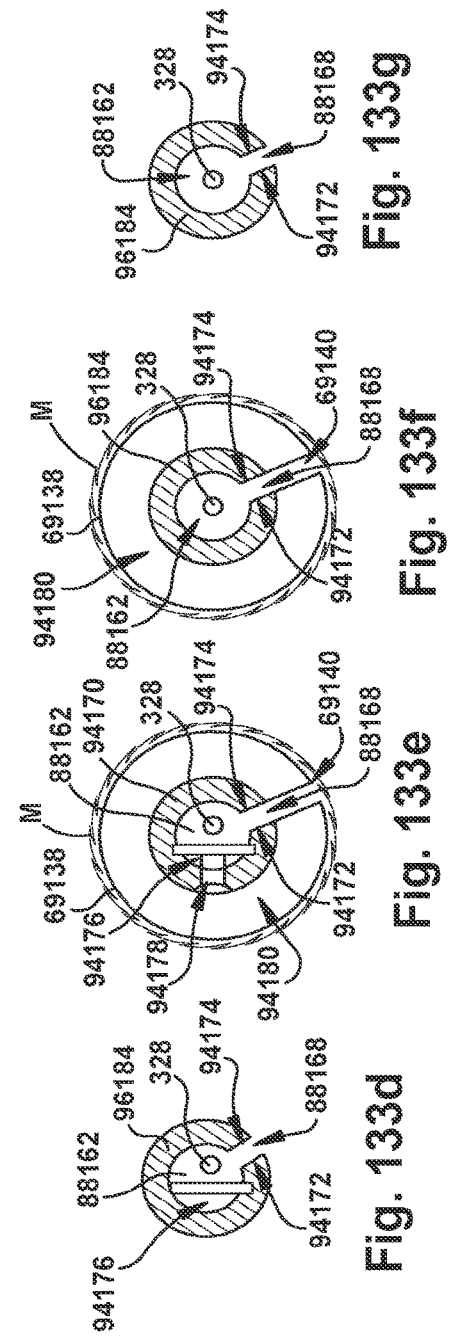

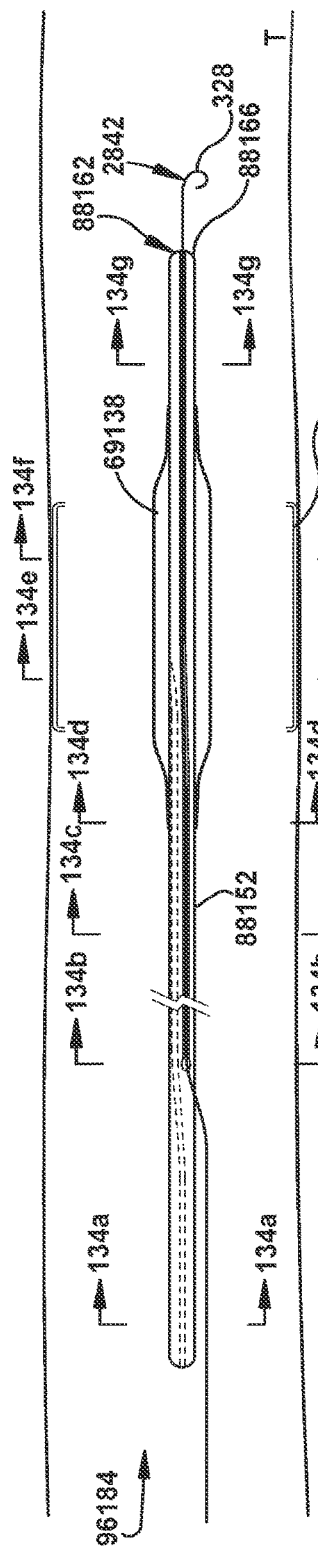

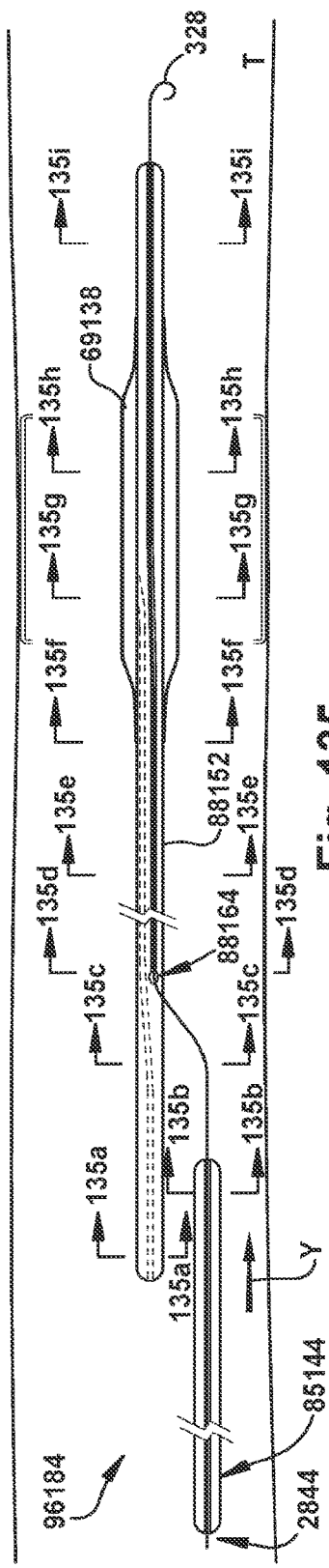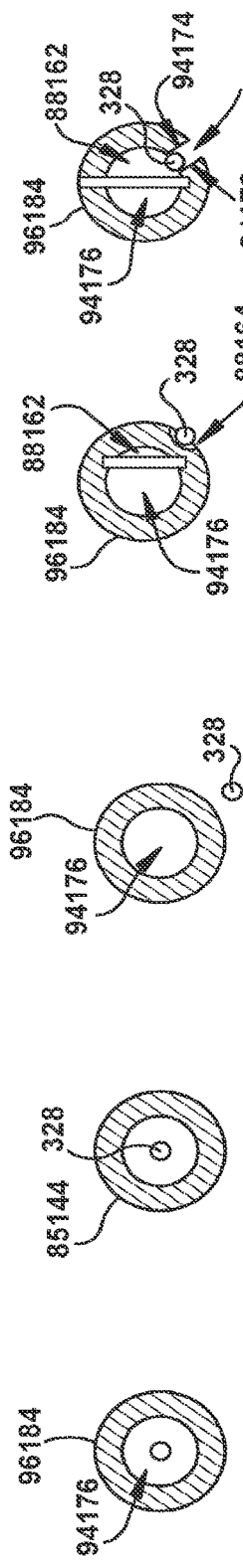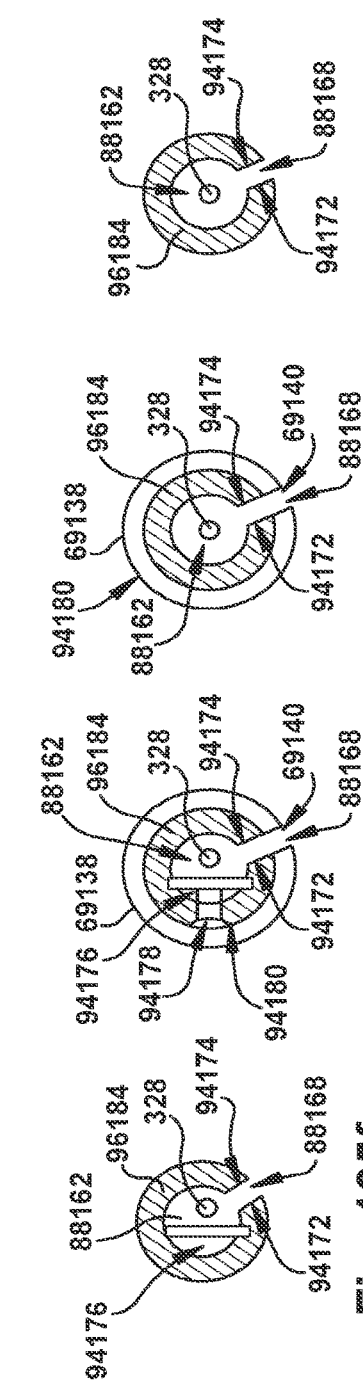

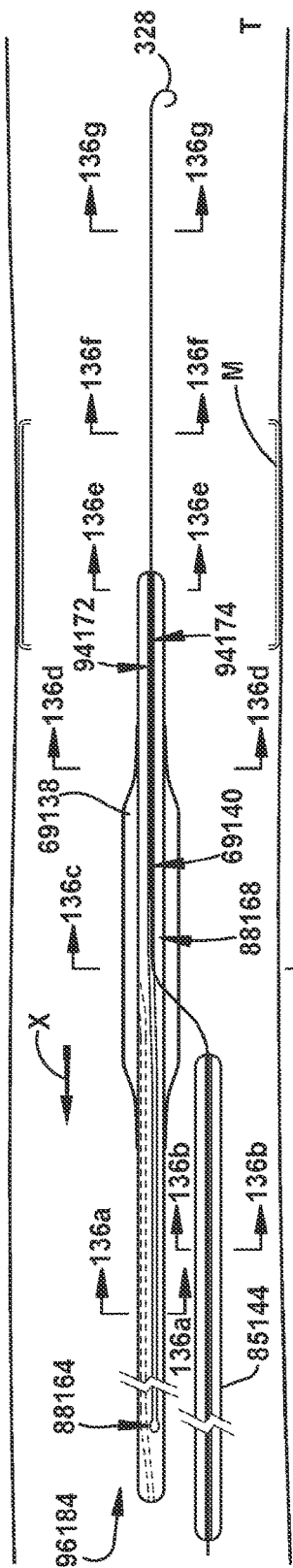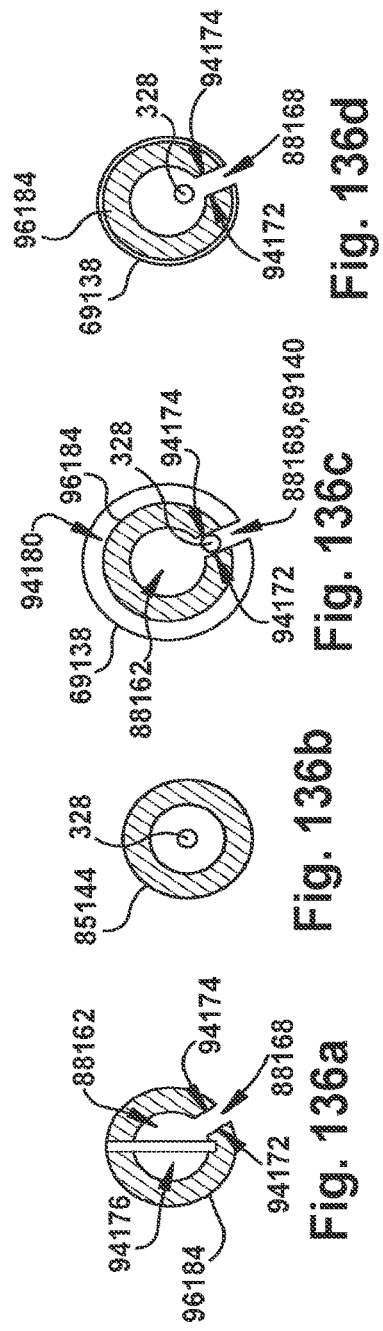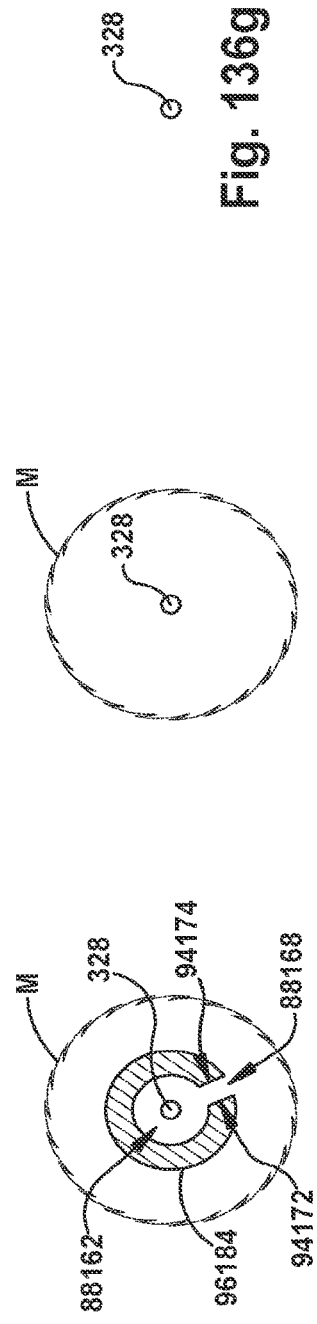

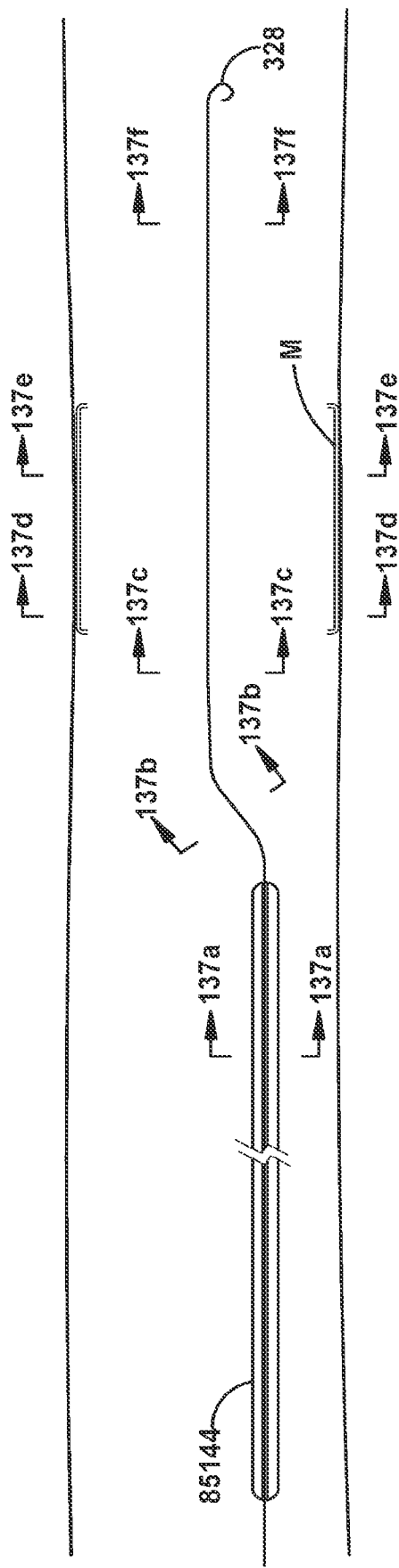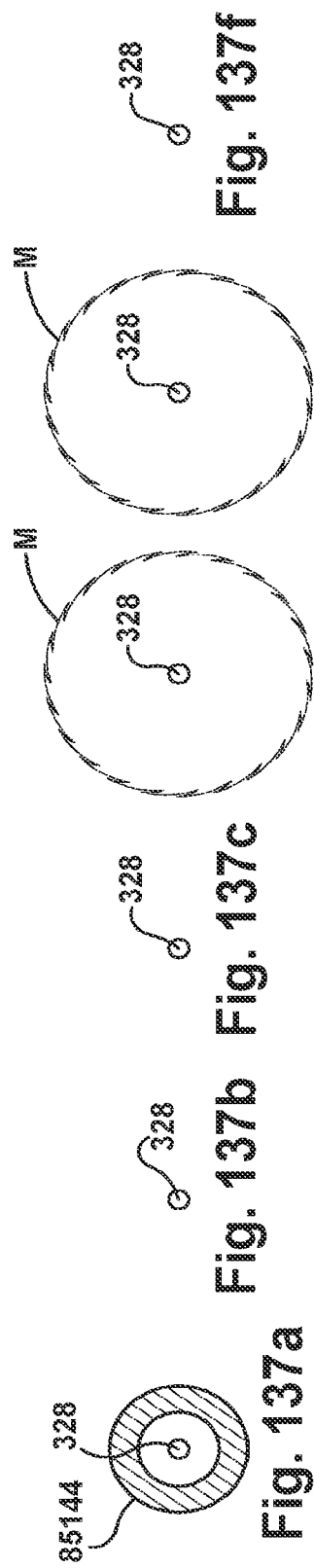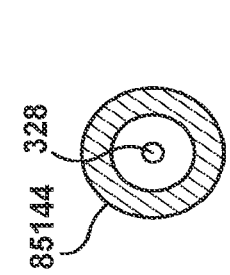

METHOD AND APPARATUSES FOR ACCESSING AND/OR MODIFYING A TARGET PATIENT TISSUE SITE

RELATED APPLICATION

This application is a continuation of U.S. application Ser. No. 16/341,975, filed, 15 Apr. 2019, which is a national phase application of and claims priority from PCT International Patent Application PCT/US2017/056564, filed Oct. 13, 2017, which claims priority from U.S. Provisional Application No. 62/408,312, filed 14 Oct. 2016; from U.S. Provisional Application No. 62/416,844, filed 3 Nov. 2016; and from U.S. Provisional Application No. 62/469,566, filed 10 Mar. 2017, the subject matter of each of which is incorporated herein by reference in its entirety.

TECHNICAL FIELD

This disclosure relates to apparatuses and methods for use of a modular dilation device, an implant delivery system, a balloon dilation device and, more particularly, to a method and device for inserting multiple dilators into a target patient tissue site, a method and device for deploying an expandable implant in a patient lumen, a method and device for constructing a balloon dilation device, and a method and device for dilating a patient lumen.

BACKGROUND

Certain medical procedures include inserting multiple medical tools into patient tissue either sequentially one after another or simultaneously. An example procedure for a sequential usage of medical instruments may include, but is not limited to, dilating a diseased patient lumen using a balloon dilation device followed by or following a stent deployed in the same lumen. A few examples of procedures for the simultaneous usage of multiple medical instruments in different sites include, but are not limited to, a procedure requiring delivering therapy to two or more patient sites simultaneously, such as thrombolysis infusion catheters to break down clots in two or more sites, or embolization catheters to block flow in two or more sites. A few examples of procedures for the simultaneous usage of multiple medical instruments at or near one diseased site may include, but are not limited to, using a diagnostic instrument such as an intravascular ultrasound catheter, and using an interventional instrument such as implant delivery catheter. Procedures that involve simultaneous usage of multiple medical instruments may include creating multiple puncture points for inserting the medical instruments. Multiple puncture points may lead to an increase in one or more of patient discomfort or complications, cost, radiation exposure, and/or procedure time. Procedures that may include the sequential operation of multiple medical instruments through a single puncture point may require the removal of one instrument outside the patient before another instrument can be advanced. This may lead to prolonged patient discomfort, increased radiation exposure, and/or increased procedure time.

SUMMARY

In an aspect, a modular dilation device is provided. A first dilator has an elongate first dilator body and a first dilator distal end. The first dilator has a first dilator outer surface and a first dilator inner lumen. The first dilator has a first dilator side wall opening. The first dilator distal end has a first dilator open tip. The first dilator side wall opening selectively places the first dilator outer surface in fluid communication with the first dilator inner lumen. The first dilator has a first dilator open slit. The first dilator open slit extends between the first dilator side wall opening and the first dilator open tip. A second dilator has an elongate second dilator body and a second dilator distal end. The second dilator has a second dilator inner lumen. The second dilator distal end having a second dilator open tip. When the second dilator is operatively joined to the first dilator, the second dilator open tip is adjacent to the first dilator side wall opening.

In an aspect, a method for collectively inserting multiple dilators into a target patient tissue site is provided. A modular dilation device is provided. A first dilator has an elongate first dilator body and a first dilator distal end. The first dilator has a first dilator outer surface and a first dilator inner lumen. The first dilator distal end has a first dilator open tip. The first dilator has a first dilator side wall opening. The first dilator side wall opening selectively places the first dilator outer surface in fluid communication with the first dilator inner lumen. The first dilator has a first dilator open slit. The first dilator open slit extends between the first dilator side wall opening and the first dilator open tip. A second dilator has an elongate second dilator body and a second dilator distal end. The second dilator has a second dilator inner lumen. The second dilator distal end has a second dilator open tip. A guidewire distal end is inserted into a target patient tissue site through a patient tissue access point. A guidewire proximal end is directed into the first dilator open tip, through at least a portion of the first dilator inner lumen, and out of the first dilator through the first dilator side wall opening. The first dilator is directed to the target patient tissue site along the guidewire. The guidewire proximal end is directed into the second dilator open tip, through at least a portion of the second dilator inner lumen, and out from the second dilator. The second dilator is directed to the target patient tissue site along the guidewire until the second dilator open tip is adjacent to the first dilator side wall opening.

In an aspect, an implant delivery system is provided. An outer sheath has an outer sheath proximal end and an outer sheath distal end. The outer sheath proximal end has an outer sheath delivery element. The outer sheath distal end has an implant holding pod. The implant holding pod has an implant holding pod proximal end and an implant holding pod distal end. The implant holding pod proximal end has an implant holding pod proximal opening. The implant holding pod distal end has an implant holding pod open tip. The implant holding pod has an implant holding pod outer surface and an implant holding pod lumen. The implant holding pod lumen extends between the implant holding pod proximal opening and the implant holding pod open tip. The implant holding pod lumen for selectively holding an expandable implant therein. The implant holding pod has an implant holding pod open slit. The implant holding pod open slit extends at least partially between the implant holding pod open tip and the implant holding pod proximal end. A shaft has a shaft proximal end, a shaft distal end, and a shaft body longitudinally extending between the shaft proximal and distal ends. The shaft proximal end has a shaft delivery element. The shaft distal end has an implant delivery element. At least one of the shaft body and the implant delivery element has a shaft open slit. When the shaft is operably joined to the outer sheath, at least a portion of the shaft open slit is selectively laterally spaced from the implant holding pod open slit.

In an aspect, a method for deploying a self-expandable implant in a patient lumen is provided. An implant delivery system is provided. An outer sheath has an outer sheath proximal end and an outer sheath distal end. The outer sheath proximal end has an outer sheath delivery element. The outer sheath distal end has an implant holding pod. The implant holding pod has an implant holding pod proximal end and an implant holding pod distal end. The implant holding pod proximal end has an implant holding pod proximal opening. The implant holding pod distal end has an implant holding pod open tip. The implant holding pod has an implant holding pod outer surface and an implant holding pod lumen. The implant holding pod lumen extends between the implant holding pod proximal opening and the implant holding pod open tip. The implant holding pod lumen for selectively holding an expandable implant therein. The implant holding pod has an implant holding pod open slit. The implant holding pod open slit extends between the implant holding pod open tip and the implant holding pod proximal end. A shaft has a shaft proximal end, a shaft distal end, and a shaft body longitudinally extends between the shaft proximal and distal ends. The shaft proximal end has a shaft delivery element. The shaft distal end has an implant delivery element. At least one of the shaft body and the implant delivery element has a shaft open slit. A collapsed expandable implant is placed within the implant holding pod lumen. At least a portion of the shaft and at least a portion of the implant delivery element are collectively inserted into the implant holding pod lumen. The shaft is aligned in the implant holding pod lumen with at least a portion of the shaft open slit being laterally spaced from the implant holding pod open slit. The collapsed expandable implant is placed in operative engagement with the implant delivery element. A guidewire distal end is inserted into a target patient tissue site in a patient lumen. A guidewire proximal end is directed through the implant delivery system. The implant delivery system is directed to the target patient tissue site along the guidewire. With the implant delivery system at the target patient tissue site, the expandable implant is exposed by directing the outer sheath delivery element in the longitudinally proximal direction to directly correspondingly cause the outer sheath to move in the longitudinally proximal direction. The guidewire, the expandable implant, and the shaft remaining in place at the target patient tissue site while the outer sheath is moved in the longitudinally proximal direction. With the expandable implant exposed, the natural properties of the expandable implant are utilized to expand the expandable implant.

In an aspect, a balloon dilation device is provided. A balloon dilation rod has a balloon dilation rod proximal end, a balloon dilation rod distal end, and an elongate balloon dilation rod body longitudinally extending between the balloon dilation rod proximal and distal ends. The balloon dilation rod has a balloon dilation rod outer surface and a balloon dilation rod lumen. The balloon dilation rod has a balloon dilation rod side wall opening. The balloon dilation rod side wall opening selectively places the balloon dilation rod outer surface in fluid communication with the balloon dilation rod lumen. The balloon dilation rod distal end has a balloon dilation rod open tip. The balloon dilation rod has a balloon dilation rod open slit. The balloon dilation rod open slit extends between the balloon dilation rod side wall opening and the balloon dilation rod open tip. An expandable balloon is positioned on at least one of the balloon dilation rod body and balloon dilation rod distal end. The balloon has a balloon open slit that extends for an entire length of the balloon. The balloon open slit is aligned with the balloon dilation rod open slit.

In an aspect, a method for constructing a balloon catheter is provided. A balloon dilation rod is provided. The balloon dilation rod has a balloon dilation rod proximal end, a balloon dilation rod distal end, and an elongate balloon dilation rod body longitudinally extending between the balloon dilation rod proximal and distal ends. The balloon dilation rod has a balloon dilation rod outer surface and a balloon dilation rod lumen. The balloon dilation rod has a balloon dilation rod side wall opening. The balloon dilation rod side wall opening selectively places the balloon dilation rod outer surface in fluid communication with the balloon dilation rod lumen. The balloon dilation rod distal end has a balloon dilation rod open tip. The balloon dilation rod has a balloon dilation rod open slit. The balloon dilation rod open slit extends between the balloon dilation rod side wall opening and the balloon dilation rod open tip. A balloon material is placed at least partially circumferentially about the balloon dilation rod outer surface so that at least a portion of the balloon material is adjacent to at least a portion of the balloon dilation rod open slit. At least a portion of the balloon material is urged through the balloon dilation rod open slit and into the balloon dilation rod lumen. At least a portion of the balloon material inserted into the balloon dilation rod lumen is attached to at least a portion of the balloon dilation rod lumen. The portion of the balloon material attached to the portion of the balloon dilation rod lumen forms at least a portion of the balloon dilation rod lumen. The balloon material forms a balloon open slit that is aligned with the balloon dilation rod open slit when the balloon material is attached to the balloon dilation rod lumen. A balloon fixer is inserted through the balloon dilation rod open slit and into the balloon dilation rod lumen. The balloon fixer has a balloon fixer lumen and a balloon fixer outer surface. The balloon fixer has a balloon fixer open slit that places the balloon fixer outer surface in fluid communication with the balloon fixer lumen. The balloon fixer lumen is in fluid communication with the balloon dilation rod lumen when the balloon fixer is inserted within at least a portion of the balloon dilation rod lumen. The balloon fixer is disposed on a portion of the balloon material that forms a portion of the balloon dilation rod lumen. The balloon fixer is aligned with the balloon fixer open slit aligned with the balloon dilation rod open slit. The balloon fixer is attached to at least one of the balloon dilation rod lumen and the portion of the balloon material that forms a portion of the balloon dilation rod lumen. At least a portion of a balloon material proximal end is circumferential attached to at least a portion the balloon dilation rod outer surface adjacent to the balloon dilation rod open slit. At least a portion of a balloon material distal end is circumferentially attached to at least a portion the balloon dilation rod outer surface adjacent to the balloon dilation rod open slit.

In an aspect, a method for dilating a patient lumen is provided. A modular dilation device is provided. A balloon dilation rod has a balloon dilation rod proximal end, a balloon dilation rod distal end, and an elongate balloon dilation rod body longitudinally extending between the balloon dilation rod proximal and distal ends. The balloon dilation rod has a balloon dilation rod outer surface and a balloon dilation rod lumen. The balloon dilation rod has a balloon dilation rod side wall opening. The balloon dilation rod side wall opening selectively places the balloon dilation rod outer surface in fluid communication with the balloon dilation rod lumen. The balloon dilation rod distal end has a balloon dilation rod open tip. The balloon dilation rod has a balloon dilation rod open slit. The balloon dilation rod open slit extends between the balloon dilation rod side wall opening and the balloon dilation rod open tip. The balloon dilation rod open slit has a balloon dilation rod open slit first surface and a balloon dilation rod open slit second surface. The balloon dilation rod open slit first surface oppositely faces and abuts the balloon dilation rod open slit second surface. The balloon dilation rod open slit first surface and the balloon dilation rod open slit second surface are selectively elastically separable. An expandable balloon is positioned on at least one of the balloon dilation rod body and balloon dilation rod distal end. The balloon has a balloon open slit that at least partially extends for an entire length of the balloon. The balloon open slit is aligned with the balloon dilation rod open slit. A guidewire distal end is inserted into a target patient tissue site in a patient lumen. A guidewire proximal end is directed into the balloon dilation rod open tip, through at least a portion of the balloon dilation rod lumen, and out from the balloon dilation rod side wall opening. The balloon dilation rod is directed to the target patient tissue site along the guidewire. With the balloon dilation rod at the target patient tissue site, the balloon is inflated to dilate the patient lumen. The balloon is deflated after the patient lumen has achieved a predetermined amount of dilation. A secondary device is directed over the guidewire until the secondary device is at least one of adjacent to and at least partially within the balloon dilation rod side wall opening. With the secondary device at least one of adjacent to and at least partially in the balloon dilation rod side wall opening, the balloon dilation rod is laterally moved toward a proximal direction to remove the balloon dilation rod from the guidewire. Movement of the balloon dilation rod toward the proximal direction causes the secondary device to selectively urge the balloon dilation rod open slit first surface elastically apart from the balloon dilation rod open slit second surface and remove the balloon dilation rod from the guidewire, while maintaining the guidewire at the target patient site. The secondary device is directed to the target patient tissue site.

BRIEF DESCRIPTION OF THE DRAWINGS

For a better understanding, reference may be made to the accompanying drawings, in which:

FIG. 9 is a side view of the element of FIG. 8;

FIG. 10 is a top view of the element of FIG. 7 in an example use configuration;

FIG. 11 is a partial side view of an element of the aspect of FIG. 1;

FIGS. 11*a-c* depict cross-sectional views of the aspect of FIG. 11;

FIGS. 28-34*e* illustrate an example sequence of operation of a portion of the aspect of FIG. 18, including cross-sectional views;

FIG. 55 is a partial side view of an element of the aspect of FIG. 1;

FIG. 56 depicts a cross-sectional view of the aspect of FIG. 55 in an alternate configuration;

FIG. 57 depicts a cross-sectional view of the aspect of FIG. 55 in an alternate configuration;

FIG. 58 is a side view of an element of the implant delivery system according to one aspect of the present invention;

FIGS. 58a-c depict cross-sectional views of the aspect of FIG. 58;

FIG. 59 is a side view of the element of FIG. 58 in an alternate configuration;

FIGS. 59a-c depict cross-sectional views of the aspect of FIG. 59;

FIG. 68 is a side view of the element of FIG. 58 in an alternate configuration;

FIG. 69 is a side view of the element of FIG. 58 in an alternate configuration;

FIG. 70 is a side view of the element of FIG. 58 in an alternate configuration;

FIGS. 70a-d depict cross-sectional views of the aspect of FIG. 70;

FIGS. 83-89c illustrate an example sequence of operation of a portion of the aspect of FIG. 77, including selected cross-sectional views;

FIG. 94 is a side cross-sectional view of a balloon dilation device according to one aspect of the present invention;

FIGS. 94a-g depict cross-sectional views of the aspect of FIG. 94;

FIG. 95 is a side cross-sectional view of the aspect of FIG. 94 in an alternate configuration;

FIGS. 95a-g depict cross-sectional views of the aspect of FIG. 95;

FIG. 96 is a side cross-sectional view of the aspect of FIG. 94 in an alternate configuration;

FIGS. 96a-g depict cross-sectional views of the aspect of FIG. 96;

FIG. 97 is a side cross-sectional view of the aspect of FIG. 94 in an alternate configuration;

FIGS. 97a-d depict cross-sectional views of the aspect of FIG. 97;

FIG. 98 is a side cross-sectional view of the aspect of FIG. 97 in an alternate configuration;

FIG. 99 is a side cross-sectional view of a portion of the aspect of FIG. 97 in an alternate configuration;

FIGS. 99a-c depict cross-sectional views of the aspect of FIG. 99;

FIGS. 100-107 depict cross-sectional views of the aspect of FIG. 94 in alternate configurations;

FIGS. 123-130d illustrate a example sequence of operation of a portion of the aspect of FIG. 94, including selected cross-sectional views;

FIG. 131 illustrates an example sequence of operation of a portion of the aspect of FIG. 95;

FIGS. 131a-g depict selected cross-sectional views of the aspect of FIG. 131; and FIGS. 132-137f illustrate an example sequence of operation of a portion of the aspect of FIG. 97, including selected cross-sectional views.

DESCRIPTION OF ASPECTS OF THE DISCLOSURE

Unless defined otherwise, all technical and scientific terms used herein have the same meaning as is commonly understood by one of skill in the art to which the present disclosure pertains.

As used herein, the term "patient" may refer to any warm-blooded organism including, but not limited to, human beings, pigs, rats, mice, dogs, goats, sheep, horses, monkeys, apes, rabbits, cattle, farm animals, livestock, etc.

As used herein, the term "user" may be used interchangeably to refer to an individual who prepares for, assists, and/or performs a procedure.

As used herein, the singular forms "a," "an" and "the" may include the plural forms as well, unless the context clearly indicates otherwise. It will be further understood that the terms "comprises" and/or "comprising," as used herein, may specify the presence of stated features, steps, operations, elements, and/or components, but do not preclude the presence or addition of one or more other features, steps, operations, elements, components, and/or groups thereof.

As used herein, the term "and/or" may include any and all combinations of one or more of the associated listed items.

As used herein, phrases such as "between X and Y" may be interpreted to include X and Y.

It will be understood that when an element is referred to as being "on," "attached" to, "contacting," etc., another element, it may be directly on, attached to or contacting the other element or intervening elements may also be present. It will also be appreciated by those of skill in the art that references to a structure or feature that is disposed "adjacent" another feature may not have portions that overlap or underlie the adjacent feature.

Spatially relative terms, such as "below," "lower," "over" and the like, may be used herein for ease of description to describe one element or feature's relationship to another element(s) or feature(s) as illustrated in the Figures. It will be understood that the spatially relative terms may encompass different orientations of a device in use or operation, in addition to the orientation depicted in the Figures. For example, if a device in the Figures is inverted, elements described as being "lower" other elements or features would then be oriented "higher" than the other elements or features.

It will be understood that, although the terms "first," "second," etc. may be used herein to describe various elements, these elements should not be limited by these terms. These terms are only used to distinguish one element from another. Thus, a "first" element discussed below could also be termed a "second" element without departing from the teachings of the present disclosure. The sequence of operations (or steps) is not limited to the order presented in the claims or Figures unless specifically indicated otherwise.

The invention comprises, consists of, or consists essentially of the following features, in any combination.

Figure 1:
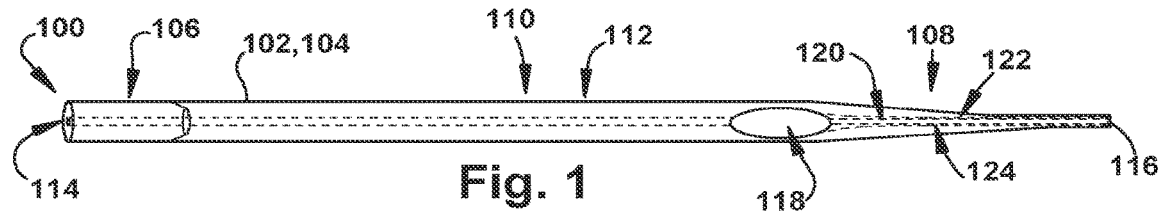
FIG. 1 is a top view of an element of a modular dilation device according to one aspect of the present invention.
Figure 2:
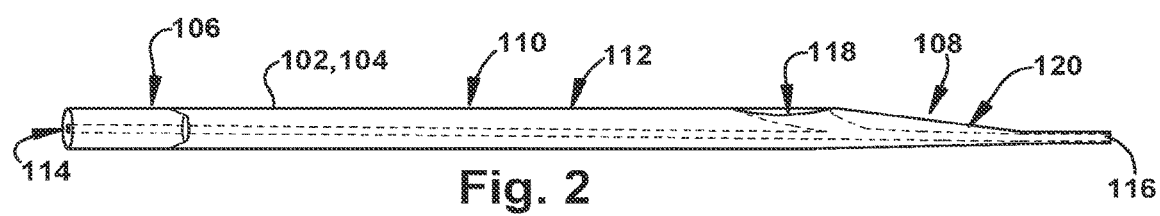
FIG. 2 is a side view of the element of FIG. 1.

A modular dilation device 100 is provided. The modular dilation device 100 may include a plurality of dilators 102 having alternate configurations, which will be discussed below. FIGS. 1, 5, 7, and 8 depict example alternate configurations of the dilators 102. FIGS. 1-2 depict an example alternate configuration for a dilator 102, referred to as a dilator A 104. The dilator A 104 has a dilator proximal end 106 and a dilator distal end 108. The dilator proximal end 106 and the dilator distal end 108 are longitudinally spaced apart by an elongate dilator body 110. The term "longitudinal" is used herein to indicate a substantially horizontal direction, in the orientation of FIG. 1. At least a portion of the dilator distal end 108 may be inwardly tapered. The term "taper" is defined herein as a gradual diminution of thickness, diameter, or width in an elongated object, as is shown by the gradual diminution in diameter of the dilator distal end in FIGS. 1-2. The term "inward" is defined herein as a taper that becomes gradually smaller, such as shown as the gradual diminution in diameter between the dilator body 110 and a dilator open tip 116, which will be discussed below, in FIGS. 1-2. Further, the inward taper, such as the taper of the dilator distal end 108, could include no expansion in diameter (or outward taper) distal to the dilator body 110. The dilator A 104 has a dilator outer surface 112 and a dilator inner lumen 114. The dilator distal end 108 has the dilator open tip 116. The dilator inner lumen 114 of the dilator A 104 may extend between the dilator proximal end 106 and the dilator open tip 116.

The dilator A 104 has a dilator side wall opening 118. The dilator side wall opening 118 is longitudinally spaced from the dilator open tip 116. The dilator side wall opening 118 is positioned on at least one of the dilator body 110 and the dilator distal end 108. The dilator side wall opening 118 selectively places the dilator outer surface 112 in fluid communication with the dilator inner lumen 114.

The dilator A 104 has a dilator open slit 120. The dilator open slit 120 extends between the dilator side wall opening 118 and the dilator open tip 116. The dilator open slit 120 has a dilator open slit first surface 122 and a dilator open slit second surface 124. The dilator open slit first surface 122 oppositely faces and abuts the dilator open slit second surface 124. The dilator open slit first surface 122 and the dilator open slit second surface 124 are elastically separable. That is, a force may be applied to separate the dilator open slit first surface 122 and the dilator open slit second surface 124, as that the dilator open slit first surface 122 will no longer be abutting the dilator open slit second surface 124. However, upon the removal of the separating force, the dilator open slit first surface 122 and the dilator open slit second surface 124 will tend to return toward their original abutting position due to the elastic nature of the material forming the dilator open slit first surface 122 and the dilator open slit second surface 124.

Figure 3:
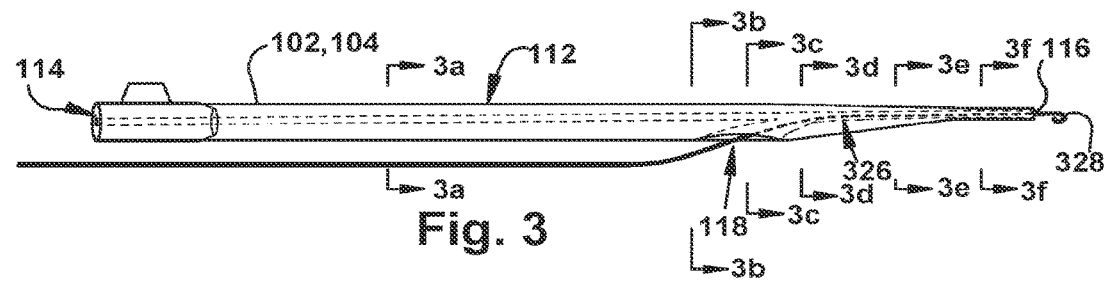
FIG. 3 is a side view of the element of FIG. 1 in an example use configuration.
Figure 3A:
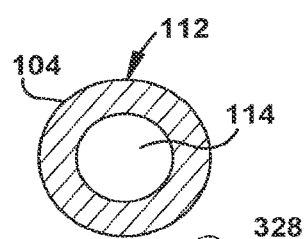
FIGS. 3*a-f* depict cross-sectional views of the aspect of FIG. 3.
Figure 3B:
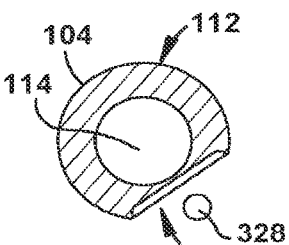
Figure 3C:
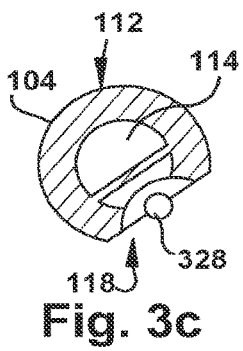
Figure 3D:
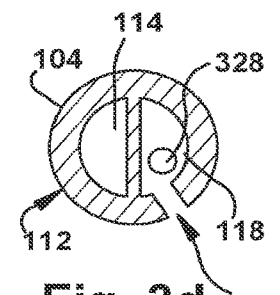
Figure 3E:
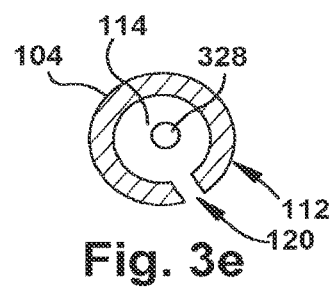
Figure 3F:
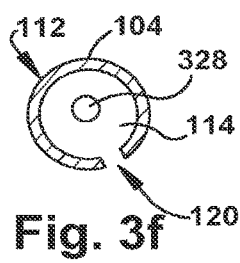
Figure 4:
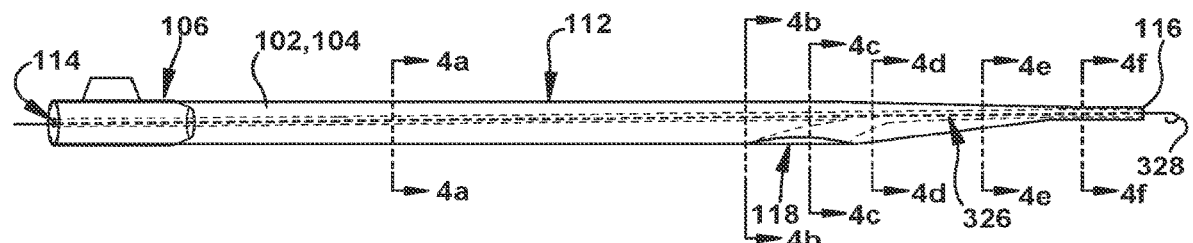
FIG. 4 is a side view of the element of FIG. 1 in an example use configuration.
Figure 4A:
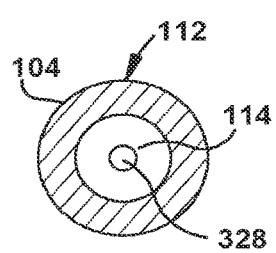
FIGS. 4*a-f* depict cross-sectional views of the aspect of FIG. 4.
Figure 4B:
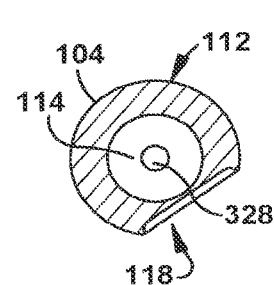
Figure 4C:
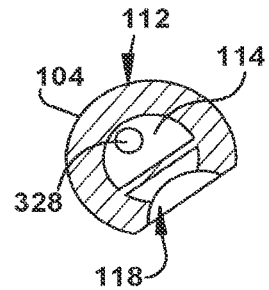
Figure 4D:
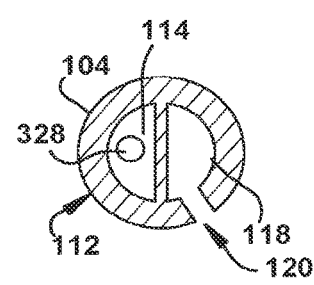
Figure 4E:
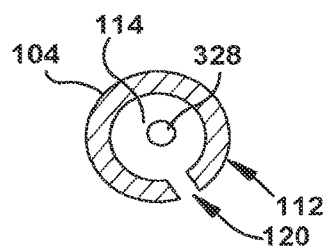
Figure 4F:
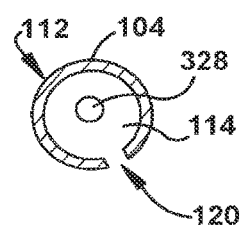

As shown in FIG. 3, the dilator A 104 may include a guidewire path 326 for a guidewire 328 to be directed through the dilator open tip 116, through at least a portion of the dilator inner lumen 114, and out from the dilator A 104, such as through the dilator side wall opening 118. FIGS. 3a-f depict cross-sectional views of various points along the dilator A 104, to show the arrangement of the dilator A 104 and the guidewire 328 in FIG. 3. As shown in FIG. 4, the dilator A may include a guidewire path 326 for a guidewire 328 to be directed through the dilator open tip 116 and the dilator inner lumen 114, and out from the dilator A 104, such as through the dilator proximal end 106 of the dilator A 104. FIGS. 4a-f depict cross-sectional views of various points along the dilator A 104, to show the arrangement of the dilator A 104 and the guidewire 328 in FIG. 4. One or more guidewires 328 may be inserted through each, or both, of the guidewire paths 326 shown in FIGS. 3 and 4.

Figure 5:
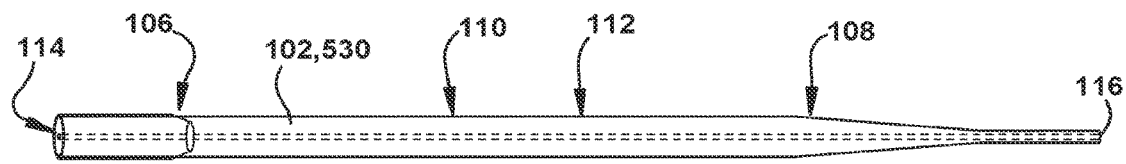
FIG. 5 is a top view of the element of FIG. 1 in an alternate configuration.
Figure 6:
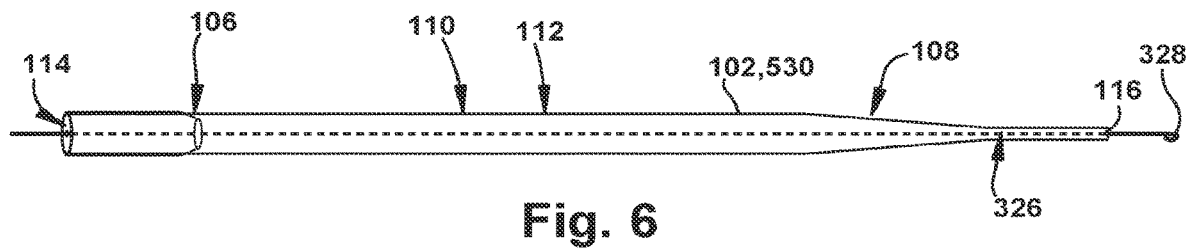
FIG. 6 is a side view of element of FIG. 5 in an example use configuration.

FIG. 5 depicts an alternate configuration for the dilator 102, referred to as a dilator B 530. Similar to the dilator A 104, the dilator B 530 has a dilator proximal end 106 and a dilator distal end 108. The dilator proximal end 106 and the dilator distal end 108 are longitudinally spaced apart by an elongate dilator body 110. At least a portion of the dilator distal end 108 may be inwardly tapered. The dilator B 530 has a dilator outer surface 112 and a dilator inner lumen 114. The dilator distal end 108 has a dilator open tip 116. The dilator inner lumen 114 of the dilator B 530 may extend between the dilator proximal end 106 and the dilator open tip 116. As shown in FIG. 6, dilator B includes a guidewire path 326 for a guidewire 328 to be directed through the dilator open tip 116 and the dilator inner lumen 114, and out from the dilator B, such as through the proximal end 106 of the dilator B 530.

Figure 7:
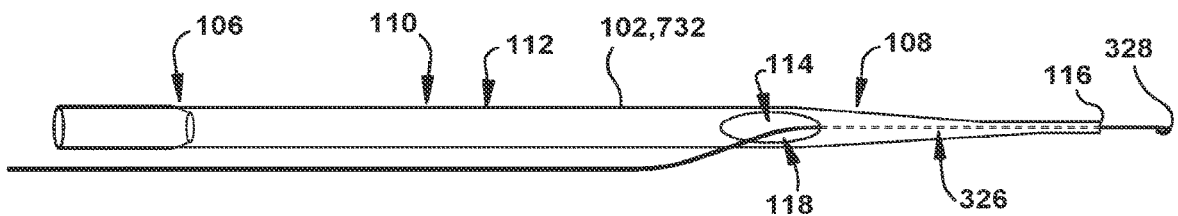
FIG. 7 is a top view of the element of FIG. 1 in an alternate configuration, in an example use configuration.

FIG. 7 depicts an example alternative configuration for the dilator 102, referred to as a dilator C 732. Similar to the dilator A 104, the dilator C 732 has a dilator proximal end 106 and a dilator distal end 108. The dilator proximal end 106 and the dilator distal end 108 are longitudinally spaced apart by an elongate dilator body 110. At least a portion of the dilator distal end 108 may be inwardly tapered. The dilator C 732 has a dilator outer surface 112 and a dilator inner lumen 114. The dilator distal end 108 has a dilator open tip 116. The dilator C 732 has a dilator side wall opening 118. The dilator side wall opening 118 is longitudinally spaced from the dilator open tip 116. The dilator side wall opening 118 is positioned on at least one of the dilator body 110 and the dilator distal end 108. The dilator side wall opening 118 selectively places the dilator outer surface 112 in fluid communication with the dilator inner lumen 114. The dilator inner lumen 114 of the dilator C 732 may extend between the dilator side wall opening 118 and the dilator open tip 116. As shown in FIG. 7, the dilator C 732 includes a guidewire path 326 for a guidewire 328 to be directed through the dilator open tip 116, through at least a portion of the dilator inner lumen 114, and out from the dilator C 732, such as through the dilator side wall opening 118.

Figure 8:
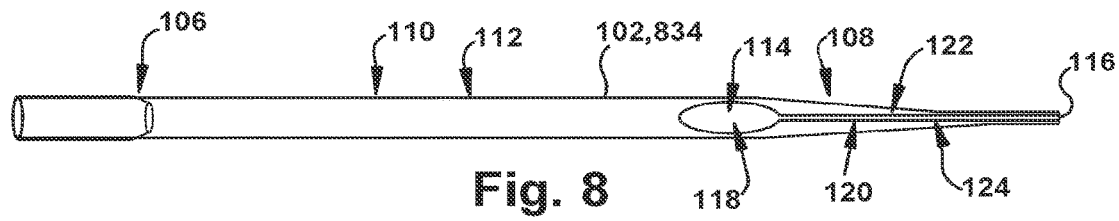
FIG. 8 is a top view of the element of FIG. 1 in an alternate configuration.
Figure 12:
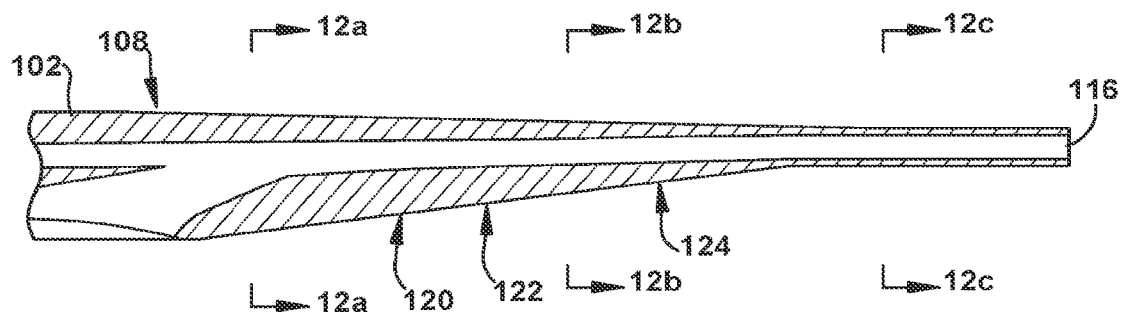
FIG. 12 is a partial side view of the element of FIG. 11 in an alternate configuration.
Figure 12A:
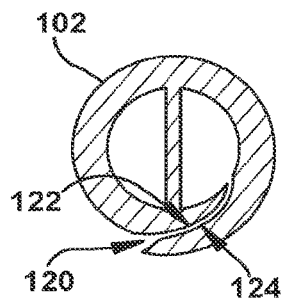
FIGS. 12*a-c* depict cross-sectional views of the aspect of FIG. 12.
Figure 12B:
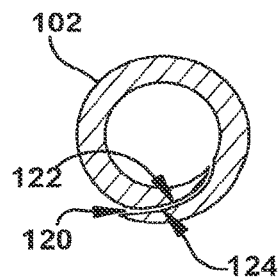
Figure 12C:
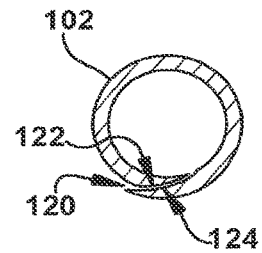

FIGS. 8-9 depict an example alternate configuration for the dilator 102, referred to as a dilator D 834. Similar to the dilator C 732, the dilator D 834 has a dilator proximal end 106 and a dilator distal end 108. The dilator proximal end 106 and the dilator distal end 108 are longitudinally spaced apart by an elongate dilator body 110. At least a portion of the dilator distal end 108 may be inwardly tapered. The dilator D 834 has a dilator outer surface 112 and a dilator inner lumen 114. The dilator distal end 108 has a dilator open tip 116. The dilator D 834 has a dilator side wall opening 118. The dilator side wall opening 118 is longitudinally spaced from the dilator open tip 116. The dilator side wall opening 118 is positioned on at least one of the dilator body 110 and the dilator distal end 108. The dilator side wall opening 118 selectively places the dilator outer surface 112 in fluid communication with the dilator inner lumen 114. The dilator inner lumen 114 of the dilator D may extend between the dilator side wall opening 118 and the dilator open tip 116.

The dilator D 834 has a dilator open slit 120. The dilator open slit 120 may extend between the dilator side wall opening 118 and the dilator open tip 116. The dilator open slit 120 has a dilator open slit first surface 122 and a dilator open slit second surface 124. The dilator open slit first surface 122 oppositely faces and abuts the dilator open slit second surface 124. The dilator open slit first surface 122 and the dilator open slit second surface 124 are elastically separable. As shown in FIG. 10, the dilator D 834 may include a guidewire path 326 for a guidewire 328 to be directed through the dilator open tip 116, through at least a portion of the dilator inner lumen 114, and out from the dilator D 834, such as through the dilator side wall opening 118.

FIGS. 11 and 11a-c depict the dilator open slit first surface 122 that oppositely faces and abuts the dilator open slit second surface 124, as described above. FIGS. 11a-c depict cross-sectional views of various points along the dilator distal end 108, to show the arrangement of the dilator open slit first surface 122 and the dilator open slit second surface 124 in FIG. 11. As shown in FIGS. 12 and 12a-c, alternatively, instead of abutting, the dilator open slit first surface 122 and the dilator open slit second surface 124 may laterally overlap to provide a labyrinth-type seal. The term "lateral" is used herein to indicate a direction substantially perpendicular to the "longitudinal" direction, and is shown as the vertical direction in the orientation of FIG. 11.

Figure 13:
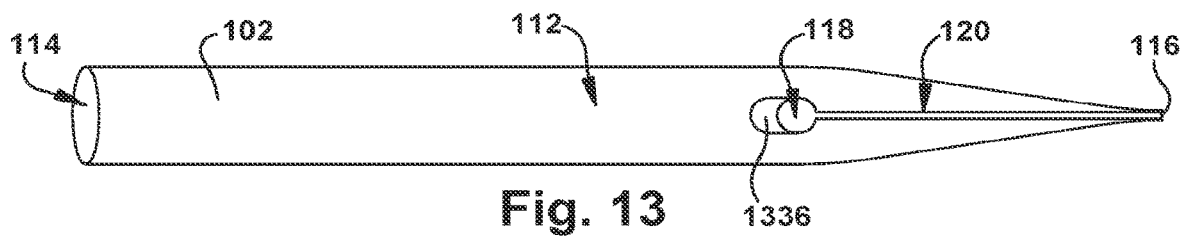
FIG. 13 is a top view of the element of FIG. 1 in an alternate configuration.
Figure 14:
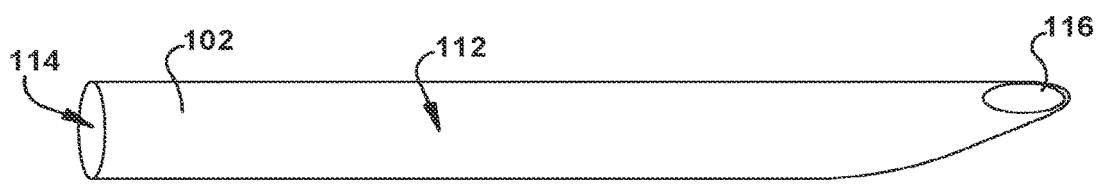
FIG. 14 is a side view of the element of FIG. 5 in an alternate configuration.

As shown in FIG. 13, the dilator side wall opening 118 may have a dilator downwardly inclined surface 1336 that extends from the dilator outer surface 112 to the dilator inner lumen 114. The term "downward" is defined herein as from a higher to a lower place or condition, as is shown by the dilator downwardly inclined surface 1336 that begins at a higher place (the dilator outer surface 112) and extends to a lower place (the dilator inner lumen 114), such as into the plane of the page in the orientation of FIG. 13. As exemplified in FIG. 14, the dilator open tip 116 may be in a side opening configuration.

Figure 15:
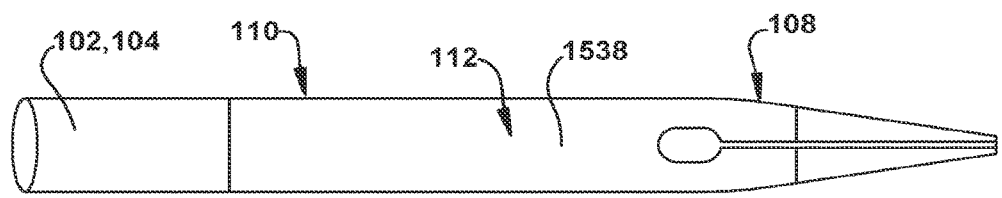
FIG. 15 is a top view of the element of FIG. 1 in an alternate configuration.
Figure 16:
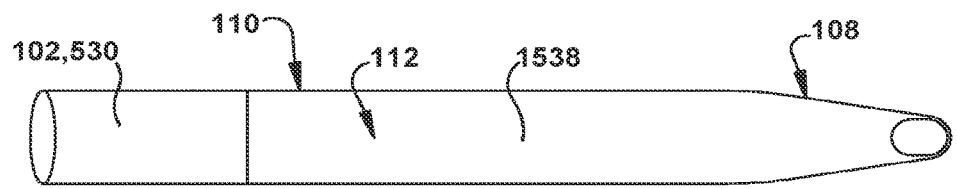
FIG. 16 is a top view of the element of FIG. 5 in an alternate configuration.

As shown in FIGS. 15-16, at least a portion of the dilator outer surface 112 may have a flat dilator abutting surface 1538. The dilator abutting surface 1538 extends between a least a portion of the dilator body 110 and at least a portion of the dilator distal end 108. That is, instead of a rounded, tubular dilator 102 as depicted in at least FIGS. 1, 5, 7, and 8, the dilator 102 may have a substantially flat surface (the dilator abutting surface 1538) that extends between at least a portion of the dilator body 110 and at least a portion of the dilator distal end 108 as shown in FIGS. 15-16. FIG. 15 depicts the dilator A 104 having the dilator abutting surface 1538. As shown in FIG. 16, at least a portion of the dilator B 530 may have the dilator abutting surface 1538. In this configuration, the dilator abutting surface 1538 of the dilator A 104 is capable of contacting the dilator abutting surface 1538 of the dilator B 530. That is, the flat dilator abutting surface 1538 of the dilator A 104 may be placed against the flat dilator abutting surface 1538 of the dilator B 530, which may provide for a more stable engagement than what the line contact between rounded, tubular surfaces might provide. Although only the dilators A and B 104, 530 have been shown as having the dilator abutting surface 1538, any of the dilators 102, such as the dilators A-D 104, 530, 732, 834, as discussed above, may have the dilator abutting surface 1538 to provide for a more stable engagement between the dilators 102.

Figure 17:
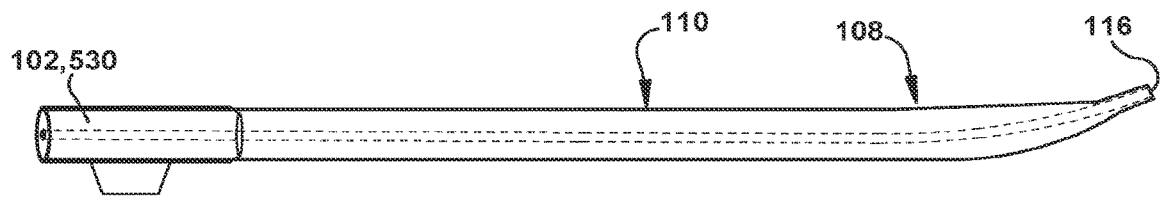
FIG. 17 is a side view of the element of FIG. 5 in an alternate configuration.

As shown in FIG. 17, at least a portion of the dilator distal end 108 of any of the dilators 102, as disclosed above, may be curved. The term "curve" is defined herein as to have a turn, change, or deviation from a straight line or plane surface without sharp breaks or angularity, as is shown by the gradual curve from the dilator body 110 to the dilator distal end 108 in FIG. 17. Although FIG. 17 depicts a curved dilator B 530, the dilator distal ends 108 of any of the dilators 102, such as the dilators A-D 104, 530, 732, 834, as discussed above, may be curved.

Figure 18:
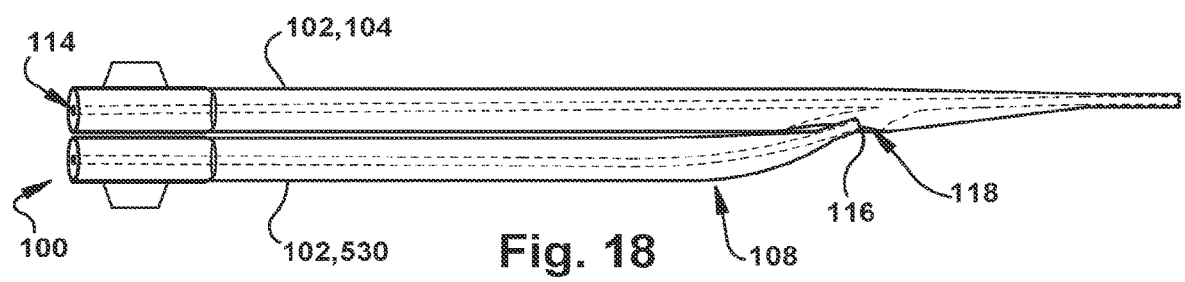
FIG. 18 is a side view of the modular dilation device in an example use configuration.
Figure 19:
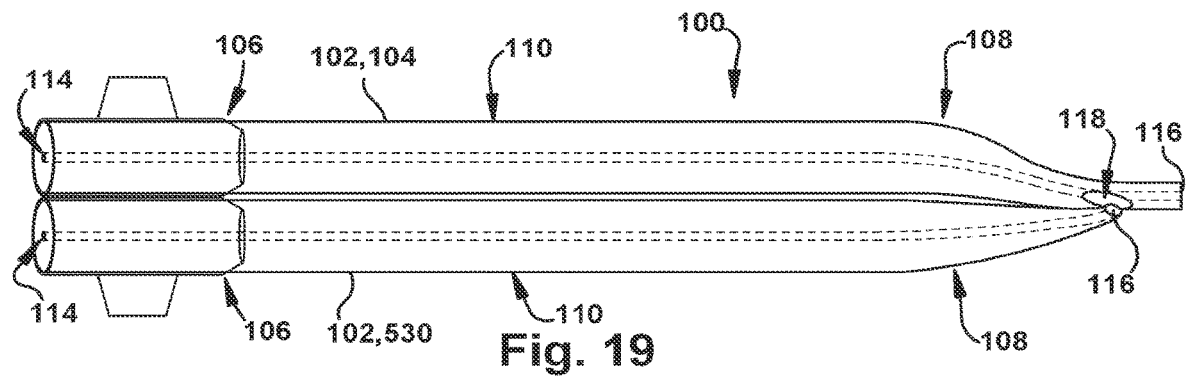
FIG. 19 is a side view of the modular dilation device in an example use configuration.
Figure 20:
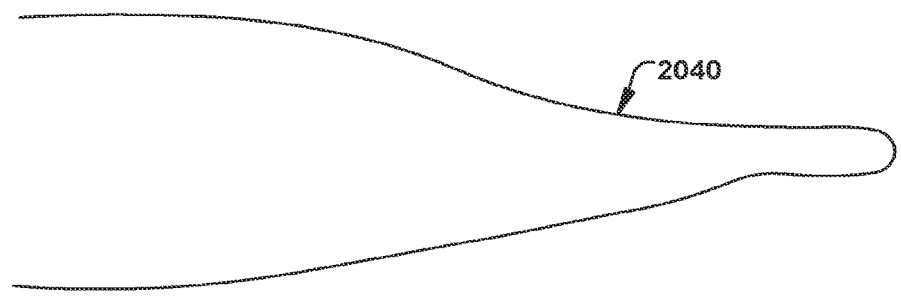
FIG. 20 is a schematic side view of an element of the aspect of FIG. 19.
Figure 21:
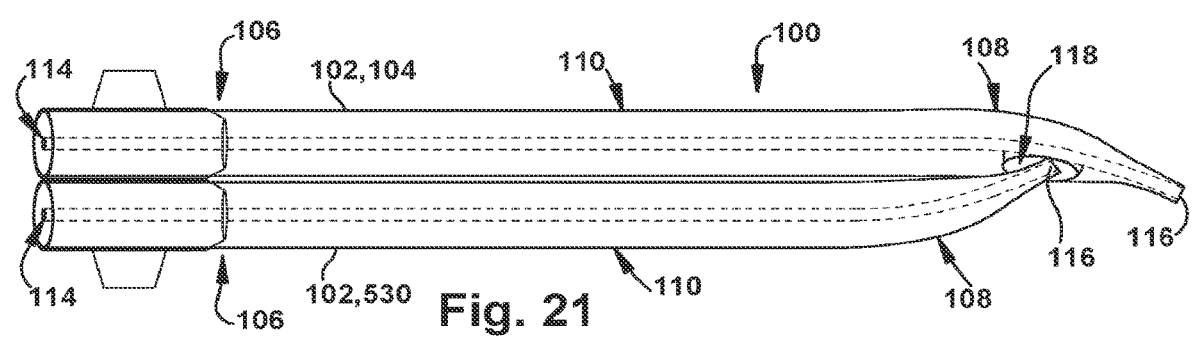
FIG. 21 is a side view of the modular dilation device in an example use configuration.
Figure 22:
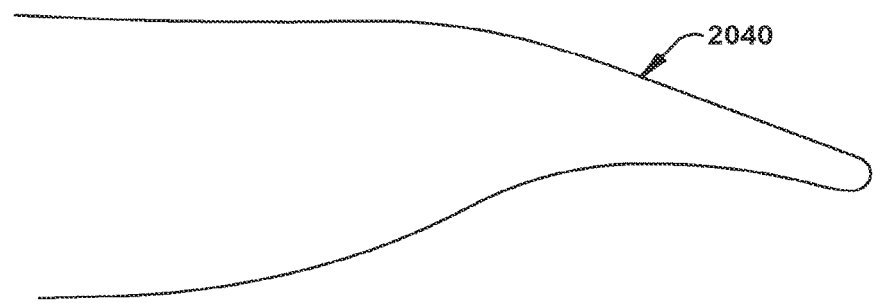
FIG. 22 is a schematic side view of an element of the aspect of FIG. 21.

The dilator open tip 116 and at least a portion of the dilator distal end 108 may each be smaller in diameter than both of the dilator side wall opening 118 and at least a portion of the dilator inner lumen 114. For example, a curved dilator B 530 may be operatively joined to a dilator A 104 by the insertion of at least a portion of the dilator distal end 108 of the curved dilator B 530 into the dilator inner lumen 114 of the dilator A 104 through the dilator side wall opening 118 of the dilator A 104. When a dilator 102 is operatively joined to another dilator 102, the dilator open tip 116 of one dilator is adjacent to the dilator side wall opening 118 of the other dilator 102. Alternatively, the insertion depth of the dilator B 530 into the dilator side wall opening 118 of the dilator A 104 may be of varying degrees. For example, as shown in FIG. 18, the dilator open tip 116 of a curved dilator B 530 and at least a portion of the dilator distal end 108 of the curved dilator B 530 may both be inserted into the dilator side wall opening 118 of the dilator A 104, without being inserted into the dilator inner lumen 114 of the dilator A 104.

As shown in FIGS. 19-22, when at least two of the dilators 102 are operatively joined together, the contours of at least one of the dilator distal ends 108, the dilator bodies 110, and the dilator proximal ends 106 may form a relatively smooth tapered surface 2040. The term "smooth" is defined herein as moving or progressing without significant breaks, sudden changes, or shifts. The smooth tapered surface 2040 may allow for a smooth dilation of a patient tissue access point P.

Figure 23:
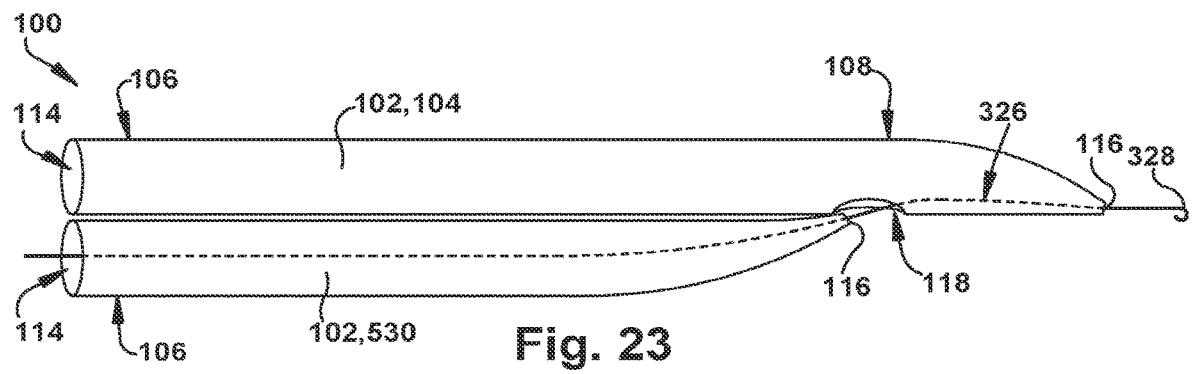
FIG. 23 is a side view of an aspect of the modular dilation device in an example use configuration.

The modular dilation device 100 including any of the dilators 102, as discussed above, may be operatively joined to any other dilator 102, including another of the same type of dilator 102. One having ordinary skill in the art may decide the order in which one dilator 102 may be joined to another dilator 102. For example, as shown in FIG. 23, when a dilator A 104 is operatively joined to a dilator B 530, the dilator open tip 116 of the dilator B 530 is adjacent to the dilator side wall opening 118 of the dilator A 104. In this configuration, the modular dilation device 100 may include a guidewire path 326 for a guidewire 328 to be directed through the dilator open tip 116 of the dilator A 104, through at least a portion of the dilator inner lumen 114 of the dilator A 104, through the dilator side wall opening 118 of the dilator A 104, through the dilator open tip 116 of the dilator B and the dilator inner lumen 114 of the dilator B 530, and out from the dilator B 530, such as through the dilator proximal end 108 of the dilator B 530.

Figure 24:
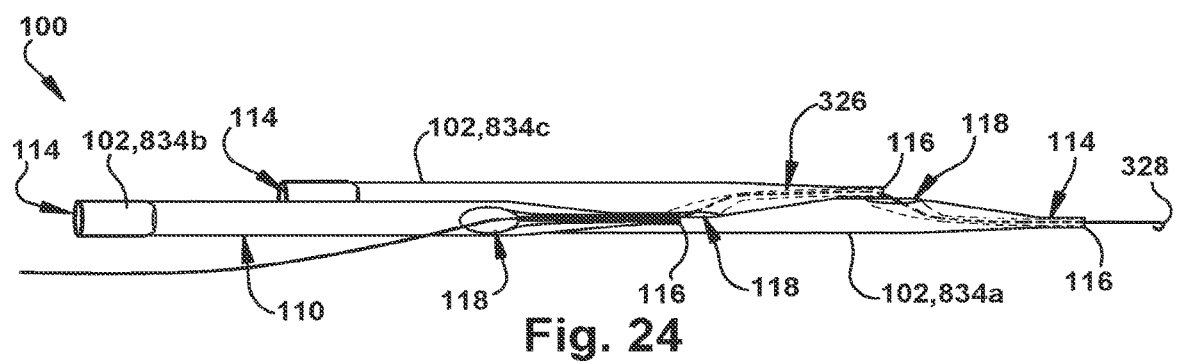
FIG. 24 is a side view of the aspect of FIG. 23 in an alternate configuration.

As shown in FIG. 24, when three of the dilators D 834 are operatively joined together, the dilator open tip 116 of a third dilator D 834c is adjacent to the dilator side wall opening 118 of a first dilator D 834a, and the dilator open tip 116 of a second dilator D 834b is adjacent to the dilator side wall opening 118 of the third dilator D 834c. In this configuration, the modular dilation device 100 may include a guidewire path 326 for a guidewire 328 to be directed through the dilator open tip 116 of the first dilator D 834a, through at least a portion of the dilator inner lumen 114 of the first dilator D 834a, through the dilator side wall opening 118 of the first dilator D 834a, through the dilator open tip 116 of the third dilator D 834c, through at least a portion of the dilator inner lumen 114 of the third dilator D 834c, through the dilator side wall opening 118 of the third dilator D 834c, through the dilator open tip 116 of the second dilator D 834b, through at least a portion of the dilator inner lumen 114 of the second dilator D 834b, and out from the second dilator D 834b, such as through the dilator side wall opening 118 of the second dilator D 834b.

Figure 25:
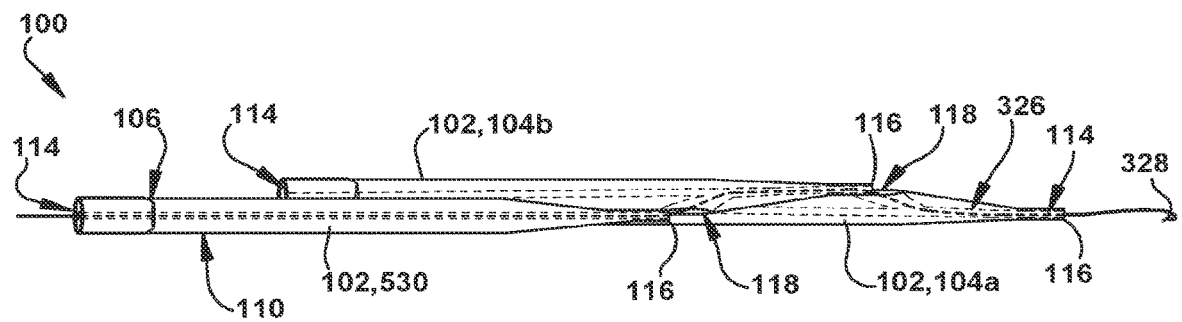
FIG. 25 is a side view of the aspect of FIG. 23 in an alternate configuration.

As shown in FIG. 25, when two dilators A 104 and a dilator B 530 are operatively joined together, the dilator open tip 116 of the dilator B 530 is adjacent to the dilator side wall opening 118 of a second dilator A 104b, and the dilator open tip 116 of the second dilator A 104b is adjacent to the dilator side wall opening 118 of a first dilator A 104a. In this configuration, the modular dilation device 100 may include a guidewire path 326 for a guidewire 328 to be directed through the dilator open tip 116 of the first dilator A 104a, through at least a portion of the dilator inner lumen 114 of the first dilator A 104a, through the dilator side wall opening 118 of the first dilator A 104a, through the dilator open tip 116 of the second dilator A 104b, through at least a portion of the dilator inner lumen 114 of the second dilator A 104b, through the dilator side wall opening 118 of the second dilator A 104b, through the dilator open tip 116 of the dilator B 530 and the dilator inner lumen 114 of the dilator B 530, and out from the dilator B 530, such as through the dilator proximal end 106 of the dilator B 530.

Figure 26:
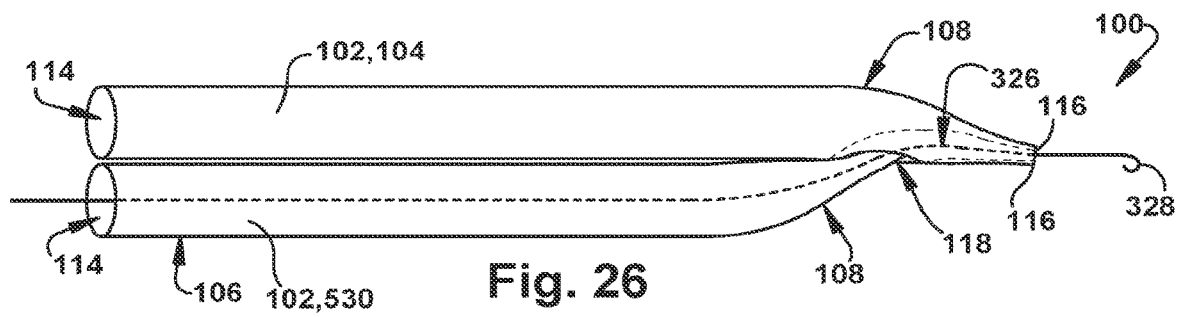
FIG. 26 is a side view of the aspect of FIG. 23 in an alternate configuration.

As shown in FIG. 26, the dilator open tip 116 and at least a portion of the dilator distal end 108 of may each be formed at least partially from an elastic material, which would allow for the dilator open tip 116 and at least a portion of the dilator distal end 108 of one dilator 102 to be inserted into the dilator inner lumen 114 of another dilator 102 through the dilator side wall opening 118 of the other dilator 102. Further, as discussed above, the dilator open tip 116 and at least a portion of the dilator distal end 108 may each be smaller in diameter than both the dilator side wall opening 118 and at least a portion of the dilator inner lumen 114. In such case, as shown in FIG. 26, when a dilator B 530, when provided, is operatively joined to a dilator A 104, when provided, the dilator open tip 116 and at least a portion of the dilator distal end 108 of the dilator B 530 is inserted into the dilator inner lumen 114 of the dilator A 104 through the dilator side wall opening 118 of the dilator A 104. In this configuration, as is shown in FIG. 26, a guidewire path 326 for a guidewire 328 may be directed through the dilator open tip 116 of the dilator A 104, through at least a portion of the dilator inner lumen 114 of the dilator A 104, through the dilator open tip 116 of the dilator B 530, and the dilator inner lumen 114 of the dilator B 530 (thus, indirectly traveling through the dilator side wall opening 118 of the dilator A 104, as well), and out from the dilator B 530, such as through the dilator proximal end 106 of the dilator B 530. Although FIG. 26 depicts the dilator A 104 and the dilator B 530, any of the dilators 102, such as the dilators A-D 104, 530, 732, 834, as discussed above, may have a similar configuration as described above for FIG. 26.

Figure 27:
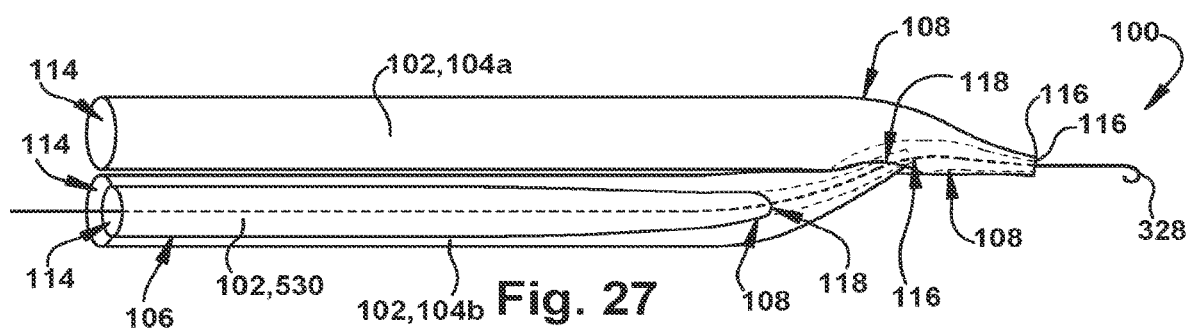
FIG. 27 is a side view of the aspect of FIG. 23 in an alternate configuration.

As shown in FIG. 27, when a dilator B 530 and two dilators A 104 are operatively joined together in a similar manner as described above for FIG. 26, the dilator open tip 116 and at least a portion of the dilator distal end 108 of the dilator B 530 may be inserted into the dilator inner lumen 114 of a second dilator A 104b through the dilator side wall opening 118 of the second dilator A 104b, and the dilator open tip 116 and at least a portion of the dilator distal end 108 of the second dilator A 104b may be inserted into the dilator inner lumen 114 of a first dilator A 104a through the dilator side wall opening 118 of the first dilator A 104a. In this configuration, as is shown in FIG. 27, a guidewire path 326 for a guidewire 328 may be directed through the dilator open tip 116 of the first dilator A 104a, through at least a portion of the dilator inner lumen 114 of the first dilator A 104a, through the dilator open tip 116 of the second dilator A 104b, through at least a portion of the dilator inner lumen 114 of the second dilator A 104b (thus, indirectly traveling through the dilator side wall opening 118 of the first dilator A 104a, as well), through the dilator open tip 116 of the dilator B 530 and the dilator inner lumen 114 of the dilator B 530 (thus, indirectly traveling through the dilator side wall opening 118 of the second dilator B 104b, as well), and out from the dilator B 530, such as through the dilator proximal end 106 of the dilator B 530. Although FIG. 27 depicts two dilators A 104a-b and a dilator B 530, any of the dilators 102, such as the dilators A-D 104, 530, 732, 834, as discussed above, may have a similar configuration as described above for FIG. 27.

In use, the modular dilation device 100, as described above, is provided to the user. The modular dilation device 100 may include at least two of any of the configurations of the dilators 102, as discussed above, in any combination, including having multiple dilators 102 with substantially the same configurations. For the sake of brevity, not every combination of the alternate dilator 102 configurations are discussed and/or depicted. However, it is to be understood that the following descriptions may be applicable to any combination of the alternate configurations of the dilators 102, as described above.

Figure 28:
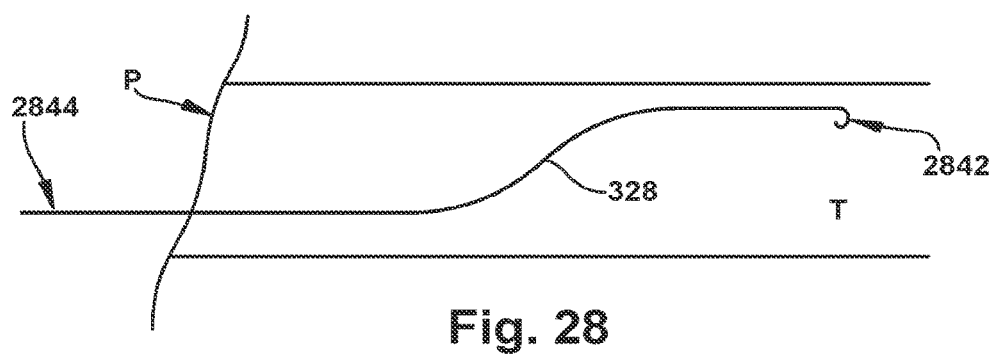

As shown in FIG. 28, a guidewire distal end 2842 is inserted into a target patient tissue site T through a patient tissue access point P. A guidewire proximal end 2844 is directed into the dilator open tip 116 of a dilator A 104, when provided, through at least a portion of the dilator inner lumen 114 of the dilator A 104, and out from the dilator A 104, such as through the dilator side wall opening 118 of the dilator A 104. As shown in FIG. 29, the dilator A 104 is directed to the target patient tissue site T along the guidewire 328. FIGS. 29a-f depict cross-sectional views of various points along the dilator A 104, to show the arrangement of the dilator A 104 and the guidewire 328 in FIG. 29.

Figure 30:
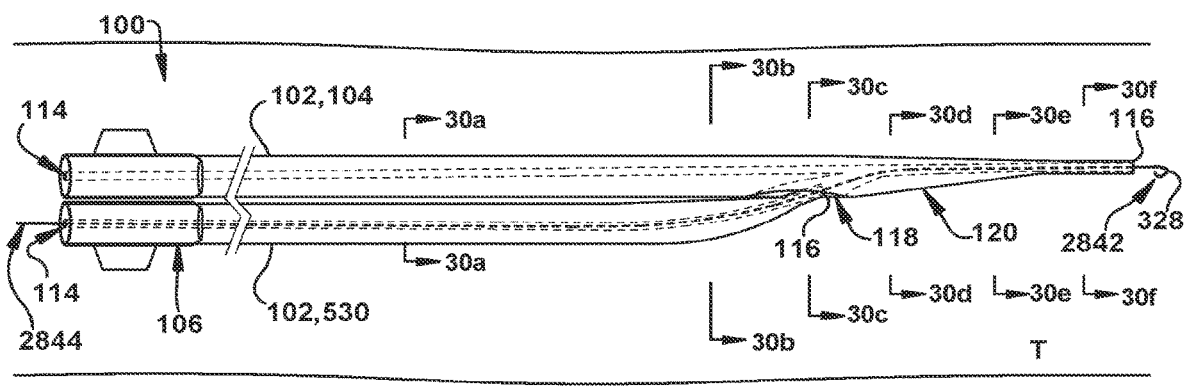
Figure 30A:
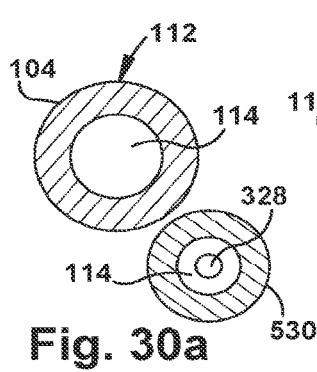
Figure 30B:
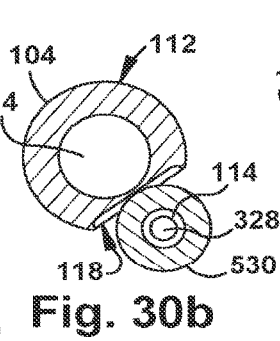
Figure 30C:
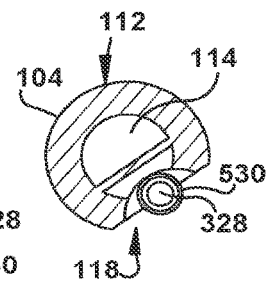
Figure 30D:
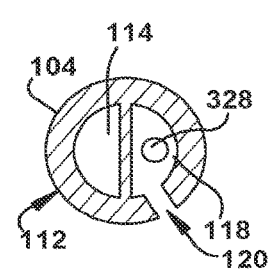
Figure 30E:
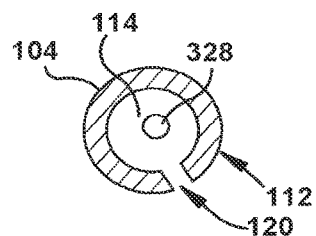
Figure 30F:
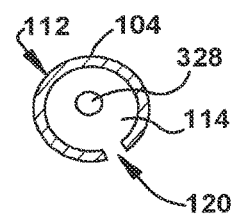

The guidewire proximal end 2844 is directed into the dilator open tip 116 of a dilator B 530, when provided, through at least a portion of the dilator inner lumen 114 of the dilator B 530, and out from the dilator B 530, such as through the dilator proximal end 106 of the dilator B 530. As shown in FIG. 30, the dilator B 530 is directed to the target patient tissue site T along the guidewire 328 until the dilator open tip 116 of the dilator B 530 is adjacent to the dilator side wall opening 118 of the dilator A 104. FIGS. 30a-f depict cross-sectional views of various points along the modular dilation device 100, to show the arrangement of the dilators 102 and the guidewire 328 in FIG. 30.

Instead of directing multiple dilators 102 to the target patient tissue site T sequentially, as described above, prior to directing the dilators 102 to the target patient tissue site T, the dilator B 530 may be placed in a predetermined relationship with the dilator A 104, wherein the dilator open tip 116 of the dilator B 530 is adjacent to the dilator side wall opening 118 of the dilator A 104. In such case, the guidewire proximal end 2844 is directed into the dilator open tip 116 of the dilator A 104 and out of the dilator proximal end 106 of the dilator B 530. In particular, the guidewire proximal end 2844 is directed through the dilator open tip 116 of the dilator A 104 and at least a portion of the dilator inner lumen 114 of the dilator A 104, through the dilator side wall opening 118 of the dilator A 104, through the dilator open tip 116 and the dilator inner lumen 114 of the dilator B 530, and out from the dilator B 530, such as through the dilator proximal end 106 of the dilator B 530. Both the dilator A 104 and the dilator B 530 are then collectively inserted into the target patient tissue site T along the guidewire 328.

Figure 31:
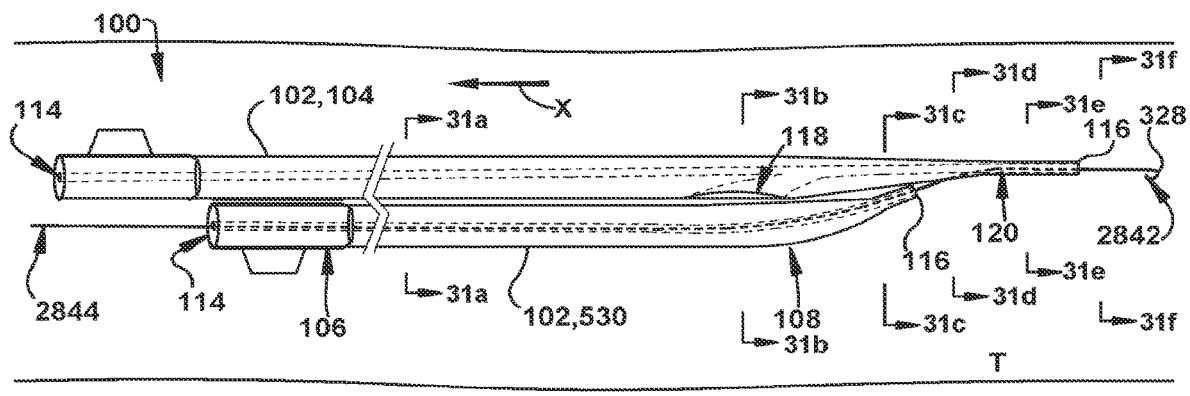
Figure 31A:
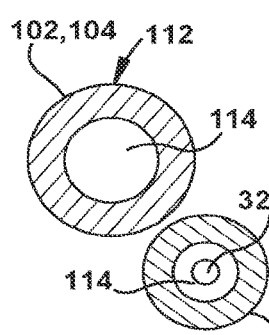
Figure 31B:
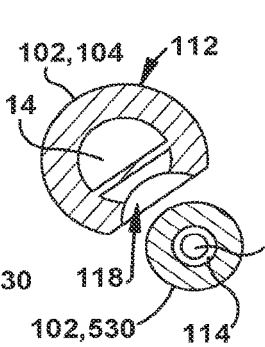
Figure 31C:
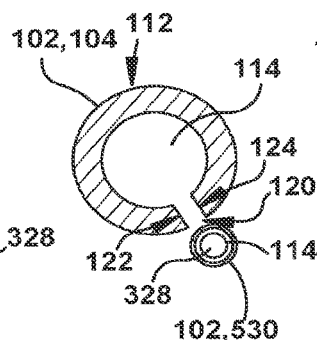
Figure 31D:
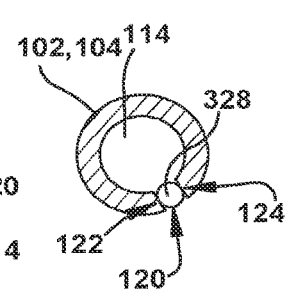
Figure 31E:
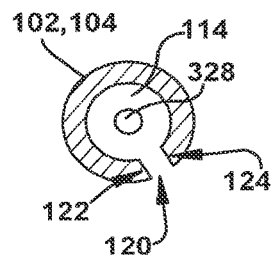
Figure 31F:
Figure 32:
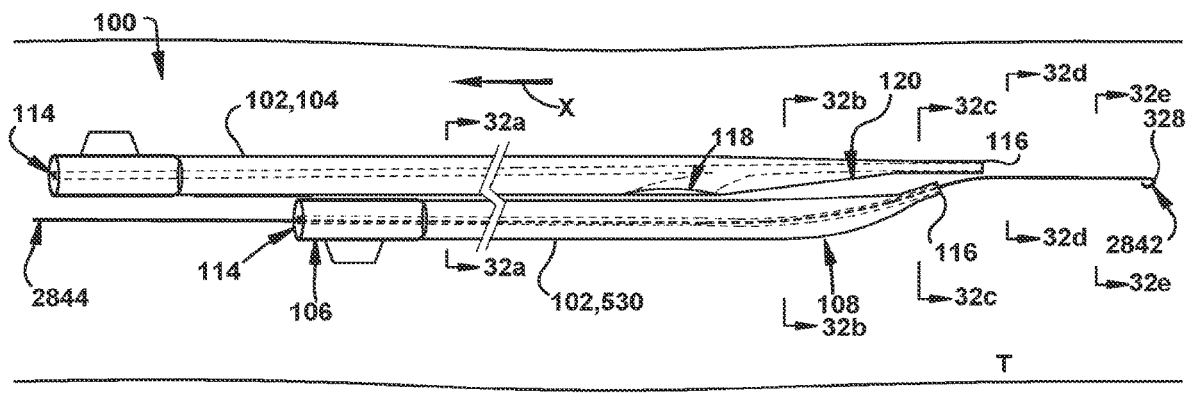
Figure 32A:
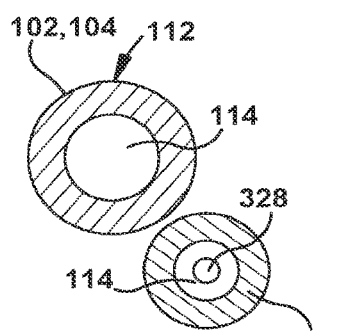
Figure 32B:
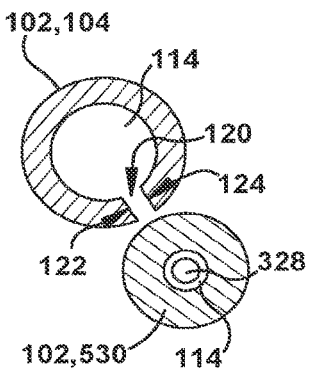
Figure 32C:
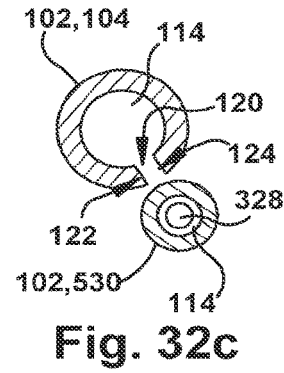
Figure 32D:
Figure 32E:

With the modular dilation device 100 at the target patient tissue site T, the dilator open tip 116 and at least a portion of the dilator distal end 108 of the dilator B 530 may each be directed at least one of adjacent to and into the dilator side wall opening 118 of the dilator A 104. As shown in FIGS. 31 and 32, with the dilator distal end 108 of the dilator B 530 at least one of adjacent to and at least partially in the dilator side wall opening 118 of the dilator A 104, the dilator A 104 is longitudinally moved toward a proximal direction (shown as the arrow X in FIGS. 31 and 32) to remove the dilator A 104 from the guidewire 328, while maintaining the guidewire 328 at the target patient tissue site T. In particular, as the dilator A 104 is moved toward the proximal direction, the dilator distal end 108 of the dilator B 530 selectively urges the dilator open slit first surface 122 of the dilator A 104 elastically apart from the dilator open slit second surface 124 of the dilator A 104 and the dilator A 104 is removed from the guidewire 328. Thus, the dilator distal end 108 of the dilator B 530 can be thought of as acting as a pivot arrangement to release the dilator A 104 from the guidewire 328. FIGS. 31a-f depict cross-sectional views of various points along the modular dilation device 100, to show the arrangement of the dilators 102 and the guidewire 328 in FIG. 31. FIGS. 32a-f depict cross-sectional views of various points along the modular dilation device 100, to show the arrangement of the dilators 102 and the guidewire 328 in FIG. 32.

Figure 33:
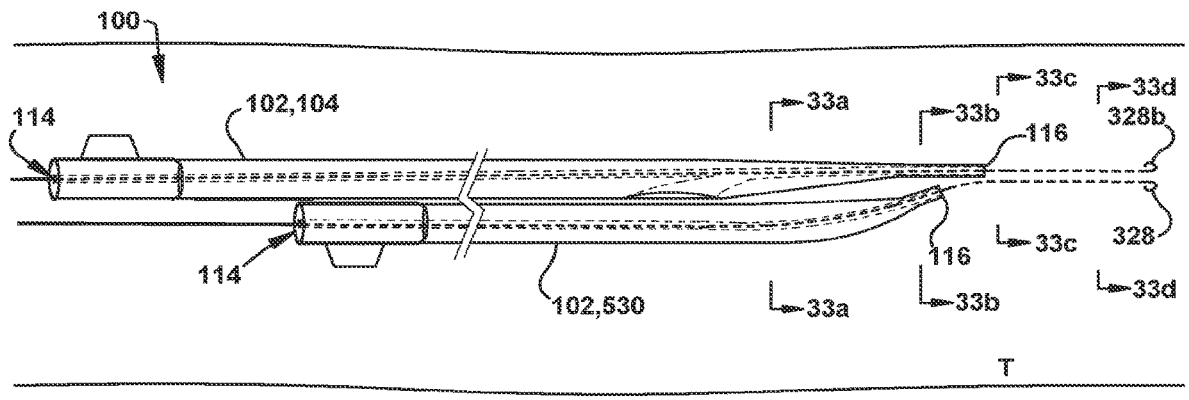
Figure 33A:
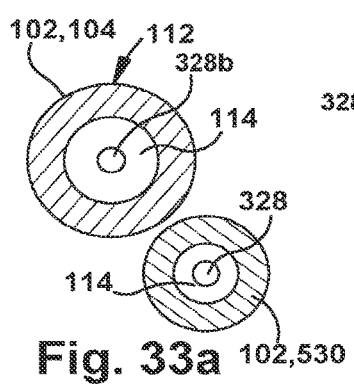
Figure 33B:
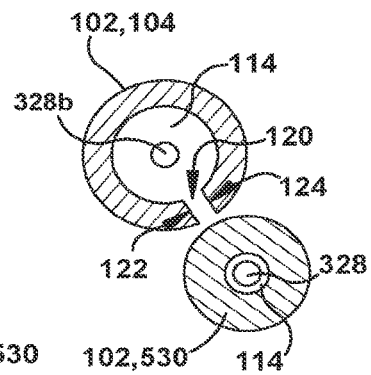
Figure 33C:
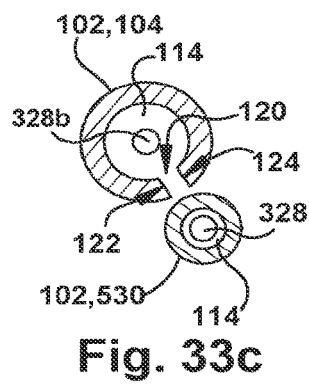
Figure 33D:
Figure 33E:
Figure 34:
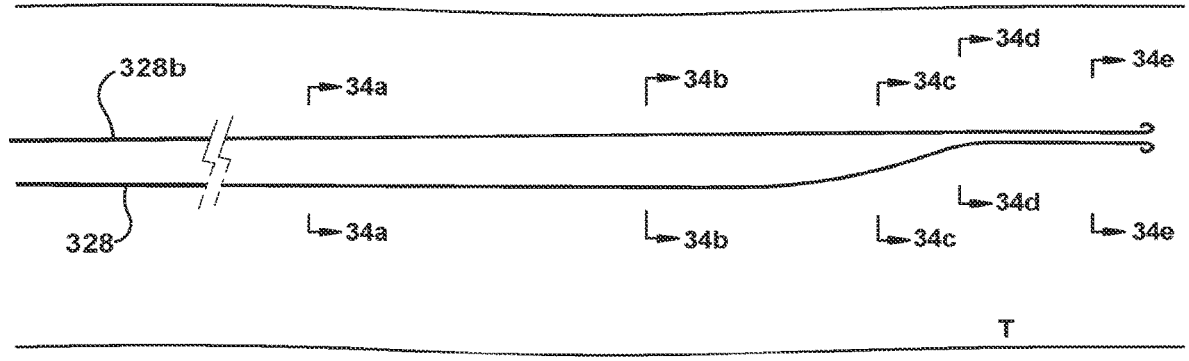
Figure 34A:
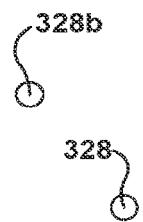
Figure 34B:
Figure 34C:
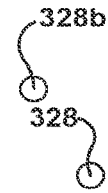
Figure 34D:
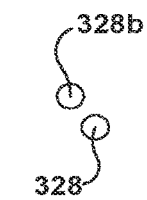
Figure 34E:
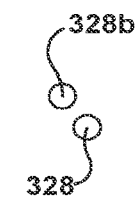

As shown in FIG. 33, once the dilator A 104 is fully removed from the guidewire 328, a second guidewire 328b may be inserted through the dilator inner lumen 114 of the dilator A 104 and into the target patent tissue site T. FIGS. 33a-f depict cross-sectional views of various points along the modular dilation device 100, to show the arrangement of the dilators 102 and the guidewires 328, 328b in FIG. 33. As shown in FIG. 34, with the second guidewire 328b at the target patient tissue site T, at least one of the dilator A 104 and the dilator B 530 may be longitudinally moved in the proximal direction over the guidewires 328, 328b to remove at least one of the dilator A and the dilator B 530 from at least one of the guidewires 328, 328b and the target patient tissue site T. FIGS. 34a-f depict cross-sectional views of various points along the guidewires 328, 328b, to show the arrangement of the guidewires 328, 328b in FIG. 34.

Figure 35:
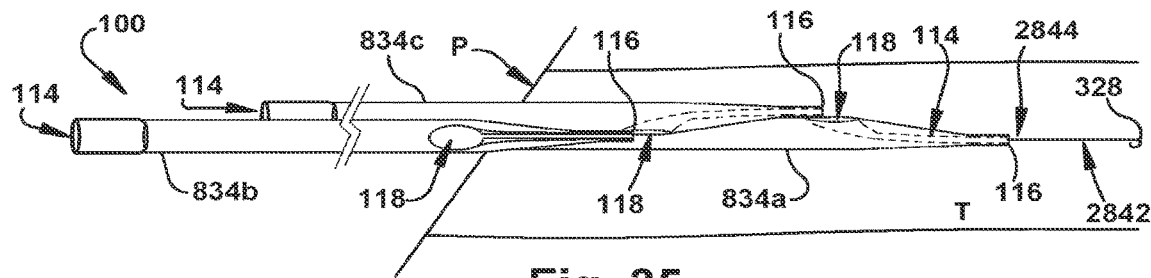
FIGS. 35-41 illustrate an example sequence operation of a portion of the aspect of FIG. 24.
Figure 36:
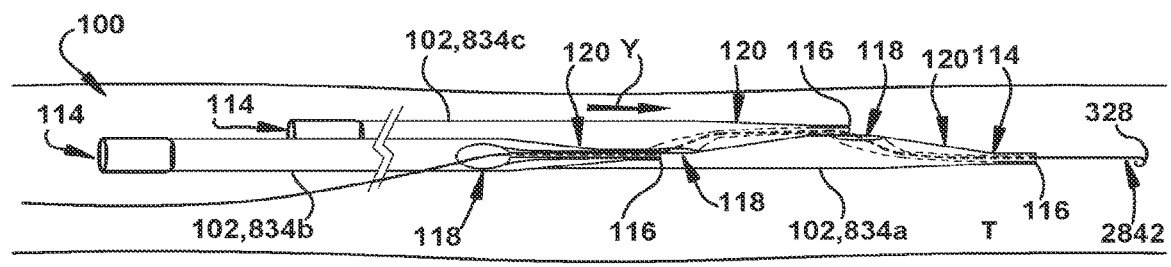

FIGS. 35-41 depict an example sequence of operation of a modular dilation device 100 having three dilators D 834. A guidewire distal end 2842 is inserted into a target patient tissue site T through a patient tissue access point P. As shown in FIG. 35, a third dilator D 834c is placed into a predetermined relationship with a first dilator D 834a, wherein the dilator open tip 116 of the third dilator D 834c is adjacent to the dilator side wall opening 118 of the first dilator D 834a. A second dilator D 834b is placed into a predetermined relationship with the third dilator D 834c, wherein the dilator open tip 116 of the second dilator D 834b is adjacent to the dilator side wall opening 118 of the third dilator D 834c. The guidewire proximal end 2844 is directed into the dilator open tip 116 of the first dilator D 834a and out of the second dilator D 834b. In particular, the guidewire proximal end 2844 is directed through the dilator open tip 116 of the first dilator D 834a and at least a portion of the dilator inner lumen 114 of the first dilator D 834a, through the dilator side wall opening 118 of the first dilator D 834a, through the dilator open tip 116 of the third dilator D 834c and at least a portion of the dilator inner lumen 114 of the third dilator D 834c, through the dilator side wall opening 118 of the third dilator D 834c, through the dilator open tip 116 and the dilator inner lumen 114 of the second dilator D 834b, and out from the second dilator D 834b, such as through the dilator side wall opening 118 of the second dilator D 834b. As shown in FIG. 36, the first dilator D 834a, the second dilator D 834b, and the third dilator D 834c are collectively inserted into the target patient tissue site T along the guidewire 328 in a longitudinally distal direction (as shown by arrow Y in FIG. 36).

Instead of collectively inserting all three of the dilators D 834a-c into the target patient tissue site T, the dilators D 834a-c may be inserted into the target patient tissue site T sequentially. For example, 2844 a guidewire proximal end is directed into the dilator open tip 116 of the first dilator D 834a, through at least a portion of the dilator inner lumen 114 of the first dilator D 834a, and out from the first dilator D 834a, such as through the dilator side wall opening 118 of the first dilator D 834a. The first dilator D 834a is directed to the target patient tissue site T along the guidewire 328. The guidewire proximal end 2844 is directed into the dilator open tip 116 of the third dilator D 834c, through at least a portion of the dilator inner lumen 114 of the third dilator D 834c, and out from the third dilator D 834c, such as through the dilator side wall opening 118 of the third dilator D 834c. The third dilator D 834c is directed into the target patient tissue site T along the guidewire 328 until the dilator open tip 116 of the third dilator D 834c is adjacent to the dilator side wall opening 118 of the first dilator D 834a. The guidewire proximal end 2842 is directed into the dilator open tip 116 of the second dilator D 834b, through at least a portion of the dilator inner lumen 114 of the second dilator D 834b, and out from the second dilator D 834b, such as through the dilator side wall opening 118 of the second dilator D 834b. The second dilator D 834b is directed to the target patient tissue site T along the guidewire 328 until the dilator open tip 116 of the second dilator D 834*b* is adjacent to the dilator side wall opening 118 of the third dilator D 834*c*.

Figure 37:
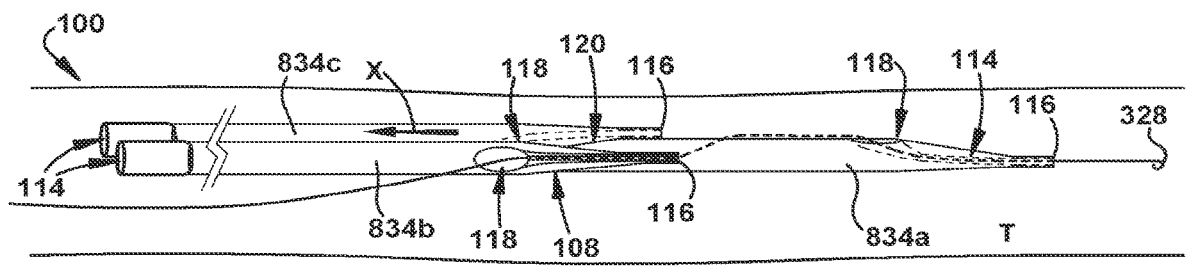
Figure 38:
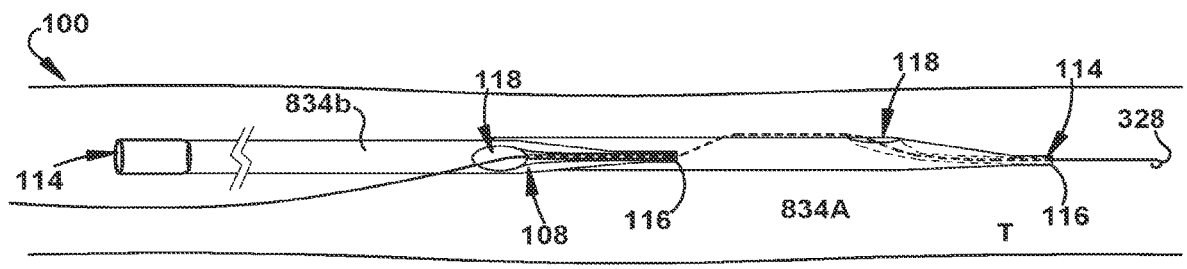

With the modular dilation device 100 at the target patient tissue site T, at least a portion of the dilator distal end 108 of the second dilator D 834*b* may be directed at least one of adjacent to and into the dilator side wall opening 118 of the third dilator D 834*c*. As shown in FIG. 37, with the dilator distal end 108 of the second dilator D 834*b* at least one of adjacent to and at least partially in the dilator side wall opening 118 of the third dilator D 834*c*, the third dilator D 834*c* is longitudinally moved toward a proximal direction (shown as the arrow X in FIG. 37) to remove the third dilator D 834*c* from the guidewire 328, while maintaining the guidewire 328 at the target patient tissue site T. In particular, as the third dilator D 834*c* is moved toward the proximal direction, the dilator distal end 108 of second dilator D 834*b* selectively urges the dilator open slit first surface 122 of the third dilator D 834*c* elastically apart from the dilator open slit second surface 124 of the third dilator D 834*c* and the third dilator D 834*c* is removed from the guidewire 328, as is shown in FIG. 38. Thus, the dilator distal end 108 of the second dilator D 834*b* can be thought of as a pivot to release the third dilator D 834*c* from the guidewire 328.

Figure 39:
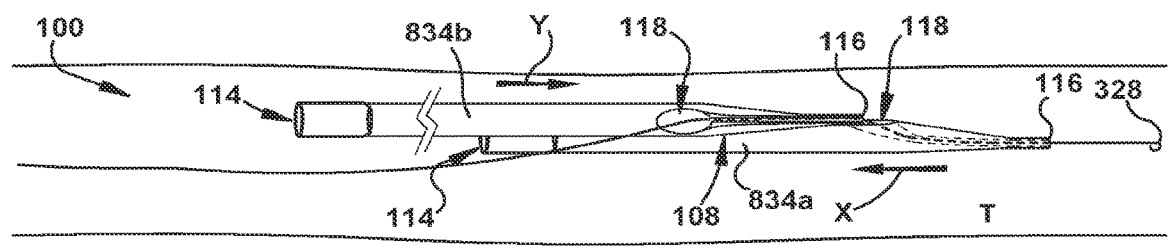
Figure 40:
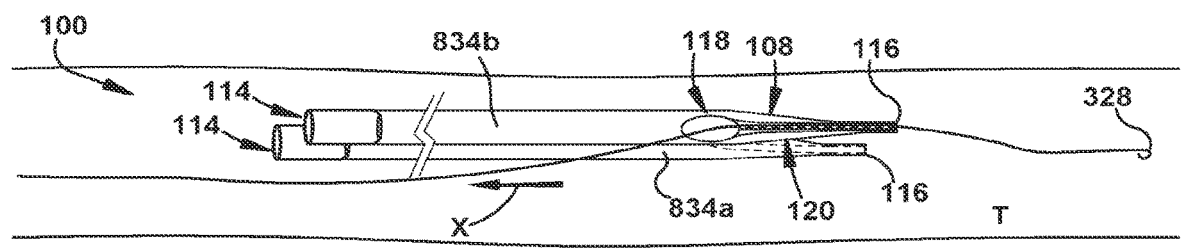
Figure 41:
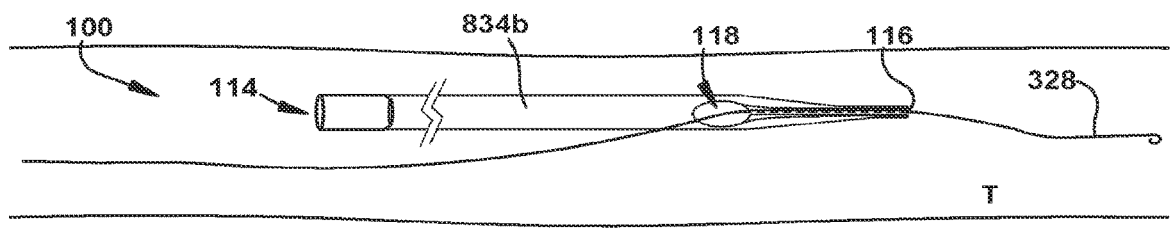

As shown in FIGS. 38-39, the dilator open tip 116 and at least a portion of the dilator distal end 108 of the second dilator D 834*b* may then be directed at least one of adjacent to and into the dilator side wall opening 118 of the first dilator D 834*a* by longitudinally moving the second dilator D 834*b* in the distal direction. As shown in FIGS. 39-40, with the second dilator distal end 108 of the second dilator D 834*b* at least one of adjacent to and at least partially in the dilator side wall opening 118 of the first dilator D 834*a*, the first dilator D 834*a* may be longitudinally moved toward the proximal direction to remove the first dilator D 834*a* from the guidewire 328. In particular, as the first dilator D 834*a* is moved toward the proximal direction, the dilator distal end 108 of the second dilator D 834*b* selectively urges the dilator open slit first surface 122 of the first dilator D 834*a* elastically apart from the dilator open slit second surface 124 of the first dilator D 834*a* and the first dilator D 834*a* is removed from the guidewire 328, while maintaining the guidewire 328 at the target patient tissue site T, as is shown in FIG. 41. Thus, the dilator distal end 108 of the second dilator D 834*b* can be thought of as a pivot to release the first dilator D 834*a* from the guidewire 328.

FIG. 41 depicts the second dilator D 834*b* maintained on the guidewire 328 at the target patient tissue site T. The second dilator D 834*b* may be removed from the guidewire 328 by directing another dilator 102 along the guidewire 328 to remove the second dilator D 834*b* from the guidewire 328, in a similar sequence as described above. The second dilator D 834*b* may be moved in the proximal direction to remove the second dilator D 834*b* from the guidewire 328 and the target patient tissue site T. Instead of removing at least one of the first and the third dilators D 834*a*, 834*c* from the target patient tissue site T after the first and the third dilators D 834*a*, 834*c* are removed from the guidewire 328, additional guidewires 328 may be directed through each of the first and third dilators D 834*a*, 834*c* to the target patient tissue site T, in a similar sequence as described above.

Figure 42:
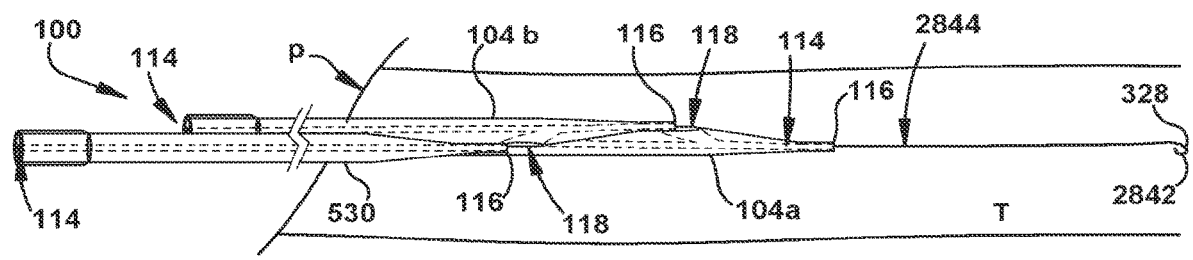
FIGS. 42-48 illustrate an example sequence of operation of a portion of the aspect of FIG. 25.
Figure 43:
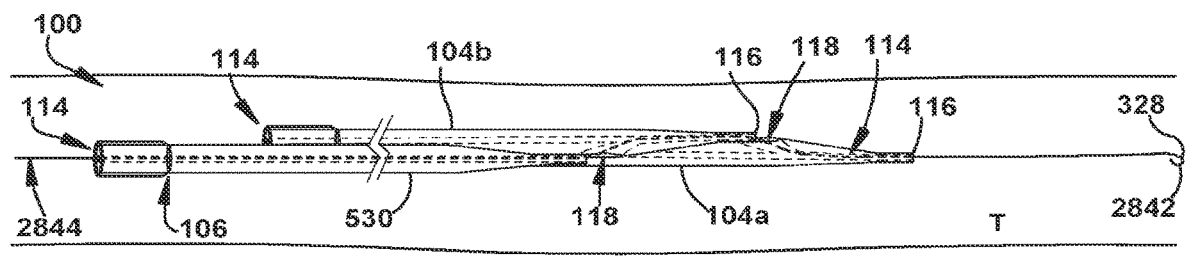

FIGS. 42-48 depict an example sequence of operation of a modular dilation device 100 that has two dilators A 104 and one dilator B 530. A guidewire distal end 2842 is inserted into a target patient tissue site T through a patient tissue access point P. As shown in FIG. 42, a second dilator A 104*b* is placed into a predetermined relationship with a first dilator A 104*a*, wherein the dilator open tip 116 of the second dilator A 104*b* is adjacent to the dilator side wall opening 118 of the first dilator A 104*a*. A dilator B 530 is placed into a predetermined relationship with the second dilator A 104*b*, wherein the dilator open tip 116 of the dilator B 530 is adjacent to the dilator side wall opening 118 of the second dilator A 104*b*. As shown in FIGS. 42-43, the guidewire proximal end 2842 is directed into the dilator open tip 116 of the first dilator A 104*a* and out of the dilator B 530. In particular, the guidewire proximal end 2844 is directed through the dilator open tip 116 of the first dilator A 104*a* and at least a portion of the dilator inner lumen 114 of the first dilator A 104*a*, through the dilator side wall opening 118 of the first dilator A 104*a*, through the dilator open tip 116 of the second dilator A 104*b* and at least a portion of the dilator inner lumen 114 of the second dilator A 104*b*, through the dilator side wall opening 118 of the second dilator A 104*b*, through the dilator open tip 116 and the dilator inner lumen 114 of the dilator B 530, and out from the dilator B 530, such as through the dilator proximal end 106 of the dilator B 530. As shown in FIG. 43, the first dilator A 104*a*, the second dilator A 104*b*, and the dilator B 530 are collectively inserted into the target patient tissue site T along the guidewire 328 in a longitudinally distal direction (as shown by arrow Y in FIG. 43).

Instead of collectively inserting the two dilators A 104*a-b* and the one dilator B 530 into the target patient tissue site T, the two dilators A 104*a-b* and the one dilator B 530 may be inserted into the target patient tissue site T sequentially. For example, a guidewire proximal end 2842 may be directed into the dilator open tip 116 of the first dilator A 104*a*, through at least a portion of the dilator inner lumen 114 of the first dilator A 104*a*, and out from the first dilator A 104, such as through the dilator side wall opening 118 of the first dilator A 104*a*. The first dilator A 104*a* is directed to the target patient tissue site T along the guidewire 328 in the longitudinally distal direction. The guidewire proximal end 2744 is directed into the dilator open tip 116 of the second dilator A 104*b*, through at least a portion of the dilator inner lumen 114 of the second dilator A 104*b*, and out from the second dilator A 104*b*, such as through the dilator side wall opening 118 of the second dilator A 104*b*. The second dilator A 104*b* is directed to the target patient tissue site T along the guidewire 328 in the longitudinally distal direction until the dilator open tip 116 of the second dilator A 104*b* is adjacent to the dilator side wall opening 118 of the first dilator A 104*a*. The guidewire proximal end 2844 is directed into the dilator open tip 116 of the dilator B 530, through at least a portion of the dilator inner lumen 114 of the dilator B 530, and out from the dilator B 530, such as through the dilator proximal end 106 of the dilator B 530. The dilator B 530 is directed to the target patient tissue site T along the guidewire 328 in the longitudinally distal direction until the dilator open tip 116 of the dilator B 530 is adjacent to the dilator side wall opening 118 of the second dilator A 104*b*.

Figure 44:
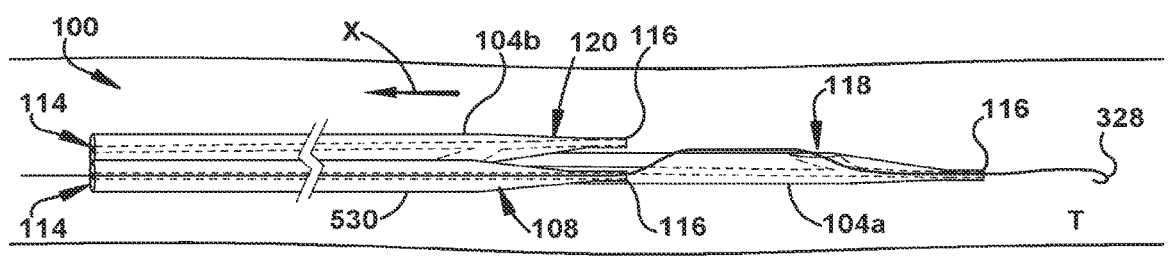
Figure 45:
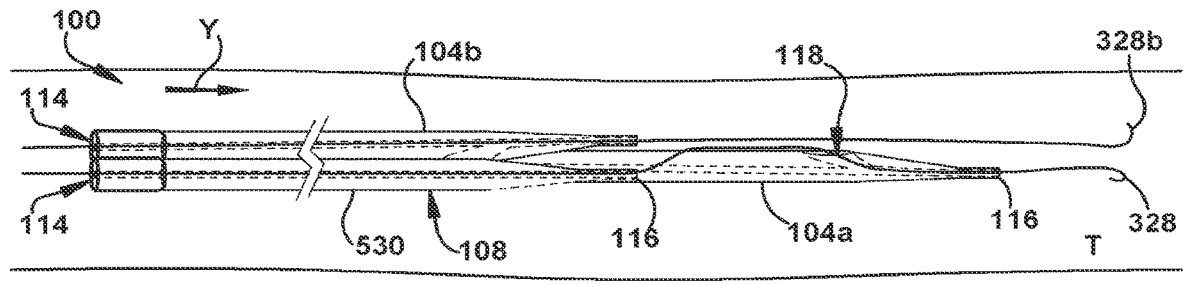

With the modular dilation device 100 at the target patient tissue site T, the dilator open tip 116 and at least a portion of the dilator distal end 108 of the dilator B 530 may be directed at least one of adjacent to and into the dilator side wall opening 118 of the second dilator A 104*b*. As shown in FIGS. 43-44, with the dilator distal end 108 of the dilator B 530 at least one of adjacent to and at least partially in the dilator side wall opening 118 of the second dilator A 104*b*, the second dilator A 104*b* is longitudinally moved toward a proximal direction (shown as the arrow X in FIG. 44) to remove the second dilator A 104*b* from the guidewire 328, while maintaining the guidewire 328 at the target patient tissue site T. In particular, as the second dilator A 104b is moved toward the proximal direction, the dilator distal end 108 of the dilator B 530 selectively urges the dilator open slit first surface 122 of the second dilator A 104b elastically apart from the dilator open slit second surface 124 of the second dilator A 104b and the second dilator A 104b is removed from the guidewire 328. Thus, the dilator distal end 108 of the dilator B 530 can be thought of as a pivot arrangement to release the second dilator A 104b from the guidewire 328. As shown in FIG. 45, with the second dilator A 104b removed from the guidewire 328, a second guidewire 328b may be directed through the second dilator A 104b to the target patient tissue site T in the longitudinally distal direction.

Figure 46:
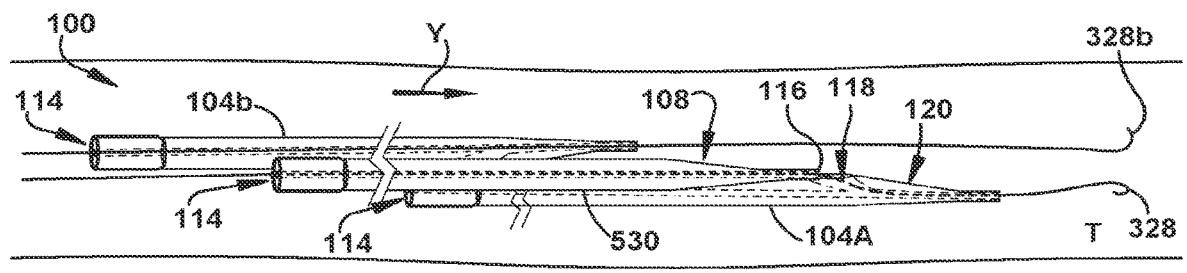
Figure 47:
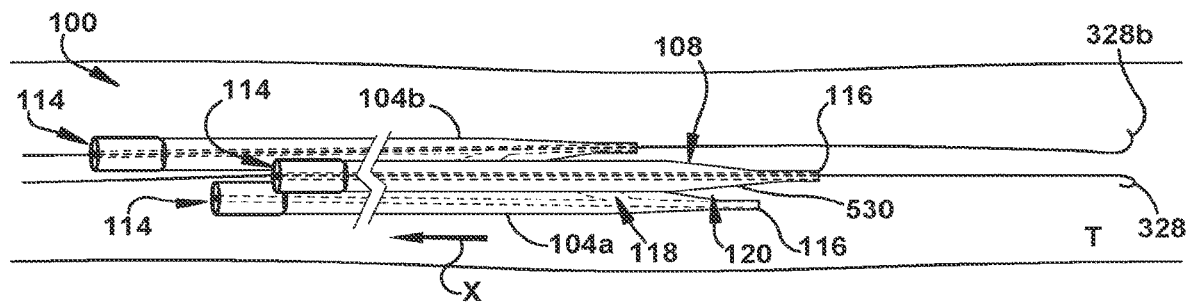
Figure 48:
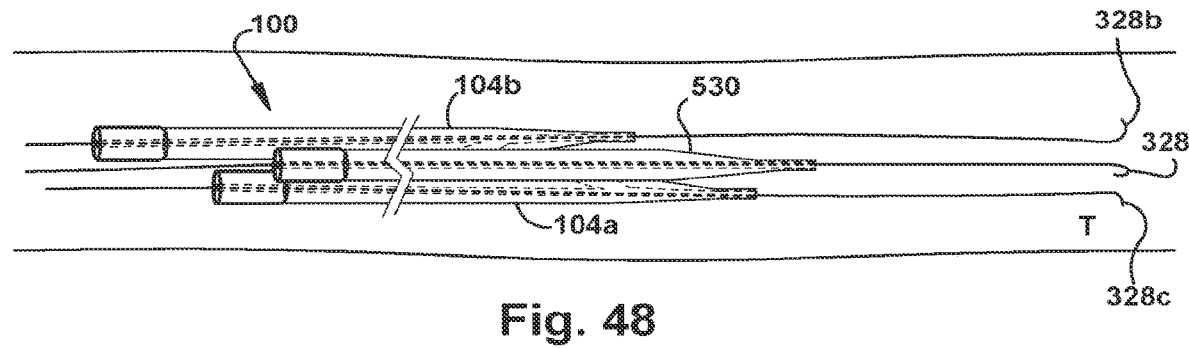

As shown in FIGS. 45-46, the dilator open tip 116 and at least a portion of the dilator distal end 108 of the dilator B 530 may then be directed at least one of adjacent to and into the dilator side wall opening 118 of the first dilator A 104a. As shown in FIGS. 46-47, with the dilator distal end 108 of the dilator B 530 at least one of adjacent to and at least partially in the dilator side wall opening 118 of the first dilator A 104a, the first dilator A 104a is longitudinally moved toward the proximal direction to remove the first dilator A 104a from the guidewire 328. In particular, as the first dilator A 104a is moved toward the proximal direction, the dilator distal end 108 of the dilator B 530 selectively urges the dilator open slit first surface 122 of the first dilator A 104a elastically apart from the dilator open slit second surface 124 of the first dilator A 104a and the first dilator A 104a is removed from the guidewire 328, while maintaining the guidewire 328 at the target patient tissue site T. Thus, the dilator distal end 108 of the dilator B 530 can be thought of as a pivot arrangement to release the first dilator A 104a from the guidewire 328. As shown in FIG. 48, with the first dilator A 104a removed from the guidewire 328, a third guidewire 328c may be directed through the first dilator A 104a to the target patient tissue site T. Each of the dilator B 530, the second dilator A 104b, and the first dilator A 104a may be moved in the longitudinally proximal direction and removed from target patient tissue site T and the guidewires 328, 328b, 328c, while maintaining the guidewires 328, 328b, 328c at the target patient tissue site T.

As previously discussed in more detail, it is contemplated that the dilator open tip 116 and at least a portion of the dilator distal end 108 of one dilator 120 may be capable of being inserted into the dilator inner lumen 114 of another dilator 102 through the dilator side wall opening 118 of the other dilator 102. To accomplish such, the user inserts the guidewire distal end 2842 into a target patient tissue site T through a patient tissue access point P. The user places the a dilator 102, such as a dilator B 530, into a predetermined relationship with another dilator 102, such as a dilator A 104, wherein the dilator open tip 116 of the dilator B 530 and at least a portion of the dilator distal end 108 of the dilator B 530 is inserted into the dilator inner lumen 114 of the dilator A 104 through the dilator side wall opening 118 of the dilator A 104. The user directs a guidewire proximal end 2844 into the dilator open tip 116 of the dilator A 104 and out of the dilator B 530, such as through the proximal end 106 of the dilator B 530. In particular, the guidewire proximal end 2844 is directed through the dilator open tip 116 and at least a portion of the dilator inner lumen 114 of the dilator A 104, through the dilator open tip 116 and the dilator inner lumen 114 of the dilator B 830 (thus, indirectly traveling through the dilator side wall opening 118 of the dilator A 104, as well), and out from the dilator B 530, such as through the dilator proximal end 106 of the dilator B 530. The user may then collectively insert both the dilator A 104 and the dilator B 530 into the target patient tissue site T along the guidewire 328. With the modular dilation device 100 at the target patient tissue site T, at least one of the dilator A 104 and the dilator B 530 may be removed from the guidewire 328, in a similar sequence as described above.

Figure 49:
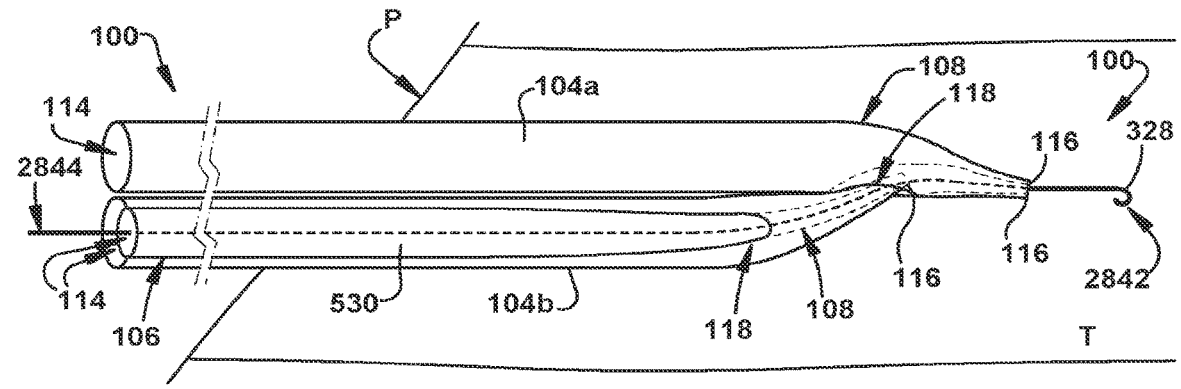
FIGS. 49-50 illustrate an example sequence of operation of a portion of the aspect of FIG. 27.
Figure 50:
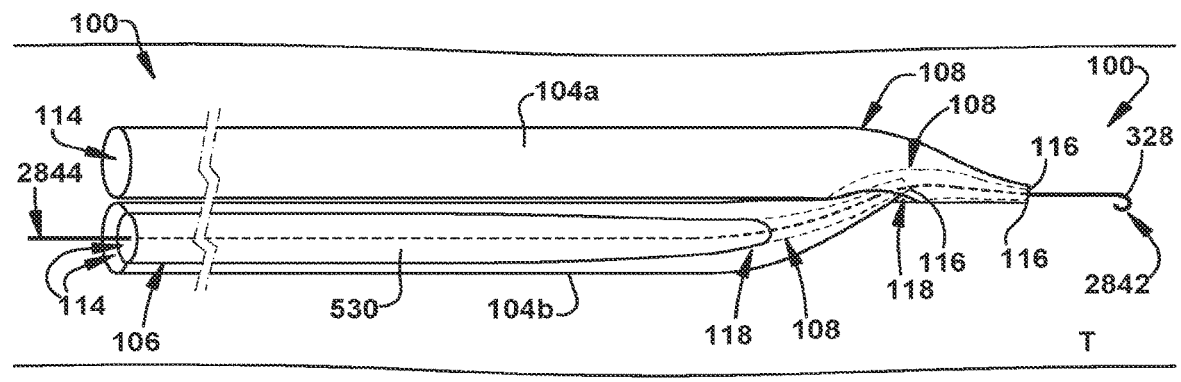

In addition to the dilator B 530 extending into the dilator inner lumen 114 of the dilator A 104, a second dilator A 104b may be provided. In such case, the user places one dilator 102, such as a dilator B 530, into a predetermined relationship with another dilator 102, such as a second dilator A 104b, wherein the dilator open tip 116 and at least a portion of the dilator distal end 108 of the dilator B 230 is inserted into the dilator inner lumen 114 of the second dilator A 104b through the dilator side wall opening 118 of the second dilator A 104b. The user places the second dilator A 104b into a predetermined relationship with another dilator 102, such as a first dilator A 104a, wherein the dilator open tip 116 of the second dilator A 104b and at least a portion of the dilator distal end 116 of the second dilator A 104b is inserted into the dilator inner lumen 114 of the first dilator A 104a through the dilator side wall opening 118 of the first dilator A 104a. The guidewire proximal end 2844 may be directed into the dilator open tip 116 of the first dilator A 104a and out of the dilator B 530, such as through the dilator proximal end 106 of the dilator B 530. In particular, the guidewire proximal end 2844 is directed through the dilator open tip 116 and at least a portion of the dilator inner lumen 114 of the first dilator A 104a, through the dilator open tip 116 and at least a portion of the dilator inner lumen 114 of the second dilator A 104b (thus, indirectly traveling through the dilator side wall opening 118 of the first dilator A 104a, as well), through the dilator open tip 116 and the dilator inner lumen 114 of the dilator B 530 (thus, indirectly traveling through the dilator side wall opening 118 of the second dilator A 104b, as well), and out from the dilator B 530, such as through the proximal end 106 of the dilator B 530. As shown in FIGS. 49-50, the first dilator A 104a, the second dilator A 104b, and the dilator B 530 may be collectively inserted into the target patient tissue site T along the guidewire 328 in a longitudinally distal direction. With the modular dilation device 100 at the target patient tissue site T, at least one of the first dilator A 104a, the second dilator A 104b, and the dilator B 530 may be utilized and/or removed from the guidewire 328, in a similar sequence as described above. For example, the second dilator A 104b may be removed from the guidewire 328 inside the patient lumen using the dilator B 530 as a pivot. After the second dilator A 104b is removed from the guidewire, the first dilator A 104a may be removed from the guidewire 328 inside the patient lumen using the dilator B 530 as a pivot. The dilator B 530 may then be longitudinally moved in the proximal direction over the guidewire to remove the dilator B 530 from the guidewire 328 outside of the patient lumen.

Any of the dilator 102 configurations of the modular dilation device 100 may be at least partially formed from silicone, polyethylene, polypropylene, stainless steel, titanium, any other biocompatible material, or any combination thereof.

It is contemplated that any of the dilator 102 configurations of the modular dilation device 100 may be a stiffener, and or may be at least a part of at least one of a sheath, catheter, tear-away sheath, any other suitable medical instrument, or any combination thereof. Further, it is contemplated that any of the dilator 102 configurations may be disposed within one or more sheaths, which allows for the insertion of multiple sheaths into a target patient tissue site T through a single access point P. In this configuration, once the sheaths, with dilators 102, such as a first dilator A 104a and a second dilator A 104b, located therein are inserted to the target patient tissue site T, a first dilator A 104a may be disengaged from the guidewire 328 within the target patient tissue site T, as previously described. Once the first dilator A 104a is disengaged from the guidewire 328, a second guidewire 328b may be separately inserted through the dilator inner lumen 114 of the first dilator A 104a into the target patient tissue site T. Once the second guidewire 328b is inserted into the target patient tissue site T, the first and second dilators A 104a-b may be removed from the target patient tissue site T, as described above. Once the dilators 102 are removed, medical instruments may be inserted through the sheaths to the target patient tissue site T.

It is contemplated that the modular dilation device 100 may provide the user with the ability to insert multiple dilators 102 into a target patient tissue site T through a single patient tissue access point P. The ability to insert multiple dilators 102 into a target patient tissue site T through a single patient tissue access point P may assist in reducing potential trauma, complications, and/or risks to the patient that result from the creation of multiple patient tissue access points P. For example, if a dilator A 104 and a dilator B 530 were inserted through two separate patient tissue access points P, the trauma, risks, and complications associated with said insertions could be increased as compared to the insertion of the dilator A 104 and the dilator B 530 through a single patient tissue access point P. Further, the ability to use a single patient tissue access point P instead of having to create multiple patient tissue access points P may reduce the procedure time and the costs that would be associated with creating multiple patient tissue access points P.

Additionally, it is contemplated that the modular dilation device 100 may allow for a smaller patient tissue access point P than what may be necessary for the insertion of multiple dilators 102 that are not operatively joined in the manner as described above. For example, when the at least two of the dilators 102 are joined as described above, the patient tissue access point P may be smaller in diameter than desirable for inserting multiple dilators that are not combined as described herein.

Figure 51:
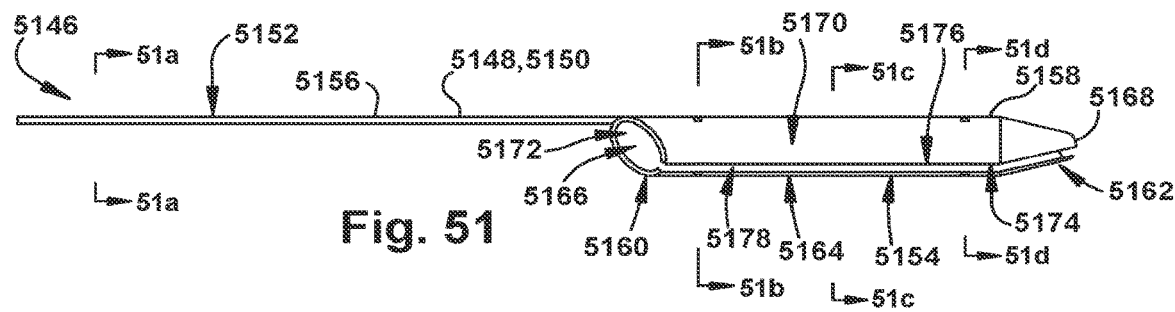
FIG. 51 is a side view of an element of an implant delivery system according to one aspect of the present invention.
Figures 51A, 51B, 51C, 51D:
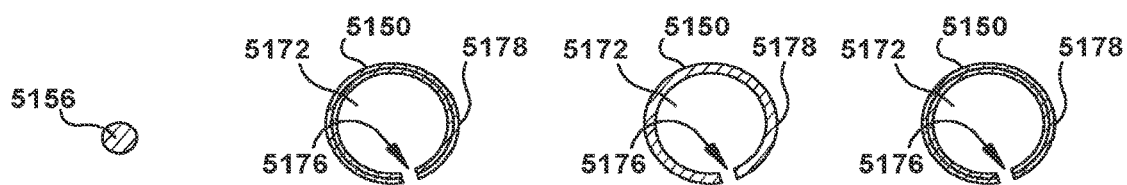
FIGS. 51*a-d* depict cross-sectional views of the aspect of FIG. 1.

An implant delivery system 5146 is provided. The implant delivery system 5146 may include a number of outer sheaths 5148 having alternate configurations, which will be discussed below. FIGS. 51, 52, 53, and 54 depict example alternative configurations of the outer sheath 5148. FIG. 51 depicts an example alternative configuration for the outer sheath 5148, referred to as an outer sheath A 5150. The outer sheath A 5150 has an outer sheath proximal end 5152 and an outer sheath distal end 5154. The outer sheath proximal end 5152 has an outer sheath delivery element 5156. The outer sheath delivery element may 5156 be a stiff wire, or any other appropriate element for delivering the outer sheath to, or from, a target patient tissue site T. The stiff wire may be, for example, a solid (i.e., non-hollow) element, such as, but not limited to, a stainless steel or plastic wire. The stiff wire may instead be, for example, an at least partially tubular or hollow element, such as, but not limited to, a catheter with an inner lumen for a guidewire.

The outer sheath distal end 5154 has an implant holding pod 5158. The implant holding pod 5158 has an implant holding pod proximal end 5160 and an implant holding pod distal end 5162. The implant holding pod 5158 has an implant holding pod body 5164 longitudinally extending between the implant holding pod proximal and distal ends 5160, 5162. The implant holding pod proximal end 5160 has an implant holding pod proximal opening 5166. The implant holding pod proximal opening 5166 of the outer sheath A 5150 may face substantially laterally downward. At least a portion of the implant holding pod distal end 5162 may be inwardly tapered.

The implant holding pod distal end 5162 has an implant holding pod open tip 5168. The implant holding pod 5158 has an implant holding pod outer surface 5170 and an implant holding pod lumen 5172. The implant holding pod lumen 5172 of the outer sheath A 5150 may extend between the implant holding pod proximal opening 5166 and the implant holding pod open tip 5168. The implant holding pod lumen 5172 is at least partially configured for selectively holding an expandable implant M therein. The expandable implant M may be a stent, an embolization coil, an embolization plug, a shunt closure device, any self-expandable device, any other expandable device, or any combination thereof.

The implant holding pod 5158 has an implant holding pod open slit 5174. The implant holding pod open slit 5174 may extend at least partially between the implant holding pod open tip 5168 and the implant holding pod proximal end 5160. In particular, the implant holding pod open slit 5147 of the outer sheath A 5150 may extend between the implant holding pod open tip 5168 and the implant holding pod proximal opening 5166. The implant holding pod open slit 5174 has an implant holding pod open slit first surface 5176 and an implant holding pod open slit second surface 5178. The implant holding pod open slit first surface 5176 oppositely faces and abuts the implant holding pod open slit second surface 5178. Alternatively, instead of abutting, the implant holding pod open slit first surface 5176 and the implant holding pod open slit second surface 5178 may laterally overlap to provide a labyrinth-type seal, similar to as previously described. The implant holding pod open slit first surface 5176 and the implant holding pod open slit second surface 5178 may be selectively elastically separable. That is, a force may be applied to separate the implant holding pod open slit first surface 5176 and the implant holding pod open slit second surface 5178, as that the implant holding pod open slit first surface 5176 will no longer be abutting the implant holding pod open slit second surface 5178. However, upon the removal of the separating force, the implant holding pod open slit first surface 5176 and the implant holding pod open slit second surface 5178 will return to their original abutting position due to the elastic nature of the material forming the implant holding pod open slit first surface 5176 and the implant holding pod open slit second surface 5178. FIGS. 51a-d depict cross-sectional views of various points along the outer sheath A 5150, to show structural features of the outer sheath A 5150.

Figure 52:
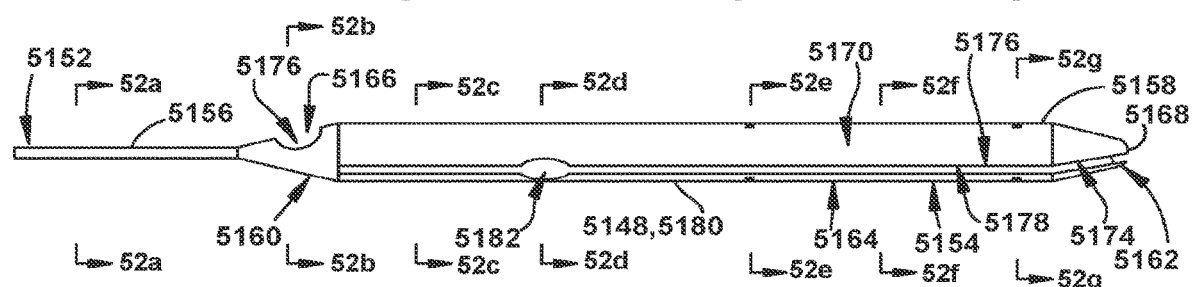
FIG. 52 is a side view of the element of FIG. 1 in an alternate configuration.
Figures 52A, 52B, 52C, 52D:
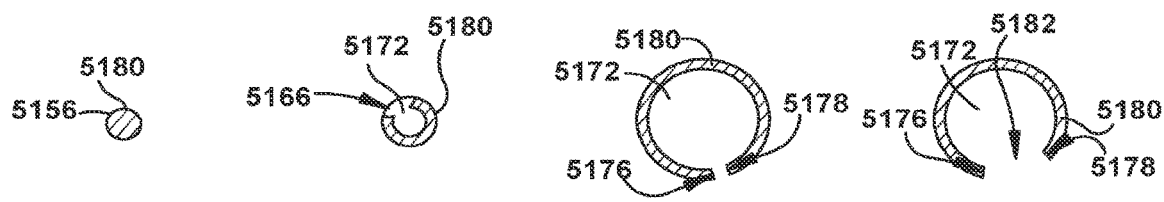
FIGS. 52*a-g* depict cross-sectional views of the aspect of FIG. 52.
Figures 52E, 52F, 52G:
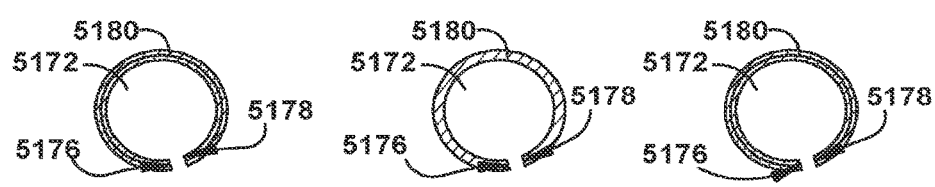

FIG. 52 depicts an alternative configuration for the outer sheath 5148, referred to as an outer sheath B 5180. Similar to the outer sheath A 5150, the outer sheath B 5180 has an outer sheath proximal end 5152 and an outer sheath distal end 5154. The outer sheath proximal end 5152 has an outer sheath delivery element 5156. The stiff wire may be, for example, a solid (i.e., non-hollow) element, such as, but not limited to, a stainless steel or plastic wire. The stiff wire may instead be, for example, an at least partially tubular or hollow element, such as, but not limited to, a catheter with an inner lumen for a guidewire.

The outer sheath distal end 5154 has an implant holding pod 5158. The implant holding pod 5158 has an implant holding pod proximal end 5160 and an implant holding pod distal end 5162. The implant holding pod 5158 has an implant holding pod body 5164 longitudinally extending between the implant holding pod proximal and distal ends 5160, 5162. The implant holding pod proximal end 5160 has an implant holding pod proximal opening 5166. The implant holding pod proximal opening 5166 of the outer sheath A may face substantially laterally upward.

At least a portion of the implant holding pod distal end 5162 may be inwardly tapered. The implant holding pod distal end 5162 has an implant holding pod open tip 5168. The implant holding pod 5158 has an implant holding pod outer surface 5170 and an implant holding pod lumen 5172. The implant holding pod lumen 5172 may extend between the implant holding pod proximal opening 5166 and the implant holding pod open tip 5168. The implant holding pod lumen 5172 is at least partially configured for selectively holding an expandable implant M therein. At least one of the implant holding pod body 5164 and the implant holding pod proximal end 5160 may have an implant holding pod side wall opening 5182. The implant holding pod side wall opening 5182 selectively places the implant holding pod outer surface 5170 in fluid communication with the implant holding pod lumen 5172.

The implant holding pod 5158 has an implant holding pod open slit 5174. The implant holding pod open slit 5174 may extend at least partially between the implant holding pod open tip 5168 and the implant holding pod proximal end 5160. In particular, the implant holding pod open slit 5174 of the outer sheath B 5180 may extend between the implant holding pod open tip 5168 and the implant holding pod side wall opening 5182. The implant holding pod open slit 5174 has an implant holding pod open slit first surface 5176 and an implant holding pod open slit second surface 5178. The implant holding pod open slit first surface 5176 oppositely faces and abuts the implant holding pod open slit second surface 5178. Alternatively, instead of abutting, the implant holding pod open slit first surface 5176 and the implant holding pod open slit second surface 5178 may laterally overlap to provide a labyrinth-type seal, similar to as previously described. The implant holding pod open slit first surface 5176 and the implant holding pod open slit second surface 5178 may be selectively elastically separable. FIGS. 52*a-g* depict cross-sectional views of various points along the outer sheath B 5180, to show structural features of the outer sheath B 5180.

Figure 53:
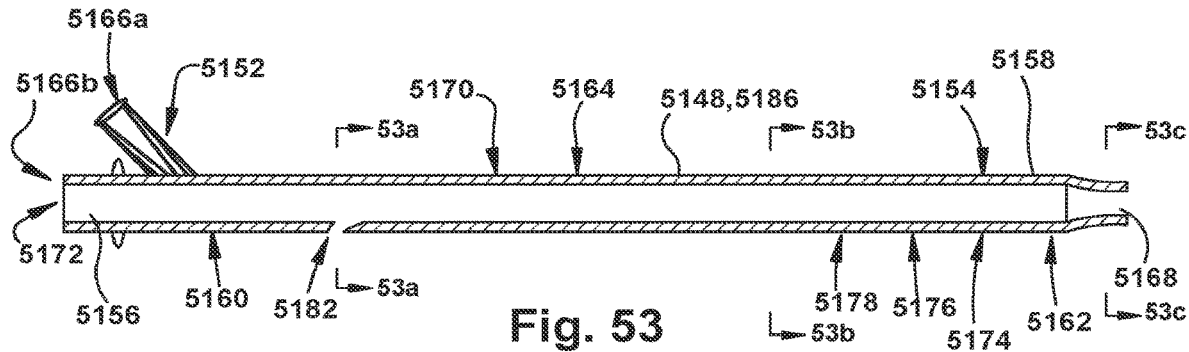
FIG. 53 is a side view of the element of FIG. 1 in an alternate configuration.
Figure 53A:
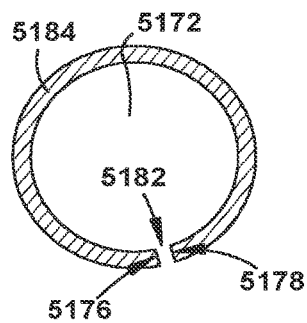
FIGS. 53*a-c* depict cross-sectional views of the aspect of FIG. 53.
Figure 53B:
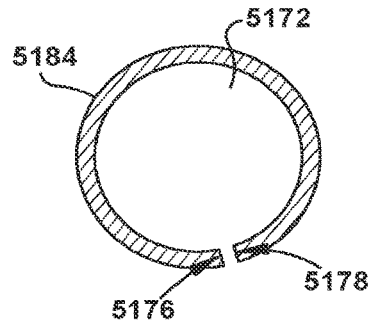
Figure 53C:
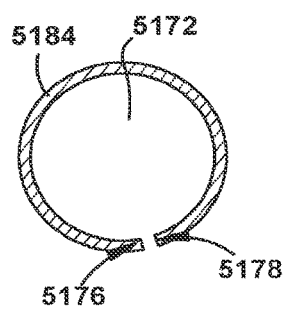

FIG. 53 depicts an alternative configuration for the outer sheath 5148, referred to as an outer sheath C 5184. Similar to the outer sheath B 5180, the outer sheath C 5184 has an outer sheath proximal end 5152 and an outer sheath distal end 5154. The outer sheath proximal end 5152 has an outer sheath delivery element 5156. At least one of the outer sheath proximal end 5152 and the outer sheath distal end 5154 has an implant holding pod 5158. The implant holding pod 5158 has an implant holding pod proximal end 5160 and an implant holding pod distal end 5162. The implant holding pod 5158 has an implant holding pod body 5164 that longitudinally extends between the implant holding pod proximal and distal ends 5160, 5162. The implant holding pod proximal end 5160 of the outer sheath C 5184 may have an implant holding pod proximal opening 5166. A first implant holding pod proximal opening 5166*a* of the outer sheath C 5184 may face substantially laterally upward. A fluid, such as saline, may be directed through the first implant holding pod proximal opening 5166*a*, when provided, to flush a target patient tissue site T when the outer sheath C 5184 is located at the target patient tissue site T. A second implant holding pod proximal opening 5166*b*, when provided, of the outer sheath C 5184 may be longitudinally facing.

At least a portion of the implant holding pod distal end 5162 may be inwardly tapered. The implant holding pod distal end 5162 has an implant holding pod open tip 5168. The implant holding pod 5158 has an implant holding pod outer surface 5170 and an implant holding pod lumen 5172. The implant holding pod lumen 5172 may extend between the implant holding pod open tip 5168 and at least one of an implant holding pod side wall opening 5182, and the first and second implant holding pod proximal openings 5166*a-b*. The implant holding pod inner lumen 5172 is at least partially configured for selectively holding an expandable implant M therein. At least one of the implant holding pod body 5164, the implant holding pod distal end 5162, and the implant holding pod proximal end 5160 may have the implant holding pod side wall opening 5182. The implant holding pod side wall opening 5182 selectively places the implant holding pod outer surface 5170 in fluid communication with the implant holding pod lumen 5172.

The implant holding pod 5158 has an implant holding pod open slit 5174. The implant holding pod open slit 8174 may extend at least partially between the implant holding pod open tip 5168 and the implant holding pod proximal end 5160. In particular, the implant holding pod open slit 5174 of the outer sheath C 5184 may extend between the implant holding pod open tip 5168 and the implant holding pod side wall opening 5182. The implant holding pod open slit 5168 has an implant holding pod open slit first surface 5176 and an implant holding pod open slit second surface 5178. The implant holding pod open slit first surface 5176 oppositely faces and abuts the implant holding pod open slit second surface 5178. The implant holding pod open slit first surface 5176 and the implant holding pod open slit second surface 5178 may be selectively elastically separable.

Figure 54:
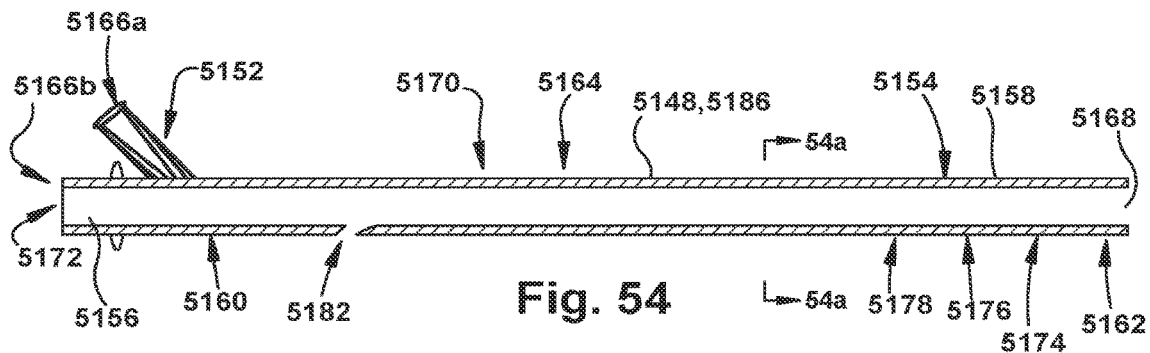
FIG. 54 is a side view of the element of FIG. 1 in an alternate configuration.
Figure 54A:
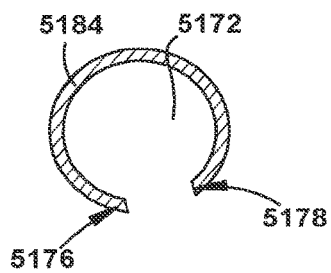
FIG. 54*a* depicts a cross-sectional view of the aspect of FIG. 54.

FIG. 54 depicts an alternative configuration for the outer sheath 5148, referred to as an outer sheath D 5186. Similar to the outer sheath C 5184, the outer sheath D 5186 has an outer sheath proximal end 5152 and an outer sheath distal end 5154. The outer sheath proximal end 5152 has an outer sheath delivery element 5156. The outer sheath delivery element 5156 may extend between the outer sheath proximal end 5152 and an implant holding pod side wall opening 5182. The outer sheath delivery element 5156 may be, but is not limited to, a stiff wire. The stiff wire may be, for example, a solid (i.e., non-hollow) element, such as, but not limited to, a stainless steel or plastic wire. The stiff wire may instead be, for example, an at least partially tubular or hollow element, such as, but not limited to a catheter with an inner lumen for a guidewire. At least one of the outer sheath proximal end 5152 and the outer sheath distal end 5154 has an implant holding pod 5158. The implant holding pod 5158 has an implant holding pod proximal end 5160 and an implant holding pod distal end 5162. The implant holding pod 5158 has an implant holding pod body 5164 that longitudinally extends between the implant holding pod proximal and distal ends 5160, 5162. The implant holding pod proximal end 5166 of the outer sheath D 5186 may have an implant holding pod proximal opening 5166. A first implant holding pod proximal opening 5166*a* of the outer sheath D 5186 may face substantially laterally upward. A fluid, such as saline, may be directed through the first implant holding pod proximal opening 5166*a*, when provided, to flush a target patient tissue site T when the outer sheath C 5184 is located at the target patient tissue site T. A second implant holding pod proximal opening 5166*b* of the outer sheath D 5186 may be longitudinally facing.

The implant holding pod distal end 5162 of the outer sheath D 5186 might not be inwardly tapered. Thus, the implant holding pod distal end 5162 and the implant holding pod body 5164 of the outer sheath D may be substantially level. The term "level" is defined herein as being substantially even or unvarying in height, as is shown by the implant holding pod distal end 5162 not having a gradual or stepwise diminution and/or increase in diameter in FIG. 54. The implant holding pod distal end 5162 has an implant holding pod open tip 5168. The implant holding pod 5158 has an implant holding pod outer surface 5170 and an implant holding pod lumen 5172. The implant holding pod lumen 5172 may extend between the implant holding pod open tip 5168 and at least one of the implant holding pod side wall opening 5182, and the first and second implant holding pod proximal openings 5166*a-b*. The implant holding pod lumen 5172 is at least partially configured for selectively holding an expandable implant M therein. At least one of the implant holding pod body 5164, the implant holding pod distal end 5162, and the implant holding pod proximal end 5160 may have the implant holding pod side wall opening 5182. The implant holding pod side wall opening 5182 selectively places the implant holding pod outer surface 5170 in fluid communication with the implant holding pod lumen 5172.

The implant holding pod 5158 has an implant holding pod open slit 5174. The implant holding pod open slit 5174 may extend at least partially between the implant holding pod open tip 5168 and the implant holding pod proximal end 5160. In particular, the implant holding pod open slit 5174 of the outer sheath D 5186 may extend between the implant holding pod open tip 5168 and the implant holding pod side wall opening 5182. The implant holding pod open slit 5174 has an implant holding pod open slit first surface 5176 and an implant holding pod open slit second surface 5178. The implant holding pod open slit first surface 5176 oppositely faces and abuts the implant holding pod open slit second surface 5178. Alternatively, instead of abutting, the implant holding pod open slit first surface 5176 and the implant holding pod open slit second surface 5178 may laterally overlap to provide a labyrinth-type seal, similar to as previously described. The implant holding pod open slit first surface 5176 and the implant holding pod open slit second surface 5178 may be selectively elastically separable.

As shown in FIG. 55, any of the outer sheath 5148 alternate configurations discussed above may have at least one c-clip 5588 selectively disposed on a portion of the implant holding pod outer surface 1570 that is adjacent to the implant holding pod open slit 5174. Instead of, or in addition to, the at least one c-clip 5588 being selectively disposed on the implant holding pod outer surface 5170, the at least one c-clip 5588 may be selectively disposed within (e.g., via overmolding) at least a portion of the implant holding pod inner lumen 5172 that is adjacent to the implant holding pod open slit 5174. Alternatively, or in addition to the above, the at least one c-clip 5588 may be embedded in the outer sheath between the implant holding pod outer surface 5170 and the implant holding pod inner lumen 5172, and adjacent to the implant holding pod open slit 5174. The c-clip 5588 at least partially selectively prevents the implant holding pod open slit first surface 5176 from elastically separating from the implant holding pod open slit second surface 5178 when a self-expanding implant M is disposed within the implant holding pod inner lumen 5172. In other words, an expandable implant M placed within the implant holding pod inner lumen 5172 in a collapsed condition may move toward an expanded condition due to the natural properties of the expandable implant M. Because the implant holding pod open slit first surface 5176 is elastically separable from the implant holding pod second surface 5178, the movement of the expandable implant M toward the expanded condition might cause the implant holding pod open slit first surface 5176 to elastically separate from the implant holding pod open slit second surface 5178. However, as shown in FIGS. 56-57, when at least one c-clip 5588 is positioned on the implant holding pod outer surface 5170 and/or within the implant holding pod inner lumen 5172, the c-clip 5588 provides a radially inward pressure or bias to at least partially selectively prevent the expandable implant M from moving from a collapsed condition toward an expanded condition, and thus at least partially prevents the expandable implant M from elastically separating the implant holding pod open slit first surface 5176 from the implant holding pod open slit second surface 5178. The term "radial" is used herein to indicate a direction substantially perpendicular to the "lateral" direction, and is shown via arrows R in FIG. 56 extending toward a central longitudinal axis LA, in the orientation of FIG. 56. FIGS. 56-57 depict that the c-clip 5588 may either partially and/or fully laterally extend circumferentially about the outer sheath 5148 from the implant holding pod open slit first surface 5176 to the implant holding pod open slit second surface 5178. The c-clip 5588 may be at least partially radiopaque, and thus visible under radiography or other intraoperative imaging techniques.

The implant delivery system 5146 may include a number of shafts 5890 having alternate configurations, which will be discussed below. FIGS. 58-70 depict example alternative configurations of the shafts 5890. FIG. 58 depicts an example alternative configuration for the shaft 5890, referred to as a shaft A 5892. The shaft A 5892 has a shaft proximal end 5894, a shaft distal end 5896, and a shaft body 5898 that longitudinally extends between the shaft proximal and distal ends 5894, 5896. The shaft proximal end 5894 has a shaft delivery element 58100. The shaft distal end 5896 has an implant delivery element 58102. The implant delivery element 58102 of the shaft A 5892 has an implant delivery element outer surface 58104 for selectively circumferentially mounting an expandable implant M thereon. The implant delivery element outer surface 58104 has at least one radially extending projection 58106. The radially extending projection 58106 of the shaft A 5892 is for substantially preventing the egress of an expandable implant M mounted circumferentially about the implant delivery element outer surface 58104 from a desired position on the implant delivery element outer surface 58104. At least one of the shaft body 5898 and the implant delivery element 58102 has a shaft open slit 58108.

The shaft body 5898 has a shaft body proximal end 58110, a shaft body distal end 58112, and a shaft body length 58114 that longitudinally extends between the shaft body proximal and distal ends 58110, 58112. At least one of the shaft body proximal end 58110, shaft body distal end 58112, and the shaft body length 58114 has a shaft side wall opening 58116. The shaft side wall opening 58116 is in selective fluid communication with the shaft open slit 58108. The shaft open slit 58108 of the shaft A 5892 may extend between the shaft side wall opening 58116 and at least one of the shaft body distal end 58112 and the at least one projection 58106. At least a portion of the shaft open slit 58108 and at least a portion of the shaft side wall opening 58116 may collectively form a shaft lumen 58118 for at least partially selectively holding a guidewire 328 therein. At least one of the shaft body proximal end 58110, the shaft body distal end 58112, and the shaft body length 58114 may have an outer sheath splitter 58120 for facilitating the elastic separation of the implant holding pod open slit first surface 5176 and the implant holding pod open slit second surface 5178. FIGS. 58a-c depict cross-sectional views of various points along the shaft A 5892, to show structural features of the shaft A 5892.

FIG. 59 depicts an alternate configuration for the shaft 5890, referred to as a shaft B 59122. Similar to the shaft A 5892, the shaft B 59122 has a shaft proximal end 5894, a shaft distal end 5896, and a shaft body 5898 that longitudinally extends between the shaft proximal and distal ends 5894, 5896. The shaft proximal end 5894 has a shaft delivery element 58100. The shaft distal end 5896 has an implant delivery element 58102. The implant delivery element 58102 of the shaft B 59122 has an implant delivery element outer surface 58104 for selectively circumferentially mounting an expandable implant M thereon. The implant delivery element outer surface 58104 has at least one radially extending projection 58106. The radially extending projection 58106 of the shaft B 59122 is for substantially preventing the egress of an expandable implant M mounted circumferentially about the implant delivery element outer surface 58104 from a desired position on the implant delivery element outer surface 58104. At least one of the shaft body 5898 and the implant delivery element 58102 has a shaft open slit 58108.

The shaft body 5898 has a shaft body proximal end 58110, a shaft body distal end 58112, and a shaft body length 58114 that longitudinally extends between the shaft body proximal end 58110 and the shaft body distal end 58112. At least one of the shaft body proximal end 58110, the shaft body distal end 58112, and the shaft body length 58114 has a shaft side wall opening 58116. The shaft side wall opening 58116 is in selective fluid communication with the shaft open slit 58108. The shaft open slit 58108 of the shaft B 59122 may extend between the shaft side wall opening 58116 and an implant delivery element open tip 59124. At least a portion of the shaft open slit 58108 and at least a portion of the shaft side wall opening 58116 may collectively form a shaft lumen 58118 for at least partially selectively holding a guidewire 328 therein. At least one of the shaft body proximal end 58110, the shaft body distal end 58112, and the shaft body length 58114 may have an outer sheath splitter 58120 for facilitating the elastic separation of the implant holding pod open slit first surface 5176 and the implant holding pod open slit second surface 5178. FIGS. 59a-c depict cross-sectional views of various points along the shaft B 59122, to show structural features of the shaft B 59122.

Figure 60:
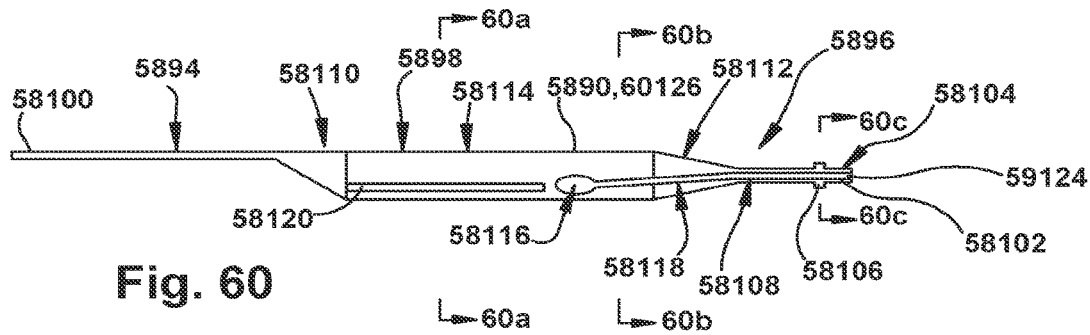
FIG. 60 is a side view of the element of FIG. 58 in an alternate configuration.

FIG. 60 depicts an alternate configuration for the shaft 5890, referred to as a shaft C 60126. Similar to the shaft A 5892, the shaft C 60126 has a shaft proximal end 5894, a shaft distal end 5896, and a shaft body 5898 that longitudinally extends between the shaft proximal and distal ends 5894, 5896. The shaft proximal end 5894 has a shaft delivery element 58100. The shaft distal end 5896 has an implant delivery element 58102. The implant delivery element 58102 of the shaft C 60126 has an implant delivery element outer surface 58104 and a radially extending projection 58106 for selectively contacting and selectively pushing an expandable implant M. At least one of the shaft body 5898 and the implant delivery element 58102 has a shaft open slit 58108.

Figure 60A:
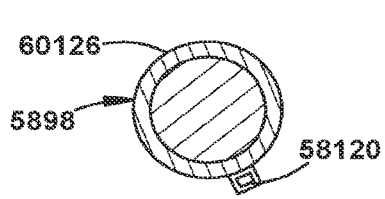
FIGS. 60a-c depict cross-sectional views of the aspect of FIG. 60.
Figure 60B:
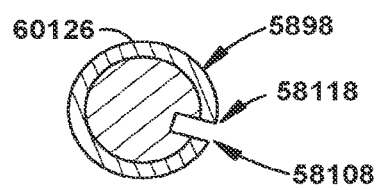
Figure 60C:
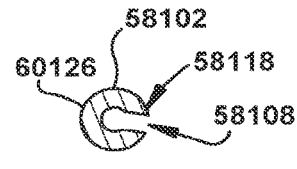

The shaft body 5898 has a shaft body proximal end 58110, a shaft body distal end 58112, and a shaft body length 58114 that longitudinally extends between the shaft body proximal end 58110 and the shaft body distal end 58112. At least one of the shaft body proximal end 58110, the shaft body distal end 58112, and the shaft body length 58114 has a shaft side wall opening 58116. The shaft side wall opening 58116 is in selective fluid communication with the shaft open slit 58108. The shaft open slit 58108 of the shaft C 60126 may extend between the shaft side wall opening 58116 and an implant delivery element open tip 59124. At least a portion of the shaft open slit 58108 and at least a portion of the shaft side wall opening 58116 may collectively form a shaft lumen 58118 for at least partially selectively holding a guidewire 328 therein. At least one of the shaft body proximal end 58110, shaft body distal end 58112, and the shaft body length 58114 may have an outer sheath splitter 58120 for facilitating the elastic separation of the implant holding pod open slit first surface 5176 and the implant holding pod open slit second surface 5178. FIGS. 60a-c depict cross-sectional views of various points along the shaft C 60126, to show structural features of the shaft B 60126.

Figure 61:
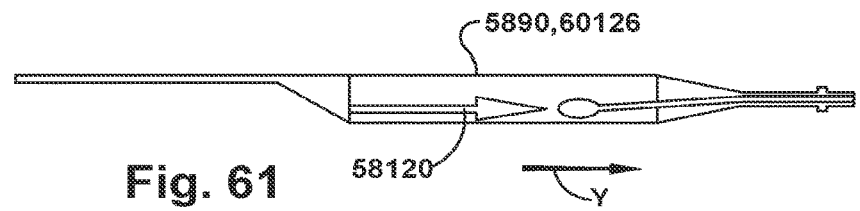
FIG. 61 is a side view of the element of FIG. 60 in an alternate configuration.

As shown in FIG. 61, the outer sheath splitter 58120 may be arrow-shaped. The term "arrow-shaped" is defined herein as a linear figure having a wedge-shaped edge, as one used on a map or architectural drawing, to indicate direction or placement. The arrow-shaped outer sheath splitter 58120 may point toward a longitudinally distal direction (shown as an arrow Y in FIG. 61). The arrow-shaped outer sheath splitter 58120 may point downward toward an implant holding pod side wall opening 5182 of an outer sheath 5148 when the shaft C 60126 is operably joined to an outer sheath 5182. Although the shaft C 60126 is shown having the arrow-shaped outer sheath splitter 58120, any of the outer sheath splitters 58120 of the alternate configurations of the shaft 5890 may be arrow-shaped.

Figure 62:
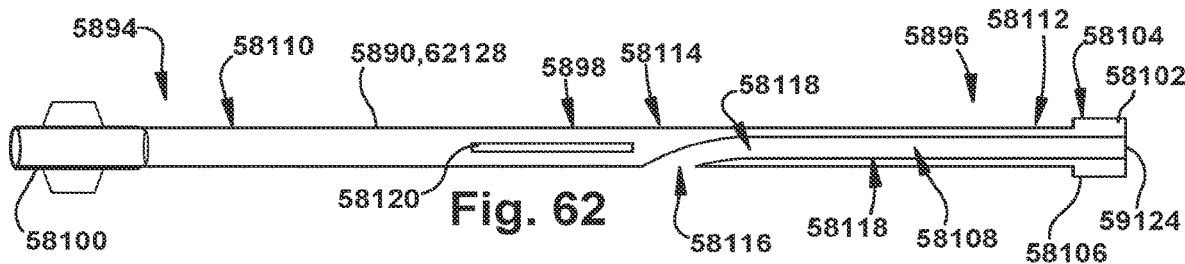
FIG. 62 is a side view of the element of FIG. 58 in an alternate configuration.

FIG. 62 depicts an alternate configuration for the shaft 5890, referred to as a shaft D 62128. Similar to the shaft C 60126, the shaft D 62128 has a shaft proximal end 5894, a shaft distal end 5896, and a shaft body 5898 longitudinally extending between the shaft proximal and distal ends 5894, 5896. The shaft proximal end 5894 has a shaft delivery element 58100. The shaft distal end 5896 has an implant delivery element 58102. The implant delivery element 58102 of the shaft A 5892 has an implant delivery element outer surface 58104 and a radially extending projection 58106 for selectively contacting and selectively pushing an expandable implant M. At least one of the shaft body 5898 and the implant delivery element 58102 has a shaft open slit 58108.

The shaft body 5898 has a shaft body proximal end 58110, a shaft body distal end 58112, and a shaft body length 58114 that longitudinally extends between the shaft body proximal end 58110 and the shaft body distal end 58112. At least one of the shaft body proximal end 58110, the shaft body distal end 58112, and the shaft body length 58114 has a shaft side wall opening 58116. The shaft side wall opening 58116 is in selective fluid communication with the shaft open slit 58108. The shaft open slit 58108 of the shaft D 62128 may extend between the shaft side wall opening 58116 and an implant delivery element open tip 59124. At least a portion of the shaft open slit 58108 and at least a portion of the shaft side wall opening 58116 may collectively form a shaft lumen 58118 for at least partially selectively holding a guidewire 328 therein. At least one of the shaft body proximal end 58110, shaft body distal end 58112, and the shaft body length 58114 may have an outer sheath splitter 58120 for facilitating the elastic separation of the implant holding pod open slit first surface 5176 and the implant holding pod open slit second surface 5178. The shaft D 62128 may have a central lumen (not shown) that extends between the shaft proximal end 5894 and the shaft distal end 5894. The central lumen (not shown) may be in fluid communication with the shaft lumen 58118, so that a guidewire 328 may be at least partially directed through the shaft D 62128.

Figure 63:
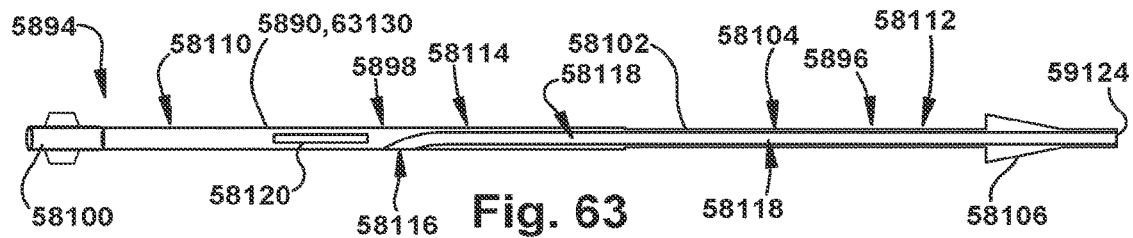
FIG. 63 is a side view of the element of FIG. 58 in an alternate configuration.

FIG. 63 depicts an alternate configuration for the shaft 5890, referred to as a shaft E 63130. Similar to the shaft A 5892, the shaft E 63130 has a shaft proximal end 5894, a shaft distal end 5896, and a shaft body 5898 that longitudinally extends between the shaft proximal and distal ends 5894, 5896. The shaft proximal end 5894 has a shaft delivery element 58100. The shaft distal end 5896 has an implant delivery element 58102. The implant delivery element 58102 of the shaft E 63130 has an implant delivery element outer surface 58104 for selectively circumferentially mounting an expandable implant M thereon. The implant delivery element outer surface 58104 may have at least one radially extending projection 58106 for substantially preventing the egress of an expandable implant M mounted circumferentially about the implant delivery element outer surface 58104 from a desired position on the implant delivery element outer surface 58104. A distal end of implant delivery element 58102 may have a radially extending projection 58106. The radially extending projection 58106 of the shaft E 63103 can be used for substantially preventing the egress of a self-expandable implant M mounted circumferentially about the implant delivery element outer surface 58104 from a desired position on the implant delivery element outer surface 58104. The radially extending projection 58106 may additionally, or instead, be used for a smooth atraumatic transition of the implant delivery system 5146 into the target patient tissue site T. The projection 58106 may be a radially extending conical head. The conical head may point, or narrow, toward a longitudinally distal direction. The term "conical" is defined herein as resembling a solid bounded by a circular or other closed plane base and the surface formed by line segments joining every point of the boundary of the base to a common vertex. At least one of the shaft body 5898 and the implant delivery element 58102 has a shaft open slit 58108.

The shaft body 5898 has a shaft body proximal end 58110, a shaft body distal end 58112, and a shaft body length 58114 that longitudinally extends between the shaft body proximal end 58110 and the shaft body distal end 58112. At least one of the shaft body proximal end 58110, the shaft body distal end 58112, and the shaft body length 58114 has a shaft side wall opening 58116. The shaft side wall opening 58116 is in selective fluid communication with the shaft open slit 58108. The shaft open slit 58108 of the shaft E 63130 may extend between the shaft side wall opening 58116 and an implant delivery element open tip 59124. At least a portion of the shaft open slit 58108 and at least a portion of the shaft side wall opening 58116 may collectively form a shaft lumen 58118 for at least partially selectively holding a guidewire 328 therein. At least one of the shaft body proximal end 58110, the shaft body distal end 58112, and the shaft body length 58114 may have an outer sheath splitter 58120 for facilitating the elastic separation of the implant holding pod open slit first surface 5176 and the implant holding pod open slit second surface 5178.

Figure 64:
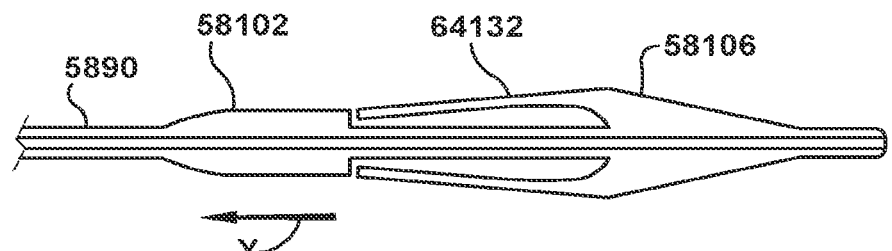
FIGS. 64-65 depict a partial side view of the element of FIG. 58 in an alternate configuration, in an example sequence of operation.
Figure 65:
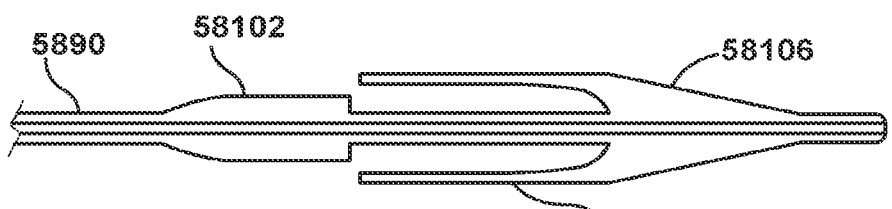
Figure 66:
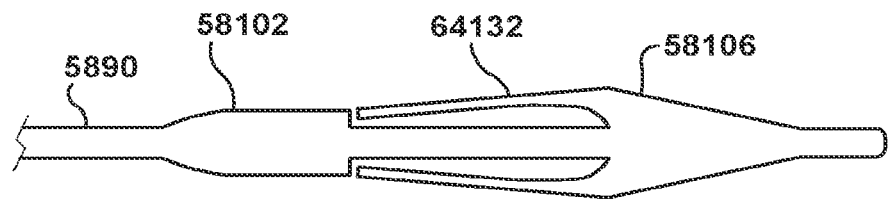
FIGS. 66-67 depict a partial side view of the element of FIG. 58 in an alternate configuration, in an example sequence of operation.
Figure 67:
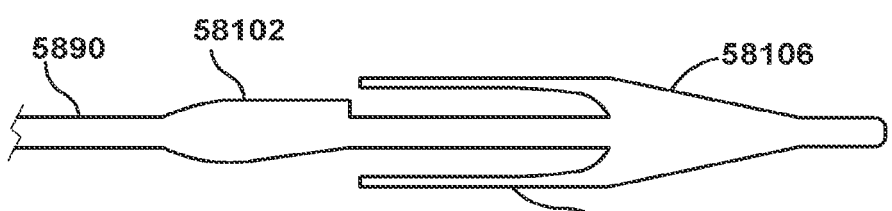

As shown in FIGS. 64-67, the conical head projection 58106 may have at least one elastic clamp 64132 that longitudinally extends in the proximal direction (shown as an arrow Y in FIG. 64). The elastic clamp 64132 is for selectively preventing the implant holding pod open slit first surface 5176 from elastically separating from an implant holding pod open slit second surface 5178 when the shaft 5890 is operably joined to the outer sheath 5148, as will be described in more detail below. The elastic clamp 64132 is capable of moving between a collapsed condition (FIGS. 64 and 66) and an expanded condition (FIGS. 65 and 67). As shown in FIGS. 66-67, at least a portion of the implant delivery element 58102 may not have an open slit.

FIG. 68 depicts an alternate configuration for the shaft 5890, referred to as a shaft F 68134. Similar to the shaft D 62128, the shaft F 68134 has a shaft proximal end 5894, a shaft distal end 5896, and a shaft body 5898 that longitudinally extends between the shaft proximal and distal ends 5894, 5896. The shaft proximal end 5894 has a shaft delivery element 58100. The shaft distal end 5896 has an implant delivery element 58102. The implant delivery element 58102 of the shaft F 68134 has an implant delivery element outer surface 58104 and a radially extending projection 58106 for selectively contacting and selectively pushing an expandable implant M. At least one of the shaft body 5898 and the implant delivery element 58102 has a shaft open slit 58108. In particular, the implant delivery element 58102 of the shaft F 68134 has the shaft open slit 58108.

The shaft body 5898 has a shaft body proximal end 58110, a shaft body distal end 58112, and a shaft body length 58114 that longitudinally extends between the shaft body proximal end 58110 and the shaft body distal end 58112. For the shaft F 68134, at least one of the shaft body proximal end 58110, the shaft body distal end 58112, the shaft body length 58114, and the implant delivery element 58102 has a shaft side wall opening 58116. The shaft side wall opening 58116 is in selective fluid communication with the shaft open slit 58108. The shaft open slit 58108 of the shaft D 62128 may extend between the shaft side wall opening 58116 and an implant delivery element open tip 59124. At least a portion of the shaft open slit 58108 and at least a portion of the shaft side wall opening 58116 may collectively form a shaft lumen 58118 for at least partially selectively holding a guidewire 328 therein.

At least one of the shaft body proximal end 58110, the shaft body distal end 58112, and the shaft body length 58114 may have an outer sheath splitter 58120 for facilitating the elastic separation of the implant holding pod open slit first surface 5176 and the implant holding pod open slit second surface 5178. As shown in FIG. 68, at least one of the shaft body 5898 and the implant delivery element 58102 of the shaft F 68134 may be at least partially curved and/or at least partially formed from an elastic material. The shaft body 5898 and/or the implant delivery element 58102 formed at least partially from an elastic material allows the shaft 5890 to be deformed from an original condition upon an application of a force, and then return to the original condition upon the removal of the force. Although FIG. 68 shows the shaft F 68134 being curved, any of the shaft 5890 alternate configurations may be curved and/or formed from an elastic material.

FIG. 69 depicts an alternate configuration for the shaft 5890, referred to as a shaft G 69136. Similar to the shaft D 62128, the shaft G 68136 has a shaft proximal end 5894, a shaft distal end 5896, and a shaft body 5898 that longitudinally extends between the shaft proximal and distal ends 5894, 5896. The shaft proximal end 5894 has a shaft delivery element 58100. The shaft distal end 5896 has an implant delivery element 58102. The implant delivery element 58102 of the shaft A 5892 has an implant delivery element outer surface 58104 and a radially extending projection 58106 for selectively contacting and selectively pushing an expandable implant M. At least one of the shaft body 5898 and the implant delivery element 58102 has a shaft open slit 58108.

The shaft body 5898 has a shaft body proximal end 58110, a shaft body distal end 58112, and a shaft body length 58114 that longitudinally extends between the shaft body proximal end 58110 and the shaft body distal end 58112. At least one of the shaft body proximal end 58110, the shaft body distal end 58112, and the shaft body length 58114 has a shaft side wall opening 58116. The shaft side wall opening 58116 is in selective fluid communication with the shaft open slit 58108. The shaft open slit 58108 of the shaft D 62128 may extend between the shaft side wall opening 58116 and an implant delivery element open tip 59124. At least a portion of the shaft open slit 58108 and at least a portion of the shaft side wall opening 58116 may collectively form a shaft lumen 58118 for at least partially selectively holding a guidewire 328 therein.

At least one of the shaft body proximal end 58110, the shaft body distal end 58112, and the shaft body length 58114 may have an outer sheath splitter 58120 for facilitating the elastic separation of the implant holding pod open slit first surface 5176 and the implant holding pod open slit second surface 5178. As shown in FIG. 69, at least one of the shaft body 5898 and the implant delivery element 58102 of the shaft G 68136 may be at least partially curved and/or at least partially formed from an elastic material. The shaft G 68136 may have an expandable balloon 69138 positioned on at least one of the shaft body 5898 and the shaft distal end 5896. The balloon 69138 may have a balloon open slit 69140 that extends for at least a partial length of the balloon 69138. The balloon open slit 69140 may be aligned with at least a portion of the shaft open slit 58108. Although FIG. 69 depicts the shaft G 68136 having the expandable balloon 69138, any of the shaft 5890 alternate configurations may have the expandable balloon 69138 positioned thereon in a similar manner. Each of the shafts 5890 having an expandable balloon 69138 may an inflation channel in fluid communication, so that an outside fluid source may direct fluid through the inflation channel, in any suitable manner, and into the expandable balloon 69138 to expand the expandable balloon 69138.

FIG. 70 depicts an alternate configuration for the shaft 5890, referred to as a shaft H 70142. Similar to the shaft G 69136, the shaft H 70142 has a shaft proximal end 5894, a shaft distal end 5896, and a shaft body 5898 that longitudinally extends between the shaft proximal and distal ends 5894, 5896. The shaft proximal end 5894 has a shaft delivery element 58100. The shaft distal end 5896 has an implant delivery element 58102. The implant delivery element 58102 of the shaft H 70142 has an implant delivery element outer surface 58104 and a radially extending projection 58106 for selectively contacting and selectively pushing a self-expandable implant M. The projection 58106 of shaft H 70142 may be a radially extending conical head. The conical head may point, or narrow, toward a longitudinally distal direction. The conical head projection 58106 of the shaft H 70142 may point downward toward an implant holding pod side wall opening 5182 of an outer sheath 5148 when the shaft H 70142 is operably joined to an outer sheath 5148. When the shaft H 70142 is operably joined to the an outer sheath 5148, the conical head projection 58106 of the shaft H 70142 may undergo a partial rotation until an outer sheath splitter 58120 engages an implant holding pod open slit 5174 of the outer sheath 5148 to facilitate the elastic separation of the implant holding pod open slit first surface 5176 and the implant holding pod open slit second surface 5178. Thus, the conical head projection 58106 may act as a "self-centering" element when the shaft H 70142 is operably joined to an outer sheath 5180. At least one of the shaft body 5898 and the implant delivery element 58102 has a shaft open slit 58108.

The shaft body 5898 has a shaft body proximal end 58110, a shaft body distal end 58112, and a shaft body length 58114 longitudinally extending between the shaft body proximal end 58110 and the shaft body distal end 58112. At least one of the shaft body proximal end 58110, the shaft body distal end 58112, and the shaft body length 58114 has a shaft side wall opening 58116. The shaft side wall opening 58116 is in selective fluid communication with the shaft open slit 58108. The shaft open slit 58108 of the shaft D 62128 may extend between the shaft side wall opening 58116 and an implant delivery element open tip 59124. At least a portion of the shaft open slit 58108 and at least a portion of the shaft side wall opening 58116 may collectively form a shaft lumen 58118 for at least partially selectively holding a guidewire 328 therein.

Figure 71:
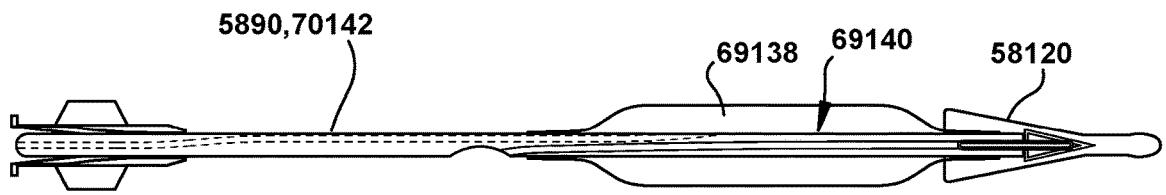
FIG. 71 is a side view of the element of FIG. 58 in an alternate configuration.

At least one of the shaft body proximal end 58110, the shaft body distal end 58112, and the shaft body length 58114 has an outer sheath splitter 58120 for facilitating the elastic separation of the implant holding pod open slit first surface 5176 and the implant holding pod open slit second surface 5178. As shown in FIG. 71, the outer sheath splitter 58120 may be arrow-shaped. The arrow-shaped outer sheath splitter 58120 may point toward a longitudinally distal direction (shown as an arrow Y in FIG. 71). The arrow-shaped outer sheath splitter 58120 may point downward toward an implant holding pod side wall opening 5182 of an outer sheath 5148 when the shaft H 70142 is operably joined to an outer sheath 5148. As shown in FIGS. 70-71, the shaft H 70142 may have an expandable balloon 69138 positioned on at least one of the shaft body 5898 and the shaft distal end 5896. The balloon 69138 may have a balloon open slit 69140 that at least partially extends for at least a partial length of the balloon 69138. The balloon open slit 69140, when provided, may be aligned with at least a portion of the shaft open slit 58108. FIGS. 70*a-d* depict cross-sectional views of various points along the shaft H 70142, to show structural features of the shaft H 70142.

As shown in FIGS. 72-79, the implant delivery system 5146 including any of the alternate configurations of the outer sheaths 5148, as discussed above, may be operatively joined to any of the alternate configurations of the shafts 5890. For the sake of brevity, not every combination of the alternate configurations of the outer sheaths 5148 and the alternate configurations of the shafts 5890 are discussed and/or depicted herein.

Figure 72:
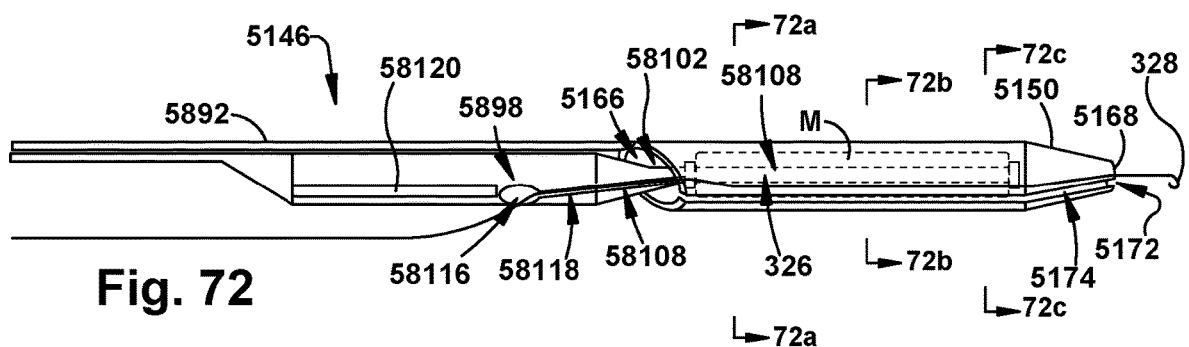
FIG. 72 is a side view of an aspect of the implant delivery system in an example use configuration.
Figure 72A:
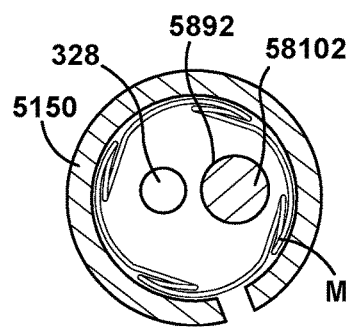
FIG. 72a-c depict cross-sectional views of the aspect of FIG. 72.
Figure 72B:
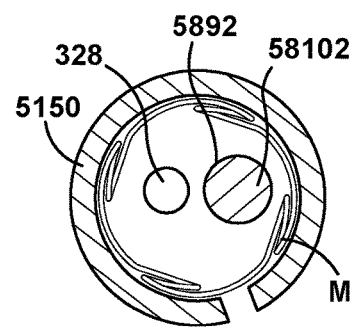
Figure 72C:
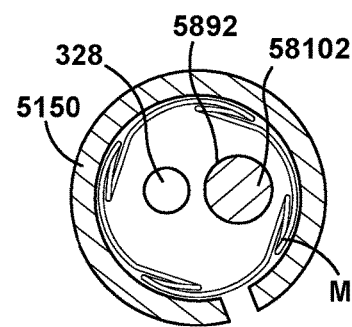

FIG. 72 depicts the outer sheath A 5150 operably joined to the shaft A 5892. When the outer sheath A 5150 is operably joined to the shaft A 5892, at least one of the shaft body 5898 and the implant delivery element 58102 may be positioned within the implant holding pod lumen 5172. The implant delivery element outer surface 58104 may have an expandable implant M disposed thereon, wherein the implant holding pod inner lumen 5172 at least partially prevents the expandable implant M from moving from a collapsed condition toward an expanded condition. At least a portion of the shaft open slit 58108 may be selectively laterally spaced from the implant holding pod open slit 5174. In this configuration, as shown in FIG. 72, the implant delivery system 5146 may include a guidewire path 326 for a guidewire 328 to be directed through the implant holding pod open tip 5168, through at least a portion of the implant holding pod lumen 5172, through the implant holding pod proximal opening 5166 and the shaft lumen 58118, and out from the shaft A 5892, such as through the shaft side wall opening 58116. FIGS. 72*a*-*c* depict cross-sectional views of various points along the implant delivery system 5146, to show the arrangement of the outer sheath A 5150, the shaft A 5892, the guidewire 328, and the expandable implant M in FIG. 72.

Figure 73:
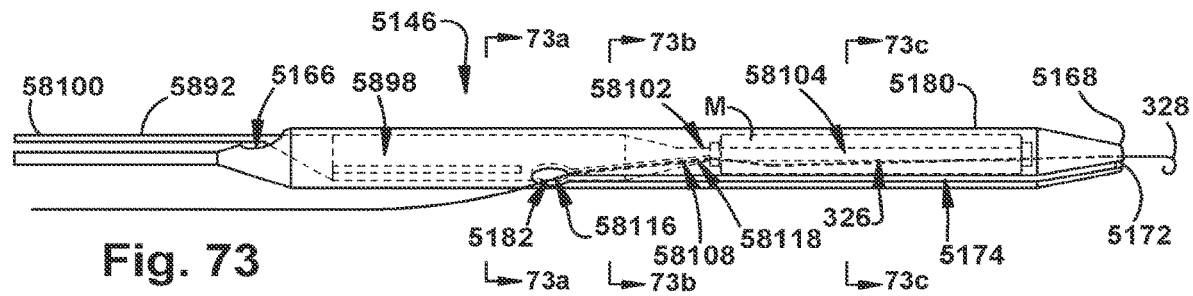
FIG. 73 is a side view of the aspect of FIG. 72 in an alternate configuration.
Figure 73A:
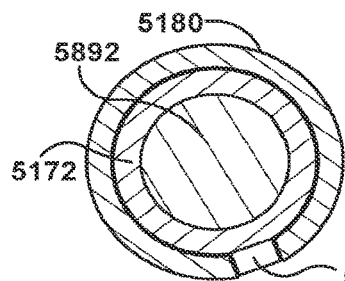
FIG. 73a-c depict cross-sectional views of the aspect of FIG. 73.
Figure 73B:
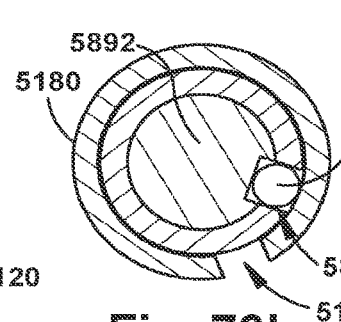
Figure 73C:
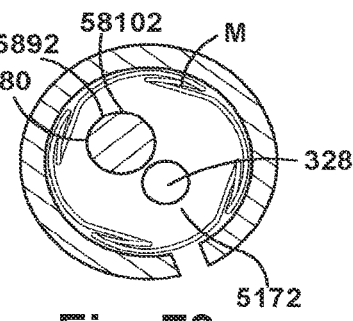

FIG. 73 depicts the outer sheath B 5180 operably joined to the shaft A 5892. When the outer sheath B 5180 is operably joined to the shaft A 5892, at least one of the shaft delivery element 58100, the shaft body 5898, and the implant delivery element 58102 may be positioned within the implant holding pod inner lumen 5172. The shaft delivery element 58100 may extend through the implant holding pod proximal opening 5166. The implant delivery element outer surface 58104 may have an expandable implant M disposed thereon, wherein the implant holding pod inner lumen 5172 at least partially prevents the expandable implant M from moving from a collapsed condition toward an expanded condition. At least a portion of the shaft open slit 58108 may be selectively laterally spaced from the implant holding pod open slit 5174. The shaft side wall opening 58116 may be aligned with the implant holding pod side wall opening 5182. In this configuration, as shown in FIG. 73, the implant delivery system 5146 may include a guidewire path 326 for a guidewire 328 to be directed through the implant holding pod open tip 5168, through at least a portion of the implant holding pod lumen 5172, through the shaft lumen 58118 (thus, indirectly traveling through the implant holding pod inner lumen 5172 of the outer sheath B 5180, as well), through the shaft side wall opening 58116, and out from the outer sheath B 5180, such as through the implant holding pod side wall opening 5182. FIGS. 73*a*-*c* depict cross-sectional views of various points along the implant delivery system 5146, to show the arrangement of the outer sheath B 5180, the shaft A 5892, the guidewire 328, and the expandable implant M in FIG. 73.

Figure 74:
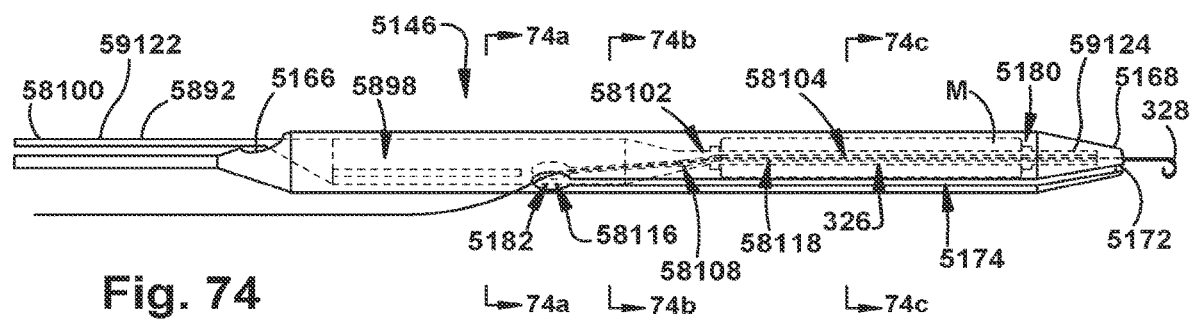
FIG. 74 is a side view of the aspect of FIG. 72 in an alternate configuration.
Figure 74A:
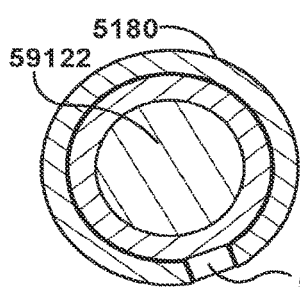
FIG. 74a-c depict cross-sectional views of the aspect of FIG. 74.
Figure 74B:
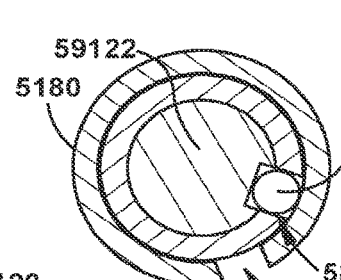
Figure 74C:
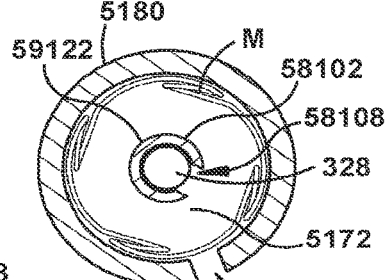

FIG. 74 depicts the outer sheath B 5180 operably joined to the shaft B 59122. When the outer sheath B 5180 is operably joined to the shaft B 59122, at least one of the shaft delivery element 58100, the shaft body 5898, and the implant delivery element 58102 may be positioned within the implant holding pod inner lumen 5172. The shaft delivery element 58100 may extend through the implant holding pod proximal opening 5166. The implant delivery element outer surface 58104 may have an expandable implant M disposed thereon, wherein the implant holding pod lumen 5172 prevents the expandable implant M from moving from a collapsed condition toward an expanded condition. At least a portion of the shaft open slit 58108 may be selectively laterally spaced from the implant holding pod open slit 5174. The shaft side wall opening 58116 may be aligned with the implant holding pod side wall opening 5182. In this configuration, as shown in FIG. 73, the implant delivery system 5146 may include a guidewire path 326 for a guidewire 328 to be directed through the implant holding pod open tip 5168, through at least a portion of the implant holding pod lumen 5172, through the implant delivery element open tip 59124, through the shaft lumen 58118 (thus, indirectly traveling through the implant holding pod lumen 5172 of the outer sheath B 5180, as well), through the shaft side wall opening 58116, and out from the outer sheath B 5180, such as through the implant holding pod side wall opening 5182. FIGS. 74*a*-*c* depict cross-sectional views of various points along the implant delivery system 5146, to show the arrangement of the outer sheath B 5180, the shaft B 59122, the guidewire 328, and the expandable implant M in FIG. 74.

Figure 75:
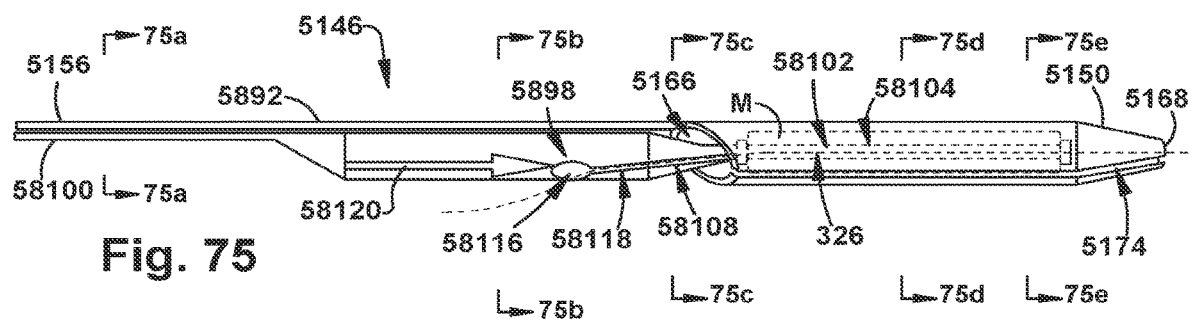
FIG. 75 is a side view of the aspect of FIG. 72 in an alternate configuration.
Figures 75A, 75B:
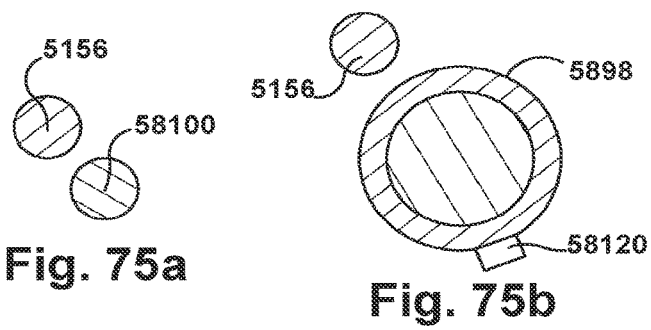
FIG. 75a-e depict cross-sectional views of the aspect of FIG. 75.
Figures 75C, 75D, 75E:
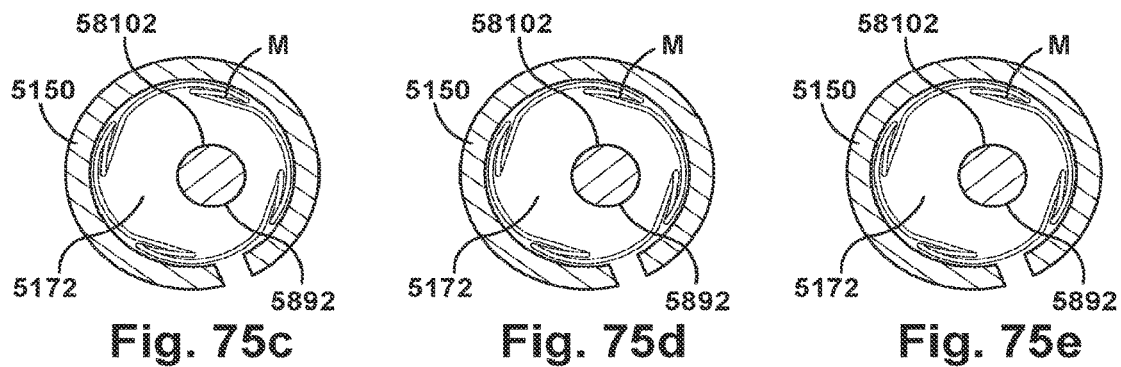

FIG. 75 depicts the outer sheath A 5150 operably joined to the shaft A 5892, which has an arrow-shaped outer sheath splitter 58120. When the outer sheath A 5150 is operably joined to the shaft A 5892, at least one of the shaft body 5898 and the implant delivery element 58102 may be positioned within the implant holding pod lumen 5172. The implant delivery element outer surface 58104 may have an expandable implant M disposed thereon, wherein the implant holding pod lumen 5172 at least partially prevents the expandable implant M from moving from a collapsed condition toward an expanded condition. At least a portion of the shaft open slit 58108 may be selectively laterally spaced from the implant holding pod open slit 5174. In this configuration, as shown in FIG. 75, the implant delivery system 5146 may include a guidewire path 326 for a guidewire 628 to be directed through the implant holding pod open tip 5168, through at least a portion of the implant holding pod lumen 5172, through the implant holding pod proximal opening 5166 and the shaft lumen 58118, and out from the shaft A 5892, such as through the shaft side wall opening 58116. FIGS. 75*a*-*e* depict cross-sectional views of various points along the implant delivery system 5146, to show the arrangement of the outer sheath A 5150, the shaft A 5892, and the expandable implant M in FIG. 75.

Figure 76:
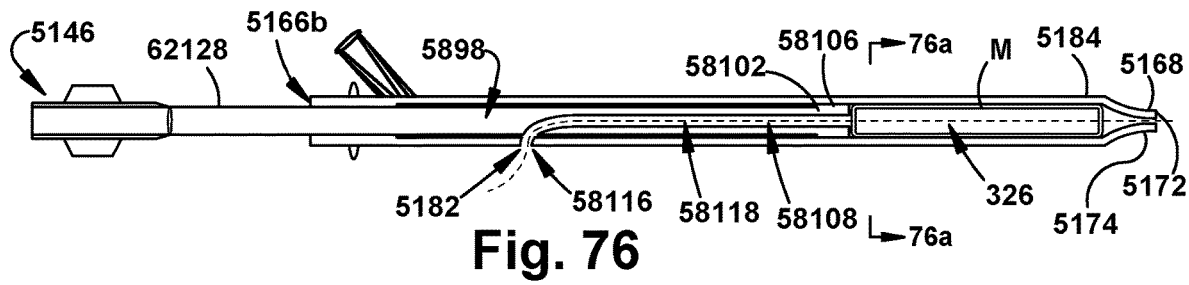
FIG. 76 is a side view of the aspect of FIG. 72 in an alternate configuration.
Figure 76A:
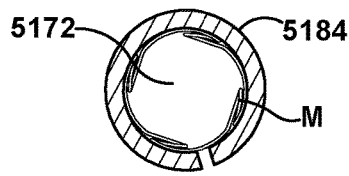
FIG. 76a depicts a cross-sectional view of the aspect of FIG. 76.

FIG. 76 depicts the outer sheath C 5184 operably joined to the shaft D 62128. When the outer sheath C 5184 is operably joined to the shaft D 62128, at least one of the shaft body 5898 and the implant delivery element 58102 may be positioned within the implant holding pod lumen 5172. The shaft body 5898 of shaft D 62128 may at least partially extend through the second implant holding pod proximal opening 5166*b*. The implant holding pod lumen 5172 may have an expandable implant M therein. The implant holding pod lumen 5172 at least partially prevents the expandable implant M from moving from a collapsed condition toward an expanded condition. The projection 58106 of the shaft D 62128 may be placed into operative engagement with the expandable implant M by locating at least a portion of the projection 58106 in abutment with the expandable implant M. At least a portion of the shaft open slit 58108 may be selectively laterally spaced from the implant holding pod open slit 5174. The shaft side wall opening 58116 may be aligned with the implant holding pod side wall opening 5182. In this configuration, as shown in FIG. 76, the implant delivery system 5146 may include a guidewire path 326 for a guidewire 328 to be directed through the implant holding pod open tip 5168, through at least a portion of the implant holding pod lumen 5172, through the implant delivery element open tip 59124, through the shaft lumen 58118 (thus, indirectly traveling through the implant holding pod lumen 5172 of the outer sheath C 5184, as well), through the shaft side wall opening 58116, and out from the outer sheath C 5184, such as through the implant holding pod side wall opening 5182. FIG. 76*a* depicts a cross-sectional view of a point along the implant delivery system 5146, to show the arrangement of the outer sheath C 5184 and the expandable implant M in FIG. 76.

Figure 77:
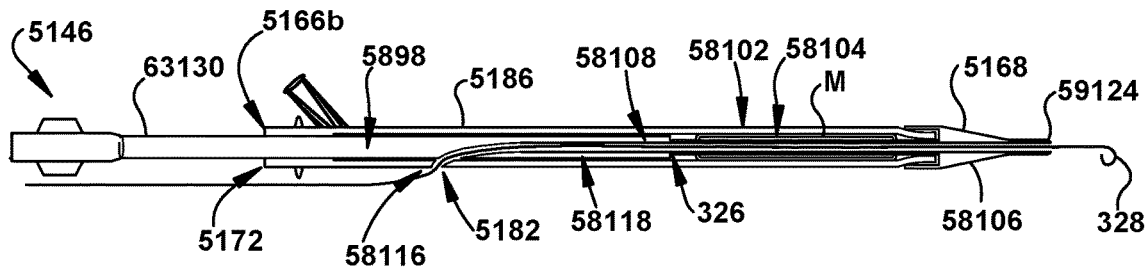
FIG. 77 is a side view of the aspect of FIG. 72 in an alternate configuration.

FIG. 77 depicts the outer sheath D 5186 operably joined to the shaft E 63130. When the outer sheath D 5186 is operably joined to the shaft E 63130, at least one of the shaft body 5898 and the implant delivery element 58102 may be positioned within the implant holding pod lumen 5172. The shaft body 5898 of shaft D 62128 may at least partially extend through the second implant holding pod proximal opening 5166*b*. The conical head projection 58106 may be longitudinally adjacent to the implant holding pod open tip 5168. The implant delivery element outer surface 58104 may have an expandable implant M disposed thereon, wherein the implant holding pod lumen 5172 at least partially prevents the expandable implant M from moving from a collapsed condition toward an expanded condition. At least a portion of the shaft open slit 58108 may be selectively laterally spaced from the implant holding pod open slit 5174. The shaft side wall opening 58116 may be aligned with the implant holding pod side wall opening 5182. In this configuration, as shown in FIG. 77, the implant delivery system 5146 may include a guidewire path 326 for a guidewire 328 to be directed through the implant delivery element open tip 59124, through at least a portion of the shaft lumen 58118 (thus, indirectly traveling through the implant holding pod open tip 5168 and the implant holding pod lumen 5172 of the outer sheath D 5186, as well), through the shaft side wall opening 58116, and out from the outer sheath D 5186, such as through the implant holding pod side wall opening 5182.

Figure 78:
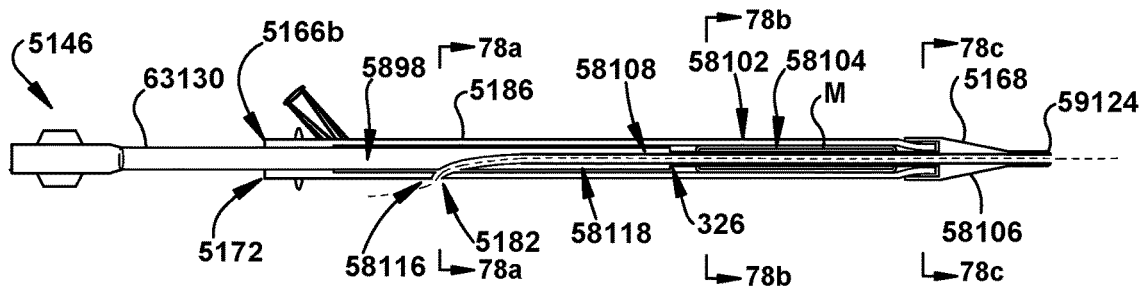
FIG. 78 is a side view of the aspect of FIG. 72 in an alternate configuration.

FIG. 78 depicts the outer sheath C 5184 operably joined to the shaft E 63130 having the at least one elastic clamp 64132. When the outer sheath C 5184 is operably joined to the shaft E 63130, at least one of the shaft body 5898 and the implant delivery element 58102 may be positioned within the implant holding pod lumen 5172. The shaft body 5898 of shaft E 63130 may at least partially extend through the second implant holding pod proximal opening 5166*b*. The conical head projection 58106 may be longitudinally adjacent to the implant holding pod open tip 5168. The implant delivery element outer surface 58104 may have an expandable implant M disposed thereon, wherein the implant holding pod lumen 5172 at least partially prevents the expandable implant M from moving from a collapsed condition toward an expanded condition.

The at least one elastic clamp 64132 may be disposed on the implant holding pod outer surface 5170 to at least partially selectively prevent the implant holding pod open slit first surface 5176 from at least partially elastically separating from the implant holding pod open slit second surface 5178 when the self-expanding implant M is disposed within the implant holding pod lumen 5172. In other words, a collapsed expandable implant M placed within the implant holding pod lumen 5172 may move toward an expanded condition due to the natural properties of the expandable implant M. Because the implant holding pod open slit first surface 5176 is elastically separable from the implant holding pod second surface 5178, the movement of the expandable implant M toward the expanded condition may cause the implant holding pod open slit first surface 5176 to at least partially elastically separate from the implant holding pod open slit second surface 5178. However, as shown in FIG. 78, when at least one elastic clamp 64132 is positioned on the implant holding pod outer surface 5170, the elastic clamp 64132 provides a radially inward force to at least partially selectively prevent the expandable implant M from at least partially elastically separating the implant holding pod open slit first surface 5176 from the implant holding pod open slit second surface 5178. At least a portion of the shaft open slit 58108 may be selectively laterally spaced from the implant holding pod open slit 5174.

Figure 78A:
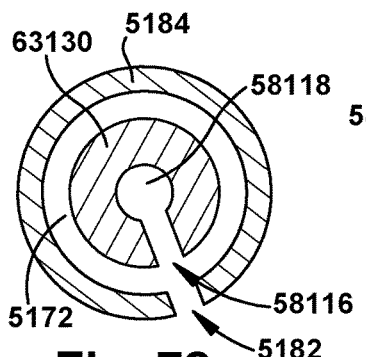
FIG. 78a-c depict cross-sectional views of the aspect of FIG. 78.
Figure 78B:
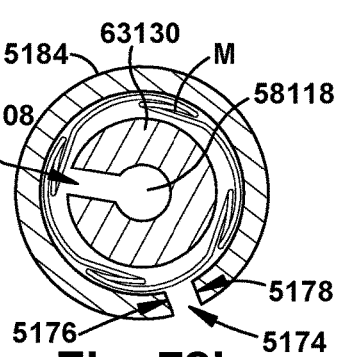
Figure 78C:
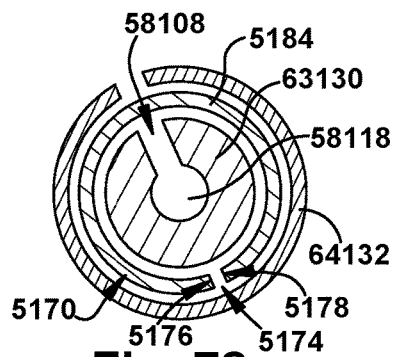

The shaft side wall opening 58116 may be aligned with the implant holding pod side wall opening 5182. In this configuration, as shown in FIG. 78, the implant delivery system 5146 may include a guidewire path 326 for a guidewire 328 to be directed through the implant delivery element open tip 59124, through at least a portion of the shaft lumen 58118 (thus, indirectly traveling through the implant holding pod open tip 5168 and the implant holding pod lumen 5172 of the outer sheath C 5184, as well), through the shaft side wall opening 58116, and out from the outer sheath C 5184, such as through the implant holding pod side wall opening 5184. FIGS. 78*a-c* depict cross-sectional views of various points along the implant delivery system 5146, to show the arrangement of the outer sheath C 5184, the shaft E 63130, the elastic clamp 64132, and the expandable implant M in FIG. 78.

Figure 79:
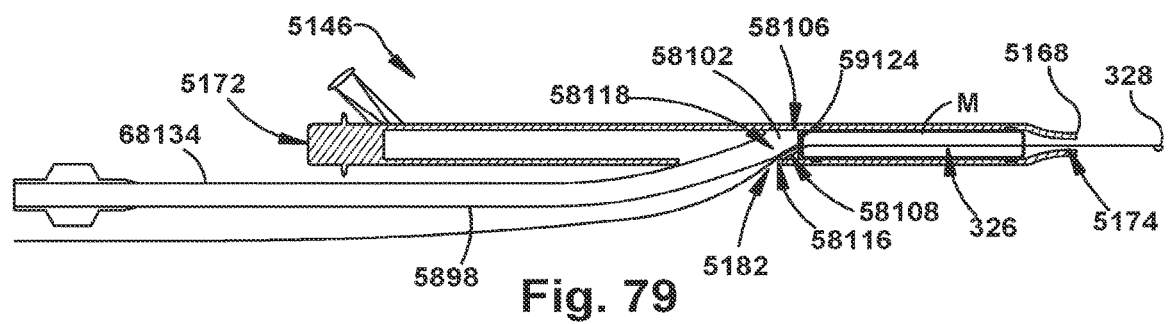
FIG. 79 is a side view of the aspect of FIG. 72 in an alternate configuration.

FIG. 79 depicts the outer sheath C 5184 operably joined to the shaft F 68134. When the outer sheath C 5184 is operably joined to the shaft F 68134, at least one of the shaft body 5898 and the implant delivery element 58102 may be positioned within the implant holding pod lumen 5172 through the implant holding pod side wall opening 5182. The implant holding pod lumen 5172 may have an expandable implant M therein. The implant holding pod lumen 5172 at least partially prevents the expandable implant M from moving from a collapsed condition toward an expanded condition. The projection 58106 of the shaft D 62128 may be in operative engagement with the expandable implant M by locating at least a portion of the projection 58106 in abutment with the expandable implant M. At least a portion of the shaft open slit 58108 may be selectively laterally spaced from the implant holding pod open slit 5174. The shaft side wall opening 58116 may be aligned with the implant holding pod side wall opening 5182. In this configuration, as shown in FIG. 79, the implant delivery system 5146 may include a guidewire path 326 for a guidewire 328 to be directed through the implant holding pod open tip 5168, through at least a portion of the implant holding pod lumen 5172, through the implant delivery element open tip 59124, through the shaft lumen 58118 (thus, indirectly traveling through the implant holding pod lumen 5172 of the outer sheath C 5184, as well), through the shaft side wall opening 58116, and out from the outer sheath C 5184, such as through the implant holding pod side wall opening 5182.

In use, the implant delivery system 5146, as described above, is provided to the user. The implant delivery system 5146 may include one of any of the alternate configurations of the outer sheaths 5148, as described above, and one of any of the alternate configurations of the shafts 5890, as described above, or a combination of individual features described above for the alternate configurations of the outer sheaths 5148 and the shafts 5890. For the sake of brevity, not every combination of the alternate configurations of the outer sheaths 5148 and the alternate configurations of the shafts 5890 are discussed and/or depicted. However, it is to be understood that the following description may be applicable to any combination of the alternate configurations of the outer sheaths 5148 and the shafts 5890, as described above.

FIGS. 80-89 depict an example sequence of operation of the implant delivery system 5146 having an outer sheath A 5150 and a shaft A 5892. A collapsed expandable implant M may be placed in operative engagement with the implant delivery element 58102. In particular, the expandable implant M may be mounted circumferentially about the implant delivery element outer surface 58104. With the expandable implant M mounted to the implant delivery element outer surface 58104, and the expandable implant M in a collapsed condition, at least one of the shaft body 5898, the implant delivery element 58102, and the expandable implant M may be collectively inserted at least partially into the implant holding pod lumen 5172. Alternatively, instead of mounting the expandable implant M to the implant delivery element outer surface 58104 prior to inserting at least a portion of the shaft 5890 into the implant holding pod lumen 5172, a collapsed expandable implant M may be placed within the implant holding pod lumen 5172 prior to inserting at least a portion of the shaft 5890 into the implant holding pod lumen 5172. In such case, after at least a portion of the shaft 5890 is inserted into the implant holding pod lumen 5172, the collapsed expandable implant M may be placed in operative engagement with the implant delivery element 58102 by mounting the expandable implant M to the implant delivery element outer surface 58104.

With at least a portion of the shaft 5890 and the expandable implant M at least partially inserted in the implant holding pod lumen 5172, the shaft 5890 may be aligned in the implant holding pod lumen 5172 with at least a portion of the shaft open slit 58108 being laterally spaced from the implant holding pod open slit 5174. A guidewire distal end 2842 is inserted into a target patient tissue site T in a patient lumen. A guidewire proximal end 2844 is directed through the implant delivery system 5146. In particular, a guidewire proximal end 2844 may be directed through the implant holding pod open tip 5168, through at least a portion of the implant holding pod lumen 5172, through the implant holding pod proximal opening 5166 and the shaft lumen 58118, and out from the shaft A 5892, such as through the shaft side wall opening 58116.

Figure 80:
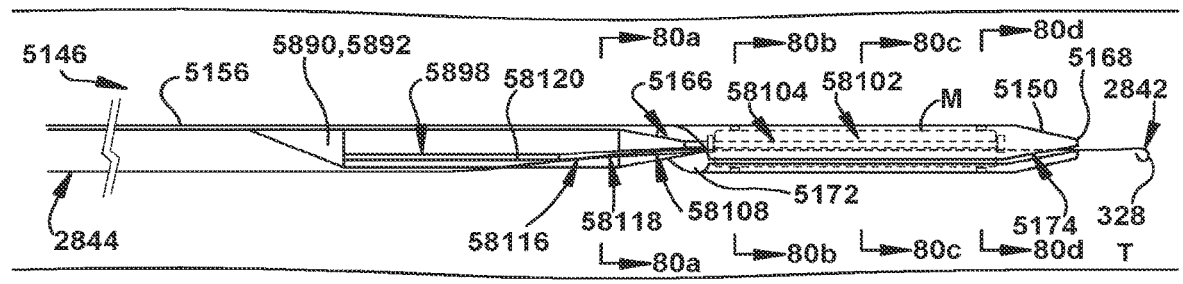
FIGS. 80-82c illustrate an example sequence of operation of a portion of the aspect of FIG. 72, including selected cross-sectional views.
Figure 80A:
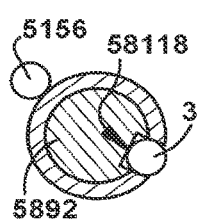
Figure 80B:
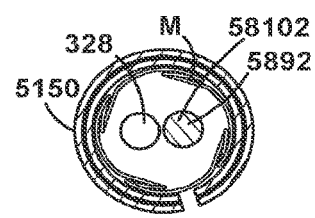
Figure 80C:
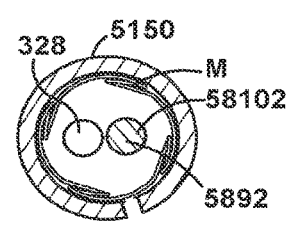
Figure 80D:
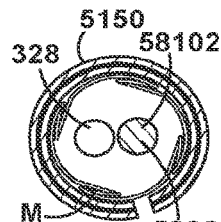

As shown in FIG. 80, the implant delivery system 5146 is directed to the target patient tissue site T along the guidewire 328. FIGS. 80a-d depict cross-sectional views of various points along the implant delivery system 5146, to show the arrangement of the outer sheath A 5150, the shaft A 5892, the guidewire 328, and the expandable implant M in FIG. 80.

Figure 81:
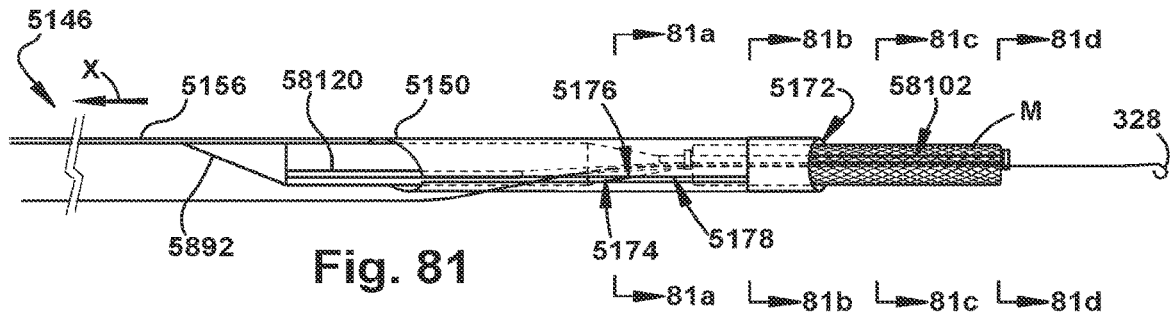
Figures 81A, 81B, 81C, 81D:
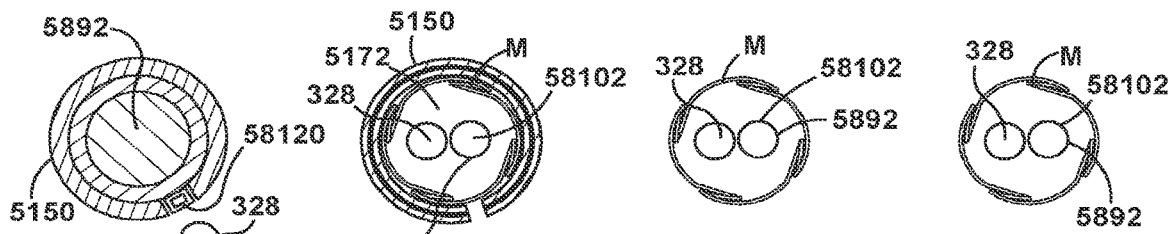
Figure 82:
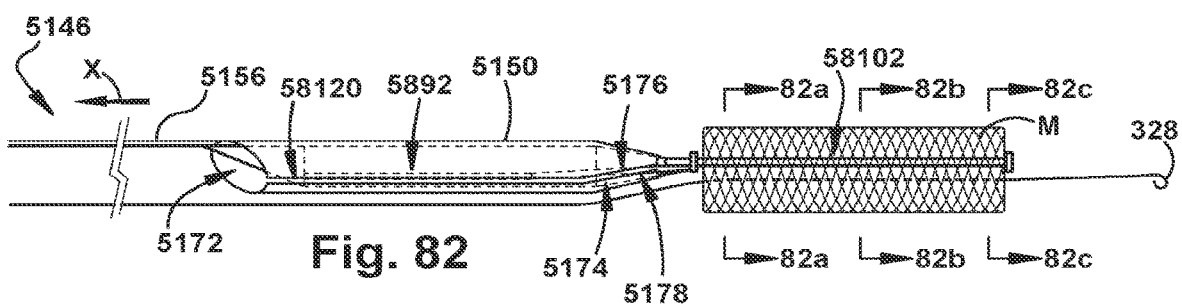

As shown in FIGS. 81 and 82, with the implant delivery system 5146 at the target patient tissue site T, the expandable implant M may be exposed by moving the outer sheath delivery element 5156 in the longitudinally proximal direction (as shown as an arrow X in FIG. 81) to directly correspondingly cause the outer sheath A 5150 to move in the longitudinally proximal direction. The guidewire 328, the expandable implant M, and the shaft A 5892 are maintained in place at the target patient tissue site T while the outer sheath A 5150 is moved in the longitudinally proximal direction.

Figures 82A, 82B, 82C:
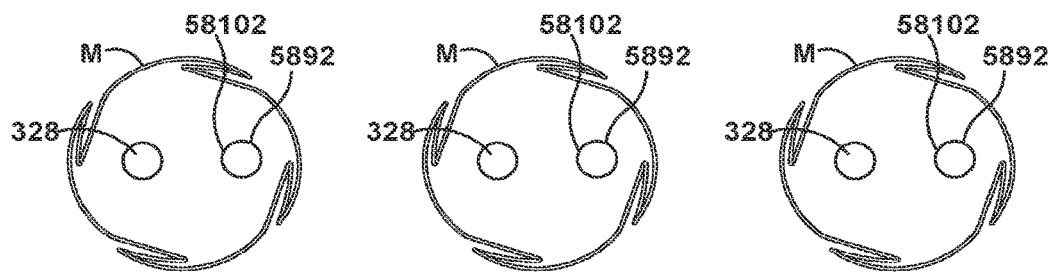

The outer sheath A 5150 may be removed from the guidewire 328 while the outer sheath A 5150 is moved in the longitudinally proximal direction. In particular, the movement of the outer sheath A 5160 in the longitudinally proximal direction causes the outer sheath splitter 58120 to move along the implant holding pod open slit 5174 to selectively urge the implant holding pod open slit first surface 5176 elastically apart from the implant holding pod open slit second surface 5178 and accordingly push the guidewire 328 from the implant holding pod lumen 5172, while maintaining the guidewire 328 and the shaft A 5892 at the target patient tissue site T. With the expandable implant M exposed, the properties of the expandable implant M are utilized to move the expandable implant M from the collapsed condition (as shown in FIGS. 80 and 81) toward the expanded condition (as shown in FIG. 82). FIGS. 81a-d depict cross-sectional views of various points along the implant delivery system 5146, to show the arrangement of the outer sheath A 5180, the shaft A 5892, the guidewire 328, and the expandable implant M in FIG. 81. FIGS. 82a-c depict cross-sectional views of various points along the implant delivery system 5146, to show the arrangement of the shaft A 5892, the guidewire 328, and the expandable implant M in FIG. 82.

FIGS. 83-89 depict an example sequence of operation of the outer sheath D 5186, the shaft E 63130, and a secondary device 85144, which will be described below. The expandable implant M may be mounted circumferentially about the implant delivery element outer surface 58104. With the expandable implant M mounted to the implant delivery element outer surface 58104, and the expandable implant M in the collapsed condition, at least one of the shaft body 5898, the implant delivery element 58102, and the expandable implant M may be collectively inserted at least partially into the implant holding pod lumen 5172.

As shown in FIG. 83, with at least a portion of the shaft E 63130 and the expandable implant M at least partially inserted in the implant holding pod lumen 5172, the shaft E 63130 may be aligned in the implant holding pod lumen 5172 with at least a portion of the shaft open slit 58108 being laterally spaced from the implant holding pod open slit 5174 and the conical head projection 58106 longitudinally adjacent to the implant holding pod open tip 5168. A guidewire distal end 2842 is inserted into a target patient tissue site T in a patient lumen. A guidewire proximal end 2844 is directed through the implant delivery system 5146. In particular, a guidewire proximal end 2842 may be directed through the implant delivery element open tip 59124, through at least a portion of the shaft lumen 58118 (thus, indirectly traveling through the implant holding pod open tip 5168 and at least a portion of the implant holding pod lumen 5172 of the outer sheath D 5186, as well), through the shaft side wall opening 58116, and out from the outer sheath D 5186, such as through the implant holding pod side wall opening 5182.

As shown in FIG. 84, the implant delivery system 5146 is directed to the target patient tissue site T along the guidewire 328. FIGS. 84a-g depict cross-sectional views of various points along the implant delivery system 5146, to show the arrangement of the outer sheath D 5186, the shaft E 63130, the guidewire 328, and the expandable implant M in FIG. 84. As shown in FIG. 85, with the implant delivery system 5146 at the target patient tissue site T, the expandable implant M may be exposed by moving the outer sheath delivery element 5156 in the longitudinally proximal direction (shown as an arrow X in FIG. 85) to directly correspondingly cause the outer sheath D 5186 to move in the longitudinally proximal direction. The guidewire 328, the expandable implant M, and the shaft E 63130 are maintained in place at the target patient tissue site T while the outer sheath D 5186 is moved in the longitudinally proximal direction. With the expandable implant M exposed, the properties of the expandable implant M are utilized to move the expandable implant M from the collapsed condition (as shown in FIG. 84) toward the expanded condition (as shown in FIG. 85).

The outer sheath D 5186 may be removed from the guidewire 328 while the outer sheath D 5186 is moved in the longitudinally proximal direction. In particular, the movement of the outer sheath D 5186 in the longitudinally proximal direction causes the outer sheath splitter 58120 to move along the implant holding pod open slit 5174 to selectively urge the implant holding pod open slit first surface 5176 at least partially elastically apart from the implant holding pod open slit second surface 5178 and accordingly push the guidewire 328 from the implant holding pod lumen 5172, while maintaining the guidewire 328 and the shaft at the target patient site T.

Alternatively, or in addition to the removal of the outer sheath D 5186, as described above, the outer sheath D 5186 may be removed from the guidewire 328 in the following sequence. As shown in FIG. 85, a secondary device 85144 may be directed over the guidewire 328 until the secondary device 85144 is at least one of adjacent to, abutting, and at least partially within the implant holding pod side wall opening 5182. With the secondary device 85144 pushing against and and/or at least partially in the implant holding pod side wall opening 5182, the outer sheath D 5186 is longitudinally moved in the proximal direction to remove the outer sheath D 5186 from the guidewire 328. In particular, the movement of the outer sheath D 5186 toward the proximal direction causes the secondary device 85144 to selectively urge the implant holding pod open slit first surface 5176 at least partially elastically apart from the implant holding pod open slit second surface 5178 and remove the outer sheath D 5186 from the guidewire 328, while leaving the guidewire 328 and the shaft E 63130 in place at the target patient tissue site T. FIGS. 85a-h depict cross-sectional views of various points along the implant delivery system 5146, to show the arrangement of the outer sheath D 5186, the shaft E 63130, the guidewire 328, the secondary device 85144, and the expandable implant M in FIG. 85.

As shown in FIG. 86, a user may then remove the shaft E 63130 from the guidewire 328 in the following sequence. At least a portion of the secondary device 85144 is directed over the guidewire 328 until the secondary device 85144 is at least one of adjacent to, abutting, and at least partially within the shaft side wall opening 58116. With the secondary device 85144 pushing against and/or located at least partially in the shaft side wall opening 58116, longitudinally the shaft E 63130 is longitudinally moved toward the proximal direction to remove the shaft E 63130 from the guidewire 328. In particular, the movement of the shaft E 63130 toward the proximal direction causes the secondary device 85144 to selectively urge a shaft open slit first surface 86146 at least partially elastically apart from a shaft open slit second surface 86148 and remove the shaft E 63130 from the guidewire 328, while maintaining the guidewire 328 at the target patient tissue site T. The shaft open slit first surface 86146 oppositely faces and abuts shaft open slit second surface 86148. The shaft open slit first surface 86146 and the shaft open slit second surface 86148 are selectively elastically separable, similar to that of the implant holding pod open slit first and second surfaces 5176, 5178. Any of the alternate configurations of the shafts 5890 may have the shaft open slit first and second surfaces 86146, 86148. FIGS. 86a-h depict cross-sectional views of various points along the implant delivery system 5146, to show the arrangement of the shaft E 63130, the guidewire 328, the secondary device 85144, and the expandable implant M in FIG. 86.

As shown in FIGS. 87 and 88, if desired by the user, the user may direct the secondary device 85144 in the longitudinally distal direction (as shown as an arrow Y in FIG. 88) to the target patient tissue site T to perform a medical procedure with the secondary device 85144 at the target patient tissue site T. The secondary device 85144 may be a balloon dilation device 88150. The balloon dilation device 88150 may have a balloon dilation rod 88152 having a balloon dilation rod proximal end 88154, a balloon dilation rod distal end 88156, and an elongate balloon dilation rod body 88158 that longitudinally extends between the balloon dilation rod proximal and distal ends 88154, 88156. The balloon dilation rod 88152 has a balloon dilation rod outer surface 88160 and a balloon dilation rod lumen 88162. The balloon dilation rod 88152 has a balloon dilation rod side wall opening 88164. The balloon dilation rod side wall opening 88164 selectively places the balloon dilation rod outer surface 88160 in fluid communication with the balloon dilation rod lumen 88162. The balloon dilation rod distal end 88156 has a balloon dilation rod open tip 88166. The balloon dilation rod 88152 has a balloon dilation rod open slit 88168. The balloon dilation rod open slit 88168 may extend between the balloon dilation rod side wall opening 88164 and the balloon dilation rod open tip 88166.

An expandable balloon 69138 may be positioned on at least one of the balloon dilation rod body 88158 and the balloon dilation rod distal end 88156. The expandable balloon 69138 may have a balloon open slit 69140 that extends for at least a partial length of the expandable balloon 69138. The balloon open slit 69140 may be aligned with the balloon dilation rod open slit 88168. The balloon dilation device 88150 may be positioned with at least a portion of the expandable balloon 69138 within a diseased segment of the patient lumen and/or adjacent to an expandable implant inner surface MI. As shown in FIG. 88, the expandable balloon 69138 may be inflated to dilate the diseased segment of the patient lumen and/or cause the expandable implant M to further expand.

Figure 89:
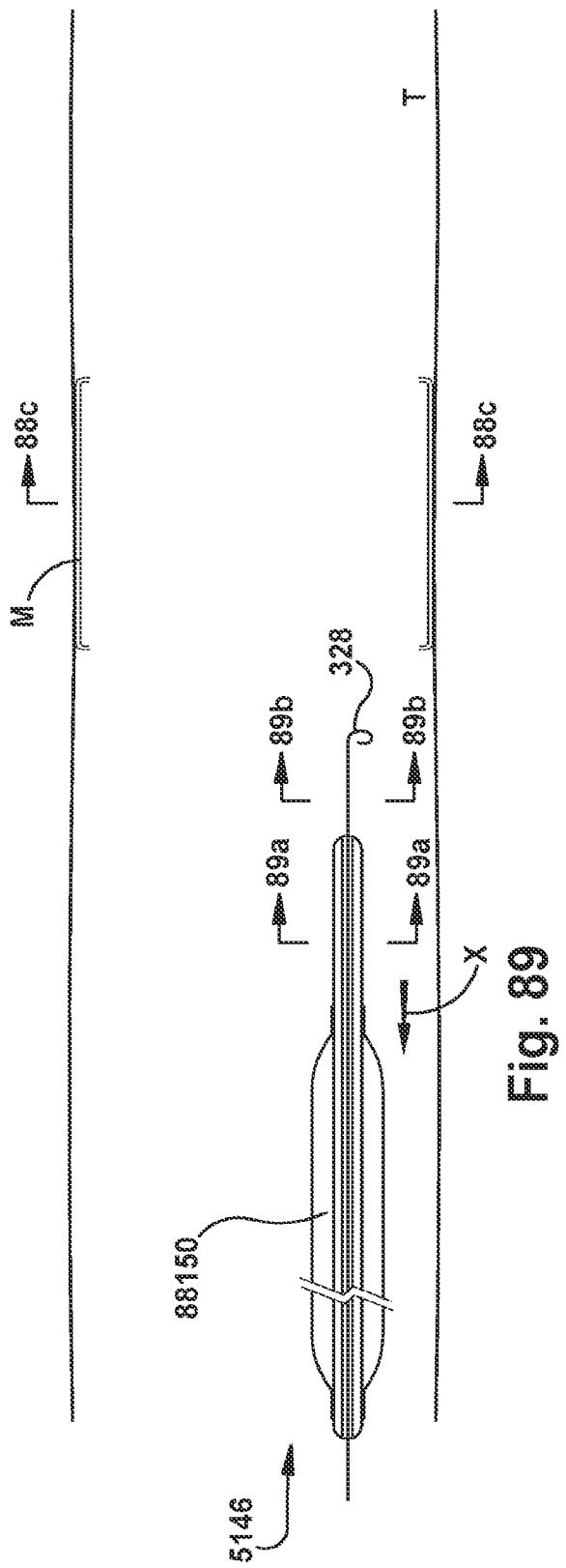
Figure 89C:
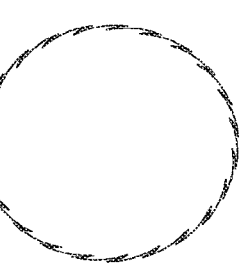
Figure 89B:
Figure 89A:
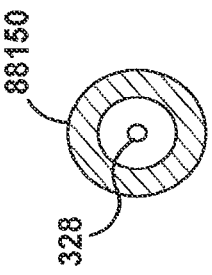

FIGS. 87a-g depict cross-sectional views of various points along the implant delivery system 5146, to show the arrangement of the secondary device 85144, the guidewire 328, and the expandable implant M in FIG. 87. FIGS. 88a-g depict cross-sectional views of various points along the implant delivery system 5146, to show the arrangement of the balloon dilation device 88150, the guidewire 328, and the expandable implant M in FIG. 88. As shown in FIG. 89, with the expandable implant M further expanded, the expandable balloon 69138 may be deflated. At least one of the balloon dilation device 88150 and the guidewire 328 may then be removed from the target patient tissue site T by moving at least one of the balloon dilation device 88159 and the guidewire 328 in the longitudinally proximal direction. FIGS. 89a-c depict cross-sectional views of various points along the implant delivery system 5146, to show the arrangement of the balloon dilation device 88150, the guidewire 328, and the expandable implant M in FIG. 89.

Figure 90:
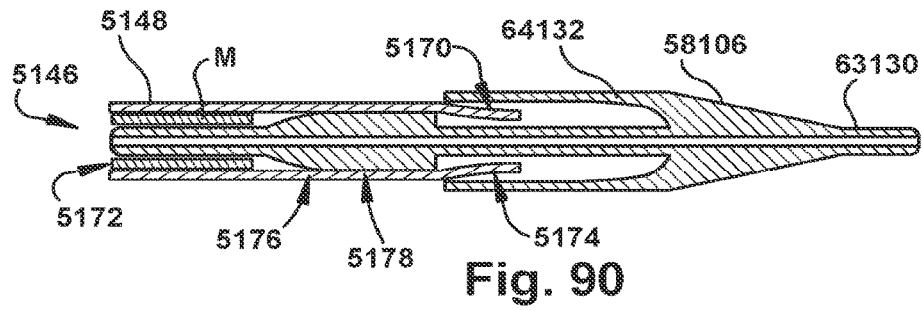
FIGS. 90-93 illustrate an example sequence of operation of a portion of the aspect of FIG. 78.

As shown in FIGS. 90-93, the conical head projection 58106 of the shaft E 63130 may have the at least one elastic clamp 64132 longitudinally extending in the proximal direction. When the shaft E 63130 is being aligned with the outer sheath 5148, as described above, the elastic clamp 64132 may be operatively engaged to the outer sheath 5148 by placing the elastic clamp 64132 on at least a portion of the implant holding pod outer surface 5170 that is adjacent to the implant holding pod open tip 5174, as is shown in FIG. 90. As shown in FIG. 90, when the elastic clamp 64132 is operatively engaged to the outer sheath, the elastic clamp 64132 is in the expanded condition. As described above, the elastic clamp 64132 at least partially selectively prevents the implant holding pod open slit first surface 5176 from elastically separating from the implant holding pod open slit second surface 5178 when the self-expanding implant M is disposed within the implant holding pod lumen 5172.

Figure 91:
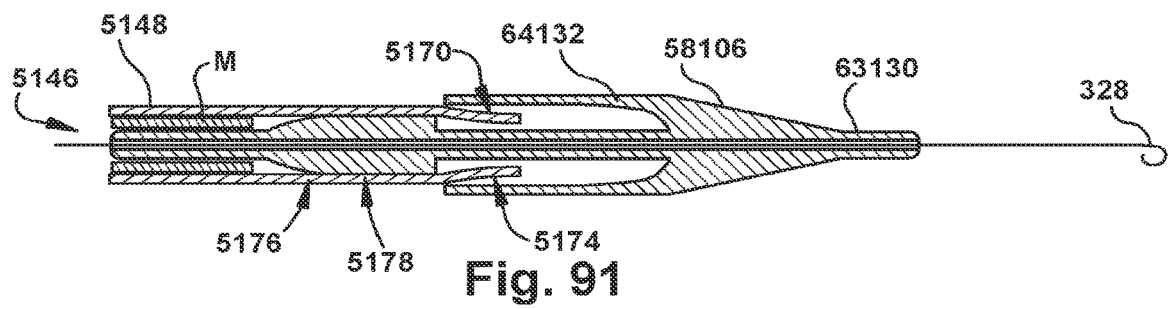
Figure 92:
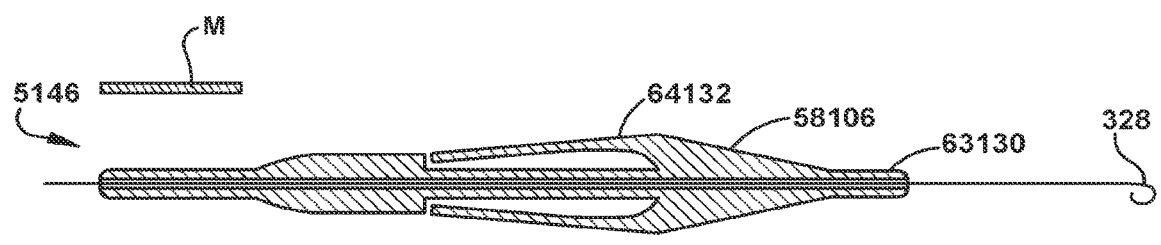
Figure 93:
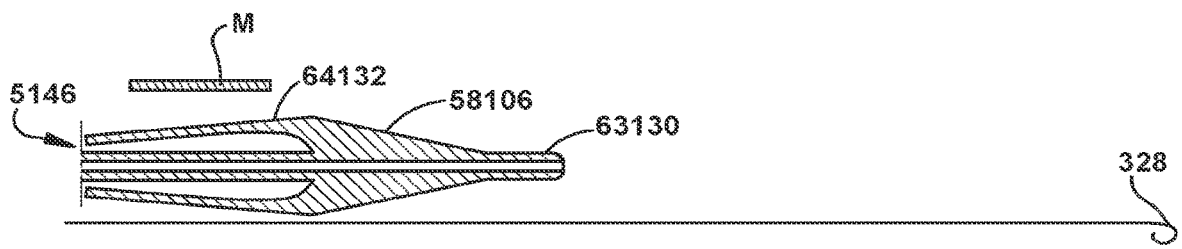

As shown in FIG. 91, the guidewire 328 may be directed through the implant delivery system 5146, as described above. When the outer sheath 5148 is directed in the longitudinally proximal direction, the outer sheath 5148 operatively disengages the elastic clamp 64132, which causes the elastic clamp 64132 to move from the expanded condition (FIG. 91) to the collapsed condition (FIG. 92). When desired by the user, as shown by FIG. 93, the implant delivery system 5146 may then be removed from the target patient tissue site T, while maintaining the guidewire 328 at the target patient tissue site T, as described above.

Although the above description of the example sequence of operation for the implant delivery system 5146 describes the shaft A 5892, the outer sheath A 5150, the shaft E 63130, and the outer sheath D 5186, any configuration for the shaft 5890 and the outer sheath 5148 may be operated in a similar sequence. For example, an example sequence of operation for the implant delivery system 5146 having a shaft B 59122 and outer sheath A 5150 may be as follows: the expandable implant M may be mounted circumferentially about the implant delivery element outer surface 58104. With the expandable implant M mounted to the implant delivery element outer surface 58104 and the expandable implant M in a collapsed condition, at least a portion of the shaft 5890 may be inserted at least partially into the implant holding pod lumen 5172. In particular, at least one of the shaft body 5898, the implant delivery element 58102, and the expandable implant M may be collectively inserted at least partially into the implant holding pod lumen 5172.

With at least a portion of the shaft B 59122 and expandable implant M at least partially inserted in the implant holding pod lumen 5172, the shaft B 59122 may be aligned in the implant holding pod lumen 5172 with at least a portion of the shaft open slit 58108 being laterally spaced from the implant holding pod open slit 5174. A guidewire distal end 2842 is inserted into a target patient tissue site T in a patient lumen. A guidewire proximal end 2844 is directed through the implant delivery system 5146. In particular, a guidewire proximal end 2844 may be directed through the implant holding pod open tip 5168, through at least a portion of the implant holding pod lumen 5172, through the implant delivery element open tip 59124, through the shaft lumen 58118 (thus, indirectly traveling through the implant holding pod lumen 5172 and the implant holding pod proximal opening 5166 of the outer sheath B 5180, as well), and out from the shaft B 59122, such as through the shaft side wall opening 58116. The implant delivery system 5146 may be directed to the target patient tissue site T as described above. The expandable implant M may be exposed to the target patient tissue site T in a similar sequence as described above. At least one of the shaft B 59122 and the outer sheath A 5150 may be removed from the guidewire 328 in a similar sequence as described above.

An example sequence of operation for the implant delivery system 5146 having a shaft A 5892 and an outer sheath B 5180 may be as follows: a collapsed expandable implant M may be placed in operative engagement with the implant delivery element 58102. In particular, the expandable implant M may be mounted circumferentially about the implant delivery element outer surface 58104. With the expandable implant M mounted to the implant delivery element outer surface 58104, and the expandable implant M in a collapsed condition, at least one of the shaft body 5898, the implant delivery element 58102, and the expandable implant M may be collectively inserted at least partially into the implant holding pod lumen 5172.

With at least a portion of the shaft A 5898 and the expandable implant M at least partially inserted in the implant holding pod lumen 5172, the shaft A 5898 may be aligned in the implant holding pod lumen 5172 with at least a portion of the shaft open slit 58108 being laterally spaced from the implant holding pod open slit 5174 and the shaft delivery element 58100 at least partially extending through the implant holding pod proximal opening 5166. A guidewire distal end 2842 is inserted into a target patient tissue site T in a patient lumen. A guidewire proximal end 2844 is directed through the implant delivery system 5146. In particular, a guidewire proximal end 2844 may be directed through the implant holding pod open tip 5168, through at least a portion of the implant holding pod lumen 5172, through the shaft lumen 58118 (thus, indirectly traveling through the implant holding pod lumen 5172 of the outer sheath B 5180, as well), through the shaft side wall opening 58116, and out from the outer sheath B 5180, such as through the implant holding pod side wall opening 5182. The implant delivery system 5146 may be directed to the target patient tissue site T as described above. The expandable implant M may be exposed to the target patient tissue site T in a similar sequence as described above. At least one of the shaft A 5892 and the outer sheath B 5180 may be removed from the guidewire 328 in a similar sequence as described above.

An example sequence of operation for the implant delivery system 5146 having a shaft C 60126 and an outer sheath A 5150 may be as follows: a collapsed expandable implant M may be placed within the implant holding pod lumen 5172. At least one of the shaft body 5898 and the implant delivery element 58102 is collectively inserted at least partially into the implant holding pod lumen 5172 of the outer sheath A 5150. The shaft C 60126 is aligned in the implant holding pod lumen 5172 with at least a portion of the shaft open slit 58108 being laterally spaced apart from the implant holding pod open slit 5174. The projection 58106 of the shaft C 60126 is placed in operative engagement with the expandable implant M by locating at least a portion of the projection 58106 in abutment with the expandable implant M.

A guidewire distal end 2842 is inserted into a target patient tissue site T in a patient lumen. A guidewire proximal end 2844 is directed through the implant delivery system 5146. In particular, a guidewire proximal end 2844 may be directed through the implant holding pod open tip 5168, through at least a portion of the implant holding pod lumen 5172, through the shaft lumen 58118, and out from the shaft C 60126, such as through the shaft side wall opening 58116. At the same time as the guidewire 328 is directed through the shaft lumen 58118, the guidewire 328 is directed through the implant holding pod proximal opening 5166. The implant delivery system 5146 may be directed to the target patient tissue site T as described above. The expandable implant M may be exposed to the target patient tissue site T in a similar sequence as described above. At least one of the shaft C 60126 and the outer sheath A 5150 may be removed from the guidewire 328 in a similar sequence as described above.

An example sequence of operation for the implant delivery system 5146 having a shaft G 68136 and an outer sheath A 5150 may be as follows: the following description may also be applicable to the shaft H 70142 and outer sheath A 5150. However, for brevity, only the shaft G 68136 and outer sheath A 5150 will be discussed below. A collapsed expandable implant M may be placed within the implant holding pod lumen 5172. At least one of the shaft body 5898 and the implant delivery element 58102 is collectively inserted at least partially into the implant holding pod lumen 5172 of the outer sheath A 5150. The shaft G 68136 is aligned in the implant holding pod lumen 5172 with at least a portion of the shaft open slit 58108 being laterally spaced apart from the implant holding pod open slit 5174. The projection 58106 of the shaft G 68136 is placed in operative engagement with the expandable implant M by locating at least a portion of the projection 58106 in abutment with the expandable implant M.

A guidewire distal end 2842 is inserted into a target patient tissue site T in a patient lumen. A guidewire proximal end 2844 is directed through the implant delivery system 5146. In particular, a guidewire proximal end 2844 may be directed through the implant holding pod open tip 5168, through at least a portion of the implant holding pod lumen 5172, through the shaft lumen 58118, and out from the shaft G 68136, such as through the shaft side wall opening 58116. At the same time as the guidewire 328 is directed through the shaft lumen 58118, the guidewire 328 is directed through the implant holding pod proximal opening 5166. The implant delivery system 5146 may be directed to the target patient tissue site T as described above. The expandable implant M may be exposed to the target patient tissue site T in a similar sequence as described above.

The expandable balloon 69138 may then be positioned adjacent to the expanded expandable implant M with at least a portion of the expandable balloon 69138 adjacent to the expandable implant inner surface MI. The expandable balloon 69138 may be inflated to cause the expandable implant M to further expand. With the expandable implant M further expanded, the expandable balloon 69138 may be deflated. At least one of the shaft G 68136 and the outer sheath A 5150 may be removed from the guidewire 328 in a similar sequence as described above.

An example sequence of operation for the implant delivery system 5146 having a shaft G 68136 and an outer sheath C 5184 may be as follows: the following description may also be applicable to a shaft H 70142 with an outer sheath C 5184, a shaft F 68134 with an outer sheath C 5184, a shaft E 63130 with an outer sheath C 5184, a shaft D 62128 with an outer sheath C 5184, a shaft G 68136 with an outer sheath D 5186, a shaft H 70142 with an outer sheath D 5186, a shaft F 68134 with an outer sheath D 5186, a shaft E 63130 with an outer sheath D 5186, a shaft D 62128 with an outer sheath D 5186. However, for brevity, only the shaft G 68136 and outer sheath C 5184 will be discussed below. A collapsed expandable implant M may be placed within the implant holding pod lumen 5172. At least one of the shaft body 5898 and the implant delivery element 58102 at least partially into the implant holding pod lumen 5172 of the outer sheath C 5184. The shaft G 68136 is aligned in the implant holding pod lumen 5172 with at least a portion of the shaft open slit 58108 being laterally spaced apart from the implant holding pod open slit 5174 and at least one of the shaft delivery element 58100 and the shaft body 5898 at least partially extending through the implant holding pod proximal opening 5166. The projection 58106 of the shaft G 68136 is placed in operative engagement with the expandable implant M by locating at least a portion of the projection 58106 in abutment with the expandable implant M.

A guidewire distal end 2842 is inserted into a target patient tissue site T in a patient lumen. A guidewire proximal end 2844 is directed through the implant delivery system 5146. In particular, a guidewire proximal end 2844 may be directed through the implant holding pod open tip 5168, through at least a portion of the implant holding pod lumen 5172, through the implant delivery element open tip 59124, through the shaft lumen 58118 (thus, indirectly traveling at least partially through the implant holding pod lumen 5172 of the outer sheath C 5184, as well), through the shaft side wall opening 58116, and out from the outer sheath C 5184, such as through the implant holding pod side wall opening 5182. The implant delivery system 5146 may be directed to the target patient tissue site T as described above. The expandable implant M may be exposed to the target patient tissue site T in a similar sequence as described above.

In the case of shafts G and H 69136, 70142, the expandable balloon 69138 may then be positioned adjacent to the expanded expandable implant M with at least a portion of the expandable balloon 69138 adjacent to the expandable implant inner surface MI. The expandable balloon 69138 may be inflated to cause the expandable implant M to further expand. With the expandable implant M further expanded, the expandable balloon 69138 may be deflated. At least one of the shaft G 68136 and the outer sheath C 5184 may be removed from the guidewire 328 in a similar sequence as described above.

Any of the alternate outer sheath 5148 configurations, the alternate shaft 5890 configurations, the secondary device 85144, when provided, and the balloon dilation device 88150, when provided, of the implant delivery system 5146 may be at least partially formed from silicone, polyethylene, polypropylene, stainless steel, titanium, rubber, latex, polychloroprene, nylon, any other biocompatible material, or any combination thereof.

The expandable implant M may be at least partially formed from a shape memory material, such as, but not limited to, Nitinol. The shape memory expandable implant M is configured to be preset in the expanded condition above a transition temperature range. The shape memory expandable implant M is able to be deformed into the collapsed condition from the expanded condition when the expandable implant M is cooled to a temperature below a transition temperature range. The transition temperature range is dependent on the particular ratio of metals and/or materials in the shape memory material. Below the transition temperature range, the shape memory material is highly ductile and may be plastically deformed into a desired shape, such as the collapsed condition. Upon reheating above the transition temperature range, the shape memory material returns to its preset shape, such as the expanded condition. In other words, the shape memory expandable implant M is configured to automatically return to the expanded condition when the expandable implant M is at a temperature above the transition temperature range. The shape memory material may be at a temperature above its transition temperature range when the temperature of the shape memory material is equal to, and/or greater than the temperature of a normal patient body. The expandable implant M may be cooled to a temperature below the transition temperature range, moved to the collapsed condition, and mounted on the implant delivery element outer surface 58108, and/or within the implant holding pod lumen 5172. When the expandable implant M is exposed at the target patient tissue site T, the temperature of the environment at the target patient tissue site T at least partially causes the expandable implant M to move from the collapsed condition toward the expanded condition.

It is contemplated that at least one of the alternate outer sheath 5148 configuration, the alternate shaft 5890 configurations, and the secondary device 85144, when provided, of the implant delivery system 5146 may be disposed within one or more conventional sheaths to deliver at least a portion of the implant delivery system 5146 to the target patient tissue site T through a patient tissue access point P.

It is contemplated that the implant delivery system 5146 may provide the user with the ability to deliver at least one of the alternate outer sheath 5148 configurations, the alternate shaft 5890 configurations, and the secondary device 85144, when provided, to a target patient tissue site T of a patient lumen along a guidewire 328 and remove at least one of the alternate outer sheath 5148 configurations, the alternate shaft 5890 configurations, and the secondary device 85144, when provided, from the guidewire 328 in the patient lumen. This allows the user to direct another alternate outer sheath 5148 configuration, alternate shaft 5890 configuration, and/or secondary device 85144, when provided, to the target patient tissue site T of the patient lumen, without having to remove at least one of the alternate outer sheath 5148 configuration, the alternate shaft 5890 configuration, and the secondary device 85144, when provided, outside of the patient lumen.

Further, the implant delivery system 5146 provides the user with the ability to direct at least one of the alternate outer sheath 5148 configurations, the alternate shaft 5890 configurations, the secondary device 85144, when provided, through a single patient tissue access point P. The ability to insert at least one of the alternate outer sheath 5148 configurations, the alternate shaft 5890 configurations, the secondary device 85144, when provided, into a target patient tissue site T over a single guidewire may assist in reducing radiation exposure, procedure time, potential trauma, complications, and/or risks to the patient that result from the need, in conventional systems, to fully remove the outer sheath with shaft outside of the patient lumen before a secondary device can be direct into the patient lumen. The ability to insert at least one of the alternate outer sheath 5148 configurations, the alternate shaft 5890 configurations, the secondary device 85144, when provided, into a target patient tissue site T through a single patient tissue access point P may assist in reducing potential trauma, complications, and/or risks to the patient that result from the creation of multiple patient tissue access points P. For example, if an outer sheath C 60126 with a shaft E 63130, and a balloon dilation device 88150 were inserted through two or more separate patient tissue access points P, the trauma, risks, and complications associated with said insertions could be increased as compared to the insertion of the outer sheath C 60126 with the shaft E 63130, and the balloon dilation device 88150 through a single patient tissue access point P. Further, the ability to use a single patient tissue access point P instead of having to create multiple patient tissue access points P may reduce the procedure time and the costs that would be associated with creating multiple patient tissue access points P.

It is contemplated that at least one of the alternate outer sheath 5148 configurations, the alternate shaft 5890 configurations, the secondary device 85144, when provided, and the expandable implant, when provided, of the implant delivery system 5146 may be prearranged, and/or pre-packaged prior to use. For example, a shaft 5890 may be prearranged with an outer sheath 5148 such that an outer sheath splitter 58120, when provided, is at least partially engaged with the implant holding pod open slit 5174 of the outer sheath 5148.

A balloon dilation device 88150, which could be similar to the balloon dilation device 88150 that is previously discussed for FIG. 88, is provided. The balloon dilation device 88150 may include a number of alternate configurations, which will be discussed below. FIGS. 94-97 depict example alternative configurations of the balloon dilation device 88150. FIG. 94 depicts an example alternative configuration for the balloon dilation device 88150, referred to as the balloon dilation device A 94170. The balloon dilation device A 94170 may have a balloon dilation rod 88152. The balloon dilation rod 88152 has a balloon dilation rod proximal end 88154, a balloon dilation rod distal end 88156, and an elongate balloon dilation rod body 88158 that longitudinally extends between the balloon dilation rod proximal and distal ends 88154, 88156. The balloon dilation rod 88152 has a balloon dilation rod outer surface 88160 and a balloon dilation rod lumen 88162.

The balloon dilation rod 88152 has a balloon dilation rod side wall opening 88164. The balloon dilation rod side wall opening 88164 selectively places the balloon dilation rod outer surface 88160 in fluid communication with the balloon dilation rod lumen 88162. The balloon dilation rod distal end 88156 has a balloon dilation rod open tip 88166. The balloon dilation rod lumen 88162 of the balloon dilation device A 94170 may extend between the balloon dilation rod side wall opening 88164 and the balloon dilation rod open tip 88168. The balloon dilation rod 88152 has a balloon dilation rod open slit 88168. The balloon dilation rod open slit 88168 may extend between the balloon dilation rod side wall opening 88164 and the balloon dilation rod open tip 88166.

The balloon dilation rod open slit 88168 has a balloon dilation rod open slit first surface 94172 and a balloon dilation rod open slit second surface 94174. The balloon dilation rod open slit first surface 94172 oppositely faces and abuts the balloon dilation rod open slit second surface 94174. The balloon dilation rod open slit first surface 94172 and the balloon dilation rod open slit second surface 94174 are selectively elastically separable. That is, a force may be applied to separate the balloon dilation rod open slit first surface 94172 and the balloon dilation rod open slit second surface 94174, as that the balloon dilation rod open slit first surface 94172 will no longer be abutting the balloon dilation rod open slit second surface 94174. However, upon the removal of the separating force, the balloon dilation rod open slit first surface 94172 and the balloon dilation rod open slit second surface 94174 will tend to return toward their original abutting position due to the elastic nature of the material forming the balloon dilation rod open slit first surface 94172 and the balloon dilation rod open slit second surface 94174.

An expandable balloon 69138 may be positioned on at least one of the balloon dilation rod body 88158 and the balloon dilation rod distal end 88156. The expandable balloon 69138 may have a balloon open slit 69140 that at least partially extends for at least a partial length of the expandable balloon 69138. The balloon open slit 69140 may be aligned with the balloon dilation rod open slit 88168. The balloon dilation device A 94170 may include a balloon inflation channel 94176 that longitudinally extends between the balloon dilation rod proximal end 88154 and a balloon inflation side wall opening 94178. The balloon inflation channel 94176 may be placed in fluid communication with an outside fluid source (not shown) in any desired manner. The balloon inflation side wall opening 94178 selectively places a balloon expanding chamber 94180 in fluid communication with at least one of the balloon inflation channel 94176 and the outside fluid source. The balloon inflation channel 94176 may be at least partially located within, or separate from, the balloon dilation rod lumen 88162.

The balloon dilation device A 94170 may include a guidewire path 326 for a guidewire 328 to be directed through the balloon dilation rod open tip 88168, through at least a portion of the balloon dilation rod lumen 88162, and out from the balloon dilation device A 94170, such as through the balloon dilation rod side wall opening 88164. FIGS. 94*a-g* depict cross-sectional views of various points along the balloon dilation device A 94170, to show the structural features of the balloon dilation device A 94170 in FIG. 94.

FIG. 95 depicts an example alternative configuration for the balloon dilation device 88150, referred to as the balloon dilation device B 95182. The balloon dilation device B 95182 may have a balloon dilation rod 88152. The balloon dilation rod 88152 has a balloon dilation rod proximal end 88154, a balloon dilation rod distal end 88156, and an elongate balloon dilation rod body 88158 that longitudinally extends between the balloon dilation rod proximal and distal ends 88154, 88156. The balloon dilation rod 88152 has a balloon dilation rod outer surface 88160 and a balloon dilation rod lumen 88162.

The balloon dilation rod 88152 has a balloon dilation rod side wall opening 88164. The balloon dilation rod side wall opening 88164 selectively places the balloon dilation rod outer surface 88160 in fluid communication with the balloon dilation rod lumen 88162. The balloon dilation rod distal end 88156 has a balloon dilation rod open tip 88166. The balloon dilation rod lumen 88162 of the balloon dilation device B 95182 may extend between the balloon dilation rod open tip 88168 and at least one of the balloon dilation rod proximal end 88154 and the balloon dilation rod side wall opening 88164. The balloon dilation rod 88152 has a balloon dilation rod open slit 88168. The balloon dilation rod open slit 88168 may extend between the balloon dilation rod side wall opening 88164 and the balloon dilation rod open tip 88166. The balloon dilation rod open slit 88168 has a balloon dilation rod open slit first surface 94172 and a balloon dilation rod open slit second surface 94174. The balloon dilation rod open slit first surface 94172 oppositely faces and abuts the balloon dilation rod open slit second surface 94174. The balloon dilation rod open slit first surface 94172 and the balloon dilation rod open slit second surface 94174 are selectively elastically separable.

An expandable balloon 69138 may be positioned on at least one of the balloon dilation rod body 88158 and the balloon dilation rod distal end 88156. The expandable balloon 69138 may have a balloon open slit 69140 that at least partially extends for at least a partial length of the expandable balloon 69138. The balloon open slit 69140 may be aligned with the balloon dilation rod open slit 88168. The balloon dilation device B 95182 may include a balloon inflation channel 94176 that longitudinally extends between the balloon dilation rod proximal end 88154 and a balloon inflation side wall opening 94178. The balloon inflation channel 94176 may be placed in fluid communication with an outside fluid source (not shown) in any desired manner. The balloon inflation side wall opening 94178 selectively places a balloon expanding chamber 94180 in fluid communication with at least one of the balloon inflation channel 94176 and the outside fluid source. The balloon inflation channel 94176 may be at least partially located within, or separate from, the balloon dilation rod lumen 88162.

The balloon dilation device B 95182 may include a guidewire path 326 for a guidewire 328 to be directed through the balloon dilation rod open tip 88168, through at least a portion of the balloon dilation rod lumen 88162, and out from the balloon dilation device A 94170, such as through at least one of the balloon dilation rod proximal end 88154 and the balloon dilation rod side wall opening 88164. One or more guidewires 328 may be inserted through each, or both, of the guidewire paths 326 shown in FIG. 95. FIGS. 95*a-g* depict cross-sectional views of various points along the balloon dilation device B 95182, to show the arrangement of the balloon dilation device B 95182 and the guidewire 328 in FIG. 95.

FIG. 96 depicts an example alternative configuration for the balloon dilation device 88150, referred to as the balloon dilation device C 96184. The balloon dilation device C 96184 may have a balloon dilation rod 88152. The balloon dilation rod 88152 has a balloon dilation rod proximal end 88154, a balloon dilation rod distal end 88156, and an elongate balloon dilation rod body 88158 that longitudinally extends between the balloon dilation rod proximal and distal ends 88154, 88156. The balloon dilation rod 88152 has a balloon dilation rod outer surface 88160 and a balloon dilation rod lumen 88162.

The balloon dilation rod 88152 has a balloon dilation rod side wall opening 88164. The balloon dilation rod side wall opening 88164 selectively places the balloon dilation rod outer surface 88160 in fluid communication with the balloon dilation rod lumen 88162. The balloon dilation rod distal end 88156 has a balloon dilation rod open tip 88166. The balloon dilation rod lumen 88162 of the balloon dilation device C 96184 may extend between the balloon dilation rod side wall opening 88164 and the balloon dilation rod open tip 88168. The balloon dilation rod 88152 has a balloon dilation rod open slit 88168. The balloon dilation rod open slit 88168 may extend between the balloon dilation rod side wall opening 88164 and the balloon dilation rod open tip 88166. The balloon dilation rod open slit 88168 has a balloon dilation rod open slit first surface 94172 and a balloon dilation rod open slit second surface 94174. The balloon dilation rod open slit first surface 94172 oppositely faces and abuts the balloon dilation rod open slit second surface 94174. The balloon dilation rod open slit first surface 94172 and the balloon dilation rod open slit second surface 94174 are selectively elastically separable.

An expandable balloon 69138 may be positioned on at least one of the balloon dilation rod body 88158 and the balloon dilation rod distal end 88156. The expandable balloon 69138 may have a balloon open slit 69140 that at least partially extends for at least a partial length of the expandable balloon 69138. The balloon open slit 69140 may be aligned with the balloon dilation rod open slit 88168. The balloon dilation device C 96184 may include a balloon inflation channel 94176 that longitudinally extends between the balloon dilation rod proximal end 88154 and a balloon inflation side wall opening 94178. The balloon inflation channel 94176 may be placed in fluid communication with an outside fluid source (not shown) in any desired manner. The balloon inflation side wall opening 94178 selectively places a balloon expanding chamber 94180 in fluid communication with at least one of the balloon inflation channel 94176 and the outside fluid source. The balloon inflation channel 94176 may be at least partially located within, or separate from, the balloon dilation rod lumen 88162.

The balloon dilation device C 96184 may include a guidewire path 326 for a guidewire 328 to be directed through the balloon dilation rod open tip 88168, through at least a portion of the balloon dilation rod lumen 88162, and out from the balloon dilation device C 96184, such as through the balloon dilation rod side wall opening 88164. An expandable implant M may be removably mounted circumferentially about at least a portion of the expandable balloon 69138 of the balloon dilation device C 96184. FIGS. 96*a-g* depict cross-sectional views of various points along the balloon dilation device C 96184, to show the arrangement of the balloon dilation device C 96184, the guidewire 328, and the expandable implant M in FIG. 96.

FIG. 97 depicts an example alternative configuration for the balloon dilation device 88150, referred to as the balloon dilation device D 97186. The configuration shown in FIG. 97 may be, for some use environments, similar to that of FIG. 70. The balloon dilation device D 97186 shown in FIG. 97 may have a balloon dilation rod 88152. The balloon dilation rod 88152 has a balloon dilation rod proximal end 88154, a balloon dilation rod distal end 88156, and an elongate balloon dilation rod body 88158 that longitudinally extends between the balloon dilation rod proximal and distal ends 88154, 88156. The balloon dilation rod 88152 has a balloon dilation rod outer surface 88160 and a balloon dilation rod lumen 88162.

The balloon dilation rod 88152 has a balloon dilation rod side wall opening 88164. The balloon dilation rod side wall opening 88164 selectively places the balloon dilation rod outer surface 88160 in fluid communication with the balloon dilation rod lumen 88162. The balloon dilation rod distal end 88156 has a balloon dilation rod open tip 88166. The balloon dilation rod lumen 88162 of the balloon dilation device D 97186 may extend between the balloon dilation rod side wall opening 88164 and the balloon dilation rod open tip 88168. The balloon dilation rod 88152 has a balloon dilation rod open slit 88168. The balloon dilation rod open slit 88168 may extend between the balloon dilation rod side wall opening 88164 and the balloon dilation rod open tip 88166. The balloon dilation rod open slit 88168 has a balloon dilation rod open slit first surface 94172 and a balloon dilation rod open slit second surface 94174. The balloon dilation rod open slit first surface 94172 oppositely faces and abuts the balloon dilation rod open slit second surface 94174. The balloon dilation rod open slit first surface 94172 and the balloon dilation rod open slit second surface 94174 are selectively elastically separable.

An expandable balloon 69138 may be positioned on at least one of the balloon dilation rod body 88158 and the balloon dilation rod distal end 88156. The expandable balloon 69138 may have a balloon open slit 69140 that at least partially extends for at least a partial length of the expandable balloon 69138. The balloon open slit 69140 may be aligned with the balloon dilation rod open slit 88168. The balloon dilation device C 96184 may include a balloon inflation channel 94176 that longitudinally extends between the balloon dilation rod proximal end 88154 and a balloon inflation side wall opening 94178. The balloon inflation channel 94176 may be placed in fluid communication with an outside fluid source (not shown) in any desired manner. The balloon inflation side wall opening 94178 selectively places a balloon expanding chamber 94180 in fluid communication with at least one of the balloon inflation channel 94176 and the outside fluid source. The balloon inflation channel 94176 may be at least partially located within, or separate from, the balloon dilation rod lumen 88162.

The balloon dilation device D 97186 may include a guidewire path 326 for a guidewire 328 to be directed through the balloon dilation rod open tip 88168, through at least a portion of the balloon dilation rod lumen 88162, and out from the balloon dilation device D 97186, such as through the balloon dilation rod side wall opening 88164. The balloon dilation rod distal end 88156 of the balloon dilation device D 97186 may have a radially extending projection 58106. The projection 58106 may be a radially extending conical head. The conical head may point, or narrow, toward a longitudinally distal direction (shown as an arrow Y in FIG. 97). The balloon dilation rod distal end 88156 may have an outer sheath splitter 58120 for facilitating the elastic separation of another device having an open slit. For example, the outer sheath splitter 58120 may facilitate the elastic separation of the implant holding pod open slit first surface 5176 and the implant holding pod open slit second surface 5178 when the balloon dilation device D 97186 is used in conjunction with an outer sheath 5148, as previously discussed. FIGS. 97*a-d* depict cross-sectional views of various points along the balloon dilation device D 97186, to show the structural features of the balloon dilation device D 97186 in FIG. 97.

As shown in FIG. 98, the outer sheath splitter 58120 of the balloon dilation device D 97186 may be arrow-shaped. The arrow-shaped outer sheath splitter 58120 may point toward a longitudinally distal direction (shown as an arrow Y in FIG. 98). As shown in FIG. 99, at least a portion of the balloon dilation rod body 88158 and the balloon dilation rod distal end 88156 of the balloon dilation device D 97186 might not have the balloon dilation rod open slit 88168. FIGS. 99*a-c* depict cross-sectional views of various points along the balloon dilation device D 97186, to show the structural features of the balloon dilation device D 97186 in FIG. 99. Although the balloon dilation device D 97186 is shown having the outer sheath splitter 58120, the arrow-shaped outer sheath splitter 58120, and/or at least one of the balloon dilation rod body 88158 and the balloon dilation rod distal end 88156 not having the balloon dilation rod open slit 88168, any of the alternate balloon dilation device 88150 configurations may have at least one of these features.

As shown in FIGS. 100-108, the expandable balloon 69138 of the balloon dilation device 88150 may include any of a number of alternate configurations, which will be discussed below, or may have any other configuration, as desired. FIG. 100 depicts an example alternative configuration for the expandable balloon 69138, referred to as the expandable balloon A 100188. The expandable balloon A 100188 may include a plurality of expandable sub-balloons 100190 positioned circumferentially about at least one of the balloon dilation rod body 88158 and the balloon dilation rod distal end 88156. The balloon open slit 69140 may be positioned between a selected one of the plurality of expandable sub-balloons 100190 and an adjacent other one of the plurality of expandable sub-balloons 100190. As previously discussed, the balloon open slit 69140 may be aligned with the balloon dilation rod open slit 88168.

FIG. 101 depicts an example alternative configuration for the expandable balloon 69138, referred to as the expandable balloon B 101192. The expandable balloon B 101192 may include a plurality of expandable sub-balloons 100190 positioned circumferentially about at least one of the balloon dilation rod body 88158 and the balloon dilation rod distal end 88156. The balloon open slit 69140 may be positioned between a selected one of the plurality of expandable sub-balloons 100190 and an adjacent other one of the plurality of expandable sub-balloons 100190. As previously discussed, the balloon open slit 69140 may be aligned with the balloon dilation rod open slit 88168.

Each of the plurality of expandable sub-balloons 100190 of the expandable balloon B 101192 may have a separate sub-balloon inflation channel 101194 therein. Each separate sub-balloon inflation channel 101194 may allow for each of the expandable sub-balloons 100190 to be separately inflated/deflated to differing degrees. Each of the separate sub-balloon inflation channels 101194 may act as a stiffener to at least partially provide stability for the plurality of expandable sub-balloons 100190. Although only the expandable balloon B 101192 is shown as having the sub-balloon inflation channels 101194, any of the alternate expandable balloon 69138 configurations may have at least one sub-balloon inflation channel 101194.

FIG. 102 depicts an example alternative configuration for the expandable balloon 69138, referred to as the expandable balloon C 102196. The expandable balloon C 102196 may include a plurality of expandable sub-balloons 100190 positioned circumferentially about at least one of the balloon dilation rod body 88158 and the balloon dilation rod distal end 88156. The expandable balloon C 102196 may include an elastic cover 102198 that at least partially encapsulates the plurality of expandable sub-balloons 100190 between an elastic cover inner surface 102200 and the balloon dilation rod outer surface 88160. At least a portion of the elastic cover 102198 may be attached to at least a portion of the balloon dilation rod lumen 88162 so that at least a portion of the elastic cover 102198 forms a portion of the balloon dilation rod lumen 88162. The elastic cover 102198 may form an elastic cover open slit 102202 that is aligned with, and at least partially contacting, the balloon dilation rod open slit 88168. The elastic cover open slit 102202 may be positioned between a chosen one of the plurality of expandable sub-balloons 100190 and an adjacent other one of the plurality of expandable sub-balloons 100190, so that the elastic cover open slit 102202 is aligned with the balloon open slit 69140.

FIG. 103 depicts an example alternative configuration for the expandable balloon 69138, referred to as the expandable balloon D 103204. The expandable balloon D 103204 may include a plurality of expandable sub-balloons 100190 positioned circumferentially about at least one of the balloon dilation rod body 88158 and the balloon dilation rod distal end 88156. The expandable balloon D 103204 may include an elastic cover 102198 that at least partially encapsulates the plurality of expandable sub-balloons 100190 between an elastic cover inner surface 102200 and the balloon dilation rod outer surface 88160. At least a portion of the elastic cover 102198 may be attached to at least a portion of the balloon dilation rod lumen 88162 so that at least a portion of the elastic cover 102198 forms a portion of the balloon dilation rod lumen 88162. At least a portion of the elastic cover 102198 may be attached to a portion of the balloon dilation rod open slit 88168 and to at least a portion of balloon dilation rod outer surface 88160 adjacent to the balloon dilation rod open slit 88168.

The elastic cover 102198 may be attached to the balloon dilation rod lumen 88162 at least partially by a balloon fixer 103206. The balloon fixer 103206 has a balloon fixer inner lumen 103208 and a balloon fixer outer surface 103210. The balloon fixer 103206 has a balloon fixer open slit 103212 that places the balloon fixer outer surface 103210 in fluid communication with the balloon fixer inner lumen 103208. The balloon fixer 103206 may be disposed within at least a portion of the balloon dilation rod lumen 88162. The balloon fixer 103206 may be disposed on the portion of the elastic cover 102198 that forms a portion of the balloon dilation rod lumen 88162. The balloon fixer inner lumen 103208 may be in fluid communication with the balloon dilation rod lumen 88162. The balloon fixer open slit 103212 may be selectively aligned with the balloon dilation rod open slit 88168. The elastic cover 102198 may form an elastic cover open slit 102202 that is aligned with, and at least partially contacting, at least one of the balloon dilation rod open slit 88168 and the balloon fixer open slit 103212. The elastic cover open slit 102202 may be positioned between a selected one of the plurality of expandable sub-balloons 100190 and an adjacent other one of the plurality of expandable sub-balloons 100190, so that the elastic cover open slit 102202 is aligned with the balloon open slit 69140. At least a portion of the elastic cover 102198 may be attached to a portion of the balloon dilation rod open slit 88168 and to at least a portion of balloon dilation rod outer surface 88160 adjacent to the balloon dilation rod open slit 88168.

FIG. 104 depicts an example alternative configuration for the expandable balloon 69138, referred to as the expandable balloon E 104214. At least a portion of the expandable balloon E 104214 may be attached to at least a portion of the balloon dilation rod lumen 88162 so that at least a portion of the expandable balloon E 104214 forms at least a portion of the balloon dilation rod lumen 88162. The expandable balloon E 104214 may be attached to the balloon dilation rod lumen 88162 at least partially by a balloon fixer 103206. The balloon fixer 103206 has a balloon fixer inner lumen 103208 and a balloon fixer outer surface 103210. The balloon fixer 103206 has a balloon fixer open slit 103212 that places the balloon fixer outer surface 103210 in fluid communication with the balloon fixer inner lumen 103208. The balloon fixer 103206 may be disposed within at least a portion of the balloon dilation rod lumen 88162. The balloon fixer 103206 may be disposed on the portion of the expandable balloon E 104214 that forms a portion of the balloon dilation rod lumen 88162. The balloon fixer inner lumen 103208 may be in fluid communication with the balloon dilation rod lumen 88162. The balloon fixer open slit 103212 may be selectively aligned with the balloon dilation rod open slit 88168.

The expandable balloon E 104214 may form a balloon open slit 69140 that is aligned with, and at least partially contacting, at least one of the balloon dilation rod open slit 88168 and the balloon fixer open slit 103212. As shown in FIG. 105, at least a portion of the expandable balloon E 104214 may be attached to a portion of the balloon dilation rod open slit 88168 and to at least a portion of the balloon dilation rod outer surface 88160 that is adjacent to the balloon dilation rod open slit 88168. FIG. 106 depicts the expandable balloon E 104214 that is at least partially attached to at least one of the balloon dilation rod lumen 88162 and the balloon dilation rod open slit 88168. FIG. 107 depicts the expandable balloon E 104214 that is at least partially attached to at least one of the balloon dilation rod lumen 88162, the balloon dilation rod open slit 88168, and the balloon dilation rod outer surface 88160.

Figure 108:
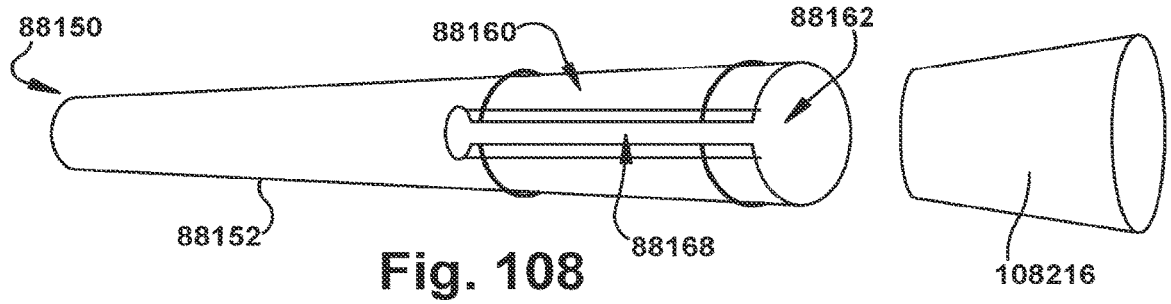
FIGS. 108-115 illustrate an example sequence of constructing a portion of the aspect of FIG. 104.
Figure 109:
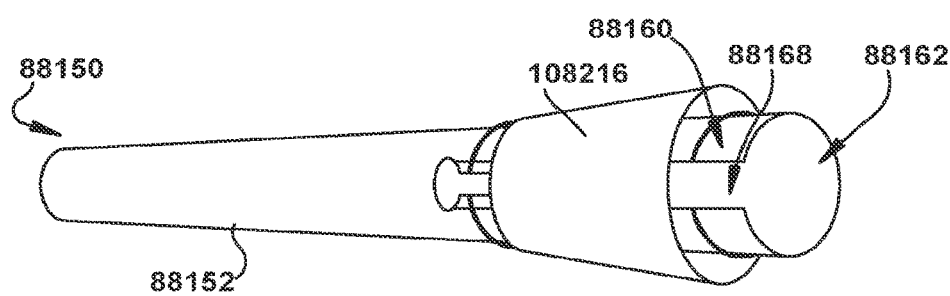
Figure 110:
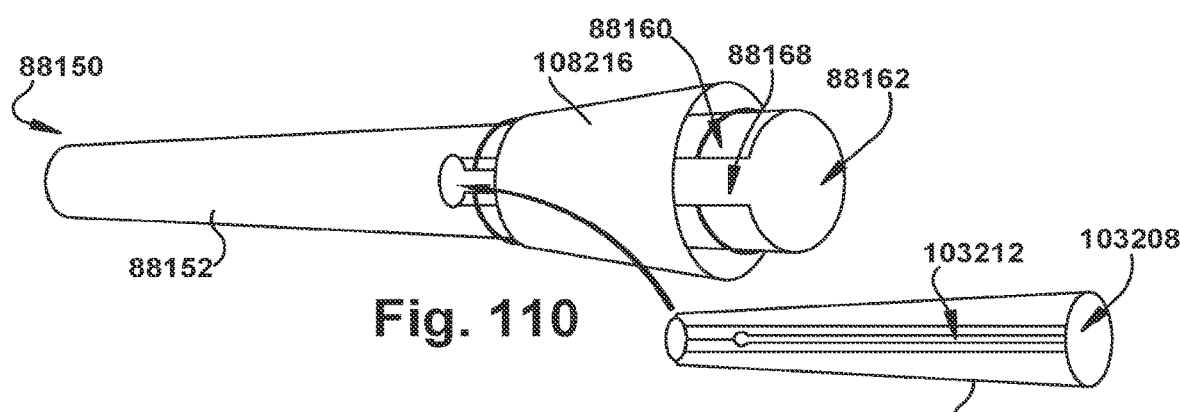
Figure 111:
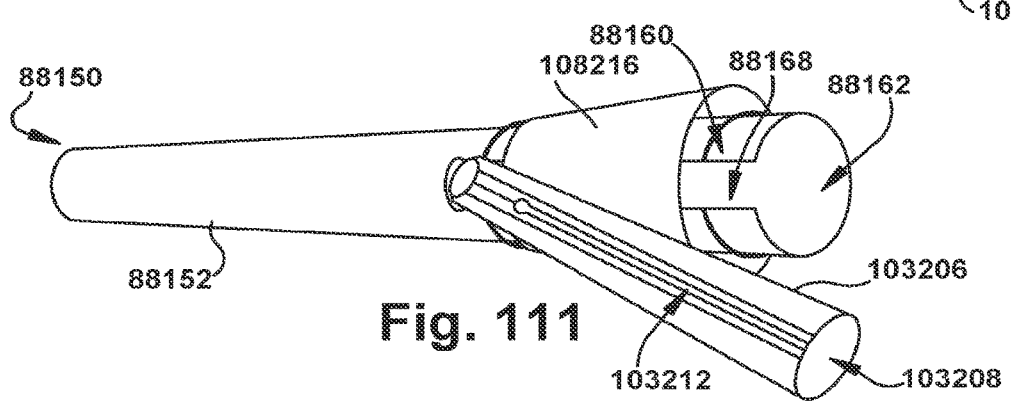

To construct the balloon dilation device 88150, a balloon dilation rod 88152, as previously described, is provided. As shown in FIGS. 108-109, a balloon material 108216 may be placed at least partially circumferentially about the balloon dilation rod outer surface 88160 so that at least a portion of the balloon material 108216 is adjacent to at least a portion of the balloon dilation rod open slit 88168. At least a portion of the balloon material 108216 is urged through the balloon dilation rod open slit 88168 and into the balloon dilation rod lumen 88162. At least a portion of the balloon material 108216 inserted into the balloon dilation rod lumen 88162 is attached to at least a portion of the balloon dilation rod lumen 88162. The portion of the balloon material 108216 attached to the portion of the balloon dilation rod lumen 88162 may form at least a portion of the balloon dilation rod lumen 88162. The balloon material 108216 may form a balloon open slit 69140 that is aligned with the balloon dilation rod open slit 88168 when the balloon material 108216 is attached to the balloon dilation rod lumen 88162.

As shown in FIGS. 110-113, a balloon fixer 103206, as previously described, may be inserted through the balloon dilation rod open slit 88168 and into the balloon dilation rod lumen 88162. The balloon fixer lumen 103208 may be in fluid communication with the balloon dilation rod lumen 88162 when the balloon fixer 103206 is inserted within at least a portion of the balloon dilation rod lumen 88162. The balloon fixer 103206 is disposed on a portion of the balloon material 108216 that forms a portion of the balloon dilation rod lumen 88162. The balloon fixer 103206 is aligned with the balloon fixer open slit 103212 aligned with the balloon dilation rod open slit 88168.

Figure 112:
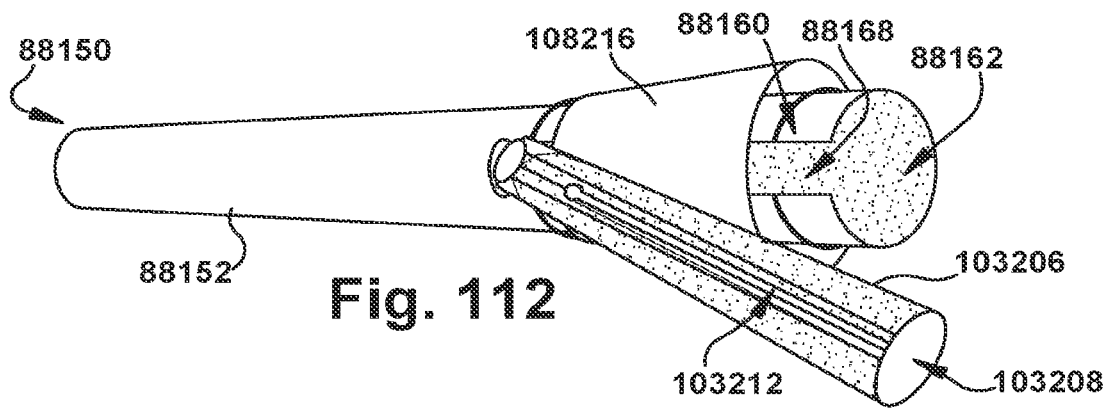
Figure 113:
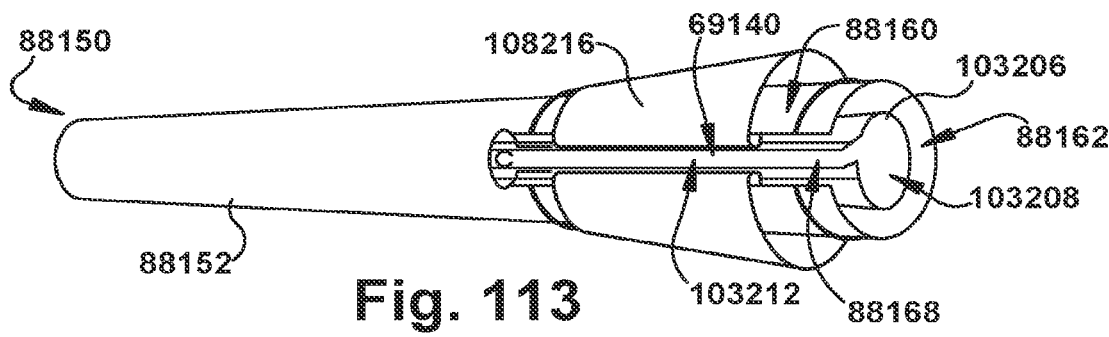
Figure 114:
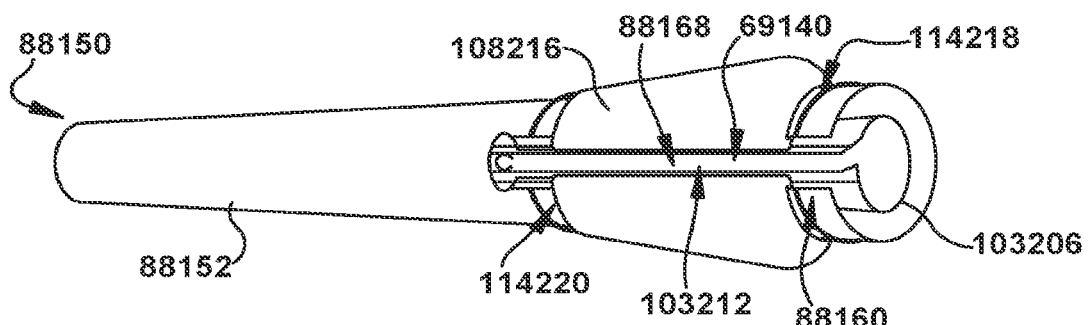
Figure 115:
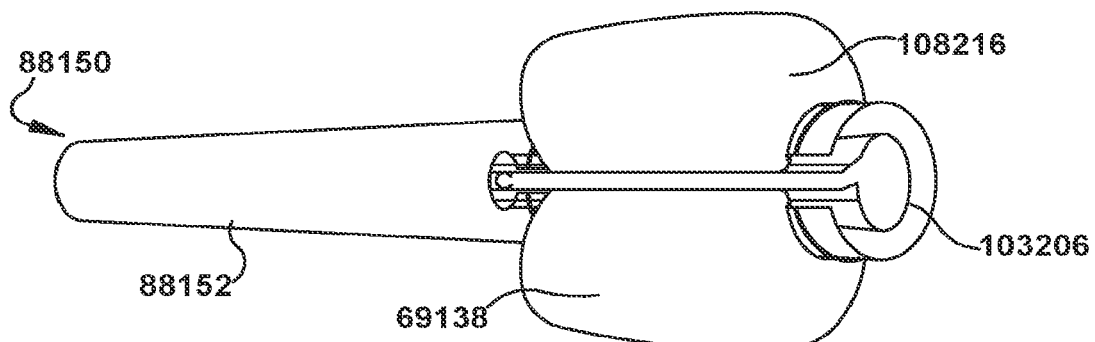

As shown in FIGS. 112-113, the balloon fixer 103206 is attached to at least one of the balloon dilation rod lumen 88162 and the portion of the balloon material 108216 that forms a portion of the balloon dilation rod lumen 88162. As shown in FIG. 114, at least a portion of a balloon material proximal end 114218 is circumferentially attached to at least a portion the balloon dilation rod outer surface 88160 adjacent to the balloon dilation rod open slit 88168. At least a portion of a balloon material distal end 114220 is circumferentially attached to at least a portion the balloon dilation rod outer surface 88160 adjacent to the balloon dilation rod open slit 88168. As shown in FIG. 115, the balloon dilation device 88150, including the expandable balloon 69138, constructed at least partially in the manner previously discussed may be inflated.

Figure 116:
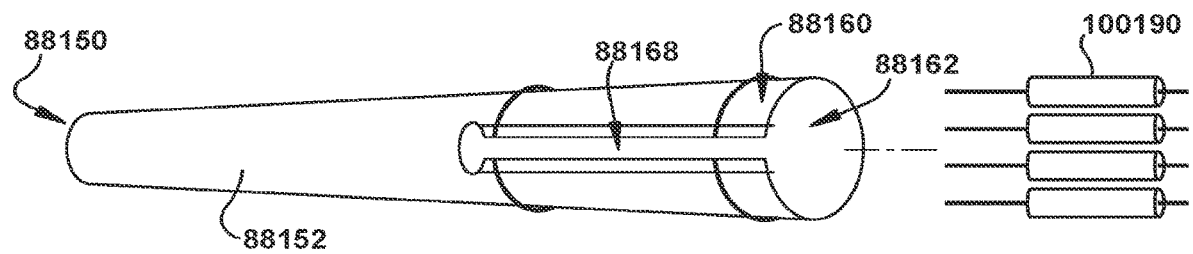
FIGS. 116-122 illustrate an example sequence of constructing a portion of the aspect of FIG. 103.
Figure 117:
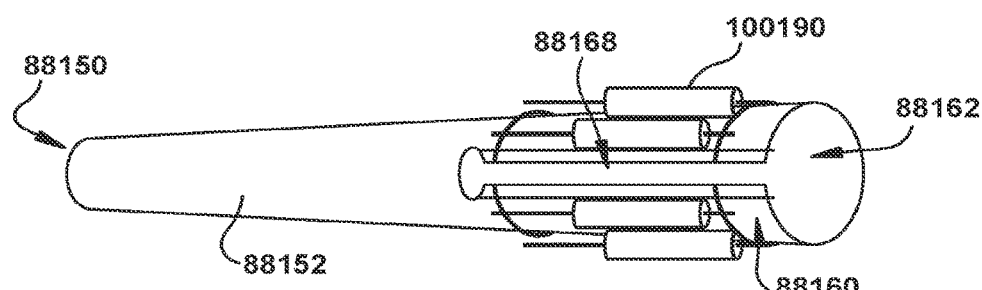
Figure 118:
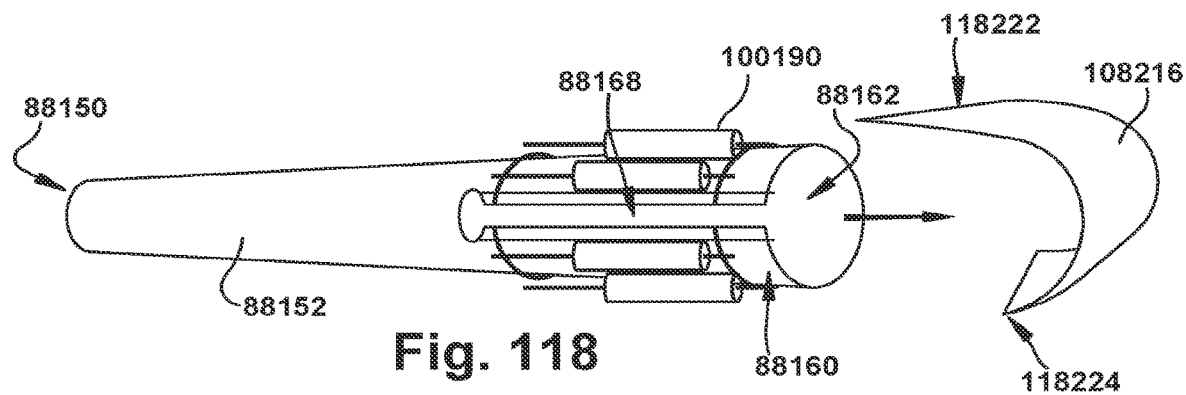

FIGS. 116-122 depict the construction of a balloon dilation device 88150 having a plurality of expandable sub-balloons 100190. A balloon dilation rod 88152, as previously described, is provided. A balloon material 108216, as previously discussed, may be an elastic cover 102198. As shown in FIGS. 116-117, prior to attaching at least a portion of the balloon material 108216 inserted into the balloon dilation rod lumen 88162 to at least a portion of the balloon dilation rod lumen 88162, a plurality of expandable sub-balloons 100190 are attached at least partially circumferentially about the balloon dilation rod outer surface 88160 adjacent to the balloon dilation rod open slit 88168.

Figure 119:
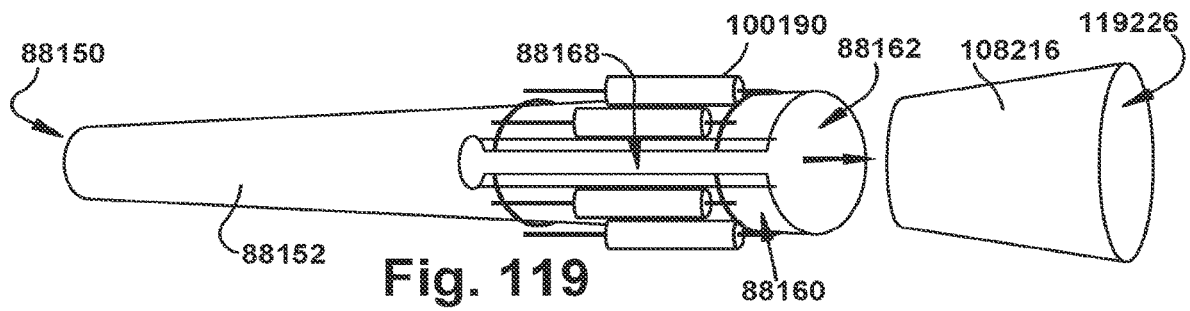

As shown in FIGS. 118-122 the balloon material 108216 may be placed at least partially circumferentially about the balloon dilation rod outer surface 88160 so that at least a portion of the balloon material 108216 is adjacent to at least a portion of the balloon dilation rod open slit 88168. As shown in FIG. 18, the balloon material 108216 may be a sheet having balloon material first and second ends 118222, 118224. Alternatively, as shown in FIG. 119, the balloon material 108216 may be ring-shaped. In such case, at least a portion of the balloon material 108216 may be inserted through the balloon dilation rod open slit 88168 and into the balloon dilation rod lumen 88162 to at least partially encapsulate the plurality of expandable sub-balloons 100190 between a balloon material inner surface 119226 and the balloon dilation rod outer surface 88160.

Figure 120:
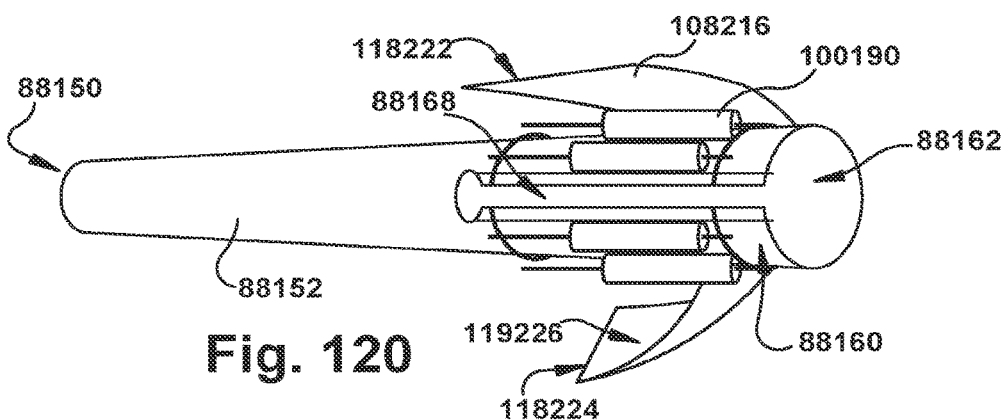
Figure 121:
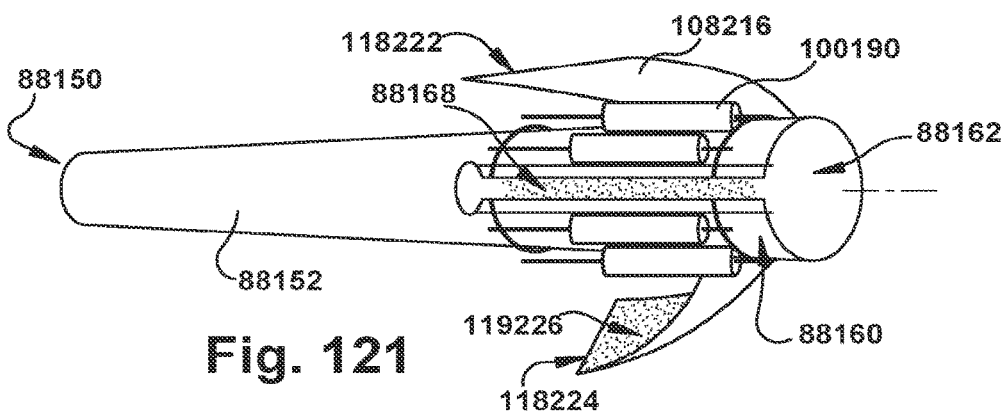
Figure 122:
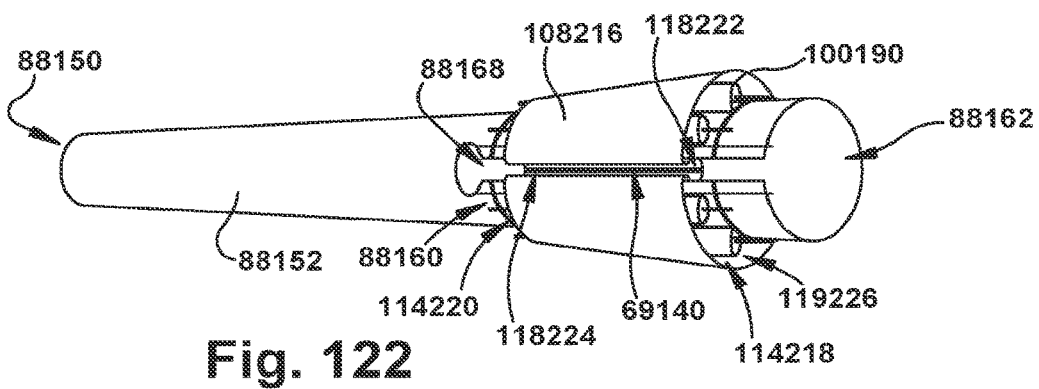

In the case of the balloon material 108216 being a sheet having balloon material first and second ends 118222, 118224, as shown in FIGS. 120-122, at least a portion of a balloon material first end 118222 is inserted through the balloon dilation rod open slit 88168 and into the balloon dilation rod lumen 88162. At least a portion of a balloon material second end 118224 is inserted through the balloon dilation rod open slit 88168 and into the balloon dilation rod lumen 88162. At least a portion of the balloon material first and second ends 118222, 118224 inserted into the balloon dilation rod lumen 88162 are attached to at least a portion of the balloon dilation rod lumen 88162. The portions of the balloon material 108216 attached to the portion of the balloon dilation rod lumen 88162 collectively forming at least a portion of the balloon dilation rod lumen 88162.

As shown in FIG. 122, the balloon material 108216 may form a balloon open slit 69140 that is aligned with the balloon dilation rod open slit 88168 when the balloon material first and second ends 118222, 118224 are attached to the balloon dilation rod lumen 88162. The portion of the balloon material 108216 inserted through the balloon dilation rod open slit 88168 and into the balloon dilation rod lumen 88162 at least partially encapsulates the plurality of expandable sub-balloons 100190 between the balloon material inner surface 119226 and the balloon dilation rod outer surface 88160. A balloon fixer 103206 may be then disposed in the balloon dilation rod 88152, and attached to at least one of the balloon dilation rod 88152 and the balloon material 108216 in similar sequence as previously discussed. At least a portion of balloon material proximal and distal ends 114218, 114220 may be circumferentially attached to at least a portion of the balloon dilation rod outer surface 88160 adjacent to the balloon dilation rod open slit 88168, with or without a balloon fixer 103206, to form the balloon dilation device 88150, including the expandable balloon 88150 that may have a plurality of expandable sub-balloons 100190.

In use, a balloon dilation device 88150, as previously described, is provided. The balloon dilation device 88150 may be any of the alternate configurations of the balloon dilation device 88150, as previously discussed. For the sake of brevity, not every alternate configuration of the balloon dilation device 88150 is discussed and/or depicted. However, it is to be understood that the following description may be applicable to any of the alternate configurations of the balloon dilation device 88150, as described above, or to any other desired configuration.

FIGS. 123-130 depict an example sequence of operation of the balloon dilation device A 94170. A guidewire distal end 2842 is inserted into a target patient tissue site T in a patient lumen. A guidewire proximal end 2844 is directed into the balloon dilation rod open tip 88166, through at least a portion of the balloon dilation rod lumen 88162, and out from the balloon dilation device A 94170, such as through the balloon dilation rod side wall opening 88164. As shown in FIG. 123, the balloon dilation device A 94170 is directed to the target patient tissue site T along the guidewire 328. FIGS. 123a-g depict cross-sectional views of various points along the balloon dilation device A 94170, to show the arrangement of the balloon dilation device A 94170 and the guidewire 328 in FIG. 123.

As shown in FIG. 124, with the balloon dilation A device 94170 at the target patient tissue site T, the expandable balloon 69138 is inflated to dilate the patient lumen at the target patient tissue site T. FIGS. 124a-g depict cross-sectional views of various points along the balloon dilation device A 94170, to show the arrangement of the balloon dilation device A 94170 and the guidewire 328 in FIG. 124. As shown in FIG. 125, the expandable balloon 69138 is deflated after the patient lumen at the target patient tissue site T has achieved a predetermined amount of dilation. As shown in FIG. 125, a secondary device 85144 may be directed over the guidewire 328 in a longitudinally distal direction (as shown as an arrow Y in FIG. 125) until the secondary device 85144 is at least one of adjacent to, abutting, and at least partially within the balloon dilation rod side wall opening 88164. FIGS. 125a-i depict cross-sectional views of various points along the balloon dilation device A 94170, to show the arrangement of the balloon dilation device A 94170, the secondary device 85144, and the guidewire 328 in FIG. 125.

As shown in FIGS. 126-127, with the secondary device 85144 at least one of adjacent to, abutting, and at least partially in the balloon dilation rod side wall opening 88164, the balloon dilation rod 88152 is longitudinally moved toward a proximal direction (as shown as an arrow X in FIG. 126) to remove the balloon dilation device A 94170 from the guidewire 328. The movement of the balloon dilation rod 88152 toward the proximal direction causes the secondary device 85144 to selectively urge the balloon dilation rod open slit first surface 94172 at least partially elastically apart from the balloon dilation rod open slit second surface 94174 and remove the balloon dilation device A 94170 from the guidewire 328, while maintaining the guidewire 328 at the target patient site T. FIGS. 126a-g depict cross-sectional views of various points along the balloon dilation device A

94170, to show the arrangement of the balloon dilation device A 94170, the secondary device 85144, and the guidewire 328 in FIG. 126.

As shown in FIGS. 127-128, the secondary device 85144 may be directed to the target patient tissue site T in the longitudinally distal direction (shown as an arrow Y in FIG. 128). FIGS. 127a-d depict cross-sectional views of various points along the secondary device 85144 and the guidewire 328 in FIG. 127. FIGS. 128a-d depict cross-sectional views of various points along the secondary device 85144 and the guidewire 328 in FIG. 128. With the secondary device 85144 located at the target patient tissue site T, a medical procedure may be performed with the secondary device 85144. For example, as shown in FIGS. 129-130, the secondary device 885144 may have an expandable implant M mounted thereon. In such case, with the secondary device 85144 at the target patient tissue site T, the expandable implant M may be expanded, i.e., moved toward the expanded condition. FIGS. 129a-d depict cross-sectional views of various points along the secondary device 85144, the expandable implant M, and the guidewire 328 in FIG. 129.

As previously discussed, the expandable implant M may be at least partially formed from a shape memory material that is capable of moving from a collapsed condition to an expanded condition because of the natural properties of the shape memory material. The expandable implant M may be cooled to a temperature below the transition temperature range, moved to the collapsed condition, and mounted on the secondary device 85144. When the expandable implant M is exposed at the target patient tissue site T, the temperature of the environment at the target patient tissue site T at least partially causes the expandable implant M to move from the collapsed condition toward the expanded condition. As shown in FIG. 130, with the expandable implant M expanded, the secondary device is longitudinally moved in the proximal direction to remove the secondary device 85144 from the target patient tissue site T, while maintaining at least one of the guidewire 328 and the expandable implant M at the target patient tissue site T. FIGS. 130a-d depict cross-sectional views of various points along the secondary device 85144, the expandable implant M, and the guidewire 328 in FIG. 130.

FIG. 131 depicts an example sequence of operation of the balloon dilation device B 95182. A guidewire distal end 2842 is inserted into a target patient tissue site T in a patient lumen. A guidewire proximal end 2844 is directed into the balloon dilation rod open tip 88166, through at least a portion of the balloon dilation rod lumen 88162, and out from the balloon dilation device 95182, such as through the balloon dilation rod side wall opening 88164. Alternatively, or in addition to the above, a guidewire proximal end 2844 may be directed into the balloon dilation rod open tip 88166, through the balloon dilation rod lumen 88162, and out from the balloon dilation device B 95182, such as through the balloon dilation rod proximal end 88154, in a similar manner to that shown in FIG. 131.

As shown in FIG. 131, the balloon dilation device B 95182 is directed to the target patient tissue site T along the guidewire 328. The balloon dilation device B 95182 may dilate the patient lumen at the target patient tissue site T as described above. When a guidewire proximal end 2844 is directed into the balloon dilation rod open tip 88166 and out from the balloon dilation device 95182, such as through the balloon dilation rod side wall opening 88164, a secondary device 85144 may be used to remove the balloon dilation device B 95182 from the guidewire 328 inside the patient lumen as described above. Alternatively, or in addition to the above, when a guidewire proximal end 2844 is directed into the balloon dilation rod open tip 88166 and out from the balloon dilation device B 95182, such as through the balloon dilation rod proximal end 88154, the balloon dilation device B 95182 may be removed from the guidewire 328 outside of the patient lumen by longitudinally moving the balloon dilation device B 95182 in the proximal direction. A secondary device 85144 may be operated and/or removed as described above.

FIGS. 132-137 depict an example sequence of operation of the balloon dilation device C 96184. A guidewire distal end 2842 is inserted into a target patient tissue site T in a patient lumen. An expandable implant M, which can be self-expandable and/or expand through external means (e.g., a balloon), is mounted circumferentially about at least a portion of the expandable balloon 69138. In the case of a shape memory expandable implant M, as previously discussed, the expandable implant M may be cooled to a temperature below the transition temperature range, moved to a collapsed condition, and mounted on the expandable balloon 69138. A guidewire proximal end 2844 is directed into the balloon dilation rod open tip 88166, through at least a portion of the balloon dilation rod lumen 88162, and out from the balloon device C 96184, such as through the balloon dilation rod side wall opening 88164. As shown in FIG. 132, the balloon dilation device C 96184 is directed to the target patient tissue site T along the guidewire 328 in a longitudinally proximal direction (as shown as an arrow Y in FIG. 132). FIGS. 132a-g depict cross-sectional views of various points along the balloon dilation device C 96184, to show the arrangement of the balloon dilation device C 96184, the expandable implant M, and the guidewire 328 in FIG. 132.

As shown in FIG. 133, with the balloon dilation C 96184 at the target patient tissue site T, the expandable balloon 69138 is inflated to dilate the patient lumen at the target patient tissue site T. Additionally, the inflating of the expandable balloon 69138 at least partially may help to cause the implant M (either self-expandable or balloon-expanded, optionally with a constraining sheath of any desired type) to expand—i.e., to at least partially move toward the expanded condition. In the case of the shape memory expandable implant M, when the expandable implant M is exposed at the target patient tissue site T, the temperature of the environment at the target patient tissue site T may at least partially cause the expandable implant M to move from the collapsed condition toward the expanded condition. FIGS. 133a-g depict cross-sectional views of various points along the balloon dilation device C 96184, to show the arrangement of the balloon dilation device C 96184, the expandable implant M, and the guidewire 328 in FIG. 133. As shown in FIG. 134, the expandable balloon 69138 is deflated after the patient lumen at the target patient tissue site T has achieved a predetermined amount of dilation and after the expandable implant M has been expanded. FIGS. 134a-g depict cross-sectional views of various points along the balloon dilation device C 96184, to show the arrangement of the balloon dilation device C 96184, the expandable implant M, and the guidewire 328 in FIG. 134.

As shown in FIG. 135, a secondary device 85144 may be directed over the guidewire 328 in a longitudinally distal direction (as shown as an arrow Y in FIG. 135) until the secondary device 85144 is at least one of adjacent to, abutting, and at least partially within the balloon dilation rod side wall opening 88164. FIGS. 135a-i depict cross-sectional views of various points along the balloon dilation device C 96184, to show the arrangement of the balloon dilation device C 96184, the expandable implant M, the secondary device 85144, and the guidewire 328 in FIG. 135. As shown in FIGS. 136-137, with the secondary device 85144 at least one of adjacent to, abutting, and at least partially in the balloon dilation rod side wall opening 88164, the balloon dilation rod 88152 is laterally moved toward a proximal direction to remove the balloon dilation device C 96184 from the guidewire 328. The movement of the balloon dilation rod 88152 toward the proximal direction causes the secondary device 85144 to selectively urge the balloon dilation rod open slit first surface 94172 at least partially elastically apart from the balloon dilation rod open slit second surface 94174 and remove the balloon dilation device C 96184 from the guidewire 328, while maintaining the guidewire 328 at the target patient site T. FIGS. 136*a-g* depict cross-sectional views of various points along the balloon dilation device C 96184, to show the arrangement of the balloon dilation device C 96184, the expandable implant M, the secondary device 85144, and the guidewire 328 in FIG. 136. FIGS. 137*a-f* depict cross-sectional views of various points along the secondary device 85144, the expandable implant M, and the guidewire 328 in FIG. 137.

The secondary device 85144 may be directed to the target patient tissue site T. With the secondary device 85144 located at the target patient tissue site T, a medical procedure may be performed with the secondary device 85144. After the secondary device 85144 is no longer desired at the target patient tissue site T, the secondary device 85144 may be longitudinally moved in the proximal direction to remove the secondary device 85144 from the target patient tissue site T, while maintaining at least one of the guidewire 328 and the expandable implant M at the target patient tissue site T.

Any of the alternate balloon dilation device 88150 configurations and/or the secondary device 85144, when provided, may be at least partially formed from silicone, polyethylene, polypropylene, stainless steel, titanium, rubber, latex, polychloroprene, nylon, any other biocompatible material, or any combination thereof.

It is contemplated that at least one of the alternate balloon dilation device 88150 configurations and the secondary device 85144, when provided, may be disposed within one or more sheaths to deliver at least a portion of the balloon dilation device 88150 to the target patient tissue site T through a patient tissue access point P.

It is contemplated that the balloon dilation device 88150 may provide the user with the ability to deliver at least one of the alternate balloon dilation device configurations and the secondary device 85144, when provided, to a target patient tissue site T of a patient lumen along a guidewire 328 and remove at least one of the alternate balloon dilation device 88150 configurations and the secondary device 85144, when provided, from the guidewire 328 in the patient lumen. This allows the user to direct another alternate balloon dilation device 88150 configuration and/or secondary device 85144, when provided, to the target patient tissue site T of the patient lumen, without having to remove the alternate balloon dilation device 88150 configuration outside of the patient lumen.

Further, the balloon dilation device 88150 provides the user with the ability to direct at least one of the alternate balloon dilation device 88150 configurations and the secondary device 85144, when provided, through a single patient tissue access point P. The ability to insert at least one of the alternate balloon dilation device 88150 configurations and the secondary device 85144, when provided, into a target patient tissue site T through a single patient tissue access point P may assist in reducing potential trauma, complications, and/or risks to the patient that result from the creation of multiple patient tissue access points P. For example, if a balloon dilation device 88150 and a secondary device 85144 were inserted through two separate patient tissue access points P, the trauma, risks, and complications associated with said insertions could be increased as compared to the insertion of the balloon dilation device 88150 and the secondary device 85144 through a single patient tissue access point P. Further, the ability to use a single patient tissue access point P instead of having to create multiple patient tissue access points P may reduce the procedure time and the costs that would be associated with creating multiple patient tissue access points P. The ability to insert at least one of the alternate balloon dilation device 88150 configurations and the secondary device 85144, when provided, into a target patient tissue site T over a single guidewire 328 may assist in reducing radiation exposure, procedure time, potential trauma, complications, and/or risks to the patient that may result from the need to fully remove the balloon dilation device 88150 outside of the patient lumen, in conventional techniques, before a secondary device can be direct into the patient lumen.

In summary, a person having ordinary skill in the art will understand that, in an aspect 1, a method for inserting multiple dilators into a target patient tissue site comprises:
  providing a modular dilation device including
    a first dilator, the first dilator having an elongate first dilator body and a first dilator distal end, the first dilator having a first dilator outer surface and a first dilator inner lumen, the first dilator distal end having a first dilator open tip, the first dilator having a first dilator side wall opening, the first dilator side wall opening selectively placing the first dilator outer surface in fluid communication with the first dilator inner lumen, the first dilator having a first dilator open slit, the first dilator open slit extending between the first dilator side wall opening and the first dilator open tip, and
    a second dilator, the second dilator having an elongate second dilator body and a second dilator distal end, the second dilator having a second dilator inner lumen, the second dilator distal end having a second dilator open tip;
  inserting a guidewire distal end into a target patient tissue site through a patient tissue access point;
  directing the guidewire proximal end into the first dilator open tip, through at least a portion of the first dilator inner lumen, and out of the first dilator through the first dilator side wall opening;
  directing the first dilator to the target patient tissue site along the guidewire;
  directing the guidewire proximal end into the second dilator open tip, through at least a portion of the second dilator inner lumen, and out from the second dilator; and
  directing the second dilator to the target patient tissue site along the guidewire until the second dilator open tip is adjacent to the first dilator side wall opening.

Aspect 2. The method of aspect 1, including:
  placing the second dilator into a predetermined relationship with the first dilator, wherein the second dilator open tip is adjacent to the first dilator side wall opening;
  directing the guidewire proximal end into the first dilator open tip and out of the second dilator, wherein the guidewire proximal end is directed through the first dilator open tip and at least a portion of the first dilator inner lumen, through the first dilator side wall opening, through the second dilator open tip and the second dilator inner lumen, and out from the second dilator; and collectively inserting both the first dilator and the second dilator into the target patient tissue site along the guidewire.

Aspect 3. The method of aspect 1, wherein the first dilator open slit includes a first dilator open slit first surface and a first dilator open slit second surface, the first dilator open slit first surface being oppositely facing and abutting the first dilator open slit second surface, the first dilator open slit first surface and the first dilator open slit second surface being selectively elastically separable, and the second dilator open tip and at least a portion of the second dilator distal end are each smaller in diameter than at least one of the first dilator inner lumen and the first dilator side wall opening, the method further including:

directing each of the second dilator open tip and at least a portion of the second dilator distal end at least one of adjacent to and at least partially into the first dilator side wall opening; and with the second dilator distal end at least one of adjacent to and at least partially in the first dilator side wall opening, longitudinally moving the first dilator toward a proximal direction to remove the first dilator from the guidewire, wherein as the first dilator is moved toward the proximal direction, the second dilator distal end selectively urges the first dilator open slit first surface elastically apart from the first dilator open slit second surface and the first dilator is removed from the guidewire, while maintaining the guidewire at the target patient site.

Aspect 4. The method of aspect 1, including:

providing a third dilator, the third dilator having an elongate third dilator body and a third dilator distal end, the third dilator having a third dilator outer surface and a third dilator inner lumen, the third dilator distal end having a third dilator open tip, the third dilator having a third dilator side wall opening, the third dilator side wall opening selectively placing the third dilator outer surface in fluid communication with the third dilator inner lumen, the third dilator having a third dilator open slit, the third dilator open slit extending between the third dilator side wall opening and the third dilator open tip;

directing the guidewire proximal end into the third dilator open tip, through at least a portion of the third dilator inner lumen, and out from the third dilator through the third dilator side wall opening;

directing the third dilator into the target patient tissue site along the guidewire until the third dilator open tip is adjacent to the first dilator side wall opening; and directing the second dilator into the target patient tissue site along the guidewire until the second dilator open tip is adjacent to the third dilator side wall opening.

Aspect 5. The method of aspect 4, including:

placing the third dilator into a predetermined relationship with the first dilator, wherein the third dilator open tip is adjacent to the first dilator side wall opening;

placing the second dilator into a predetermined relationship with the third dilator, wherein the second dilator open tip is adjacent to the third dilator side wall opening;

directing the guidewire proximal end into the first dilator open tip and out of the second dilator, wherein the guidewire proximal end is directed through the first dilator open tip and at least a portion of the first dilator inner lumen, through the first dilator side wall opening, through the third dilator open tip and at least a portion of the third dilator inner lumen, through the third dilator side wall opening, through the second dilator open tip and the second dilator inner lumen, and out from the second dilator; and collectively inserting the first dilator, the second dilator, and the third dilator into the target patient tissue site along the guidewire.

Aspect 6. The method of aspect 4, wherein the first dilator open slit includes a first dilator open slit first surface and a first dilator open slit second surface, the first dilator open slit first surface being oppositely facing and abutting the first dilator open slit second surface, the first dilator open slit first surface and the first dilator open slit second surface being selectively elastically separable, and the third dilator open slit includes a third dilator open slit first surface and a third dilator open slit second surface, the third dilator open slit first surface being oppositely facing and abutting the third dilator open slit second surface, the third dilator open slit first surface and the third dilator open slit second surface being selectively elastically separable, the method further including:

directing at least a portion of the second dilator distal end at least one of adjacent to and at least partially into the third dilator side wall opening;

with the second dilator distal end at least one of adjacent to and at least partially in the third dilator side wall opening, longitudinally moving the third dilator toward a proximal direction to remove the third dilator from the guidewire, wherein as the third dilator is moved toward the proximal direction, the second dilator distal end selectively urges the third dilator open slit first surface elastically apart from the third dilator open slit second surface and the third dilator is removed from the guidewire, while maintaining the guidewire at the target patient site;

directing at least a portion of the second dilator distal end at least one of adjacent to and at least partially into the first dilator side wall opening; and with the second dilator distal end at least one of adjacent to and at least partially in the first dilator side wall opening, longitudinally moving the first dilator toward a proximal direction to remove the first dilator from the guidewire, wherein as the first dilator is moved toward the proximal direction, the second dilator distal end selectively urges the first dilator open slit first surface elastically apart from the first dilator open slit second surface and the first dilator is removed from the guidewire, while maintaining the guidewire at the target patient site.

Aspect 7. The method of aspect 1, wherein the second dilator open tip and at least a portion of the second dilator distal end that are each smaller in diameter than at least one of a third dilator inner lumen and a third dilator side wall opening, the method further including:

providing a third dilator, the third dilator having an elongate third dilator body and a third dilator distal end, the third dilator having a third dilator outer surface and a third dilator inner lumen, the third dilator distal end having a third dilator open tip, the third dilator having a third dilator side wall opening, the third dilator side wall opening selectively placing the third dilator outer surface in fluid communication with the third dilator inner lumen, the third dilator having a third dilator open slit, the third dilator open slit extending between the third dilator side wall opening and the third dilator open tip, the third dilator open tip and at least a portion of the third dilator distal end each being smaller in diameter than at least one of the first dilator inner lumen and the first dilator side wall opening;

inserting the second dilator open tip and at least a portion of the second dilator distal end into the third dilator inner lumen through the third dilator side wall opening;

inserting the third dilator open tip and at least a portion of the third dilator distal end into the first dilator inner lumen through the first dilator side wall opening;

directing the guidewire proximal end into the first dilator open tip and out of the second dilator, wherein the guidewire proximal end is directed through the first dilator open tip and at least a portion of the first dilator inner lumen, through the third dilator open tip and at least a portion of the third dilator inner lumen, through the second dilator open tip and the second dilator inner lumen, and out from the second dilator; and collectively inserting the first dilator, the second dilator, and the third dilator into the target patient tissue site along the guidewire.

Aspect 8. The method of aspect 7, wherein the first dilator open slit includes a first dilator open slit first surface and a first dilator open slit second surface, the first dilator open slit first surface being oppositely facing and abutting the first dilator open slit second surface, the first dilator open slit first surface and the first dilator open slit second surface being selectively elastically separable, and the third dilator open slit including a third dilator open slit first surface and a third dilator open slit second surface, the third dilator open slit first surface being oppositely facing and abutting the third dilator open slit second surface, the third dilator open slit first surface and the third dilator open slit second surface being selectively elastically separable, the method further including:

with the third dilator distal end at least partially in the first dilator side wall opening, longitudinally moving the first dilator toward a proximal direction to remove the first dilator from the guidewire, wherein as the first dilator is moved toward the proximal direction, the third dilator distal end selectively urges the first dilator open slit first surface elastically apart from the first dilator open slit second surface and the first dilator is removed from the guidewire, while maintaining the guidewire at the target patient site; and with the second dilator distal end at least partially in the third dilator side wall opening, longitudinally moving the third dilator toward a proximal direction to remove the third dilator from the guidewire, wherein as the third dilator is moved toward the proximal direction, the second dilator distal end selectively urges the third dilator open slit first surface elastically apart from the third dilator open slit second surface and the third dilator is removed from the guidewire, while maintaining the guidewire at the target patient site.

In summary, a person having ordinary skill in the art will understand that, in an aspect 9, an implant delivery system comprises:

an outer sheath having a outer sheath proximal end and an outer sheath distal end, the outer sheath proximal end having an outer sheath delivery element, the outer sheath distal end having an implant holding pod, the implant holding pod having an implant holding pod proximal end and an implant holding pod distal end, the implant holding pod proximal end having an implant holding pod proximal opening, the implant holding pod distal end having an implant holding pod open tip, the implant holding pod having an implant holding pod outer surface and an implant holding pod lumen, the implant holding pod lumen extending between the implant holding pod proximal opening and the implant holding pod open tip, the implant holding pod lumen for selectively holding an expandable implant therein, the implant holding pod having an implant holding pod open slit, the implant holding pod open slit extending at least partially between the implant holding pod open tip and the implant holding pod proximal end;

a shaft having an shaft proximal end, a shaft distal end, and a shaft body longitudinally extending between the shaft proximal and distal ends, the shaft proximal end having a shaft delivery element, the shaft distal end having an implant delivery element, at least one of the shaft body and the implant delivery element having a shaft open slit;

wherein when the shaft is operably joined to the outer sheath, at least a portion of the shaft open slit is selectively laterally spaced from the implant holding pod open slit.

Aspect 10. The implant delivery system of aspect 9, wherein the implant holding pod has an implant holding pod body longitudinally extending between the implant holding pod proximal and distal ends, at least one of the implant holding pod body and the implant holding pod proximal end having an implant holding pod side wall opening, the implant holding pod side wall opening selectively placing the implant holding pod outer surface in fluid communication with the implant holding pod lumen, the implant holding pod open slit extending from the implant holding pod open tip to at least one of the implant holding pod side wall opening and the implant holding pod proximal end.

Aspect 11. The implant delivery system of aspect 9, wherein the shaft body has a shaft body proximal end, a shaft body distal end, and a shaft body length longitudinally extending between the shaft body proximal end and the shaft body distal end, at least one of the shaft body proximal end, shaft body distal end, and the shaft body length having an outer sheath splitter for facilitating the separation of an implant holding pod open slit first surface and an implant holding pod open slit second surface, the implant holding pod open slit first surface being oppositely facing and abutting the implant holding pod open slit second surface, the implant holding pod open slit first surface and the implant holding pod open slit second surface being selectively elastically separable.

Aspect 12. The implant delivery system of aspect 11, wherein the outer sheath splitter is arrow-shaped, the arrow-shaped splitter pointing toward a longitudinally distal direction.

Aspect 13. The implant delivery system of aspect 9, wherein the implant delivery element has an implant delivery element outer surface and a radially extending projection for selectively contacting and selectively pushing an expandable implant.

Aspect 14. The implant delivery system of claim 13, wherein the implant delivery element has the shaft open slit, at least a portion of the shaft body and the shaft distal end each being at least one of the same diameter as, smaller in diameter than, at least one of the implant holding pod lumen and the implant holding pod side wall opening, the implant holding pod side wall opening selectively placing the implant holding pod outer surface in fluid communication with the implant holding pod lumen, the implant holding pod side wall opening being located on at least one of the implant holding pod proximal end and an implant holding pod body, the implant holding pod body longitudinally extending between the implant holding pod proximal and distal ends, the implant holding pod open slit extending from the implant holding pod open tip to at least one of the implant holding pod side wall opening and the implant holding pod proximal end.

Aspect 15. The implant delivery system of aspect 13, wherein the shaft body has a shaft side wall opening, the shaft side wall opening being in fluid communication with the shaft open slit, the shaft open slit extending between the shaft side wall opening and an implant delivery element open tip, at least a portion of the shaft open slit and at least a portion of the shaft side wall opening collectively forming a shaft lumen for at least partially selectively holding a guidewire therein.

Aspect 16. The implant delivery system of aspect 15, including an expandable balloon positioned on at least one of the shaft body and the shaft distal end, the balloon having a balloon open slit that extends for at least a partial length of the balloon, the balloon open slit being aligned with at least a portion of the shaft open slit.

Aspect 17. The implant delivery system of aspect 16, wherein at least a portion of the shaft body and at least a portion of the shaft distal end are each smaller in diameter than at least one of the implant holding pod lumen and the implant holding pod side wall opening, the implant holding pod side wall opening selectively placing the implant holding pod outer surface in fluid communication with the implant holding pod lumen, the implant holding pod side wall opening being located on at least one of the implant holding pod proximal end and an implant holding pod body, the implant holding pod body longitudinally extending between the implant holding pod proximal and distal ends, the implant holding pod open slit extending from the implant holding pod open tip to at least one of the implant holding pod side wall opening and the implant holding pod proximal end.

Aspect 18. The implant delivery system of aspect 16, wherein the projection is a radially extending conical head, the conical head pointing toward a longitudinally distal direction.

Aspect 19. The implant delivery system of aspect 9, wherein the implant delivery element has an implant delivery element outer surface for selectively circumferentially mounting an expandable implant thereon.

Aspect 20. The implant delivery system of aspect 19, wherein the implant delivery element outer surface has at least one radially extending projection, the radially extending projection for substantially preventing the egress of an expandable implant mounted circumferentially about the implant delivery element outer surface from a desired position on the implant delivery element outer surface.

Aspect 21. The implant delivery system of aspect 20, wherein the shaft body has a shaft side wall opening, the shaft side wall opening being in selective fluid communication with the shaft open slit, the shaft open slit extending between the shaft side wall opening and an implant delivery element open tip, at least a portion of the shaft open slit and at least a portion of the shaft side wall opening collectively forming a shaft lumen for at least partially selectively holding a guidewire therein.

Aspect 22. The implant delivery system of aspect 19, the implant delivery element having a radially extending conical head, the conical head pointing toward a longitudinally distal direction.

Aspect 23. The implant delivery system of aspect 22, wherein the shaft body has a shaft side wall opening, the shaft side wall opening being in selective fluid communication with the shaft open slit, the shaft open slit extending between the shaft side wall opening and an implant delivery element open tip, at least a portion of the shaft open slit and at least a portion of the shaft side wall opening collectively forming a shaft lumen for at least partially selectively holding a guidewire therein.

Aspect 24. The implant delivery system of aspect 23, wherein the conical head has at least one elastic clamp longitudinally extending in the proximal direction, the elastic clamp for selectively preventing an implant holding pod open slit first surface from separating from an implant holding pod open slit second surface when the shaft is operably joined to the outer sheath, the implant holding pod open slit first surface being oppositely facing and abutting the implant holding pod open slit second surface, the implant holding pod open slit first surface and the implant holding pod open slit second surface being selectively elastically separable.

Aspect 25. The implant delivery system of aspect 9, wherein the implant holding pod open slit has an implant holding pod open slit first surface and an implant holding pod open slit second surface, the implant holding pod open slit first surface being oppositely facing and abutting the implant holding pod open slit second surface, the implant holding pod open slit first surface and the implant holding pod open slit second surface being selectively elastically separable, and wherein at least one c-clip is selectively disposed on at least a portion of the implant holding pod outer surface that is adjacent to the implant holding pod open slit, the c-clip at least partially selectively preventing the implant holding open slit first surface from separating from the implant holding pod open slit second surface.

Aspect 26. The implant delivery system of aspect 9, wherein the implant holding pod open slit has an implant holding pod open slit first surface and an implant holding pod open slit second surface, the implant holding pod open slit first surface being oppositely facing and abutting the implant holding pod open slit second surface, the implant holding pod open slit first surface and the implant holding pod open slit second surface being selectively elastically separable, and wherein at least one c-clip is selectively disposed within at least a portion of the implant holding pod lumen that is adjacent to the implant holding pod open slit, the c-clip at least partially selectively preventing the implant holding open slit first surface from separating from the implant holding pod open slit second surface.

Aspect 27. The implant delivery system of aspect 9, wherein at least one of the outer sheath delivery element and the shaft delivery element is a stiff wire.

Aspect 28. The implant delivery system of claim 9, wherein the implant holding pod proximal opening is facing laterally downward.

In summary, a person having ordinary skill in the art will understand that, in an aspect 29, an method for deploying an expandable implant in a patient lumen comprises:
  providing an implant delivery system including
    an outer sheath having a outer sheath proximal end and an outer sheath distal end, the outer sheath proximal end having an outer sheath delivery element, the outer sheath distal end having an implant holding pod, the implant holding pod having an implant holding pod proximal end and an implant holding pod distal end, the implant holding pod proximal end having an implant holding pod proximal opening, the implant holding pod distal end having an implant holding pod open tip, the implant holding pod having an implant holding pod outer surface and an implant holding pod lumen, the implant holding pod lumen extending between the implant holding pod proximal opening and the implant holding pod open tip, the implant holding pod lumen for selectively holding an expandable implant therein, the implant holding pod having an implant holding pod open slit, the implant holding pod open slit extending between the implant holding pod open tip and the implant holding pod proximal end, and a shaft having an shaft proximal end, a shaft distal end, and a shaft body longitudinally extending between the shaft proximal and distal ends, the shaft proximal end having a shaft delivery element, the shaft distal end having an implant delivery element, at least one of the shaft body and the implant delivery element having a shaft open slit;

placing a collapsed expandable implant within the implant holding pod lumen;

collectively inserting at least one of the shaft body and the implant delivery element at least partially into the implant holding pod lumen;

aligning the shaft in the implant holding pod lumen with at least a portion of the shaft open slit being laterally spaced apart from the implant holding pod open slit;

placing the collapsed expandable implant in operative engagement with the implant delivery element;

inserting a guidewire distal end into a target patient tissue site in a patient lumen;

directing a guidewire proximal end through the implant delivery system;

directing the implant delivery system to the target patient tissue site along the guidewire;

with the implant delivery system at the target patient tissue site, exposing the expandable implant by directing the outer sheath delivery element in the longitudinally proximal direction to directly correspondingly cause the outer sheath to move in the longitudinally proximal direction, the guidewire, the expandable implant, and the shaft remaining in place at the target patient tissue site while the outer sheath is moved in the longitudinally proximal direction; and with the expandable implant exposed, utilizing the properties of the expandable implant to move the expandable implant toward an expanded condition.

Aspect 30. The method of aspect 29, wherein the implant holding pod has an implant holding pod body longitudinally extending between the implant holding pod proximal and distal ends, at least one of the implant holding pod body and the implant holding pod proximal end having an implant holding pod side wall opening, the implant holding pod side wall opening selectively placing the implant holding pod outer surface in fluid communication with the implant holding pod lumen, the implant holding pod open slit extending from the implant holding pod open tip to at least one of the implant holding pod side wall opening and the implant holding pod proximal end, the implant delivery element has an implant delivery element outer surface for selectively circumferentially mounting an expandable implant thereon, the implant delivery element having a radially extending conical head, the conical head pointing toward a longitudinally distal direction, and the shaft body has a shaft side wall opening, the shaft side wall opening being in fluid communication with the shaft open slit, the shaft open slit extending between the shaft side wall opening and an implant delivery element open tip, at least a portion of the shaft open slit and at least a portion of the shaft side wall opening collectively forming a shaft lumen for at least partially selectively holding a guidewire therein, the method further including:

mounting the expandable implant circumferentially about the implant delivery element outer surface;

with the expandable implant mounted to the implant delivery element outer surface, inserting at least a portion of the shaft into the implant holding pod lumen;

aligning the shaft with the outer sheath with the shaft side wall opening aligned with the implant holding pod side wall opening and the conical head longitudinally adjacent to the implant holding pod open tip;

directing a guidewire proximal end through the implant delivery element open tip, through at least a portion of the shaft lumen, through the shaft side wall opening, and out of the outer sheath through the implant holding pod side wall opening;

directing a secondary device over the guidewire until the secondary device is at least one of adjacent to and at least partially within the implant holding pod side wall opening;

with the secondary device at least one of adjacent to and at least partially in the implant holding pod side wall opening, longitudinally moving the outer sheath in the proximal direction to remove the outer sheath from the guidewire, movement of the outer sheath toward the proximal direction causing the secondary device to selectively urge an implant holding pod open slit first surface elastically apart from an implant holding pod open slit second surface and remove the outer sheath from the guidewire, while leaving the guidewire and the shaft in place at the target patient site, the implant holding pod open slit first surface being oppositely facing and abutting the implant holding pod open slit second surface, the implant holding pod open slit first surface and the implant holding pod open slit second surface being selectively elastically separable;

directing at least a portion of the secondary device over the guidewire until the secondary device is at least one of adjacent to and at least partially within the shaft side wall opening;

with the secondary device located at least one of adjacent to and at least partially in the shaft side wall opening, longitudinally moving the shaft toward a proximal direction to remove the shaft from the guidewire, movement of the shaft toward the proximal direction causing the secondary device to selectively urge an shaft open slit first surface elastically apart from an shaft open slit second surface and remove the shaft from the guidewire, while maintaining the guidewire at the target patient site, the shaft open slit first surface being oppositely facing and abutting shaft open slit second surface, the shaft open slit first surface and the shaft open slit second surface being selectively elastically separable;

directing the secondary device to the target patient tissue site; and performing a medical procedure with the secondary device.

Aspect 31. The method of aspect 30, wherein the conical head has at least one elastic clamp longitudinally extending in the proximal direction, the elastic clamp for selectively preventing the implant holding pod open slit first surface from separating from the implant holding pod open slit second surface when the shaft is operably joined to the outer sheath, the method further including:

operatively engaging the elastic clamp to the outer sheath by placing the elastic clamp on at least a portion of the implant pod outer surface adjacent to the implant holding pod open tip;

wherein as the outer sheath is longitudinally directed in the longitudinal direction, the outer sheath operatively disengages the elastic clamp.

Aspect 32. The method of aspect 30, wherein the secondary device is a balloon dilation device including a balloon dilation rod having a balloon dilation rod proximal end, a balloon dilation rod distal end, and an elongate balloon dilation rod body longitudinally extending between the balloon dilation rod proximal and distal ends, the balloon dilation rod having a balloon dilation rod outer surface and a balloon dilation rod lumen, the balloon dilation rod having a balloon dilation rod side wall opening, the balloon dilation rod side wall opening selectively placing the balloon dilation rod outer surface in fluid communication with the balloon dilation rod lumen, the balloon dilation rod distal end having a balloon dilation rod open tip, the balloon dilation rod having a balloon dilation rod open slit, the balloon dilation rod open slit extending between the balloon dilation rod side wall opening and the balloon dilation rod open tip; and an expandable balloon positioned on at least one of the balloon dilation rod body and balloon dilation rod distal end, the expandable balloon having a balloon open slit that at least partially extends for at least a partial length of the balloon, the balloon open slit being aligned with the balloon dilation rod open slit.

Aspect 33. The method of aspect 32, including:
inflating the expandable balloon to cause the expandable implant to further expand; and
with the expandable implant further expanded, deflating the expandable balloon.

Aspect 34. The method of aspect 29, wherein the shaft body has a shaft body proximal end, a shaft body distal end, and a shaft body length longitudinally extending between the shaft body proximal end and the shaft body distal end, at least one of the shaft body proximal end, the shaft body distal end, and the shaft body length having an outer sheath splitter for selectively facilitating the separation of an implant holding pod open slit first surface and an implant holding pod open slit second surface, the implant holding pod open slit first surface oppositely facing and abutting the implant holding pod open slit second surface, the implant holding pod open slit first surface and the implant holding pod open slit second surface being selectively elastically separable, and the implant delivery element having an implant delivery element outer surface for selectively circumferentially mounting an expandable implant thereon, the implant delivery element outer surface having at least one radially extending projection, the radially extending projection for substantially preventing the egress of an expandable implant mounted circumferentially about the implant delivery element outer surface from a desired position on the implant delivery element outer surface.

Aspect 35. The method of aspect 34, including:
mounting the expandable implant circumferentially about the implant delivery element outer surface;
with the expandable implant mounted to the implant delivery element outer surface, inserting at least a portion of the shaft into the implant holding pod lumen;

directing a guidewire proximal end through the implant holding pod open tip, through at least a portion of the implant holding pod lumen, through the implant holding pod proximal opening and the shaft open slit, and out from the shaft open slit;

removing the outer sheath from the guidewire by moving the outer sheath in the longitudinally proximal direction, movement of the outer sheath in the longitudinally proximal direction causing the outer sheath splitter to move along the implant holding pod open slit to selectively urge the implant holding pod open slit first surface elastically apart from the implant holding pod open slit second surface and accordingly push the guidewire from the implant holding pod lumen, while maintaining the guidewire and the shaft at the target patient site.

Aspect 36. The method of aspect 35, wherein the implant holding pod has an implant holding pod body longitudinally extending between the implant holding pod proximal and distal ends, at least one of the implant holding pod body and the implant holding pod proximal end having an implant holding pod side wall opening, the implant holding pod side wall opening selectively placing the implant holding pod outer surface in fluid communication with the implant holding pod lumen, the implant holding pod open slit extending from the implant holding pod open tip to at least one of the implant holding pod side wall opening and the implant holding pod proximal end, the method further including:

aligning the shaft in the implant holding pod lumen with at least a portion of the shaft open slit being laterally spaced apart from the implant holding pod open slit and the shaft delivery element at least partially extending through the implant holding pod proximal opening; and directing a guidewire proximal end through the implant holding pod open tip, through at least a portion of the implant holding pod lumen, through the shaft lumen, through the shaft side wall opening, and out from the implant holding pod side wall opening.

Aspect 37. The method of aspect 34, wherein the shaft body has a shaft side wall opening, the shaft side wall opening being in fluid communication with the shaft open slit, the shaft open slit extending between the shaft side wall opening and an implant delivery element open tip, at least a portion of the shaft open slit and at least a portion of the shaft side wall opening collectively forming a shaft lumen for at least partially selectively holding a guidewire therein, the method further including:

mounting the expandable implant circumferentially about the implant delivery element outer surface;

with the expandable implant mounted to the implant delivery element outer surface, inserting at least a portion of the shaft into the implant holding pod lumen;

directing a guidewire proximal end through the implant holding pod open tip, through at least a portion of the implant holding pod lumen, through the shaft lumen, and out from the shaft side wall opening, as the guidewire is directed through the shaft lumen, the guidewire is directed through the implant holding pod proximal end; and removing the outer sheath from the guidewire by moving the outer sheath in the longitudinally proximal direction, movement of the outer sheath in the longitudinally proximal direction causing the outer sheath splitter to move along the implant holding pod open slit to selectively urge the implant holding pod open slit first surface elastically apart from the implant holding pod open slit second surface and accordingly push the guidewire from the implant holding pod lumen, while maintaining the guidewire and the shaft at the target patient site.

Aspect 38. The method of claim 37, wherein the implant holding pod has an implant holding pod body longitudinally extending between the implant holding pod proximal and distal ends, at least one of the implant holding pod body and the implant holding pod proximal end having an implant holding pod side wall opening, the implant holding pod side wall opening selectively placing the implant holding pod outer surface in fluid communication with the implant holding pod lumen, the implant holding pod open slit extending from the implant holding pod open tip to at least one of the implant holding pod side wall opening and the implant holding pod proximal end, the method further including:
- aligning the shaft in the implant holding pod lumen with at least a portion of the shaft open slit being laterally spaced apart from the implant holding pod open slit and the shaft delivery element at least partially extending through the implant holding pod proximal opening; and
- directing a guidewire proximal end through the implant holding pod open tip, through at least a portion of the implant holding pod lumen, through the shaft lumen, through the shaft side wall opening, and out from the implant holding pod side wall opening.

Aspect 39. The method of claim 29, wherein the shaft body has a shaft body proximal end, a shaft body distal end, and a shaft body length longitudinally extending between the shaft body proximal end and the shaft body distal end, at least one of the shaft body proximal end, the shaft body distal end, and the shaft body length having an outer sheath splitter for facilitating the separation of an implant holding pod open slit first surface and an implant holding pod open slit second surface, the implant holding pod open slit first surface being oppositely facing and abutting the implant holding pod open slit second surface, the shaft body having a shaft side wall opening, the shaft side wall opening being in selective fluid communication with the shaft open slit, the shaft open slit extending between the shaft side wall opening and an implant delivery element open tip, at least a portion of the shaft open slit and at least a portion of the shaft side wall opening collectively forming a shaft lumen for at least partially selectively holding a guidewire therein, the implant holding pod open slit first surface and the implant holding pod open slit second surface being selectively elastically separable, and the implant delivery element having an implant delivery element outer surface and a radially extending projection for selectively contacting and selectively pushing an expandable implant.

Aspect 40. The method of aspect 39, including:
- placing the projection in operative engagement with the expandable implant by locating a least a portion of the projection in abutment with the expandable implant;
- directing a guidewire proximal end through the implant holding pod open tip, through at least a portion of the implant holding pod lumen, through the shaft lumen, and out from the shaft side wall opening, at the same time as the guidewire is directed through the shaft lumen, the guidewire is directed through the implant holding pod proximal end; and
- removing the outer sheath from the guidewire by moving the outer sheath in the longitudinally proximal direction, movement of the outer sheath in the longitudinally proximal direction causing the outer sheath splitter to move along the implant holding pod open slit to selectively urge the implant holding pod open slit first surface elastically apart from the implant holding pod open slit second surface and accordingly push the guidewire from the implant holding pod lumen, while maintaining the guidewire and the shaft at the target patient site.

Aspect 41. The method of aspect 40, wherein the implant holding pod has an implant holding pod body longitudinally extending between the implant holding pod proximal and distal ends, at least one of the implant holding pod body and the implant holding pod proximal end having an implant holding pod side wall opening, the implant holding pod side wall opening selectively placing the implant holding pod outer surface in fluid communication with the implant holding pod lumen, the implant holding pod open slit extending from the implant holding pod open tip to at least one of the implant holding pod side wall opening and the implant holding pod proximal end, the method further including:
- aligning the shaft in the implant holding pod lumen with at least a portion of the shaft open slit being laterally spaced apart from the implant holding pod open slit and the shaft delivery element at least partially extending through the implant holding pod proximal opening; and
- directing a guidewire proximal end through the implant holding pod open tip, through at least a portion of the implant holding pod lumen, through the shaft lumen, through the shaft side wall opening, and out from the implant holding pod side wall opening.

Aspect 42. The method of aspect 40, including:
- providing an expandable balloon positioned on at least one of the shaft body and the shaft distal end, the balloon having a balloon open slit that extends for at least a partial length of the balloon, the balloon open slit being aligned with at least a portion of the shaft open slit;
- positioning the expandable balloon radially adjacent to the expanded expandable implant;
- inflating the expandable balloon to further expand the expandable implant; and
- deflating the expandable balloon.

Aspect 43. The method of aspect 42, wherein the projection is a radially extending conical head, the conical head pointing toward a longitudinally distal direction.

Aspect 44. The method of aspect 42, wherein the implant holding pod has an implant holding pod body longitudinally extending between the implant holding pod proximal and distal ends, at least one of the implant holding pod body and the implant holding pod proximal end having an implant holding pod side wall opening, the implant holding pod side wall opening selectively placing the implant holding pod outer surface in fluid communication with the implant holding pod lumen, the implant holding pod open slit extending from the implant holding pod open tip to at least one of the implant holding pod side wall opening and the implant holding pod proximal end, the method further including:
- aligning the shaft in the implant holding pod lumen with at least a portion of the shaft open slit being laterally spaced apart from the implant holding pod open slit and at least one of the shaft delivery element and the shaft body at least partially extending through the implant holding pod proximal opening; and
- directing a guidewire proximal end through the implant holding pod open tip, through at least a portion of the implant holding pod lumen, through the shaft lumen, through the shaft side wall opening, and out from the implant holding pod side wall opening.

In summary, a person having ordinary skill in the art will understand that, in an aspect 45, a balloon dilation device comprises:

a balloon dilation rod having a balloon dilation rod proximal end, a balloon dilation rod distal end, and an elongate balloon dilation rod body longitudinally extending between the balloon dilation rod proximal and distal ends, the balloon dilation rod having a balloon dilation rod outer surface and a balloon dilation rod lumen, the balloon dilation rod having a balloon dilation rod side wall opening, the balloon dilation rod side wall opening selectively placing the balloon dilation rod outer surface in fluid communication with the balloon dilation rod lumen, the balloon dilation rod distal end having a balloon dilation rod open tip, the balloon dilation rod having a balloon dilation rod open slit, the balloon dilation rod open slit extending between the balloon dilation rod side wall opening and the balloon dilation rod open tip; and an expandable balloon positioned on at least one of the balloon dilation rod body and balloon dilation rod distal end, the balloon having a balloon open slit that at least partially extends for at least a partial length of the balloon, the balloon open slit being aligned with the balloon dilation rod open slit.

Aspect 46. The balloon dilation device of aspect 45, wherein the balloon dilation rod lumen extends between the balloon dilation rod side wall opening and the balloon dilation rod open tip.

Aspect 47. The balloon dilation device of aspect 45, wherein the balloon dilation rod lumen extends between the balloon dilation rod proximal end and the balloon dilation rod open tip.

Aspect 48. The balloon dilation device of aspect 45, including a balloon inflation channel longitudinally extending between the balloon dilation rod proximal end and a balloon inflation side wall opening, the balloon inflation side wall opening selectively placing a balloon expanding chamber in fluid communication with the balloon inflation channel.

Aspect 49. The balloon dilation device of aspect 48, wherein the balloon inflation channel is at least partially located within the balloon dilation rod lumen.

Aspect 50. The balloon dilation device of aspect 45, wherein an expandable implant is removably mounted circumferentially about at least a portion of the expandable balloon.

Aspect 51. The balloon dilation device of aspect 45, wherein the balloon dilation rod distal end has a conical head, the conical head pointing toward a longitudinally distal direction.

Aspect 52. The balloon dilation device of aspect 45, wherein the balloon dilation rod distal end has an outer sheath splitter disposed thereon.

Aspect 53. The balloon dilation device of aspect 52, wherein the outer sheath splitter is arrow-shaped, the arrow-shaped outer sheath splitter pointing toward a longitudinally distal direction.

Aspect 54. The balloon dilation device of aspect 45, wherein the expandable balloon includes a plurality of expandable sub-balloons positioned circumferentially about at least one of the balloon dilation rod body and the balloon dilation rod distal end, the balloon open slit being positioned between at least one of the plurality of expandable sub-balloons and another one of the plurality of expandable sub-balloons.

Aspect 55. The balloon dilation device of aspect 54, wherein each of the plurality of expandable sub-balloons has a separate sub-balloon inflation channel therein.

Aspect 56. The balloon dilation device of aspect 54, wherein the expandable balloon includes an elastic cover encapsulating the plurality of expandable sub-balloons between an elastic cover inner surface and the balloon dilation rod outer surface, at least a portion of the elastic cover being attached to at least a portion of the balloon dilation rod lumen so that at least a portion of the elastic cover forms a portion of the balloon dilation rod lumen, the elastic cover forming an elastic cover open slit that is aligned with, and at least partially contacting, the balloon dilation rod open slit.

Aspect 57. The balloon dilation device of aspect 56, wherein the elastic cover is attached to the balloon dilation rod lumen at least partially by a balloon fixer, the balloon fixer having a balloon fixer inner lumen and a balloon fixer outer surface, the balloon fixer having a balloon fixer open slit that places the balloon fixer outer surface in fluid communication with the balloon fixer inner lumen, the balloon fixer being disposed within at least a portion of the balloon dilation rod lumen, the balloon fixer being disposed on the portion of the elastic cover that forms a portion of the balloon dilation rod lumen, the balloon fixer inner lumen being in fluid communication with the balloon dilation rod lumen, the balloon fixer open slit being selectively aligned with the balloon dilation rod open slit.

Aspect 58. The balloon dilation device of aspect 57, wherein at least a portion of the elastic cover is attached to a portion of the balloon dilation rod open slit and to at least a portion of balloon dilation rod outer surface adjacent to the balloon dilation rod open slit.

Aspect 59. The balloon dilation device of aspect 45, wherein at least a portion of the expandable balloon is attached to at least a portion of the balloon dilation rod lumen so that at least a portion of the expandable balloon forms at least a portion of the balloon dilation rod lumen.

60. The balloon dilation device of aspect 59, wherein the expandable balloon is attached to the balloon dilation rod lumen at least partially by a balloon fixer, the balloon fixer having a balloon fixer lumen and a balloon fixer outer surface, the balloon fixer having a balloon fixer open slit that places the balloon fixer outer surface in fluid communication with the balloon fixer lumen, the balloon fixer being disposed within at least a portion of the balloon dilation rod lumen, the expandable balloon fixer being disposed on the portion of the balloon material that forms a portion of the balloon dilation rod lumen, the balloon fixer lumen being in fluid communication with the balloon dilation rod lumen, the balloon fixer open slit being selectively aligned with the balloon dilation rod open slit.

Aspect 61. The balloon dilation device of aspect 60, wherein a least a portion of the expandable balloon is attached to a portion of the balloon dilation rod open slit and to at least a portion of the balloon dilation rod outer surface adjacent to the balloon dilation rod open slit.

Aspect 62. The balloon dilation device of aspect 45, wherein the balloon dilation rod open slit has a balloon dilation rod open slit first surface and a balloon dilation rod open slit second surface, the balloon dilation rod open slit first surface being oppositely facing and abutting the balloon dilation rod open slit second surface, the balloon dilation rod open slit first surface and the balloon dilation rod open slit second surface being selectively elastically separable.

In summary, a person having ordinary skill in the art will understand that, in an aspect 63, a method for constructing a balloon dilation device comprises:
- providing a balloon dilation rod including a balloon dilation rod proximal end, a balloon dilation rod distal end, and an elongate balloon dilation rod body longitudinally extending between the balloon dilation rod proximal and distal ends, the balloon dilation rod having a balloon dilation rod outer surface and a balloon dilation rod lumen, the balloon dilation rod having a balloon dilation rod side wall opening, the balloon dilation rod side wall opening selectively placing the balloon dilation rod outer surface in fluid communication with the balloon dilation rod lumen, the balloon dilation rod distal end having a balloon dilation rod open tip, the balloon dilation rod having a balloon dilation rod open slit, the balloon dilation rod open slit extending between the balloon dilation rod side wall opening and the balloon dilation rod open tip;
- placing a balloon material at least partially circumferentially about the balloon dilation rod outer surface so that at least a portion of the balloon material is adjacent to at least a portion of the balloon dilation rod open slit;
- urging at least a portion of the balloon material through the balloon dilation rod open slit and into the balloon dilation rod lumen;
- attaching at least a portion of the balloon material inserted into the balloon dilation rod lumen to at least a portion of the balloon dilation rod lumen, the portion of the balloon material attached to the portion of the balloon dilation rod lumen forming at least a portion of the balloon dilation rod lumen, the balloon material forming a balloon open slit that is aligned with the balloon dilation rod open slit when the balloon material is attached to the balloon dilation rod lumen;
- inserting a balloon fixer through the balloon dilation rod open slit and into the balloon dilation rod lumen, the balloon fixer having a balloon fixer lumen and a balloon fixer outer surface, the balloon fixer having a balloon fixer open slit that places the balloon fixer outer surface in fluid communication with the balloon fixer lumen, the balloon fixer lumen being in fluid communication with the balloon dilation rod lumen when the balloon fixer is inserted within at least a portion of the balloon dilation rod lumen;
- disposing the balloon fixer on a portion of the balloon material that forms a portion of the balloon dilation rod lumen;
- aligning the balloon fixer with the balloon fixer open slit aligned with the balloon dilation rod open slit;
- attaching the balloon fixer to at least one of the balloon dilation rod lumen and the portion of the balloon material that forms a portion of the balloon dilation rod lumen;
- circumferentially attaching at least a portion of a balloon material proximal end to at least a portion the balloon dilation rod outer surface adjacent to the balloon dilation rod open slit; and
- circumferentially attaching at least a portion of a balloon material distal end to at least a portion the balloon dilation rod outer surface adjacent to the balloon dilation rod open slit.

Aspect 64. The method of claim 63, wherein the balloon material is an elastic cover, the method further including:
prior to attaching at least a portion of the balloon material inserted into the balloon dilation rod lumen to at least a portion of the balloon dilation rod lumen, attaching a plurality of expandable sub-balloons at least partially circumferentially about the balloon dilation rod outer surface adjacent to the balloon dilation rod open slit; and
inserting at least a portion of the balloon material through the balloon dilation rod open slit and into the balloon dilation rod lumen to at least partially encapsulate the plurality of expandable sub-balloons between a balloon material inner surface and the balloon dilation rod outer surface.

Aspect 65. The method of aspect 64, including:
inserting at least a portion of a balloon material first end through the balloon dilation rod open slit and into the balloon dilation rod lumen;
inserting at least a portion of a balloon material second end through the balloon dilation rod open slit and into the balloon dilation rod lumen; and
attaching at least a portion of the balloon material first and second ends inserted into the balloon dilation rod lumen to at least a portion of the balloon dilation rod lumen, the portions of the balloon material attached to the portion of the balloon dilation rod lumen collectively forming at least a portion of the balloon dilation rod lumen, the balloon material forming a balloon open slit that is aligned with the balloon dilation rod open slit when the balloon material first and second ends are attached to the balloon dilation rod lumen.

Aspect 66. The method of aspect 64, wherein the balloon material is ring-shaped.

Aspect 67. The method of aspect 63, wherein the balloon material is ring-shaped.

In summary, a person having ordinary skill in the art will understand that, in an aspect 64, a method for dilating a patient lumen comprises:
providing a balloon dilation device including
a balloon dilation rod having a balloon dilation rod proximal end, a balloon dilation rod distal end, and an elongate balloon dilation rod body longitudinally extending between the balloon dilation rod proximal and distal ends, the balloon dilation rod having a balloon dilation rod outer surface and a balloon dilation rod lumen, the balloon dilation rod having a balloon dilation rod side wall opening, the balloon dilation rod side wall opening selectively placing the balloon dilation rod outer surface in fluid communication with the balloon dilation rod lumen, the balloon dilation rod distal end having a balloon dilation rod open tip, the balloon dilation rod having a balloon dilation rod open slit, the balloon dilation rod open slit extending between the balloon dilation rod side wall opening and the balloon dilation rod open tip, a balloon dilation rod open slit first surface and a balloon dilation rod open slit second surface, the balloon dilation rod open slit first surface being oppositely facing and abutting the balloon dilation rod open slit second surface, the balloon dilation rod open slit first surface and the balloon dilation rod open slit second surface being selectively elastically separable, and
an expandable balloon positioned on at least one of the balloon dilation rod body and balloon dilation rod distal end, the balloon having a balloon open slit that at least partially extends for at least a partial length of the balloon, the balloon open slit being aligned with the balloon dilation rod open slit;

inserting a guidewire distal end into a target patient tissue site in a patient lumen;
directing a guidewire proximal end into the balloon dilation rod open tip, through at least a portion of the balloon dilation rod lumen, and out from the balloon dilation rod side wall opening;
directing the balloon dilation device to the target patient tissue site along the guidewire; and
with the balloon dilation device at the target patient tissue site, inflating the expandable balloon to dilate the patient lumen;
deflating the balloon after the patient lumen has achieved a predetermined amount of dilation;
directing a secondary device over the guidewire until the secondary device is at least one of adjacent to and at least partially within the balloon dilation rod side wall opening;
with the secondary device at least one of adjacent to and at least partially in the balloon dilation rod side wall opening, longitudinally moving the balloon dilation rod toward a proximal direction to remove the balloon dilation device from the guidewire, movement of the balloon dilation rod toward the proximal direction causing the secondary device to selectively urge the balloon dilation rod open slit first surface elastically apart from the balloon dilation rod open slit second surface and remove the balloon dilation device from the guidewire, while maintaining the guidewire at the target patient site; and
directing the secondary device to the target patient tissue site.

Aspect 65. The method of claim 64, wherein the secondary device has an expandable implant mounted thereon, the method further including:
with the secondary device at the target patient tissue site, expanding the expandable implant; and
with the expandable implant expanded, longitudinally moving the secondary device in the proximal direction to remove the secondary device from the target patient tissue site, while maintaining at least one of the guidewire and the expandable implant at the target patient tissue site.

Aspect 66. The method of aspect 64, wherein the balloon dilation rod lumen extends entirely between the balloon dilation rod proximal end and the balloon dilation rod open tip.

Aspect 67. The method of claim 64, including:
mounting an expandable implant circumferentially about at least a portion of the balloon;
inflating the balloon to cause the expandable implant to expand; and
with the expandable implant expanded, deflating the balloon.

Aspect 68. The method of aspect 64, including with the secondary device located at the target patient tissue site, performing a medical procedure with the secondary device.

While aspects of this disclosure have been particularly shown and described with reference to the example aspects above, it will be understood by those of ordinary skill in the art that various additional aspects may be contemplated. For example, the specific methods described above for using the apparatus are merely illustrative; one of ordinary skill in the art could readily determine any number of tools, sequences of steps, or other means/options for placing the above-described apparatus, or components thereof, into positions substantively similar to those shown and described herein. In an effort to maintain clarity in the Figures, certain ones of duplicative components shown have not been specifically numbered, but one of ordinary skill in the art will realize, based upon the components that were numbered, the element numbers which should be associated with the unnumbered components; no differentiation between similar components is intended or implied solely by the presence or absence of an element number in the Figures. Any of the described structures and components could be integrally formed as a single unitary or monolithic piece or made up of separate sub-components, with either of these formations involving any suitable stock or bespoke components and/or any suitable material or combinations of materials; however, the chosen material(s) should be biocompatible for many applications. Any of the described structures and components could be disposable or reusable as desired for a particular use environment. Any component could be provided with a user-perceptible marking to indicate a material, configuration, at least one dimension, or the like pertaining to that component, the user-perceptible marking potentially aiding a user in selecting one component from an array of similar components for a particular use environment. A "predetermined" status may be determined at any time before the structures being manipulated actually reach that status, the "predetermination" being made as late as immediately before the structure achieves the predetermined status. The term "substantially" is used herein to indicate a quality that is largely, but not necessarily wholly, that which is specified—a "substantial" quality admits of the potential for some relatively minor inclusion of a non-quality item. Though certain components described herein are shown as having specific geometric shapes, all structures of this disclosure may have any suitable shapes, sizes, configurations, relative relationships, cross-sectional areas, or any other physical characteristics as desirable for a particular application. Any structures or features described with reference to one aspect or configuration could be provided, singly or in combination with other structures or features, to any other aspect or configuration, as it would be impractical to describe each of the aspects and configurations discussed herein as having all of the options discussed with respect to all of the other aspects and configurations. A device or method incorporating any of these features should be understood to fall under the scope of this disclosure as determined based upon the claims below and any equivalents thereof.

Other aspects, objects, and advantages may be obtained from a study of the drawings, the disclosure, and the appended claims.

What is claimed is:

1. A method for inserting multiple dilators into a target patient tissue site, the method comprising:
providing a modular dilation device including a first dilator, the first dilator having an elongate first dilator body and a first dilator distal end, the first dilator having a first dilator outer surface and a first dilator inner lumen, the first dilator distal end having a first dilator open tip, the first dilator having a first dilator side wall opening, the first dilator side wall opening selectively placing the first dilator outer surface in fluid communication with the first dilator inner lumen, and
a second dilator, the second dilator having an elongate second dilator body and a second dilator distal end, the second dilator having a second dilator inner lumen, the second dilator distal end having a second dilator open tip;
inserting a guidewire distal end of a guidewire into a target patient tissue site through a patient tissue access point;

directing a guidewire proximal end into the first dilator open tip, through at least a portion of the first dilator inner lumen, and out of the first dilator through the first dilator side wall opening;

directing the first dilator to the target patient tissue site along the guidewire;

directing the guidewire proximal end into the second dilator open tip, through at least a portion of the second dilator inner lumen, and out from the second dilator;

and directing the second dilator to the target patient tissue site along the guidewire until the second dilator open tip is adjacent to the first dilator side wall opening.

2. The method of claim 1, including:

placing the second dilator into a predetermined relationship with the first dilator, wherein the second dilator open tip is adjacent to the first dilator side wall opening;

directing the guidewire proximal end into the first dilator open tip and out of the second dilator, wherein the guidewire proximal end is directed through the first dilator open tip and at least a portion of the first dilator inner lumen, through the first dilator side wall opening, through the second dilator open tip and the second dilator inner lumen, and out from the second dilator; and collectively inserting both the first dilator and the second dilator into the target patient tissue site along the guidewire.

3. The method of claim 1, wherein the first dilator has a first dilator open slit, the first dilator open slit extending between the first dilator side wall opening and the first dilator open tip, the first dilator open slit including a first dilator open slit first surface and a first dilator open slit second surface, the first dilator open slit first surface being oppositely facing and abutting the first dilator open slit second surface, the first dilator open slit first surface and the first dilator open slit second surface being selectively elastically separable, and the second dilator open tip and at least a portion of the second dilator distal end are each smaller in diameter than at least one of the first dilator inner lumen and the first dilator side wall opening, the method further including:

directing each of the second dilator open tip and at least a portion of the second dilator distal end at least one of adjacent to and at least partially into the first dilator side wall opening; and with the second dilator distal end at least one of adjacent to and at least partially in the first dilator side wall opening, longitudinally moving the first dilator toward a proximal direction to remove the first dilator from the guidewire, wherein as the first dilator is moved toward the proximal direction, the second dilator distal end selectively urges the first dilator open slit first surface elastically apart from the first dilator open slit second surface and the first dilator is removed from the guidewire, while maintaining the guidewire at the target patient site.

4. The method of claim 1, including:

providing a third dilator, the third dilator having an elongate third dilator body and a third dilator distal end, the third dilator having a third dilator outer surface and a third dilator inner lumen, the third dilator distal end having a third dilator open tip, the third dilator having a third dilator side wall opening, the third dilator side wall opening selectively placing the third dilator outer surface in fluid communication with the third dilator inner lumen, the third dilator having a third dilator open slit, the third dilator open slit extending between the third dilator side wall opening and the third dilator open tip;

directing the guidewire proximal end into the third dilator open tip, through at least a portion of the third dilator inner lumen, and out from the third dilator through the third dilator side wall opening;

directing the third dilator into the target patient tissue site along the guidewire until the third dilator open tip is adjacent to the first dilator side wall opening; and directing the second dilator into the target patient tissue site along the guidewire until the second dilator open tip is adjacent to the third dilator side wall opening.

5. The method of claim 4, including:

placing the third dilator into a predetermined relationship with the first dilator, wherein the third dilator open tip is adjacent to the first dilator side wall opening;

placing the second dilator into a predetermined relationship with the third dilator, wherein the second dilator open tip is adjacent to the third dilator side wall opening;

directing the guidewire proximal end into the first dilator open tip and out of the second dilator, wherein the guidewire proximal end is directed through the first dilator open tip and at least a portion of the first dilator inner lumen, through the first dilator side wall opening, through the third dilator open tip and at least a portion of the third dilator inner lumen, through the third dilator side wall opening, through the second dilator open tip and the second dilator inner lumen, and out from the second dilator; and collectively inserting the first dilator, the second dilator, and the third dilator into the target patient tissue site along the guidewire.

6. The method of claim 4, wherein first dilator has a first dilator open slit, the first dilator open slit extending between the first dilator side wall opening and the first dilator open tip, the first dilator open slit including a first dilator open slit first surface and a first dilator open slit second surface, the first dilator open slit first surface being oppositely facing and abutting the first dilator open slit second surface, the first dilator open slit first surface and the first dilator open slit second surface being selectively elastically separable, and the third dilator open slit includes a third dilator open slit first surface and a third dilator open slit second surface, the third dilator open slit first surface being oppositely facing and abutting the third dilator open slit second surface, the third dilator open slit first surface and the third dilator open slit second surface being selectively elastically separable, the method further including:

directing at least a portion of the second dilator distal end at least one of adjacent to and at least partially into the third dilator side wall opening;

with the second dilator distal end at least one of adjacent to and at least partially in the third dilator side wall opening, longitudinally moving the third dilator toward a proximal direction to remove the third dilator from the guidewire, wherein as the third dilator is moved toward the proximal direction, the second dilator distal end selectively urges the third dilator open slit first surface elastically apart from the third dilator open slit second surface and the third dilator is removed from the guidewire, while maintaining the guidewire at the target patient site;

directing at least a portion of the second dilator distal end at least one of adjacent to and at least partially into the first dilator side wall opening; and with the second dilator distal end at least one of adjacent to and at least partially in the first dilator side wall opening, longitudinally moving the first dilator toward a proximal direction to remove the first dilator from the guidewire, wherein as the first dilator is moved toward the proximal direction, the second dilator distal end selectively urges the first dilator open slit first surface elastically apart from the first dilator open slit second surface and the first dilator is removed from the guidewire, while maintaining the guidewire at the target patient site.

7. The method of claim 1, wherein the second dilator open tip and at least a portion of the second dilator distal end that are each smaller in diameter than at least one of a third dilator inner lumen and a third dilator side wall opening, the method further including:

provMiding a third dilator, the third dilator having an elongate third dilator body and a third dilator distal end, the third dilator having a third dilator outer surface and a third dilator inner lumen, the third dilator distal end having a third dilator open tip, the third dilator having a third dilator side wall opening, the third dilator side wall opening selectively placing the third dilator outer surface in fluid communication with the third dilator inner lumen, the third dilator having a third dilator open slit, the third dilator open slit extending between the third dilator side wall opening and the third dilator open tip, the third dilator open tip and at least a portion of the third dilator distal end each being smaller in diameter than at least one of the first dilator inner lumen and the first dilator side wall opening;

inserting the second dilator open tip and at least a portion of the second dilator distal end into the third dilator inner lumen through the third dilator side wall opening;

inserting the third dilator open tip and at least a portion of the third dilator distal end into the first dilator inner lumen through the first dilator side wall opening;

directing the guidewire proximal end into the first dilator open tip and out of the second dilator, wherein the guidewire proximal end is directed through the first dilator open tip and at least a portion of the first dilator inner lumen, through the third dilator open tip and at least a portion of the third dilator inner lumen, through the second dilator open tip and the second dilator inner lumen, and out from the second dilator; and collectively inserting the first dilator, the second dilator, and the third dilator into the target patient tissue site along the guidewire.

8. The method of claim 7, wherein first dilator has a first dilator open slit, the first dilator open slit extending between the first dilator side wall opening and the first dilator open tip, the first dilator open slit including a first dilator open slit first surface and a first dilator open slit second surface, the first dilator open slit first surface being oppositely facing and abutting the first dilator open slit second surface, the first dilator open slit first surface and the first dilator open slit second surface being selectively elastically separable, and the third dilator open slit including a third dilator open slit first surface and a third dilator open slit second surface, the third dilator open slit first surface being oppositely facing and abutting the third dilator open slit second surface, the third dilator open slit first surface and the third dilator open slit second surface being selectively elastically separable, the method further including:

with the third dilator distal end at least partially in the first dilator side wall opening, longitudinally moving the first dilator toward a proximal direction to remove the first dilator from the guidewire, wherein as the first dilator is moved toward the proximal direction, the third dilator distal end selectively urges the first dilator open slit first surface elastically apart from the first dilator open slit second surface and the first dilator is removed from the guidewire, while maintaining the guidewire at the target patient site; and with the second dilator distal end at least partially in the third dilator side wall opening, longitudinally moving the third dilator toward a proximal direction to remove the third dilator from the guidewire, wherein as the third dilator is moved toward the proximal direction, the second dilator distal end selectively urges the third dilator open slit first surface elastically apart from the third dilator open slit second surface and the third dilator is removed from the guidewire, while maintaining the guidewire at the target patient site.

\* \* \* \* \*